US012570630B2

(12) United States Patent

Kim et al.

(10) Patent No.: US 12,570,630 B2
(45) Date of Patent: Mar. 10, 2026

(54) HETEROCYLIC COMPOUND AND LIGHT-EMITTING DEVICE AND ELECTRONIC APPARATUS INCLUDING THE HETEROCYCLIC COMPOUND

(71) Applicant: Samsung Display Co., Ltd., Yongin-si (KR)

(72) Inventors: Taeil Kim, Yongin-si (KR); Munki Sim, Yongin-si (KR); Sunyoung Pak, Yongin-si (KR); Junha Park, Yongin-si (KR); Jangyeol Baek, Yongin-si (KR); Kyoung Sunwoo, Yongin-si (KR); Chanseok Oh, Yongin-si (KR); Minjung Jung, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 939 days.

(21) Appl. No.: 17/693,418

(22) Filed: Mar. 14, 2022

(65) Prior Publication Data

US 2022/0340602 A1 Oct. 27, 2022

(30) Foreign Application Priority Data

Mar. 16, 2021 (KR) ........................ 10-2021-0034236

(51) Int. Cl.
*H01L 51/50* (2006.01)
*C07C 15/28* (2006.01)
(Continued)

(52) U.S. Cl.
CPC ............ *C07D 401/14* (2013.01); *C07C 15/28* (2013.01); *C07C 15/30* (2013.01); *C07C 15/38* (2013.01);
(Continued)

(58) Field of Classification Search
None
See application file for complete search history.

(56) References Cited

U.S. PATENT DOCUMENTS

| | | | | |
|---|---|---|---|---|
| 2006/0124924 A1* | 6/2006 | Suh | ...................... | H10K 10/466 257/40 |
| 2010/0001301 A1* | 1/2010 | Karg | ...................... | H10K 50/86 257/40 |

(Continued)

FOREIGN PATENT DOCUMENTS

| | | |
|---|---|---|
| JP | 2019119680 | 7/2019 |
| KR | 10-2016-0119683 | 10/2016 |

(Continued)

OTHER PUBLICATIONS

Pershin, Anton, et al. "Highly Emissive Excitons with Reduced Exchange Energy in Thermally Activated Delayed Fluorescent Molecules." Nature Communications, vol. 10, No. 1, 2019 Deep-Blue Organic Light-Emitting Diode Featuring an Organoboron-Based 10, 2019, pp. 678-682.

(Continued)

*Primary Examiner* — Gregory D Clark
(74) *Attorney, Agent, or Firm* — Womble Bond Dickinson (US) LLP

(57) ABSTRACT

A light-emitting device includes: a first electrode; a second electrode facing the first electrode; and an interlayer between the first electrode and the second electrode and including an emission layer, wherein the interlayer includes a heterocyclic compound of Formula 1:

$$A_1 \text{-}[B_1]_{n1}$$ Formula 1 wherein, in Formula 1, the variables are defined herein.

18 Claims, 3 Drawing Sheets

10

(51) Int. Cl.

| | |
|---|---|
| ***C07C 15/30*** | (2006.01) |
| ***C07C 15/38*** | (2006.01) |
| ***C07C 15/46*** | (2006.01) |
| ***C07C 211/54*** | (2006.01) |
| ***C07D 209/82*** | (2006.01) |
| ***C07D 213/22*** | (2006.01) |
| ***C07D 213/74*** | (2006.01) |
| ***C07D 235/08*** | (2006.01) |
| ***C07D 251/24*** | (2006.01) |
| ***C07D 307/91*** | (2006.01) |
| ***C07D 333/76*** | (2006.01) |
| ***C07D 401/04*** | (2006.01) |
| ***C07D 401/10*** | (2006.01) |
| ***C07D 401/12*** | (2006.01) |
| ***C07D 401/14*** | (2006.01) |
| ***C07D 403/10*** | (2006.01) |
| ***C07D 403/14*** | (2006.01) |
| ***C07D 405/12*** | (2006.01) |
| ***C07D 409/12*** | (2006.01) |
| ***C07D 487/04*** | (2006.01) |
| ***C07D 491/048*** | (2006.01) |
| ***C07D 495/04*** | (2006.01) |
| ***C07F 1/02*** | (2006.01) |
| ***C07F 3/00*** | (2006.01) |
| ***C07F 5/02*** | (2006.01) |
| ***C07F 5/06*** | (2006.01) |
| ***C07F 7/08*** | (2006.01) |
| ***C07F 11/00*** | (2006.01) |
| ***C07F 15/00*** | (2006.01) |
| ***H10K 50/12*** | (2023.01) |
| ***H10K 50/16*** | (2023.01) |
| ***H10K 85/30*** | (2023.01) |
| ***H10K 85/40*** | (2023.01) |
| ***H10K 85/60*** | (2023.01) |

(52) U.S. Cl.

CPC ............ *C07C 15/46* (2013.01); *C07C 211/54* (2013.01); *C07D 209/82* (2013.01); *C07D 213/22* (2013.01); *C07D 213/74* (2013.01); *C07D 235/08* (2013.01); *C07D 251/24* (2013.01); *C07D 307/91* (2013.01); *C07D 333/76* (2013.01); *C07D 401/04* (2013.01); *C07D 401/10* (2013.01); *C07D 401/12* (2013.01); *C07D 403/10* (2013.01); *C07D 403/14* (2013.01); *C07D 405/12* (2013.01); *C07D 409/12* (2013.01); *C07D 487/04* (2013.01); *C07D 491/048* (2013.01); *C07D 495/04* (2013.01); *C07F 1/02* (2013.01); *C07F 3/006* (2013.01); *C07F 5/027* (2013.01); *C07F 5/069* (2013.01); *C07F 7/0803* (2013.01); *C07F 7/0812* (2013.01); *C07F 11/00* (2013.01); *C07F 15/002* (2013.01); *C07F 15/0033* (2013.01); *C07F 15/0086* (2013.01); *C07F 15/0093* (2013.01); *H10K 50/12* (2023.02); *H10K 50/16* (2023.02); *H10K 85/30* (2023.02); *H10K 85/324* (2023.02); *H10K 85/342* (2023.02); *H10K 85/346* (2023.02); *H10K 85/348* (2023.02); *H10K 85/40* (2023.02); *H10K 85/615* (2023.02); *H10K 85/622* (2023.02); *H10K 85/624* (2023.02); *H10K 85/631* (2023.02); *H10K 85/633* (2023.02); *H10K 85/636* (2023.02); *H10K 85/652* (2023.02); *H10K 85/654* (2023.02); *H10K 85/657* (2023.02); *H10K 85/6572* (2023.02); *H10K 85/6574* (2023.02); *H10K 85/6576* (2023.02); *H10K 85/658* (2023.02); *C07B 2200/05* (2013.01)

(56) References Cited

U.S. PATENT DOCUMENTS

| | | | | |
|---|---|---|---|---|
| 2018/0019408 | A1 | 1/2018 | Ko | |
| 2019/0119312 | A1 | 4/2019 | Chen et al. | |
| 2020/0119289 | A1 | 4/2020 | Lin et al. | |
| 2020/0144513 | A1 | 5/2020 | Hatakeyama et al. | |
| 2020/0176679 | A1 | 6/2020 | Jeong et al. | |
| 2020/0190115 | A1 * | 6/2020 | Hatakeyama ........ | H10K 85/322 |
| 2020/0283463 | A1 | 9/2020 | Lee et al. | |
| 2021/0277026 | A1 | 9/2021 | Geum et al. | |

FOREIGN PATENT DOCUMENTS

| | | | |
|---|---|---|---|
| KR | 10-2018-0007735 | A | 1/2018 |
| KR | 101876763 | | 7/2018 |
| KR | 102058028 | | 12/2019 |
| KR | 10-2020-0006965 | | 1/2020 |
| KR | 10-2020-0011383 | | 2/2020 |
| KR | 10-2020-0108147 | | 9/2020 |
| KR | 10-2020-0141983 | A | 12/2020 |
| KR | 10-2020-0143653 | A | 12/2020 |
| WO | 2018212169 | | 11/2018 |
| WO | 2020/040298 | A1 | 2/2020 |
| WO | 2020/045681 | A1 | 3/2020 |

OTHER PUBLICATIONS

Kondo, Yasuhiro, et al. “Narrowband Emitter.” Nature Photonics, vol. 13, no.

Notice of Allowance issued in corresponding KR Patent Application No. 10-2021-0034236, dated Jan. 27, 2026, 8pp.

* cited by examiner

HETEROCYLIC COMPOUND AND LIGHT-EMITTING DEVICE AND ELECTRONIC APPARATUS INCLUDING THE HETEROCYCLIC COMPOUND

CROSS-REFERENCE TO RELATED APPLICATION

This application claims priority from and the benefit of Korean Patent Application No. 10-2021-0034236, filed on Mar. 16, 2021, which is hereby incorporated by reference for all purposes as if fully set forth herein.

BACKGROUND

Field

Embodiments of the invention relate generally to display devices, and more particularly, to a heterocyclic compound and to a light-emitting device and an electronic apparatus including the heterocyclic compound.

Discussion of the Background

Organic light-emitting devices (OLEDs) are self-emissive devices that have wide viewing angles, high contrast ratios, short response times, and excellent characteristics in terms of luminance, driving voltage, and response speed, compared to devices in the art.

Organic light-emitting devices may include a first electrode located on a substrate, and a hole transport region, an emission layer, an electron transport region, and a second electrode sequentially stacked on the first electrode. Holes provided from the first electrode may move toward the emission layer through the hole transport region, and electrons provided from the second electrode may move toward the emission layer through the electron transport region. Carriers, such as holes and electrons, recombine in the emission layer to produce excitons. These excitons transition from an excited state to a ground state to thereby generate light.

The above information disclosed in this Background section is only for understanding of the background of the inventive concepts, and, therefore, it may contain information that does not constitute prior art.

SUMMARY

When light-emitting devices and electronic apparatuses constructed according to the principles and illustrative implementations of the invention include a heterocyclic compound represented by one or more of the formula disclosed herein, the light-emitting devices may have low driving voltage, high emission efficiency, and high external quantum efficiency, and high-quality electronic apparatuses may be manufactured.

Additional features of the inventive concepts will be set forth in the description which follows, and in part will be apparent from the description, or may be learned by practice of the inventive concepts.

According to one aspect of the invention, a light-emitting device includes: a first electrode; a second electrode facing the first electrode; and an interlayer between the first electrode and the second electrode and including an emission layer, wherein the interlayer includes a heterocyclic compound of Formula 1:

Formula 1

$A_1-[B_1]_{n1}$

Formula 1-1

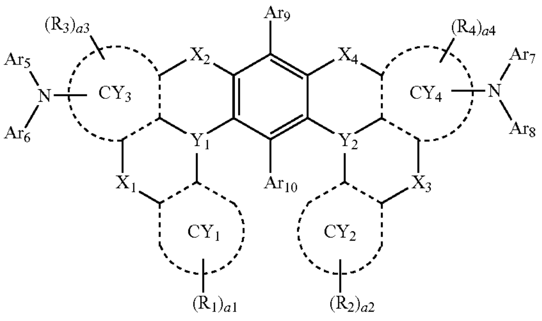

Formula 1-2

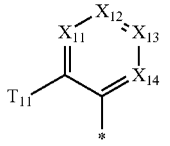

wherein, in Formulae 1, 1-1, and 1-2, the variables are defined herein.

The heterocyclic compound of Formula 1 may be included in the emission layer.

The organometallic compound of Formula 401 may be further included in the emission layer:

Formula 401

$M(L_{401})_{xc1}(L_{402})_{xc2}$

Formula 402

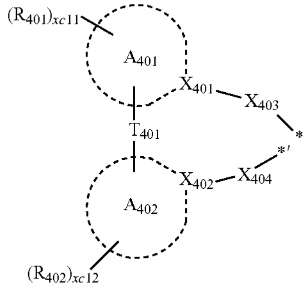

wherein, in Formulae 401 and 402, the variables are defined herein.

The emission layer may be configured to emit blue light.

The emission layer may further include a host, and an amount of the host may be greater than an amount of the heterocyclic compound of Formula 1.

The host may include two different host compounds.

The host may include a hole transport host compound and an electron transport host compound.

The interlayer may further include a hole transport region between the first electrode and the emission layer and an electron transport region between the emission layer and the second electrode, the hole transport region may include a hole injection layer, a hole transport layer, an emission auxiliary layer, an electron blocking layer, or any combination thereof, and the electron transport region may include a buffer layer, a hole blocking layer, an electron control layer, an electron transport layer, an electron injection layer, or any combination thereof.

The emission layer may include the heterocyclic compound of Formula 1, the hole transport region may include a compound of Formula 201, a compound of Formula 202, or any combination thereof:

Formula 201

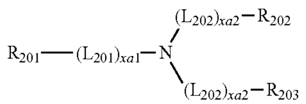

Formula 202

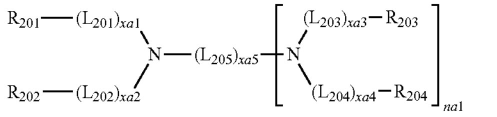

wherein, in Formulae 201 and 202, the variables are defined herein.

Each of Formulae 201 and 202 may include at least one group of Formulae CY201 to CY217, as defined herein.

The emission layer may include the heterocyclic compound of Formula 1, the electron transport region includes a compound of Formula 601:

$[Ar_{601}]_{xe11}\text{-}[(L_{601})_{xe1}\text{-}R_{601}]_{xe21}$ Formula 601 wherein, in Formula 601, the variables are defined herein.

The electron transport layer in the electron transport region may include a compound of Formula 601, and the electron transport layer may further include a material including a metal.

The material may include a post-transition metal complex, an alkali metal complex, an alkaline earth metal complex, or any combination thereof.

The variables $Y_1$ and $Y_2$ may each be boron.

The Formula 1-2 may be of Formula 1-2-1 or 1-2-2:

Formula 1-2-1

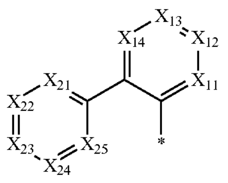

Formula 1-2-2

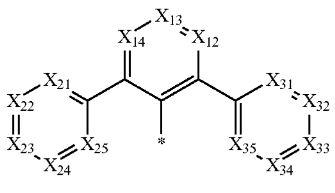

wherein, in Formulae 1-2-1 and 1-2-2, the variables are defined herein.

The Formula 1-2 may be one of Formulae 2-1 to 2-57, the variables are defined herein.

The Formula 1-1 may be of Formula 1-1-1:

Formula 1-1-1

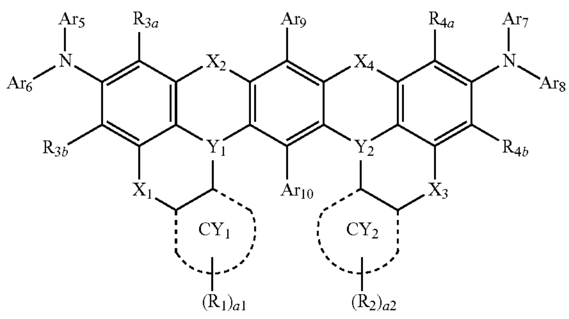

wherein, in Formula 1-1-1, the variables are defined herein.

The light-emitting device may further include a capping layer outside the first electrode or the second electrode, and the capping layer may include one or more carbocyclic compounds, heterocyclic compounds, amine-based compounds, porphyrin derivatives, phthalocyanine derivatives, naphthalocyanine derivatives, alkali metal complexes, alkaline earth-based complexes, or any combination thereof.

An electronic apparatus may include the light-emitting device, as described above.

The electronic apparatus may further include a thin-film transistor, wherein the thin-film transistor may include a source electrode and a drain electrode, and the first electrode of the light-emitting device may be electrically connected to at least one of the source electrode and the drain electrode of the thin-film transistor.

It is to be understood that both the foregoing general description and the following detailed description are illustrative and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate illustrative embodiments of the invention, and together with the description serve to explain the inventive concepts.

DETAILED DESCRIPTION

Figure 1:
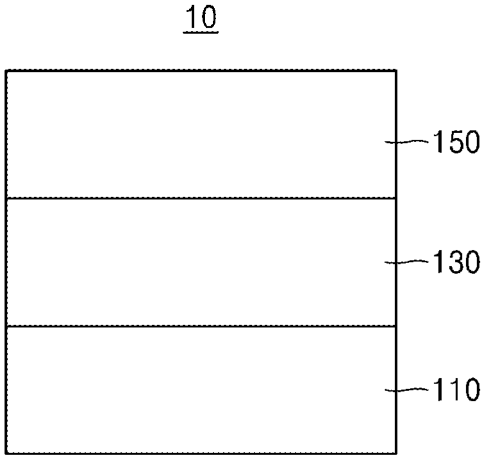
FIG. 1 is a schematic cross-sectional view of an embodiment of a light-emitting device constructed according to the principles of the invention.

In the following description, for the purposes of explanation, numerous specific details are set forth in order to provide a thorough understanding of various embodiments or implementations of the invention. As used herein "embodiments" and "implementations" are interchangeable words that are non-limiting examples of devices or methods employing one or more of the inventive concepts disclosed herein. It is apparent, however, that various embodiments may be practiced without these specific details or with one or more equivalent arrangements. In other instances, well-known structures and devices are shown in block diagram form in order to avoid unnecessarily obscuring various embodiments. Further, various embodiments may be different, but do not have to be exclusive. For example, specific shapes, configurations, and characteristics of an embodiment may be used or implemented in another embodiment without departing from the inventive concepts.

Unless otherwise specified, the illustrated embodiments are to be understood as providing illustrative features of varying detail of some ways in which the inventive concepts may be implemented in practice. Therefore, unless otherwise specified, the features, components, modules, layers, films, panels, regions, and/or aspects, etc. (hereinafter individually or collectively referred to as "elements"), of the various embodiments may be otherwise combined, separated, interchanged, and/or rearranged without departing from the inventive concepts.

The use of cross-hatching and/or shading in the accompanying drawings is generally provided to clarify boundaries between adjacent elements. As such, neither the presence nor the absence of cross-hatching or shading conveys or indicates any preference or requirement for particular materials, material properties, dimensions, proportions, commonalities between illustrated elements, and/or any other characteristic, attribute, property, etc., of the elements, unless specified. Further, in the accompanying drawings, the size and relative sizes of elements may be exaggerated for clarity and/or descriptive purposes. When an embodiment may be implemented differently, a specific process order may be performed differently from the described order. For example, two consecutively described processes may be performed substantially at the same time or performed in an order opposite to the described order. Also, like reference numerals denote like elements, and duplicative explanations are omitted to avoid redundancy.

When an element, such as a layer, is referred to as being "on," "connected to," or "coupled to" another element or layer, it may be directly on, connected to, or coupled to the other element or layer or intervening elements or layers may be present. When, however, an element or layer is referred to as being "directly on," "directly connected to," or "directly coupled to" another element or layer, there are no intervening elements or layers present. To this end, the term "connected" may refer to physical, electrical, and/or fluid connection, with or without intervening elements. Further, the D1-axis, the D2-axis, and the D3-axis are not limited to three axes of a rectangular coordinate system, such as the x, y, and z-axes, and may be interpreted in a broader sense. For example, the D1-axis, the D2-axis, and the D3-axis may be perpendicular to one another, or may represent different directions that are not perpendicular to one another. For the purposes of this disclosure, "at least one of X, Y, and Z" and "at least one selected from the group consisting of X, Y, and Z" may be construed as X only, Y only, Z only, or any combination of two or more of X, Y, and Z, such as, for instance, XYZ, XYY, YZ, and ZZ. As used herein, the term "and/or" includes any and all combinations of one or more of the associated listed items.

Although the terms "first," "second," etc. may be used herein to describe various types of elements, these elements should not be limited by these terms. These terms are used to distinguish one element from another element. Thus, a first element discussed below could be termed a second element without departing from the teachings of the disclosure.

Spatially relative terms, such as "beneath," "below," "under," "lower," "above," "upper," "over," "higher," "side" (e.g., as in "sidewall"), and the like, may be used herein for descriptive purposes, and, thereby, to describe one elements relationship to another element(s) as illustrated in the drawings. Spatially relative terms are intended to encompass different orientations of an apparatus in use, operation, and/or manufacture in addition to the orientation depicted in the drawings. For example, if the apparatus in the drawings is turned over, elements described as "below" or "beneath" other elements or features would then be oriented "above" the other elements or features. Thus, the term "below" can encompass both an orientation of above and below. Furthermore, the apparatus may be otherwise oriented (e.g., rotated 90 degrees or at other orientations), and, as such, the spatially relative descriptors used herein interpreted accordingly.

The terminology used herein is for the purpose of describing particular embodiments and is not intended to be limiting. As used herein, the singular forms, "a," "an," and "the" are intended to include the plural forms as well, unless the context clearly indicates otherwise. Moreover, the terms "comprises," "comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof. It is also noted that, as used herein, the terms "substantially," "about," and other similar terms, are used as terms of approximation and not as terms of degree, and, as such, are utilized to account for inherent deviations in measured, calculated, and/or provided values that would be recognized by one of ordinary skill in the art.

Various embodiments are described herein with reference to sectional and/or exploded illustrations that are schematic illustrations of idealized embodiments and/or intermediate structures. As such, variations from the shapes of the illustrations as a result, for example, of manufacturing techniques and/or tolerances, are to be expected. Thus, embodiments disclosed herein should not necessarily be construed as limited to the particular illustrated shapes of regions, but are to include deviations in shapes that result from, for instance, manufacturing. In this manner, regions illustrated in the drawings may be schematic in nature and the shapes of these regions may not reflect actual shapes of regions of a device and, as such, are not necessarily intended to be limiting.

Unless otherwise defined, all terms (including technical and scientific terms) used herein have the same meaning as commonly understood by one of ordinary skill in the art to which this disclosure is a part. Terms, such as those defined in commonly used dictionaries, should be interpreted as having a meaning that is consistent with their meaning in the context of the relevant art and should not be interpreted in an idealized or overly formal sense, unless expressly so defined herein.

A light-emitting device (for example, an organic light-emitting device) may include a first electrode; a second electrode facing the first electrode; an interlayer between the first electrode and the second electrode and including the emission layer, and a heterocyclic compound represented by Formula 1.

First, the heterocyclic compound may be represented by Formula 1:

$$A_1 \left[ B_1 \right]_{n1} \qquad \text{Formula 1}$$

wherein, in Formula 1, $A_1$ may be a group represented by Formula 1-1, $B_1$ may be a group represented by Formula 1-2, and n1 may be an integer from 1 to 10.

Formula 1-1

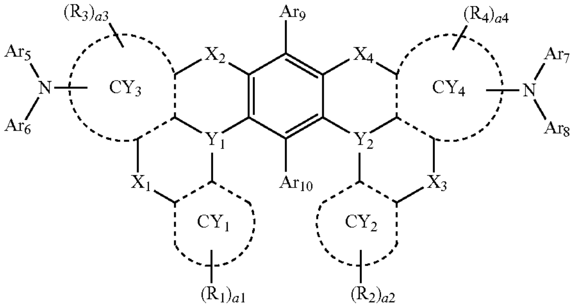

Formula 1-2

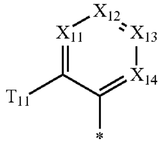

* in Formula 1-2 indicates a binding site to $A_1$ Formula 1.

Although not wanting to be bound by theory, because the heterocyclic compound represented by Formula 1 includes a group represented by Formula 1-2 as a substituent of Formula 1-1, light-emitting devices including such heterocyclic compounds may have excellent driving voltage, emission efficiency, color purity, and lifespan characteristics. Next, in Formulae 1-1 and 1-2, $CY_1$ to $CY_4$ in Formula 1-1 may each independently be a $C_5$-$C_{30}$ carbocyclic group or a $C_1$-$C_{30}$ heterocyclic group. For example, $CY_1$ to $CY_4$ may each independently be a benzene group, a naphthalene group, an anthracene group, a dibenzofuran group, a dibenzothiophene group, a carbazole group, a fluorene group, or dibenzosilole group.

In an embodiment, $CY_1$ and $CY_2$ may be identical to each other. For example, $CY_1$ and $CY_2$ may be a benzene group. In one or more embodiments, $CY_3$ and $CY_4$ may be identical to each other. For example, $CY_3$ and $CY_4$ may each be a benzene group. In one or more embodiments, $CY_1$ to $CY_4$ may be identical to each other. For example, $CY_1$ to $CY_4$ may each be a benzene group. The variables $Y_1$ and $Y_2$ in Formula 1-1 may each independently be B, P(=O), or P(=S). In an embodiment, $Y_1$ and $Y_2$ may be identical to each other. For example, $Y_1$ and $Y_2$ may each be B.

The variable $X_1$ in Formula 1-1 may be O, S, Se, Te, $N(Ar_1)$, $Al(Ar_1)$, or $P(Ar_1)$, $X_2$ may be O, S, Se, Te, $N(Ar_2)$, $Al(Ar_2)$, or $P(Ar_2)$, $X_3$ may be O, S, Se, Te, $N(Ar_3)$, $Al(Ar_3)$, or $P(Ar_3)$, and $X_4$ may be O, S, Se, Te, $N(Ar_4)$, $Al(Ar_4)$, or $P(Ar_4)$. In an embodiment, in Formula 1, $X_1$ may be $N(Ar_1)$, $X_2$ may be $N(Ar_2)$, $X_3$ may be $N(Ar_3)$, and $X_4$ may be $N(Ar_4)$; $X_1$ may be $N(Ar_1)$, $X_2$ may be $N(Ar_2)$, $X_3$ may be $N(Ar_3)$, and $X_4$ may be O, S, Se, or Te; $X_1$ may be $N(Ar_1)$, $X_2$ may be $N(Ar_2)$, $X_3$ may be O, S, Se, or Te, and $X_4$ may be $N(Ar_4)$; $X_1$ may be $N(Ar_1)$, $X_2$ may be O, S, Se, or Te, $X_3$ may be $N(Ar_3)$, and $X_4$ may be $N(Ar_4)$; or $X_1$ may be O, S, Se, or Te, $X_2$ may be $N(Ar_2)$, $X_3$ may be $N(Ar_3)$, and $X_4$ may be $N(Ar_4)$;

The variable $X_1$ may be $N(Ar_1)$, $X_2$ may be $N(Ar_2)$, $X_3$ may be O, S, Se, or Te, $X_4$ may be O, S, Se, or Te; $X_1$ may be $N(Ar_1)$, $X_2$ may be O, S, Se, or Te, $X_3$ may be $N(Ar_3)$, and $X_4$ may be O, S, Se, or Te; $X_1$ may be $N(Ar_1)$, $X_2$ may be O, S, Se, or Te, $X_3$ may be O, S, Se, or Te, and $X_4$ may be $N(Ar_4)$; $X_1$ may be O, S, Se, or Te, $X_2$ may be $N(Ar_2)$, $X_3$ may be $N(Ar_3)$, and $X_4$ may be O, S, Se, or Te; or $X_1$ may be O, S, Se, or Te, $X_2$ may be O, S, Se, or Te, $X_3$ may be $N(Ar_3)$, and $X_4$ may be $N(Ar_4)$; $X_1$ may be $N(Ar_1)$, $X_2$ may be O, S, Se, or Te, $X_3$ may be O, S, Se, or Te, and $X_4$ may be O, S, Se, or Te; $X_1$ may be O, S, Se, or Te, $X_2$ may be $N(Ar_2)$, $X_3$ may be O, S, Se, or Te, and $X_4$ may be O, S, Se, or Te; or $X_1$ may be O, S, Se, or Te, $X_2$ may be O, S, Se, or Te, $X_3$ may be O, S, Se, or Te, and $X_4$ may be $N(Ar_4)$; or $X_1$ may be O, S, Se, or Te, $X_2$ may be O, S, Se, or Te, $X_3$ may be O, S, Se, or Te, and $X_4$ may be O, S, Se, or Te.

The groups $Ar_1$ to $Ar_{10}$ in Formula 1-1 may each independently be a binding site to $B_1$ in Formula 1, hydrogen, deuterium, —F, —Cl, —Br, —I, a hydroxyl group, a cyano group, a nitro group, a $C_1$-$C_6$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, $—C(Q_1)(Q_2)(Q_3)$, $—Si(Q_1)(Q_2)(Q_3)$, $—N(Q_1)(Q_2)$, $—B(Q_1)(Q_2)$, $—C(=O)(Q_1)$, $—S(=O)_2(Q_1)$, or $—P(=O)(Q_1)(Q_2)$, and at least one of $Ar_1$ to $Ar_{10}$ may be a binding site to $B_1$ in Formula 1.

In an embodiment, $Ar_1$ to $Ar_{10}$ may each independently be: a binding site to $B_1$ in Formula 1; hydrogen, deuterium, —F, —Cl, —Br, —I, a cyano group, a $C_1$-$C_{20}$ alkyl group, or a $C_1$-$C_{20}$ alkoxy group; a $C_1$-$C_{20}$ alkyl group or a $C_1$-$C_{20}$ alkoxy group substituted with deuterium, $—CD_3$, $—CD_2H$, $—CDH_2$, —F, $—CF_3$, $—CF_2H$, $—CFH_2$, —Cl, $—CCl_3$, $—CCl_2H$, $—CClH_2$, —Br, $—CBr_3$, $—CBr_2H$, $—CBrH_2$, —I, $—CI_3$, $—CI_2H$, $—CIH_2$, a cyano group, or any combination thereof; a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, a terphenyl group, a $C_1$-$C_{20}$ alkylphenyl group, a naphthyl group, a fluorenyl group, a phenanthrenyl group, an anthracenyl group, a thiophenyl group, a furanyl group, an indenyl group, an isoindolyl group, an indolyl group, a carbazolyl group, a benzofuranyl group, a benzothiophenyl group, a benzosilolyl group, a dibenzofuranyl group, a dibenzothiophenyl group, a dibenzosilolyl group, a benzofluorenyl group, a benzocarbazolyl group, a naphthobenzofuranyl group, a naphthobenzothiophenyl group, a naphthobenzosilolyl group, a dibenzofluorenyl group, a dibenzocarbazolyl group, a dinaphthofuranyl group, a dinaphthothiophenyl group, a dinaphthosilolyl group, an indenocarbazolyl group, an indolocarbazolyl group, a benzofuranocarbazolyl group, a benzothienocarbazolyl group, a benzosilolocarbazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, a benzoisoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, an acridinyl group, a phenanthrolinyl group, a phenazinyl group, a phenoxazinyl group, a phenothiazinyl group, a phenoxathinyl group, a benzimidazolyl group, a benzofuranyl group, a benzothiophenyl group, a benzosilolyl group, a benzothiazolyl group, a benzoisothiazolyl group, a benzoxazolyl group, a benzoisoxazolyl group, a triazolyl group, a tetrazolyl group, a thiadiazolyl group, an oxadiazolyl group, a triazinyl group, an imidazopyridinyl group, an imidazopyrimidinyl group, an oxazolopyridinyl group, a thiazolopyridinyl group, a benzonaphthyridinyl group, an azafluorenyl group, an azaspiro-bifluorenyl group, an azacarbazolyl group, an azadibenzofuranyl group, an azadibenzothiophenyl group, an azadibenzosilolyl group, an indenopyrrolyl group, or an indolopyrrolyl group, each unsubstituted or substituted with deuterium, $—CD_3$, $—CD_2H$, $—CDH_2$, —F, $—CF_3$, $—CF_2H$, $—CFH_2$, —Cl, $—CCl_3$, $—CCl_2H$, $—CClH_2$, —Br, $—CBr_3$, $—CBr_2H$, $—CBrH_2$, —I, $—CI_3$, $—CI_2H$, $—CIH_2$, a cyano group, a $C_1$-$C_{20}$ alkyl group, a $C_1$-$C_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, a terphenyl group, a $C_1$-$C_{20}$ alkylphenyl group, a naphthyl group, a fluorenyl group, a phenanthrenyl group, an anthracenyl group, a thiophenyl group, a furanyl group, an indenyl group, an isoindolyl group, an indolyl group, a carbazolyl group, a benzofuranyl group, a benzothiophenyl group, a benzosilolyl group, a dibenzofuranyl group, a dibenzothiophenyl group, a dibenzosilolyl group, a benzofluorenyl group, a benzocarbazolyl group, a naphthobenzofuranyl group, a naphthobenzothiophenyl group, a naphthobenzosilolyl group, a dibenzofluorenyl group, a dibenzocarbazolyl group, a dinaphthofuranyl group, a dinaphthothiophenyl group, a dinaphthosilolyl group, an indenocarbazolyl group, an indolocarbazolyl group, a benzofuranocarbazolyl group, a benzothienocarbazolyl group, a benzosilolocarbazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, a benzoisoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, an acridinyl group, a phenanthrolinyl group, a phenazinyl group, a phenoxazinyl group, a phenothiazinyl group, a phenoxathinyl group, a benzimidazolyl group, a benzofuranyl group, a benzothiophenyl group, a benzosilolyl group, a benzothiazolyl group, a benzoisothiazolyl group, a benzoxazolyl group, a benzoisoxazolyl group, a triazolyl group, a tetrazolyl group, a thiadiazolyl group, an oxadiazolyl group, a triazinyl group, an imidazopyridinyl group, an imidazopyrimidinyl group, an oxazolopyridinyl group, a thiazolopyridinyl group, a benzonaphthyridinyl group, an azafluorenyl group, an azaspiro-bifluorenyl group, an azacarbazolyl group, an azadibenzofuranyl group, an azadibenzothiophenyl group, an azadibenzosilolyl group, an indenopyrrolyl group, an indolopyrrolyl group, $—Si(Q_{31})(Q_{32})(Q_{33})$, $—N(Q_{31})(Q_{32})$, $—B(Q_{31})(Q_{32})$, $—C(=O)(Q_{31})$, $—S(=O)_2(Q_{31})$, $—P(=O)(Q_{31})(Q_{32})$, or any combination thereof; or $—C(Q_1)(Q_2)(Q_3)$, $—Si(Q_1)(Q_2)(Q_3)$, $—N(Q_1)(Q_2)$, $—B(Q_1)(Q_2)$, $—C(=O)(Q_1)$, $—S(=O)_2(Q_1)$, or $—P(=O)(Q_1)(Q_2)$.

For example, $Ar_1$ to $Ar_{10}$ may each independently be: a binding site to $B_1$ in Formula 1; a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, a terphenyl group, a $C_1$-$C_{20}$alkylphenyl group, a naphthyl group, a fluorenyl group, a phenanthrenyl group, an anthracenyl group, a thiophenyl group, a furanyl group, an indenyl group, an isoindolyl group, an indolyl group, a carbazolyl group, a benzofuranyl group, a benzothiophenyl group, a benzosilolyl group, a dibenzofuranyl group, a dibenzothiophenyl group, a dibenzosilolyl group, a benzofluorenyl group, a benzocarbazolyl group, a naphthobenzofuranyl group, a naphthobenzothiophenyl group, a naphthobenzosilolyl group, a dibenzofluorenyl group, a dibenzocarbazolyl group, a dinaphthofuranyl group, a dinaphthothiophenyl group, a dinaphthosilolyl group, an indeno carbazolyl group, an indolocarbazolyl group, a benzofuranocarbazolyl group, a benzothienocarbazolyl group, or a benzosilolocarbazolyl group, each unsubstituted or substituted with hydrogen, deuterium, $—CD_3$, $—CD_2H$, $—CDH_2$, —F, $—CF_3$, $—CF_2H$, $—CFH_2$, —Cl, $—CCl_3$, $—CCl_2H$, $—CClH_2$, —Br, $—CBr_3$, $—CBr_2H$, $—CBrH_2$, —I, $—CI_3$, $—CI_2H$, $—CIH_2$, a cyano group, a $C_1$-$C_{20}$ alkyl group, a $C_1$-$C_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, a terphenyl group, a $C_1$-$C_{20}$ alkylphenyl group, a naphthyl group, a fluorenyl group, a phenanthrenyl group, an anthracenyl group, a thiophenyl group, a furanyl group, an indenyl group, an isoindolyl group, an indolyl group, a carbazolyl group, a benzofuranyl group, a benzothiophenyl group, a benzosilolyl group, a dibenzofuranyl group, a dibenzothiophenyl group, a dibenzosilolyl group, a benzofluorenyl group, a benzocarbazolyl group, a naphthobenzofuranyl group, a naphthobenzothiophenyl group, a naphthobenzosilolyl group, a dibenzofluorenyl group, a dibenzocarbazolyl group, a dinaphthofuranyl group, a dinaphthothiophenyl group, a dinaphthosilolyl group, an indenocarbazolyl group, an indolocarbazolyl group, a benzofuranocarbazolyl group, a benzothienocarbazolyl group, a benzosilolocarbazolyl group, $—Si(Q_{31})(Q_{32})(Q_{33})$, $—N(Q_{31})(Q_{32})$, $—B(Q_{31})(Q_{32})$, $—C(=O)(Q_{31})$, $—S(=O)_2(Q_{31})$, $—P(=O)(Q_{31})(Q_{32})$, or any combination thereof; or $—C(Q_1)(Q_2)(Q_3)$, $—Si(Q_1)(Q_2)(Q_3)$, $—N(Q_1)(Q_2)$, $—B(Q_1)(Q_2)$, $—C(=O)(Q_1)$, $—S(=O)_2(Q_1)$, or $—P(=O)(Q_1)(Q_2)$.

In an embodiment, $Ar_{10}$ may be hydrogen. In an embodiment, when $Ar_9$ indicates a binding site to $B_1$ in Formula 1, $X_2$ and $X_4$ may each independently be O, S, Se, or Te. The variable $T_{11}$ in Formula 1-2 may be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$.

In an embodiment, $T_{11}$ may be i) a group T1, ii) a condensed cyclic group in which two or more groups T1(s) are condensed with each other, iii) a group T2, iv) a condensed cyclic group in which two or more groups T2(s) are condensed with each other, or v) a condensed cyclic group in which one or more groups T2(s) and one or more groups T1(s) are condensed with each other, each unsubstituted or substituted with at least one $R_{10a}$.

The group T1 may be a cyclopropane group, a cyclobutane group, a cyclopentane group, a cyclohexane group, a cycloheptane group, a cyclooctane group, a cyclobutene group, a cyclopentene group, a cyclopentadiene group, a cyclohexene group, a cyclohexadiene group, a cycloheptene group, an adamantane group, a norbornane (or a bicyclo [2.2.1]heptane) group, a norbornene group, a bicyclo[1.1.1]

pentane group, a bicyclo[2.1.1]hexane group, a bicyclo [2.2.2]octane group, or a benzene group.

The group T2 may be a furan group, a thiophene group, a 1H-pyrrole group, a silole group, a borole group, a 2H-pyrrole group, a 3H-pyrrole group, an imidazole group, a pyrazole group, a triazole group, a tetrazole group, an oxazole group, an isoxazole group, an oxadiazole group, a thiazole group, an isothiazole group, a thiadiazole group, an azasilole group, an azaborole group, a pyridine group, a pyrimidine group, a pyrazine group, a pyridazine group, a triazine group, a tetrazine group, a pyrrolidine group, an imidazolidine group, a dihydropyrrole group, a piperidine group, a tetrahydropyridine group, a dihydropyridine group, a hexahydropyrimidine group, a tetrahydropyrimidine group, a dihydropyrimidine group, a piperazine group, a tetrahydropyrazine group, a dihydropyrazine group, a tetrahydropyridazine group, or a dihydropyridazine group.

In Formula 1-2, $X_{11}$ may be N or $C(R_{11})$, $X_{12}$ may be N or $C(R_{12})$, $X_{13}$ may be N or $C(R_{13})$, and $X_{14}$ may be N or $C(R_{14})$. In an embodiment, $X_{11}$ to $X_{14}$ may be identical to each other. For example, $X_{11}$ may be $C(R_{11})$, $X_{12}$ may be $C(R_{12})$, $X_{13}$ may be $C(R_{13})$, and $X_{14}$ may be $C(R_{14})$.

The variables $R_1$ to $R_4$ and $R_{11}$ to $R_{14}$ in Formulae 1-1 and 1-2 may each independently be hydrogen, deuterium, —F, —Cl, —Br, —I, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, $—C(Q_1)(Q_2)(Q_3)$, $—Si(Q_1)(Q_2)(Q_3)$, $—N(Q_1)(Q_2)$, $—B(Q_1)(Q_2)$, $—C(=O)(Q_1)$, $—S(=O)_2(Q_1)$, or $—P(=O)(Q_1)(Q_2)$.

In an embodiment, $R_1$ to $R_4$ and $R_{11}$ to $R_{14}$ may each independently be: hydrogen, deuterium, —F, —Cl, —Br, —I, a cyano group, a $C_1$-$C_{20}$ alkyl group, or a $C_1$-$C_{20}$ alkoxy group; a $C_1$-$C_{20}$ alkyl group or a $C_1$-$C_{20}$ alkoxy group substituted with deuterium, $—CD_3$, $—CD_2H$, $—CDH_2$, —F, $—CF_3$, $—CF_2H$, $—CFH_2$, —Cl, $—CCl_3$, $—CCl_2H$, $—CClH_2$, —Br, $—CBr_3$, $—CBr_2H$, $—CBrH_2$, —I, $—CI_3$, $—CI_2H$, $—CIH_2$, a cyano group, or any combination thereof; a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, a terphenyl group, a $C_1$-$C_{20}$ alkylphenyl group, a naphthyl group, a fluorenyl group, a phenanthrenyl group, an anthracenyl group, a thiophenyl group, a furanyl group, an indenyl group, an isoindolyl group, an indolyl group, a carbazolyl group, a benzofuranyl group, a benzothiophenyl group, a benzosilolyl group, a dibenzofuranyl group, a dibenzothiophenyl group, a dibenzosilolyl group, a benzofluorenyl group, a benzocarbazolyl group, a naphthobenzofuranyl group, a naphthobenzothiophenyl group, a naphthobenzosilolyl group, a dibenzofluorenyl group, a dibenzocarbazolyl group, a dinaphthofuranyl group, a dinaphthothiophenyl group, a dinaphthosilolyl group, an indenocarbazolyl group, an indolocarbazolyl group, a benzofuranocarbazolyl group, a benzothienocarbazolyl group, a benzosilolocarbazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, a benzoisoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, an acridinyl group, a phenanthrolinyl group, a phenazinyl group, a phenoxazinyl group, a phenothiazinyl group, a phenoxathinyl group, a benzimidazolyl group, a benzofuranyl group, a benzothiophenyl group, a benzosilolyl group, a benzothiazolyl group, a benzoisothiazolyl group, a benzoxazolyl group, a benzoisoxazolyl group, a triazolyl group, a tetrazolyl group, a thiadiazolyl group, an oxadiazolyl group, a triazinyl group, an imidazopyridinyl group, an imidazopyrimidinyl group, an oxazolopyridinyl group, a thiazolopyridinyl group, a benzonaphthyridinyl group, an azafluorenyl group, an azaspiro-bifluorenyl group, an azacarbazolyl group, an azadibenzofuranyl group, an azadibenzothiophenyl group, an azadibenzosilolyl group, an indenopyrrolyl group, or an indolopyrrolyl group, each unsubstituted or substituted with deuterium, $—CD_3$, $—CD_2H$, $—CDH_2$, —F, $—CF_3$, $—CF_2H$, $—CFH_2$, —Cl, $—CCl_3$, $—CCl_2H$, $—CClH_2$, —Br, $—CBr_3$, $—CBr_2H$, $—CBrH_2$, —I, $—CI_3$, $—CI_2H$, $—CIH_2$, a cyano group, a $C_1$-$C_{20}$ alkyl group, a $C_1$-$C_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, a terphenyl group, a $C_1$-$C_{20}$ alkylphenyl group, a naphthyl group, a fluorenyl group, a phenanthrenyl group, an anthracenyl group, a thiophenyl group, a furanyl group, an indenyl group, an isoindolyl group, an indolyl group, a carbazolyl group, a benzofuranyl group, a benzothiophenyl group, a benzosilolyl group, a dibenzofuranyl group, a dibenzothiophenyl group, a dibenzosilolyl group, a benzofluorenyl group, a benzocarbazolyl group, a naphthobenzofuranyl group, a naphthobenzothiophenyl group, a naphthobenzosilolyl group, a dibenzofluorenyl group, a dibenzocarbazolyl group, a dinaphthofuranyl group, a dinaphthothiophenyl group, a dinaphthosilolyl group, an indenocarbazolyl group, an indolocarbazolyl group, a benzofuranocarbazolyl group, a benzothienocarbazolyl group, a benzosilolocarbazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, a benzoisoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, an acridinyl group, a phenanthrolinyl group, a phenazinyl group, a phenoxazinyl group, a phenothiazinyl group, a phenoxathinyl group, a benzimidazolyl group, a benzofuranyl group, a benzothiophenyl group, a benzosilolyl group, a benzothiazolyl group, a benzoisothiazolyl group, a benzoxazolyl group, a benzoisoxazolyl group, a triazolyl group, a tetrazolyl group, a thiadiazolyl group, an oxadiazolyl group, a triazinyl group, an imidazopyridinyl group, an imidazopyrimidinyl group, an oxazolopyridinyl group, a thiazolopyridinyl group, a benzonaphthyridinyl group, an azafluorenyl group, an azaspiro-bifluorenyl group, an azacarbazolyl group, an azadibenzofuranyl group, an azadibenzothiophenyl group, an azadibenzosilolyl group, an indenopyrrolyl group, an indolopyrrolyl group, $—Si(Q_{31})(Q_{32})(Q_{33})$, $—N(Q_{31})(Q_{32})$, $—B(Q_{31})(Q_{32})$, $—C(=O)(Q_{31})$, $—S(=O)_2(Q_{31})$, $—P(=O)(Q_{31})(Q_{32})$, or any combination thereof; or —$C(Q_1)(Q_2)(Q_3)$, —$Si(Q_1)(Q_2)(Q_3)$, —$N(Q_1)(Q_2)$, —$B(Q_1)(Q_2)$, —$C(=O)(Q_1)$, —$S(=O)_2(Q_1)$, or —$P(=O)(Q_1)(Q_2)$.

The variables a1 and a4 in Formula 1-1 may each independently be an integer from 0 to 10. The variable a1 indicates the number of $R_1$(s), when a1 is an integer of 2 or more, two or more $R_1$(s) may be identical to or different from each other, a2 indicates the number of $R_2$(s), when a2 is an integer of 2 or more, two or more $R_2$(s) may be identical to or different from each other, a3 indicates the number of $R_3$(s), when a3 is an integer of 2 or more, two or more $R_3$(s) may be identical to or different from each other, a4 indicates the number of $R_4$(s), when a4 is an integer of 2 or more, two or more $R_4$(s) may be identical to or different from each other.

If two or more of a1(s), $R_1$(s) in Formula 1-1 may optionally be linked to each other to form a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, two or more of a2 $R_2$(s) may optionally be linked to each other to form a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, two or more of a3 $R_3$(s) may optionally be linked to each other to form a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, two or more of a4 $R_4$(s) may optionally be linked to each other to form a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$.

Two or more neighboring groups of $R_{11}$ to $R_{14}$ in Formula 1-1 may optionally be linked to each other to form a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$.

Formula 1-1 may be represented by Formula 1-1-1:

Formula 1-1-1

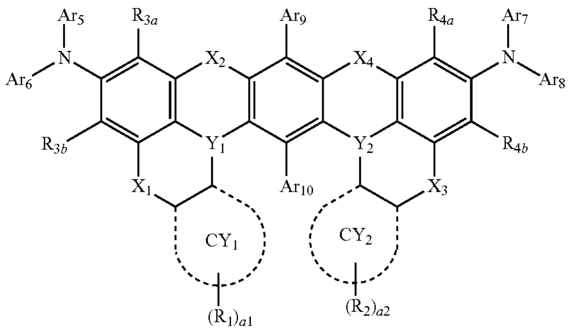

wherein, in Formula 1-1-1, $CY_1$, $CY_2$, $X_1$ to $X_4$, $Y_1$, $Y_2$, $Ar_1$ to $Ar_{10}$, $R_1$, $R_2$, a1, and a2 are each the same as described herein, $R_{3a}$ and $R_{3b}$ are each the same as described in connection with $R_3$, and $R_{4a}$ and $R_{4b}$ are each the same as described in connection with $R_4$.

In an embodiment, a group represented by

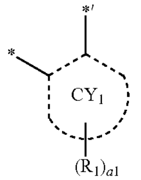

in Formula 1-1 may be a group represented by one of Formulae CY1-1 to CY1-10:

CY1-1

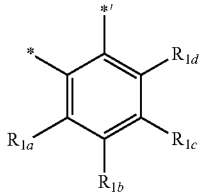

CY1-2

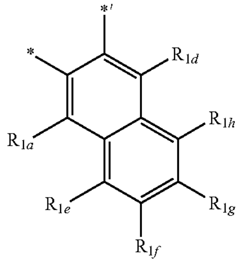

CY1-3

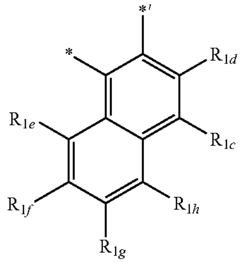

CY1-4

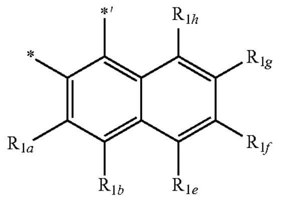

CY1-5

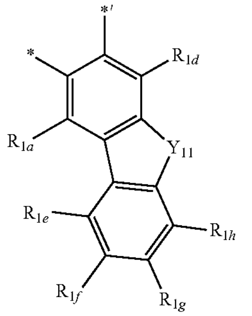

-continued

CY1-6

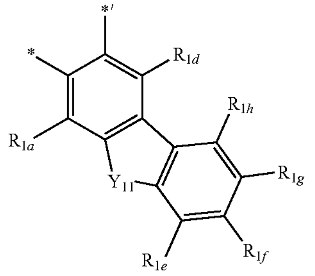

CY1-7

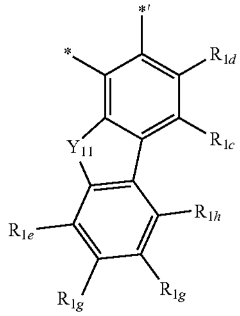

CY1-8

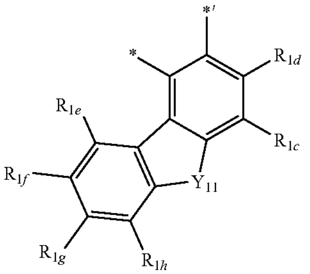

CY1-9

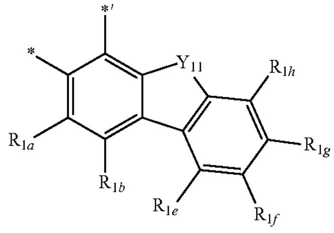

CY1-10

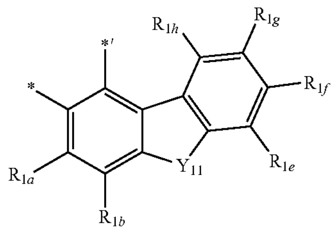

wherein, in Formulae CY1-1 to CY1-10, $Y_{11}$ may be O, S, Se, Te, $N(R_{11a})$, $C(R_{11a})(R_{11b})$, or $Si(R_{11a})(R_{11b})$, $R_{1a}$ to $R_{1h}$, $R_{11a}$, and $R_{11b}$ may each be the same as described in connection with $R_1$,

* indicates a binding site to $X_1$ in Formula 1-1, and

*' indicates a binding site to $Y_1$ in Formula 1-1.

In an embodiment, a group represented by

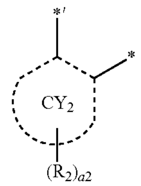

in Formula 1-1 may be a group represented by one of Formulae CY2-1 to CY2-10:

CY2-1

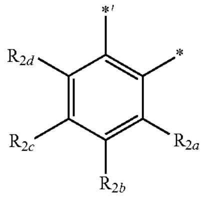

CY2-2

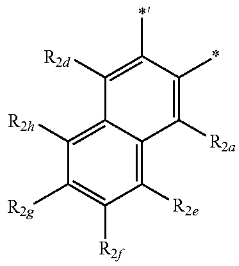

CY2-3

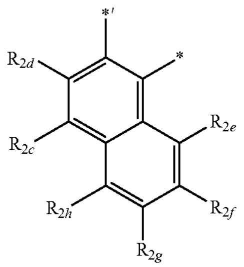

CY2-4

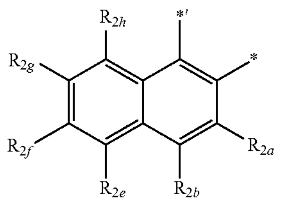

CY2-5

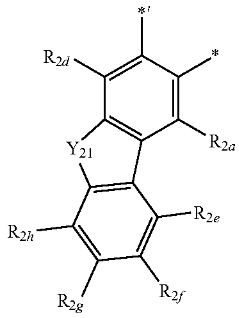

-continued

CY2-6

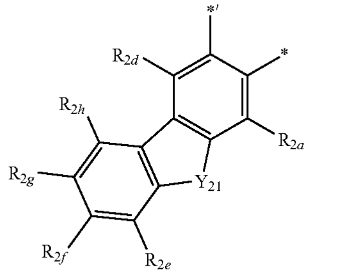

CY2-7

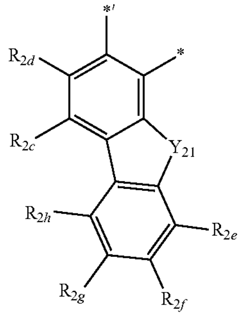

CY2-8

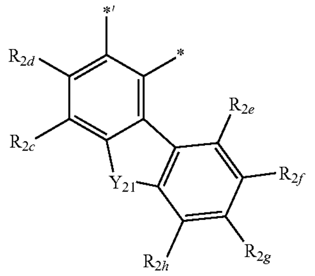

CY2-9

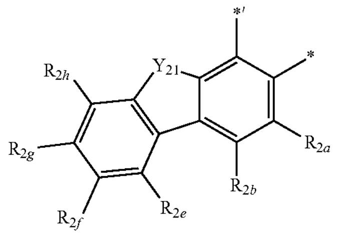

CY2-10

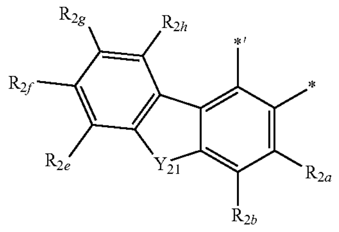

wherein, in Formulae CY2-1 to CY2-10, $Y_{21}$ may be O, S, Se, Te, $N(R_{21a})$, $C(R_{21a})(R_{21b})$, or $Si(R_{21a})(R_{21b})$, $R_{2a}$ to $R_{2h}$, $R_{21a}$, and $R_{21b}$ are each the same as described in connection with $R_2$,

* indicates a binding site to $X_3$ in Formula 1-1, and

*' indicates a binding site to $Y_2$ in Formula 1-1.

In an embodiment, Formula 1-2 may be represented by Formula 1-2-1 or 1-2-2:

Formula 1-2-1

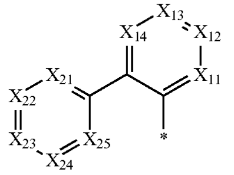

Formula 1-2-2

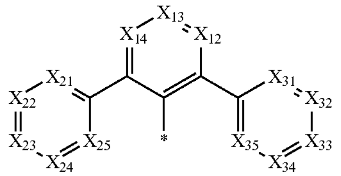

wherein, in Formulae 1-2-1 and 1-2-2, $X_{11}$ to $X_{14}$ are each the same as described herein, $X_{21}$ may be N or $C(R_{21})$, $X_{22}$ may be N or $C(R_{22})$, $X_{23}$ may be N or $C(R_{23})$, $X_{24}$ may be N or $C(R_{24})$, and $X_{25}$ may be N or $C(R_{25})$, $X_{31}$ may be N or $C(R_{31})$, $X_{32}$ may be N or $C(R_{32})$, $X_{33}$ may be N or $C(R_{33})$, $X_{34}$ may be N or $C(R_{34})$, and $X_{35}$ may be N or $C(R_{35})$, $R_{21}$ to $R_{25}$ and $R_{31}$ to $R_{35}$ are each the same as described in connection with $R_{10a}$, two or more neighboring groups of $R_{21}$ to $R_{25}$ may be optionally linked to each other to form a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, and two or more neighboring groups of $R_{31}$ to $R_{35}$ may be optionally linked to each other to form a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$.

For example, Formula 1-2 may be a group selected from Formulae 2-1 to 2-57:

2-1

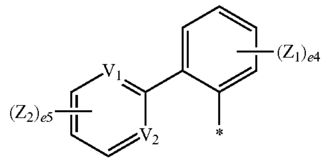

2-2

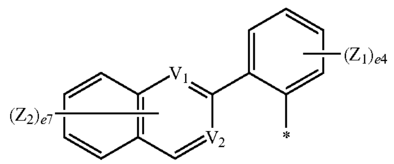

2-3

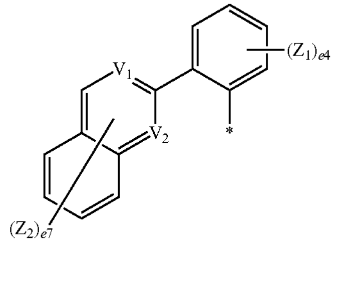

-continued
2-4
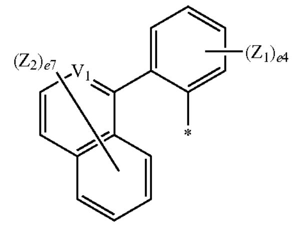
2-5
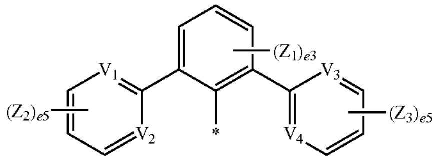
2-6
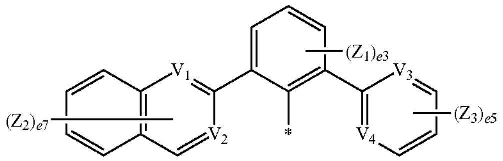
2-7
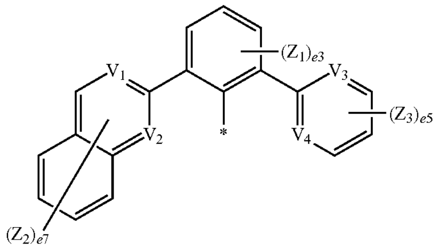
2-8
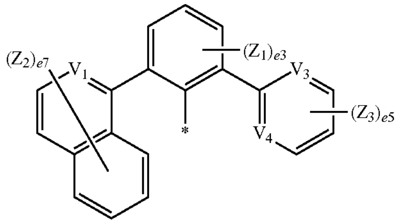
2-9
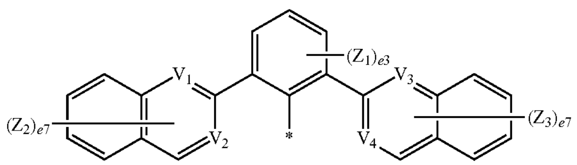
2-10
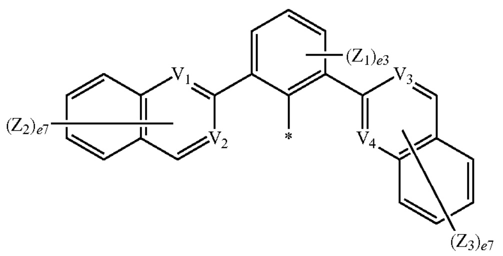
-continued
2-11
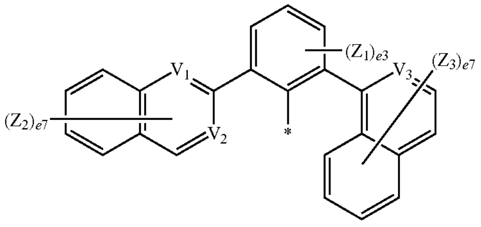
2-12
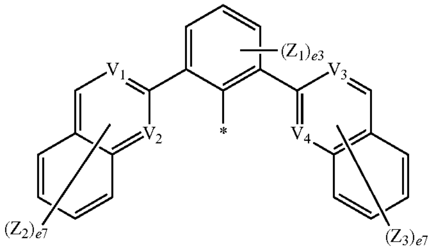
2-13
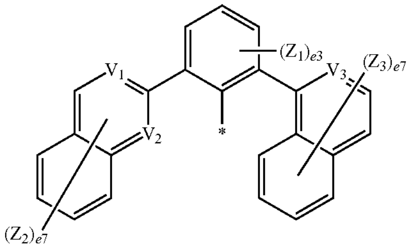
2-14
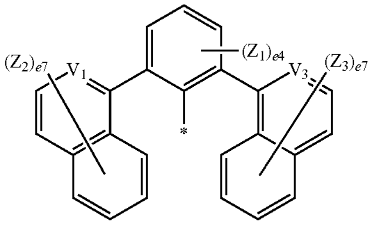
2-15
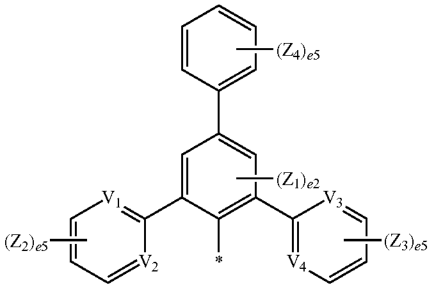
2-16
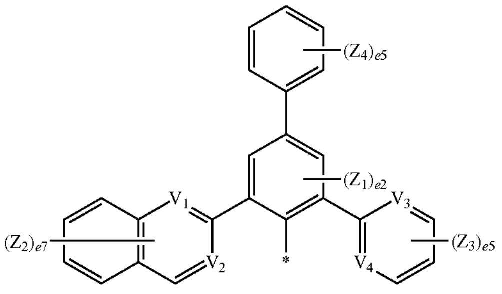

-continued
2-17
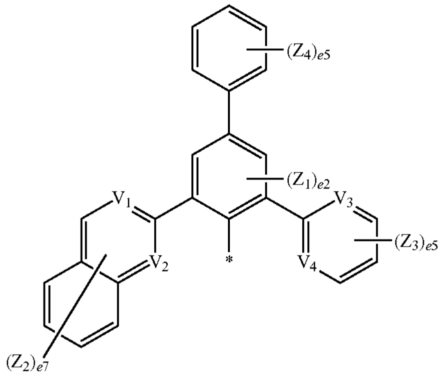
2-18
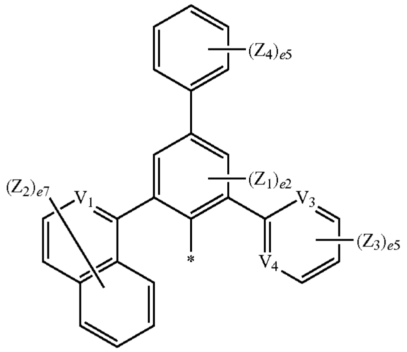
2-19
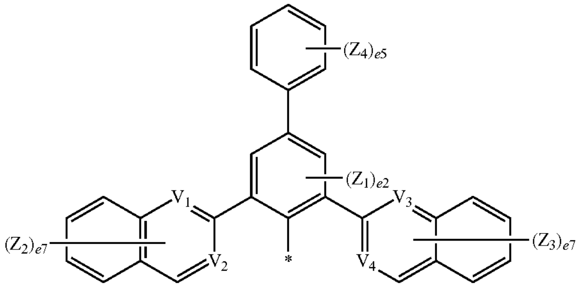
2-20
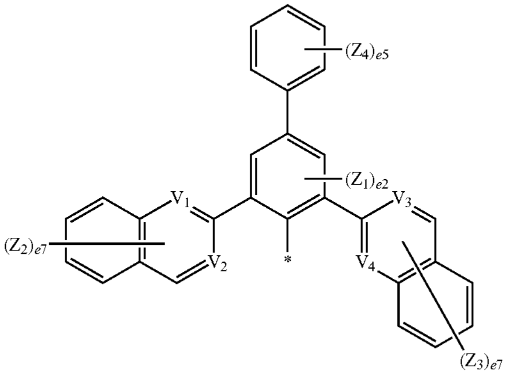
-continued
2-21
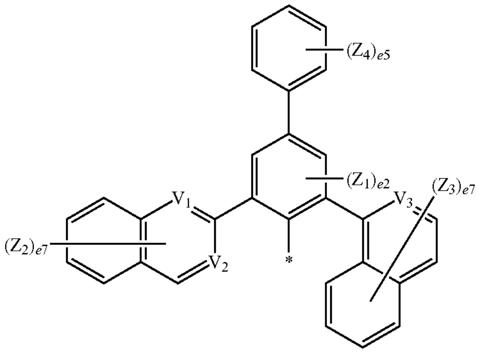
2-22
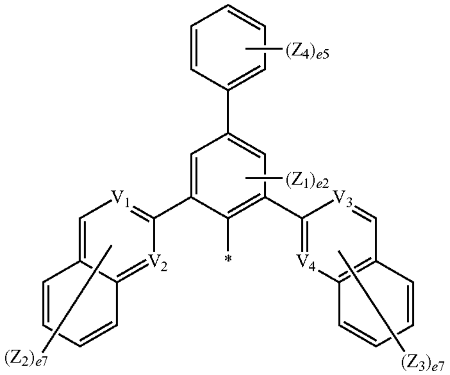
2-23
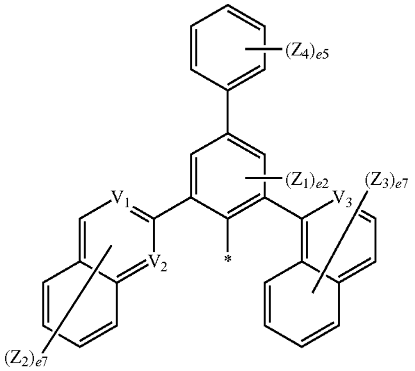
2-24
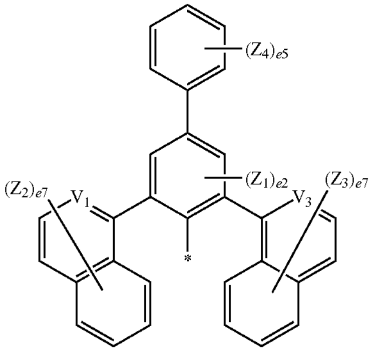

-continued
2-25
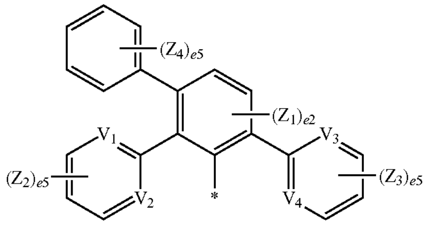
2-26
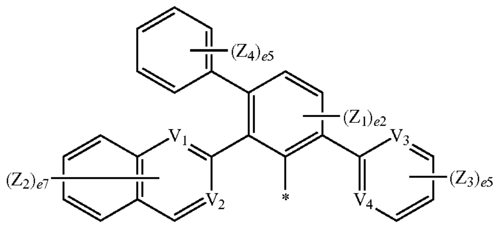
2-27
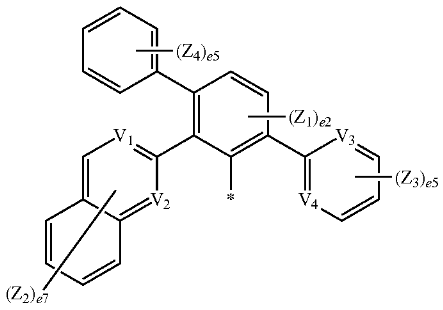
2-28
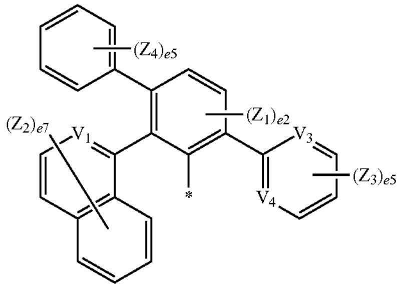
2-29
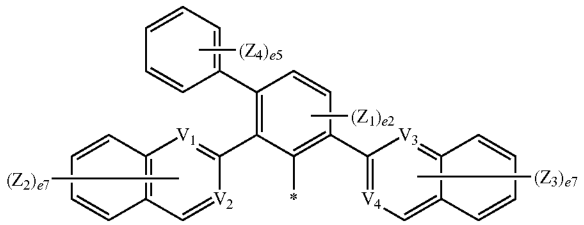
-continued
2-30
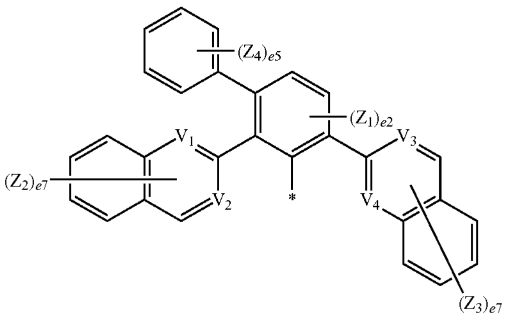
2-31
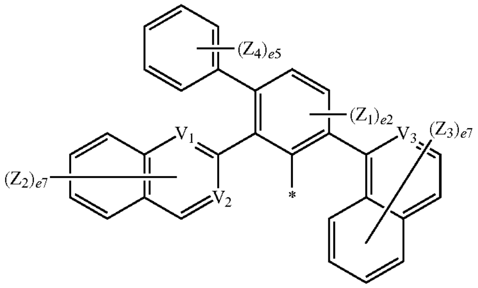
2-32
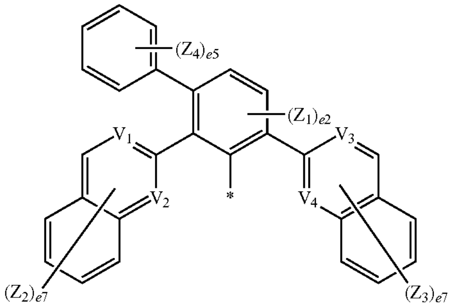
2-33
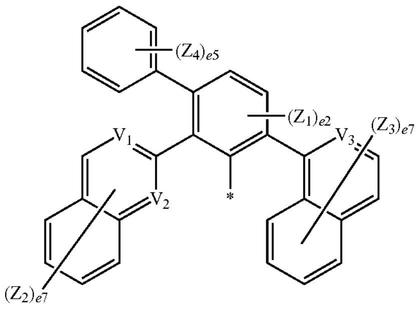
2-34
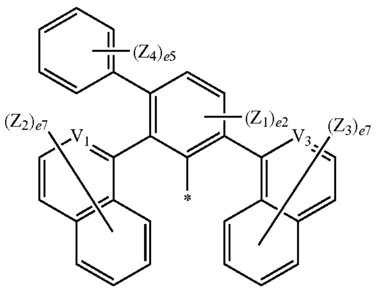

-continued
2-35
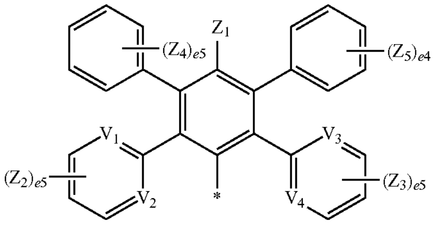
2-36
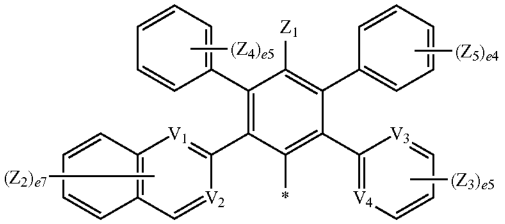
2-37
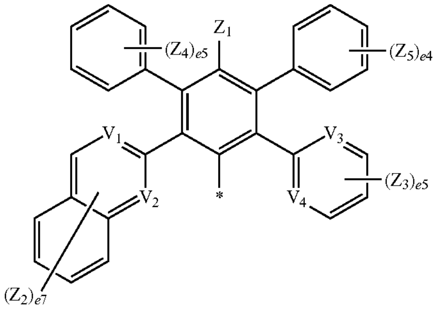
2-38
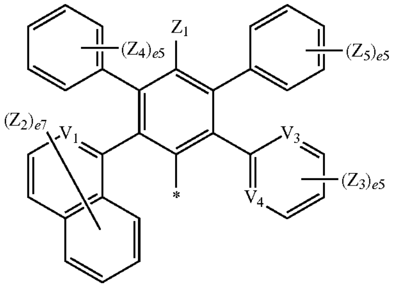
2-39
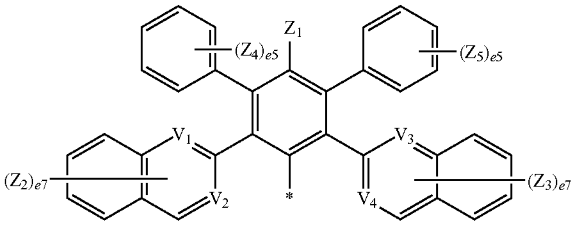
-continued
2-40
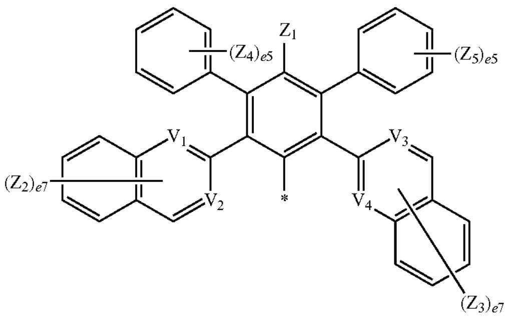
2-41
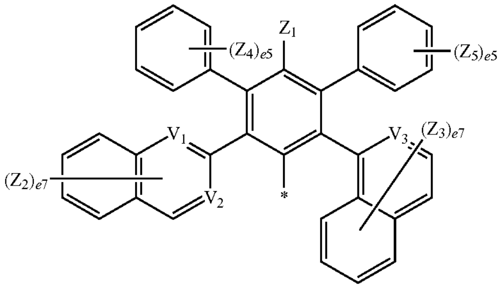
2-42
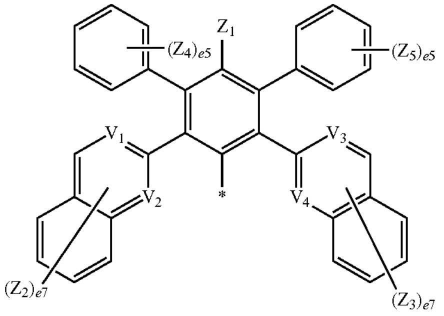
2-43
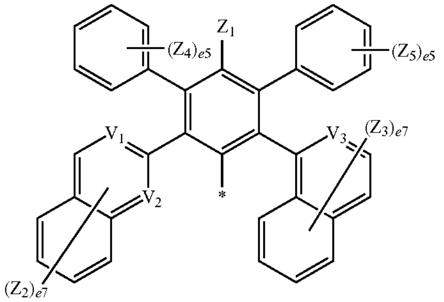
2-45
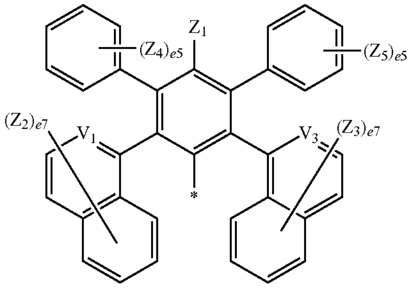

-continued 2-46

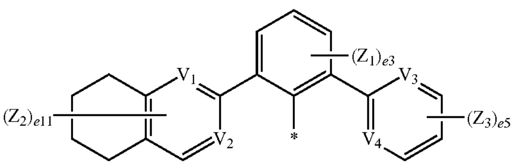

2-47

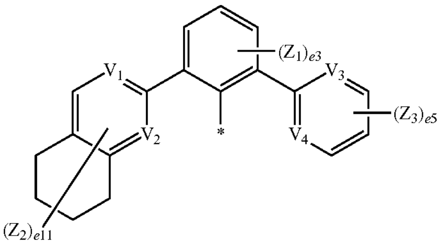

2-48

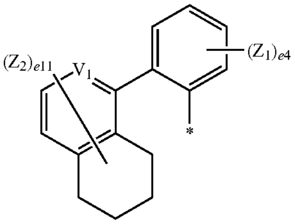

2-49

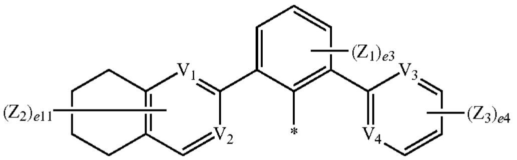

2-50

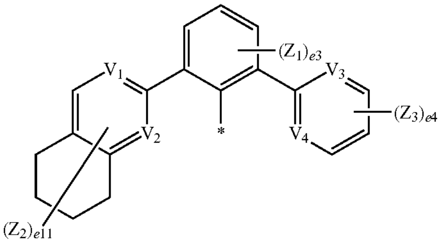

2-51

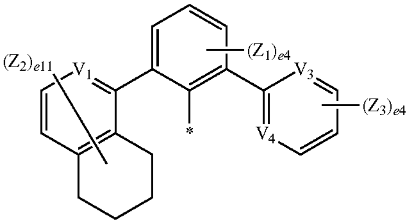

2-52

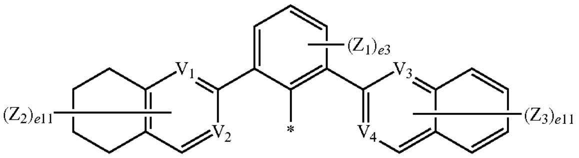

-continued 2-53

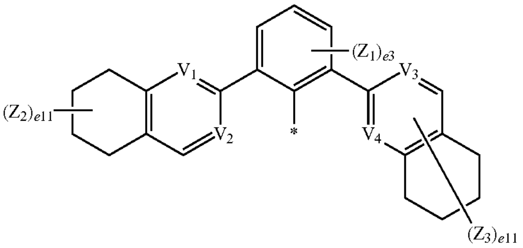

2-54

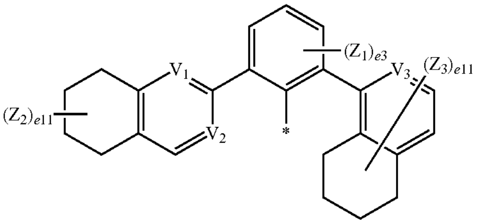

2-55

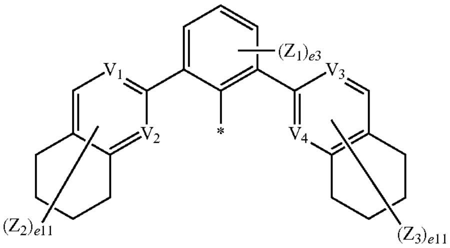

2-56

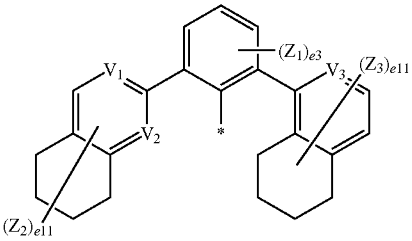

2-57

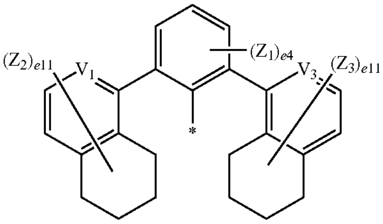

wherein, in Formulae 2-1 to 2-57, $V_1$ to $V_4$ may each independently be C or N, $Z_1$ to $Z_5$ may each independently be:

deuterium, —F, —Cl, —Br, —I, a cyano group, a $C_1$-$C_{20}$ alkyl group, or a $C_1$-$C_{20}$ alkoxy group;

a $C_1$-$C_{20}$ alkyl group or a $C_1$-$C_{20}$ alkoxy group each substituted with deuterium, $—CD_3$, $—CD_2H$, $—CDH_2$, —F, $—CF_3$, $—CF_2H$, $—CFH_2$, —Cl, $—CCl_3$, $—CCl_2H$, $—CClH_2$, —Br, $—CBr_3$, $—CBr_2H$, $—CBrH_2$, —I, $—CI_3$, $—CI_2H$, $—CIH_2$, a cyano group, or any combination thereof;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, a terphenyl group, a $C_1$-$C_{20}$ alkylphenyl group, a naphthyl group, a fluorenyl group, a phenanthrenyl group, an anthracenyl group, a thiophenyl group, a furanyl group, an indenyl group, an isoindolyl group, an indolyl group, a carbazolyl group, a benzofuranyl group, a benzothiophenyl group, a benzosilolyl group, a dibenzofuranyl group, a dibenzothiophenyl group, a dibenzosilolyl group, a benzofluorenyl group, a benzocarbazolyl group, a naphthobenzofuranyl group, a naphthobenzothiophenyl group, a naphthobenzosilolyl group, a dibenzofluorenyl group, a dibenzocarbazolyl group, a dinaphthofuranyl group, a dinaphthothiophenyl group, a dinaphthosilolyl group, an indenocarbazolyl group, an indolocarbazolyl group, a benzofuranocarbazolyl group, a benzothienocarbazolyl group, a benzosilolocarbazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, a benzoisoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, an acridinyl group, a phenanthrolinyl group, a phenazinyl group, a phenoxazinyl group, a phenothiazinyl group, a phenoxathinyl group, a benzimidazolyl group, a benzofuranyl group, a benzothiophenyl group, a benzosilolyl group, a benzothiazolyl group, a benzoisothiazolyl group, a benzoxazolyl group, a benzoisoxazolyl group, a triazolyl group, a tetrazolyl group, a thiadiazolyl group, an oxadiazolyl group, a triazinyl group, an imidazopyridinyl group, an imidazopyrimidinyl group, an oxazolopyridinyl group, a thiazolopyridinyl group, a benzonaphthyridinyl group, an azafluorenyl group, an azaspiro-bifluorenyl group, an azacarbazolyl group, an azadibenzofuranyl group, an azadibenzothiophenyl group, an azadibenzosilolyl group, an indenopyrrolyl group, or an indolopyrrolyl group, each unsubstituted or substituted with deuterium, $-CD_3$, $-CD_2H$, $-CDH_2$, —F, $-CF_3$, $-CF_2H$, $-CFH_2$, —Cl, $-CCl_3$, $-CCl_2H$, $-CClH_2$, —Br, $-CBr_3$, $-CBr_2H$, $-CBrH_2$, —I, $-CI_3$, $-CI_2H$, $-CIH_2$, a cyano group, a $C_1$-$C_{20}$ alkyl group, a $C_1$-$C_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, a terphenyl group, a $C_1$-$C_{20}$ alkylphenyl group, a naphthyl group, a fluorenyl group, a phenanthrenyl group, an anthracenyl group, a thiophenyl group, a furanyl group, an indenyl group, an isoindolyl group, an indolyl group, a carbazolyl group, a benzofuranyl group, a benzothiophenyl group, a benzosilolyl group, a dibenzofuranyl group, a dibenzothiophenyl group, a dibenzosilolyl group, a benzofluorenyl group, a benzocarbazolyl group, a naphthobenzofuranyl group, a naphthobenzothiophenyl group, a naphthobenzosilolyl group, a dibenzofluorenyl group, a dibenzocarbazolyl group, a dinaphthofuranyl group, a dinaphthothiophenyl group, a dinaphthosilolyl group, an indenocarbazolyl group, an indolocarbazolyl group, a benzofuranocarbazolyl group, a benzothienocarbazolyl group, a benzosilolocarbazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, a benzoisoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, an acridinyl group, a phenanthrolinyl group, a phenazinyl group, a phenoxazinyl group, a phenothiazinyl group, a phenoxathinyl group, a benzimidazolyl group, a benzofuranyl group, a benzothiophenyl group, a benzosilolyl group, a benzothiazolyl group, a benzoisothiazolyl group, a benzoxazolyl group, a benzoisoxazolyl group, a triazolyl group, a tetrazolyl group, a thiadiazolyl group, an oxadiazolyl group, a triazinyl group, an imidazopyridinyl group, an imidazopyrimidinyl group, an oxazolopyridinyl group, a thiazolopyridinyl group, a benzonaphthyridinyl group, an azafluorenyl group, an azaspiro-bifluorenyl group, an azacarbazolyl group, an azadibenzofuranyl group, an azadibenzothiophenyl group, an azadibenzosilolyl group, an indenopyrrolyl group, an indolopyrrolyl group, $-Si(Q_{31})(Q_{32})(Q_{33})$, $-N(Q_{31})(Q_{32})$, $-B(Q_{31})(Q_{32})$, $-C(=O)(Q_{31})$, $-S(=O)_2(Q_{31})$, $-P(=O)(Q_{31})(Q_{32})$, or any combination thereof; or $-C(Q_1)(Q_2)(Q_3)$, $-Si(Q_1)(Q_2)(Q_3)$, $-N(Q_1)(Q_2)$, $-B(Q_1)(Q_2)$, $-C(=O)(Q_1)$, $-S(=O)_2(Q_1)$, or $-P(=O)(Q_1)(Q_2)$, wherein $Q_1$ to $Q_3$ and $Q_{31}$ to $Q_{33}$ may each independently be hydrogen; deuterium; —F; —Cl; —Br; —I; a hydroxyl group; a cyano group; a nitro group; a $C_1$-$C_{60}$ alkyl group; a $C_2$-$C_{60}$ alkenyl group; a $C_2$-$C_{60}$ alkynyl group; a $C_1$-$C_{60}$ alkoxy group; or a $C_3$-$C_{60}$ carbocyclic group or a $C_1$-$C_{60}$ heterocyclic group, each unsubstituted or substituted with deuterium, —F, a cyano group, a $C_1$-$C_{60}$ alkyl group, a $C_1$-$C_{60}$ alkoxy group, a phenyl group, a biphenyl group, or any combination thereof, e2 may be an integer from 0 to 2, e3 may be an integer from 0 to 3, e4 may be an integer from 0 to 4, e5 may be an integer from 0 to 5, e7 may be an integer from 0 to 7, e11 may be an integer from 0 to 11, and

* indicates a binding site to a neighboring group.

In one embodiment, the heterocyclic compound may be selected from Compounds 1 to 110:

21
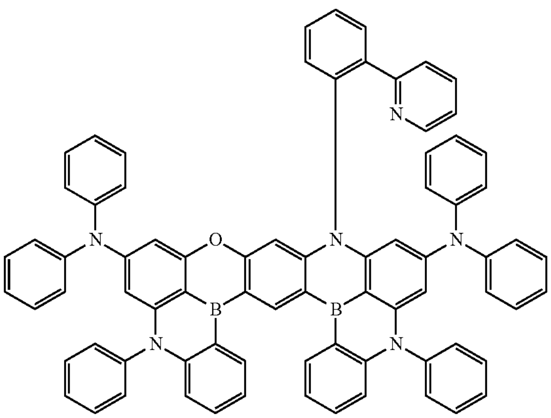
22
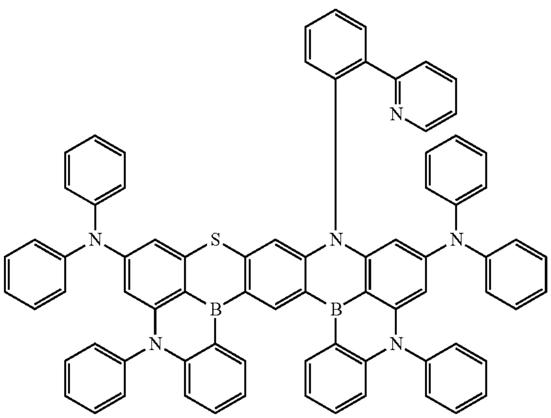
23
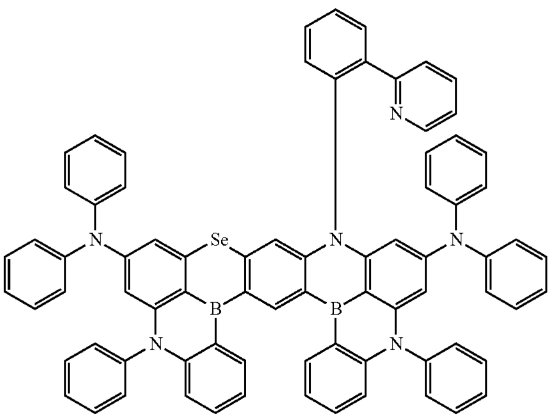
24
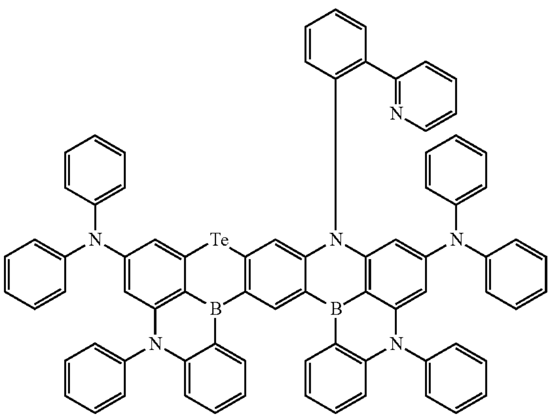
25
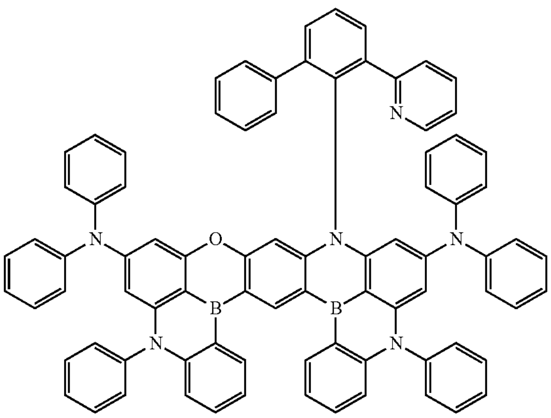
26
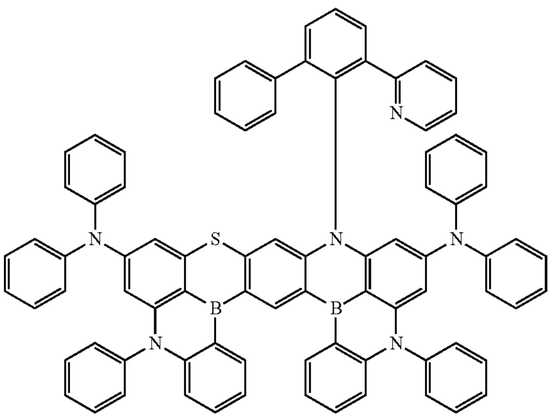

-continued
27
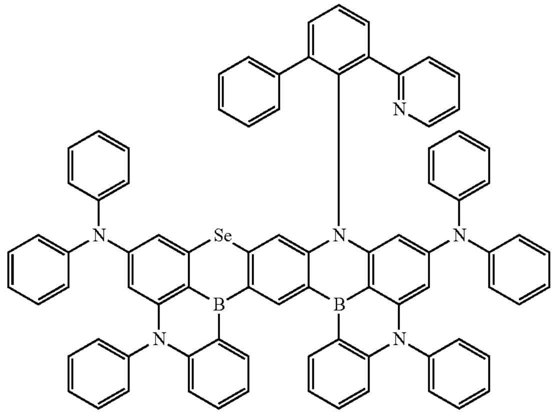
28
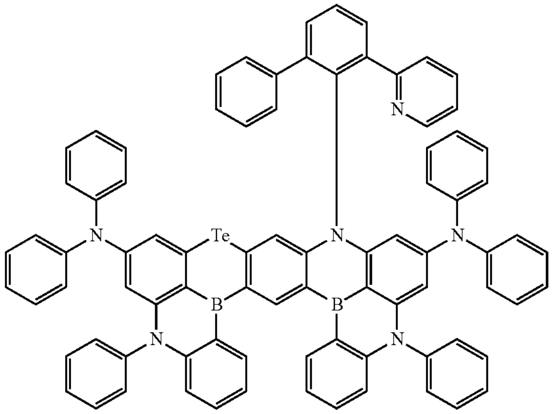
29
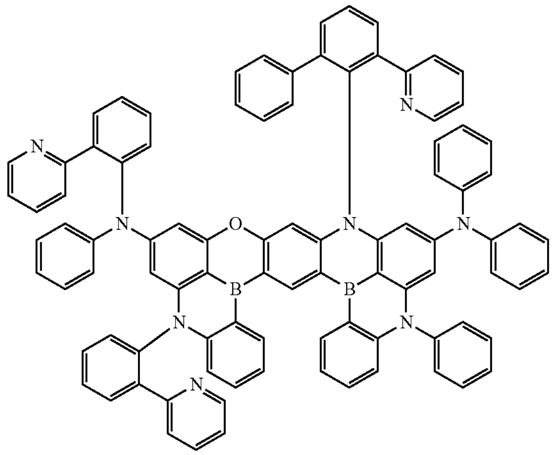
30
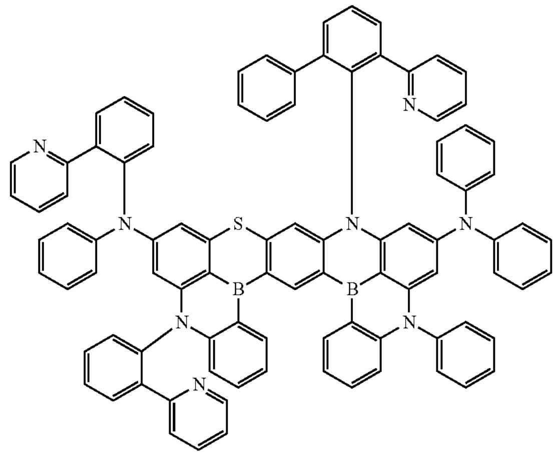
31
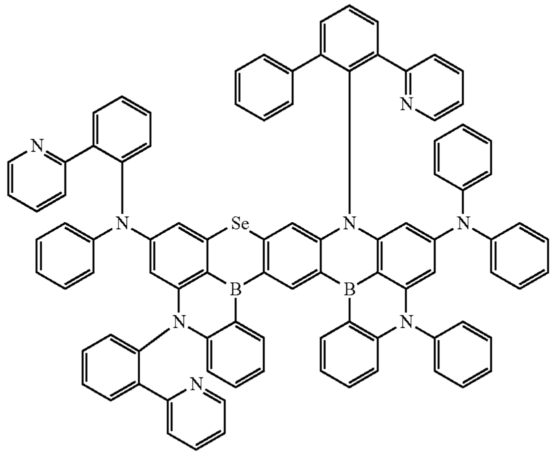
32
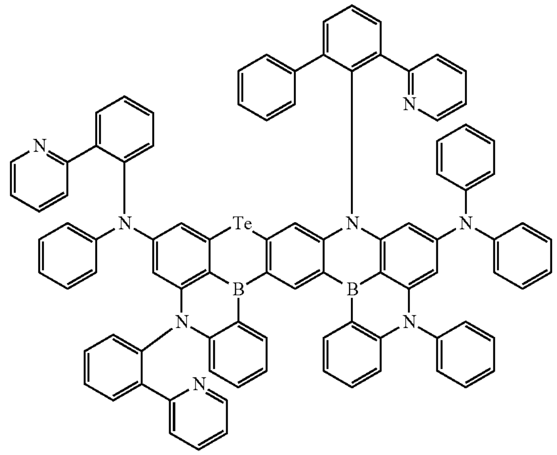

-continued
33
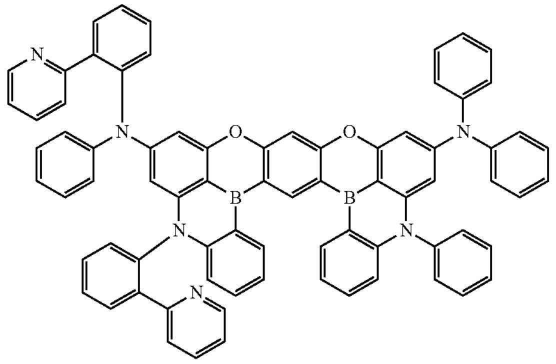
34
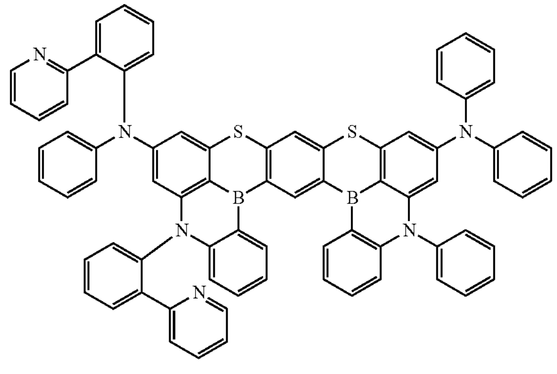
35
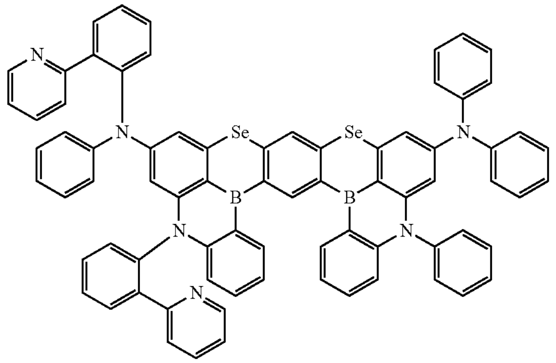
36
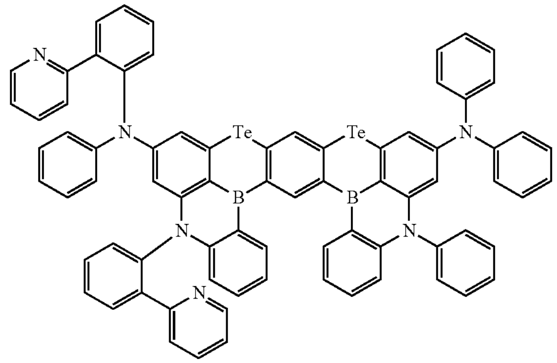
37
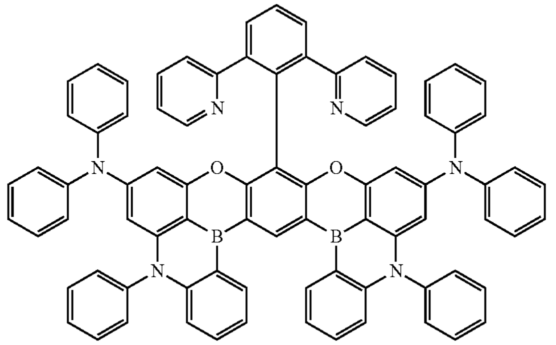
38
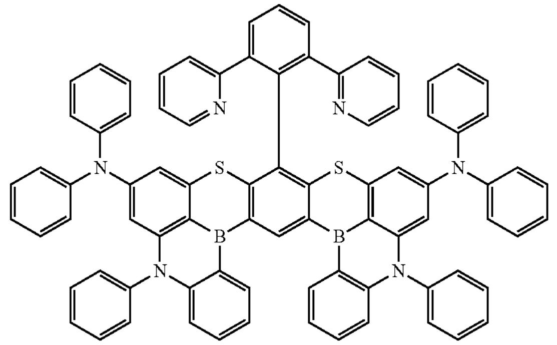
39
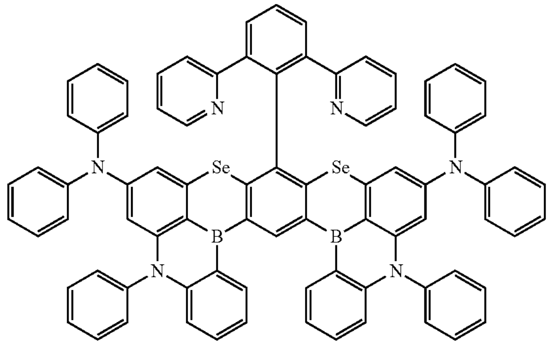
40
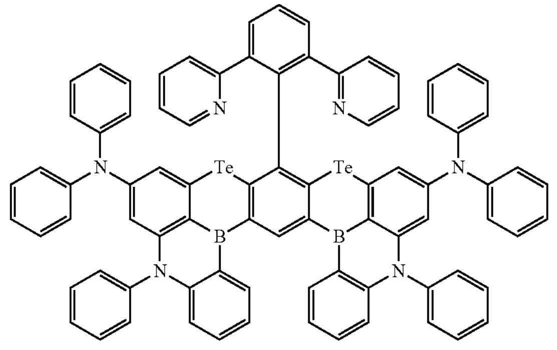

-continued
1
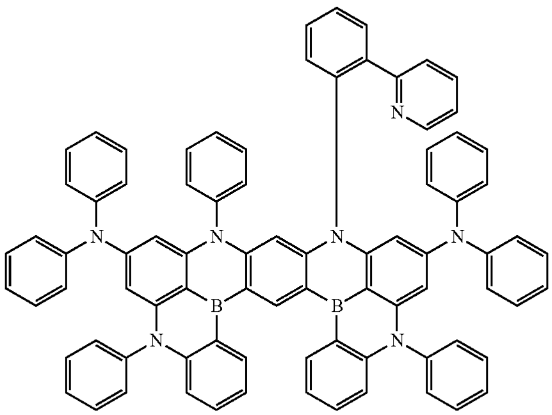
2
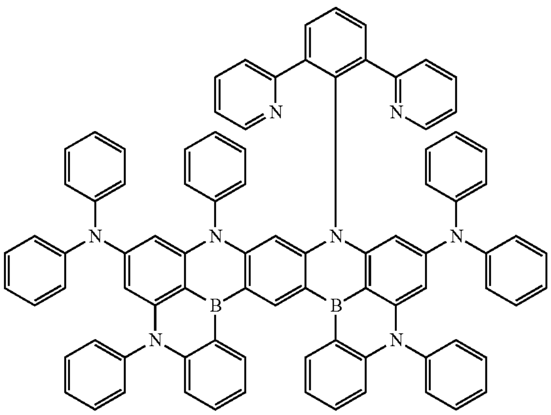
3
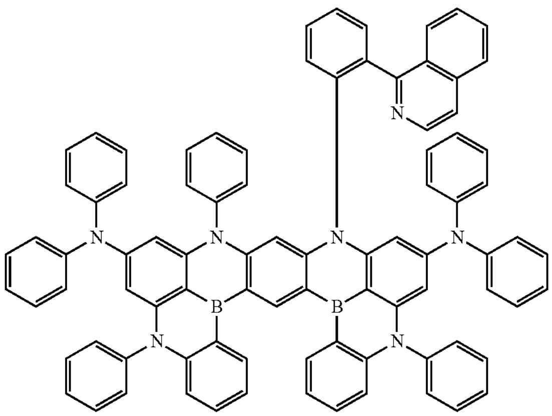
4
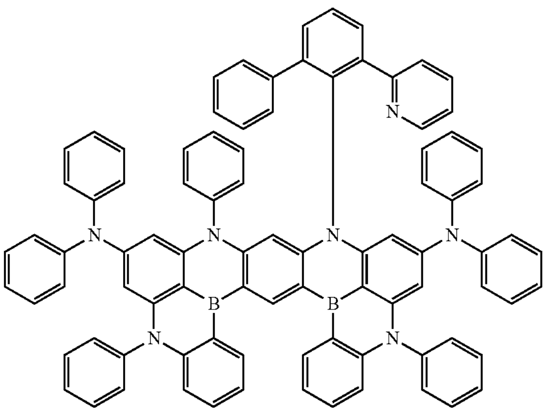
5
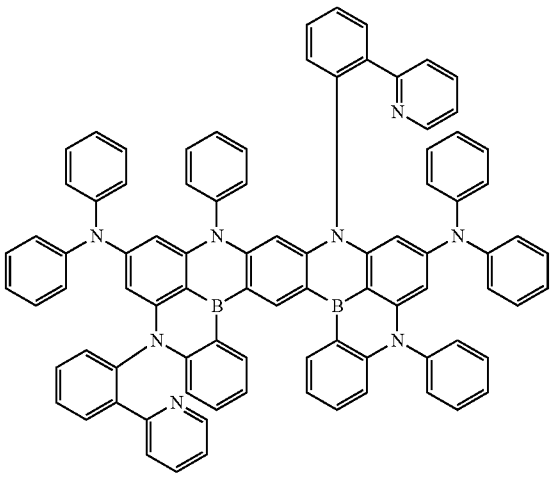
6
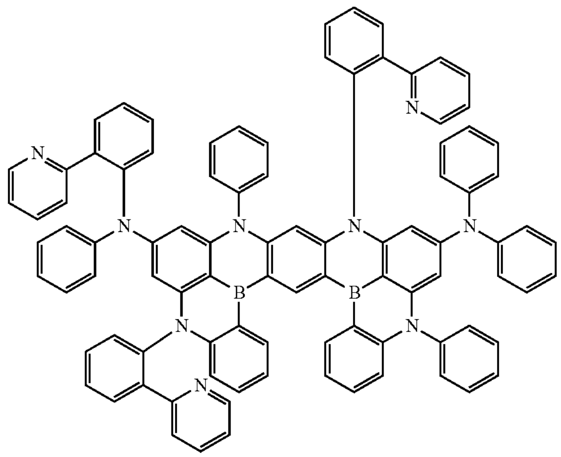

-continued
7
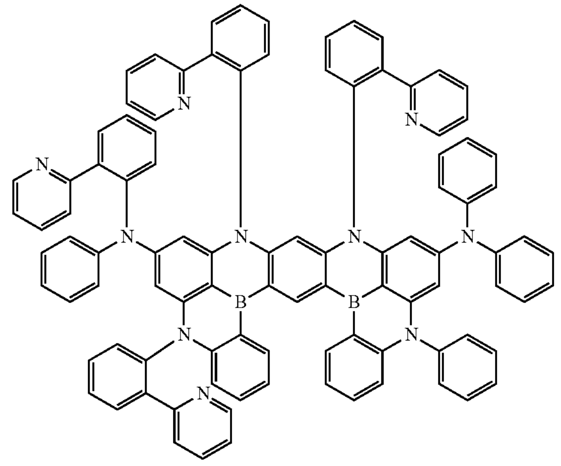
8
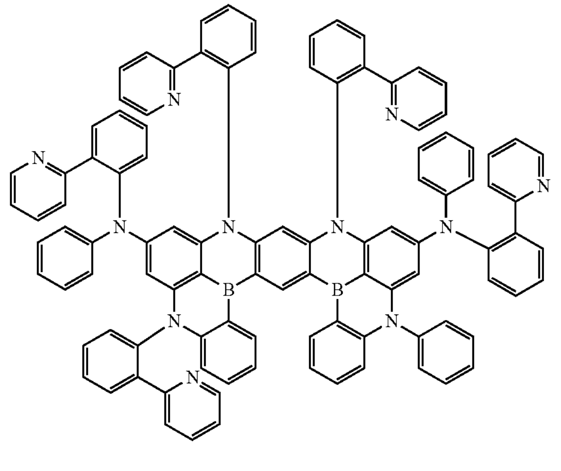
9
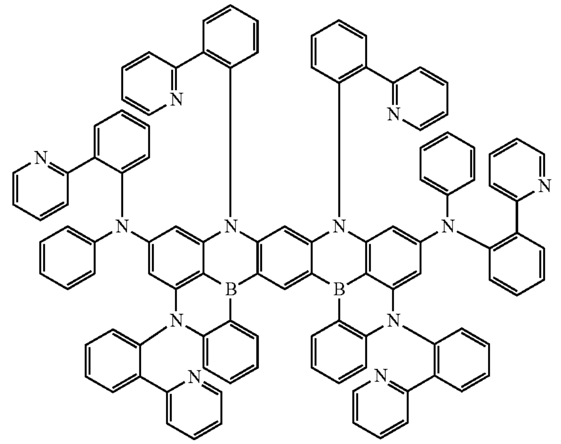
10
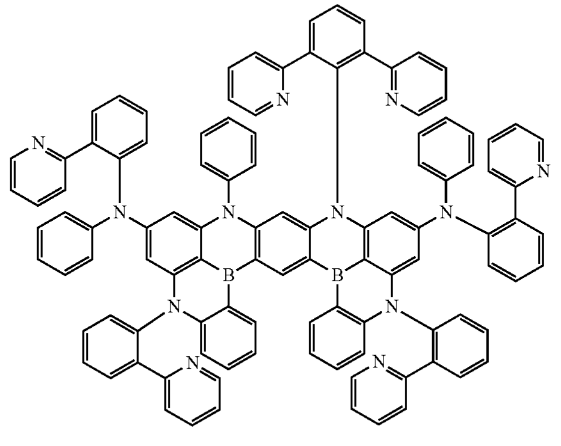
11
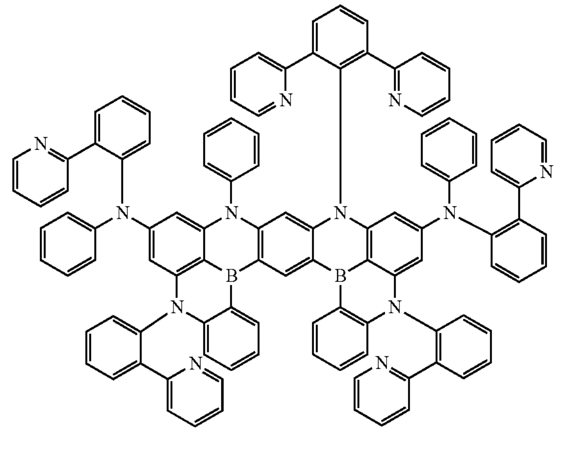
12
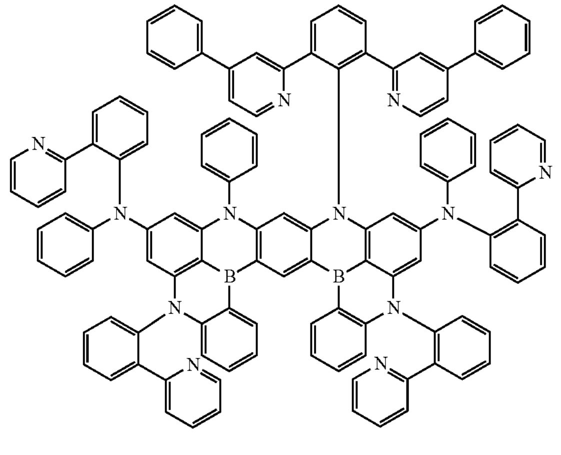

-continued
13
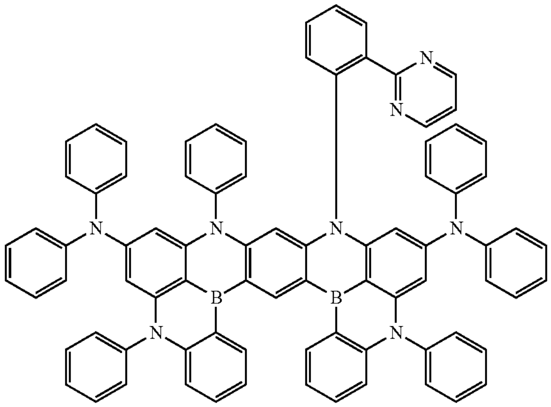
14
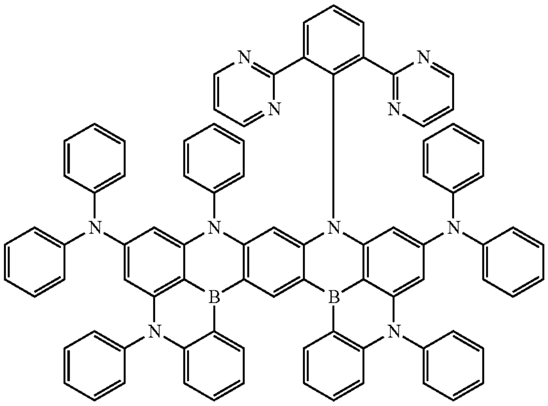
15
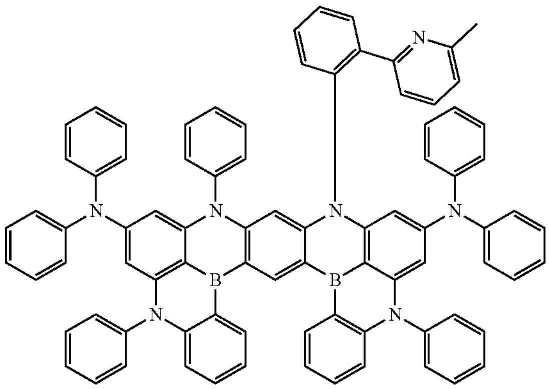
16
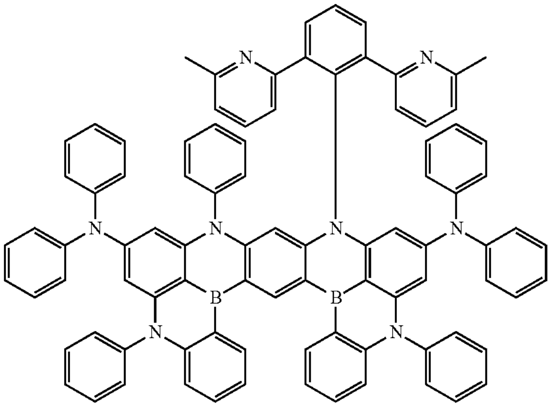
17
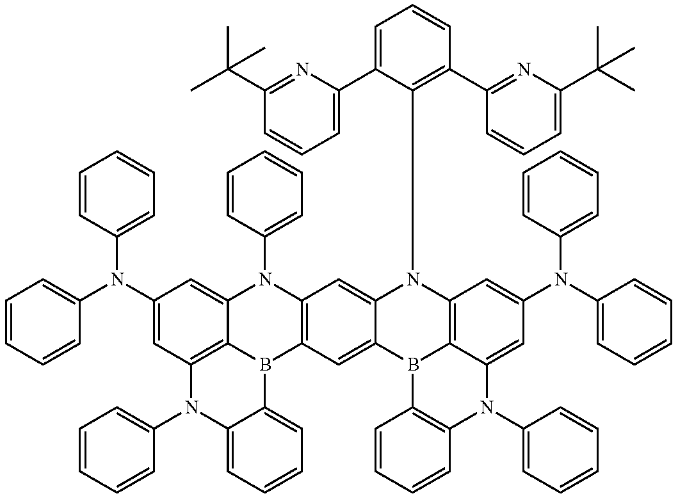

-continued
18
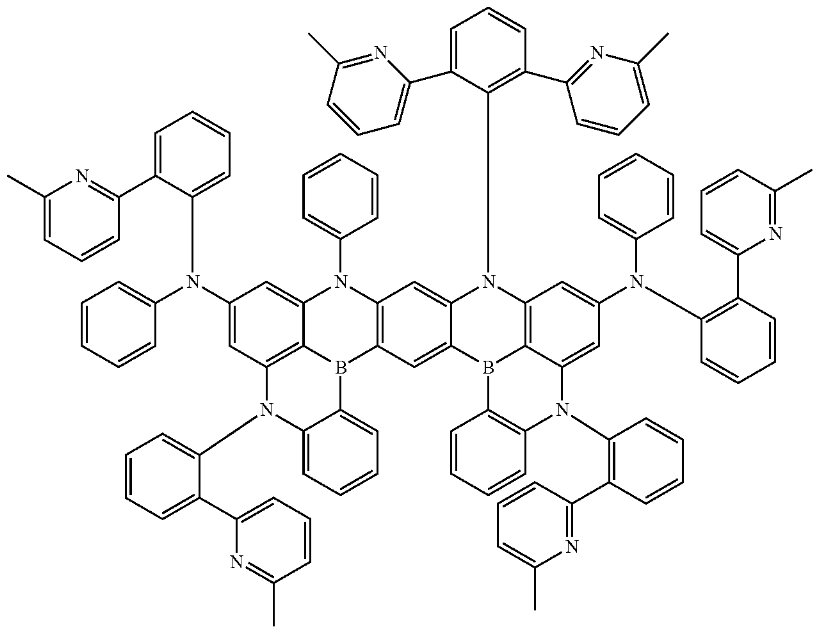
19
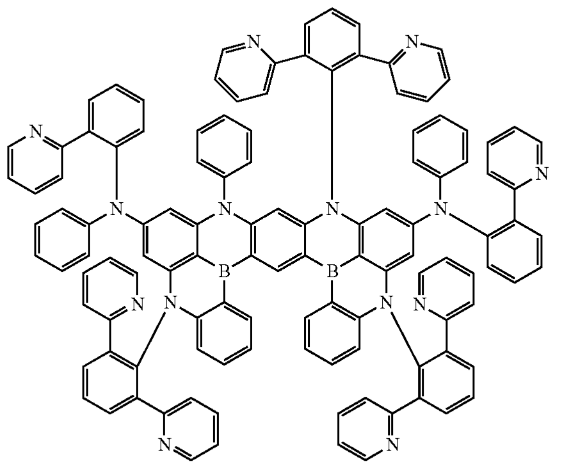
20
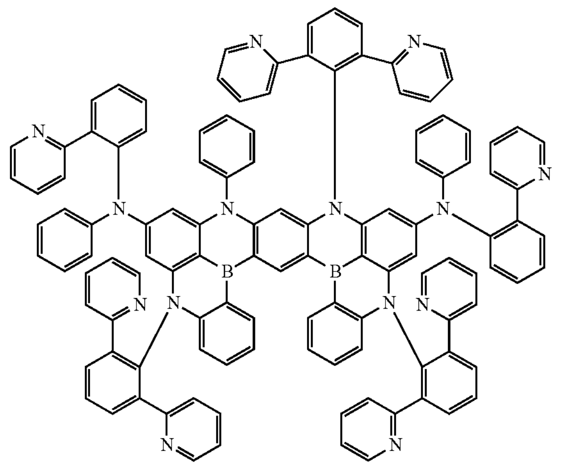
41
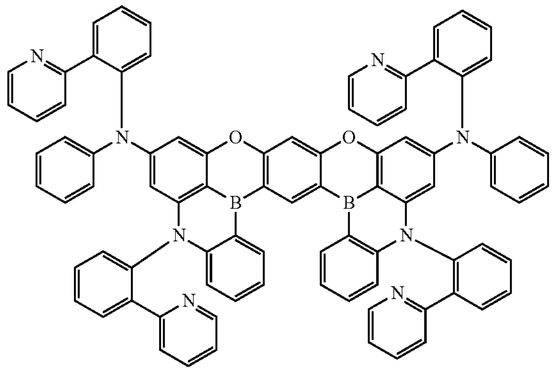
42
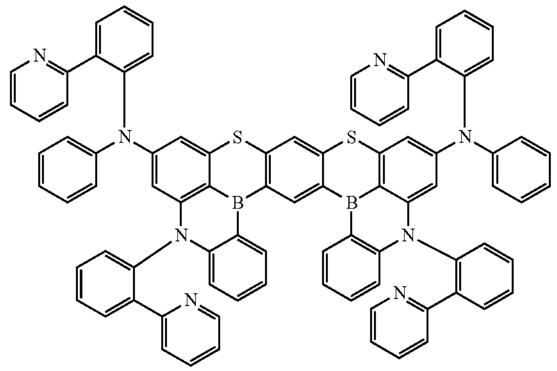

-continued
43
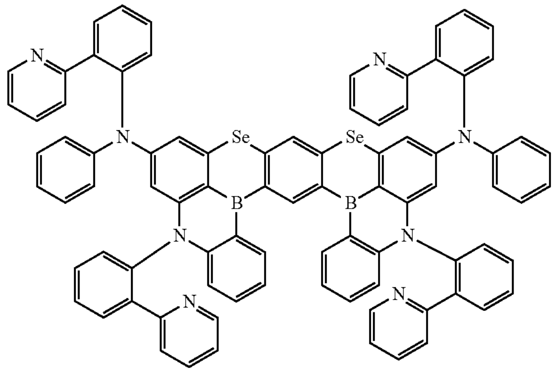
44
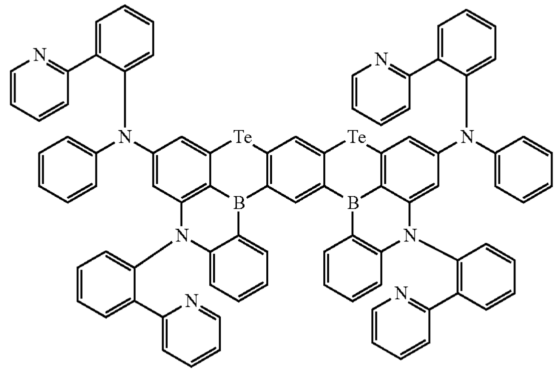
45
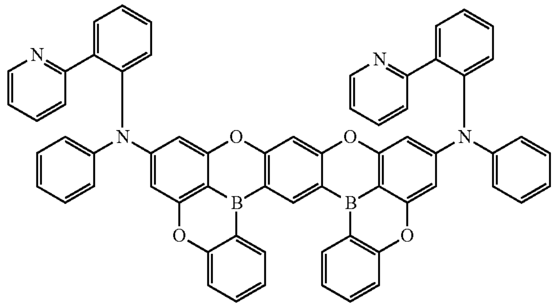
46
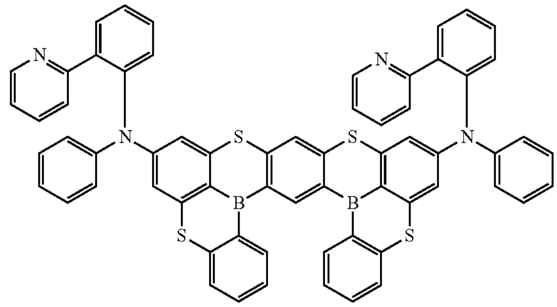
47
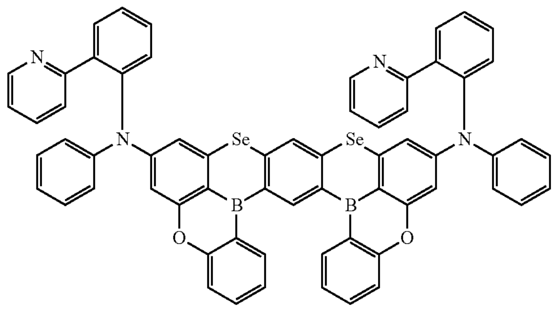
48
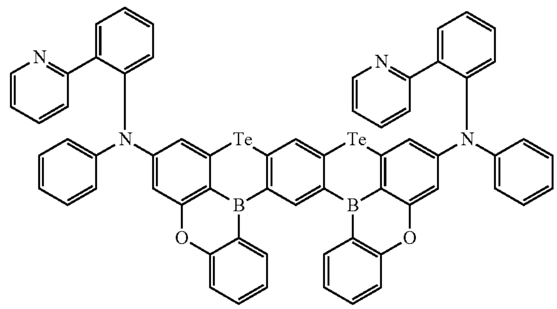
49
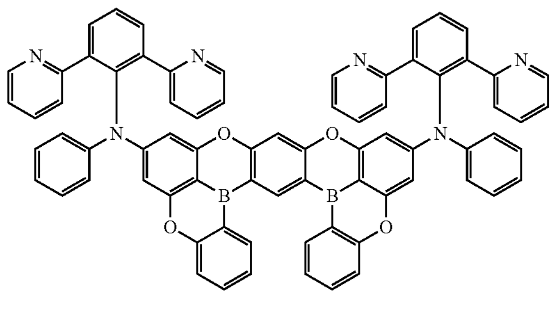
50
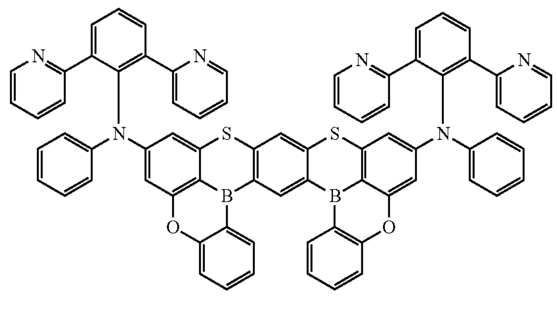

-continued
51
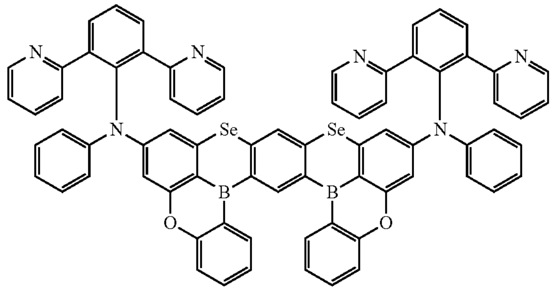
52
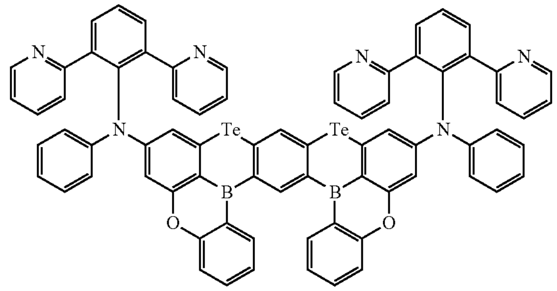
53
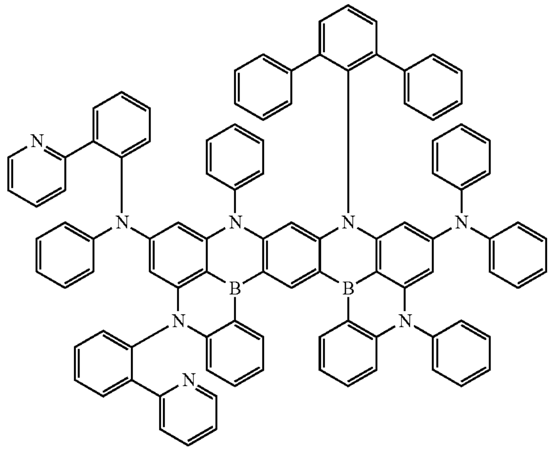
54
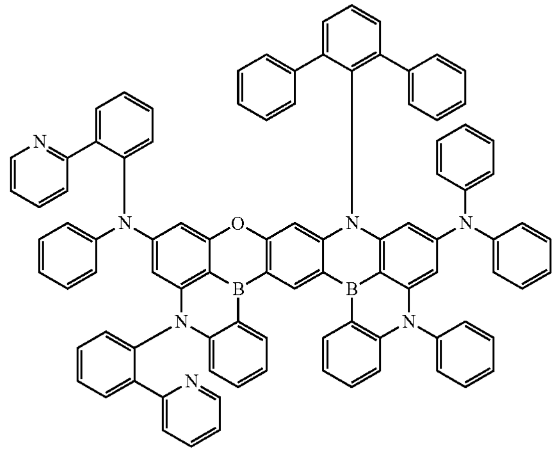
55
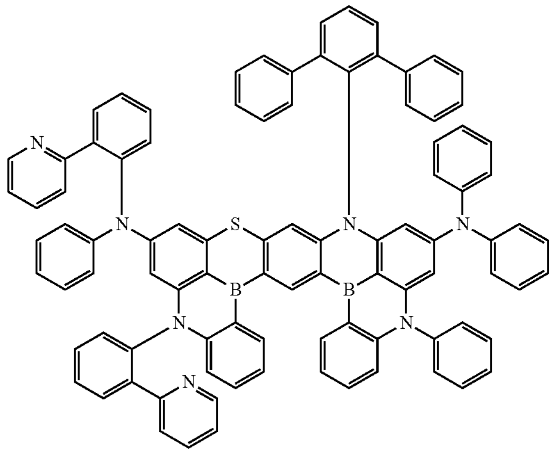
56
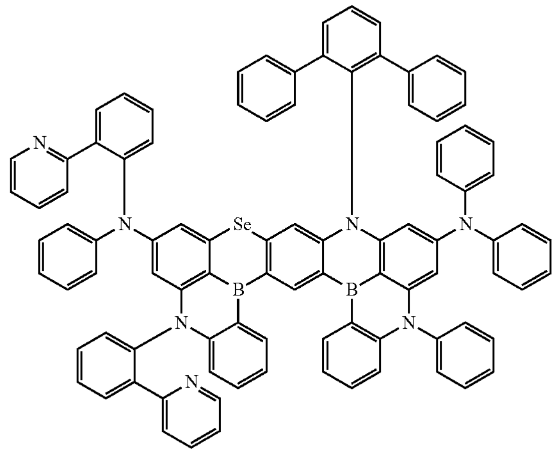

-continued
57
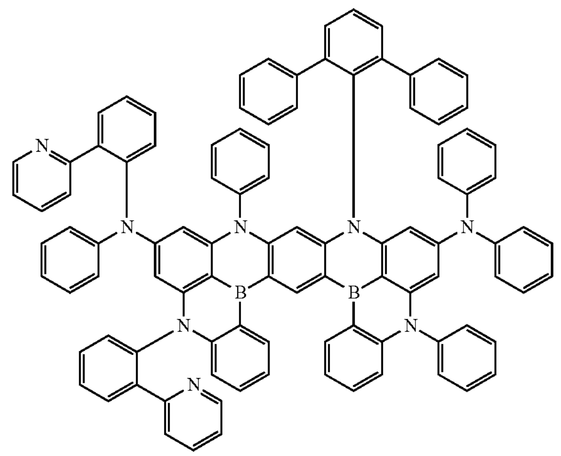
58
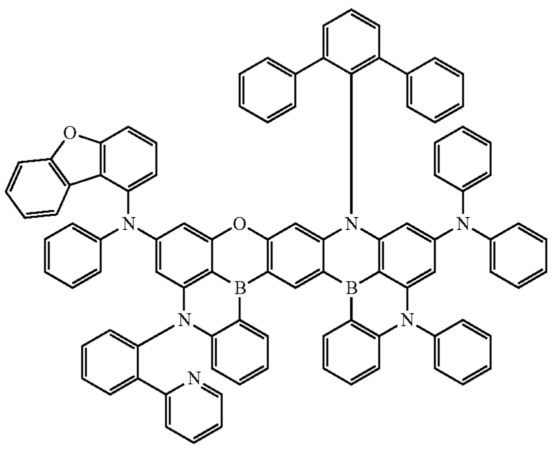
59
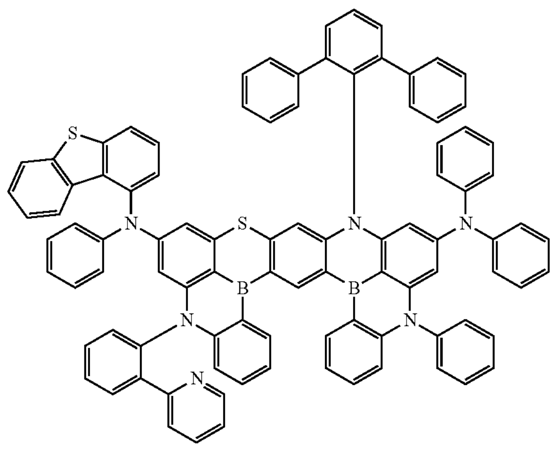
60
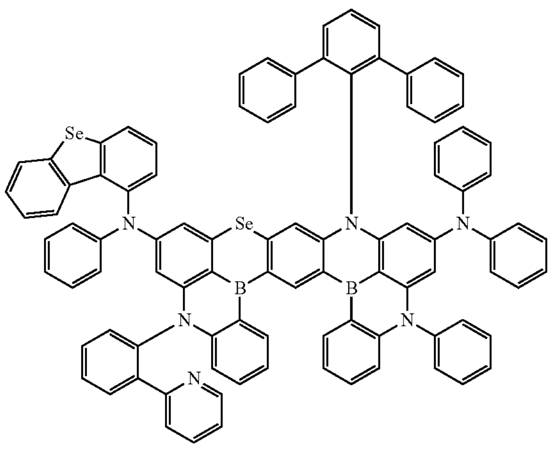
61
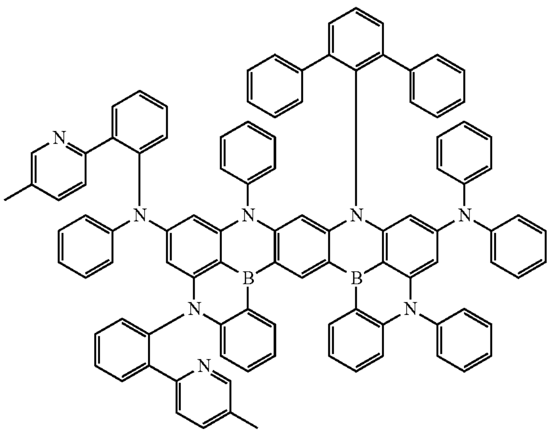
62
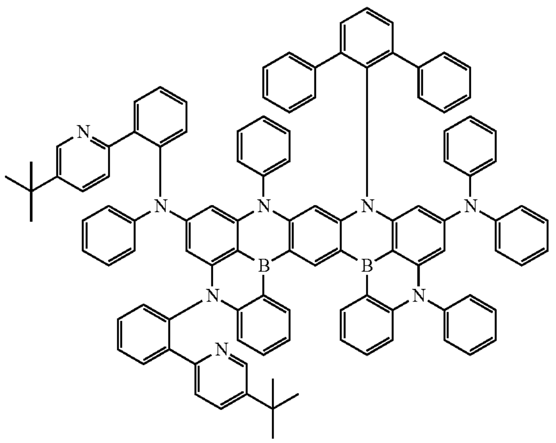

-continued
63
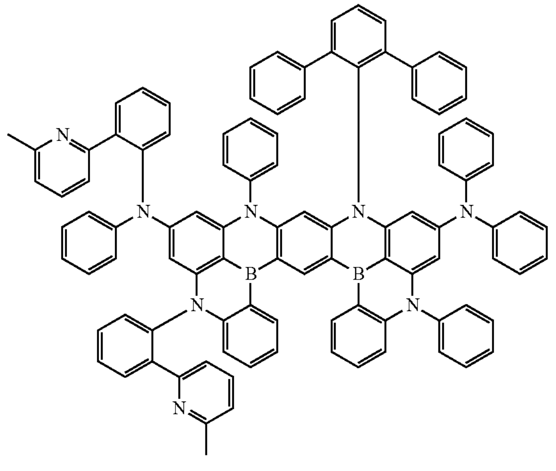
64
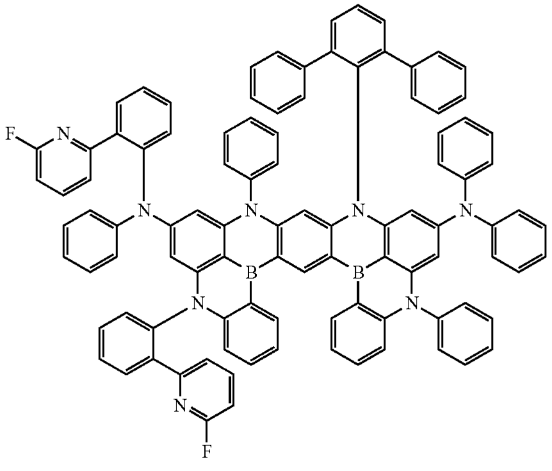
65
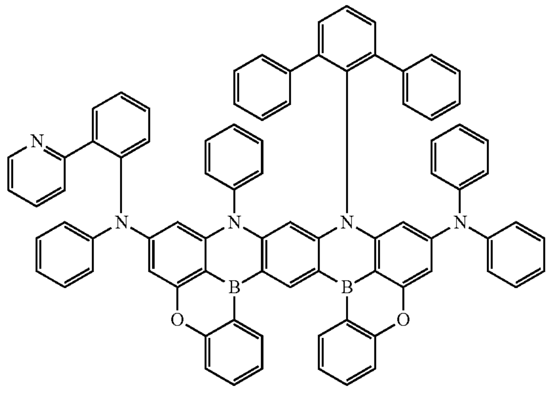
66
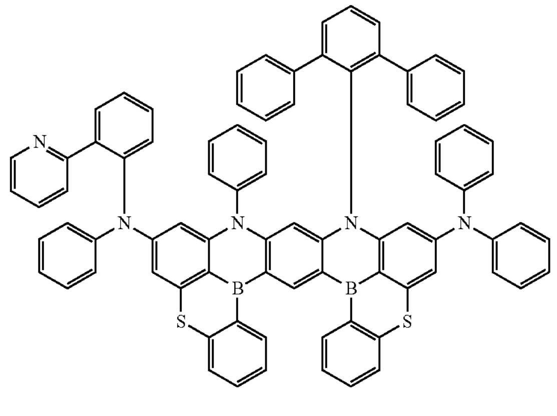
67
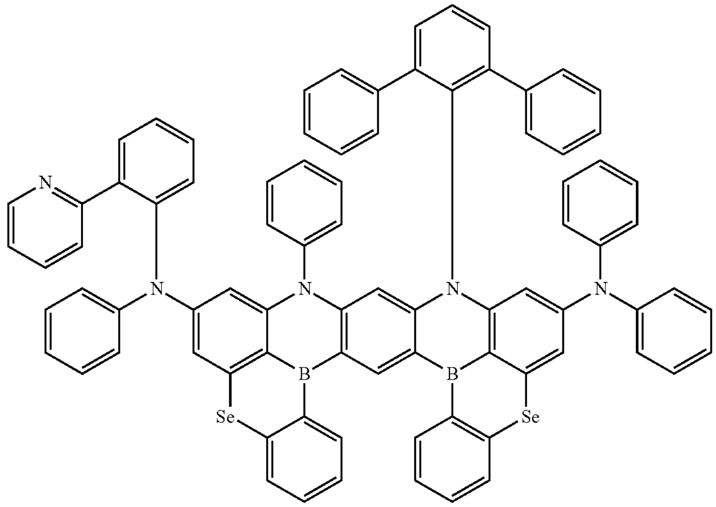

-continued
68
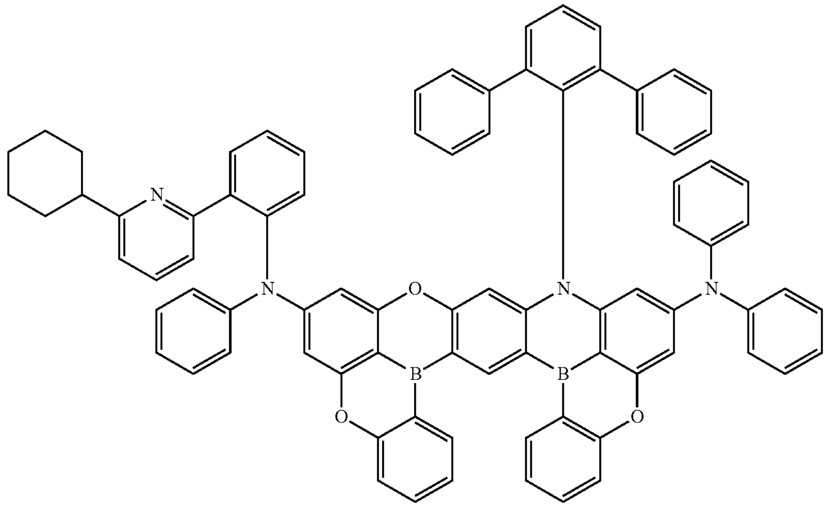
69
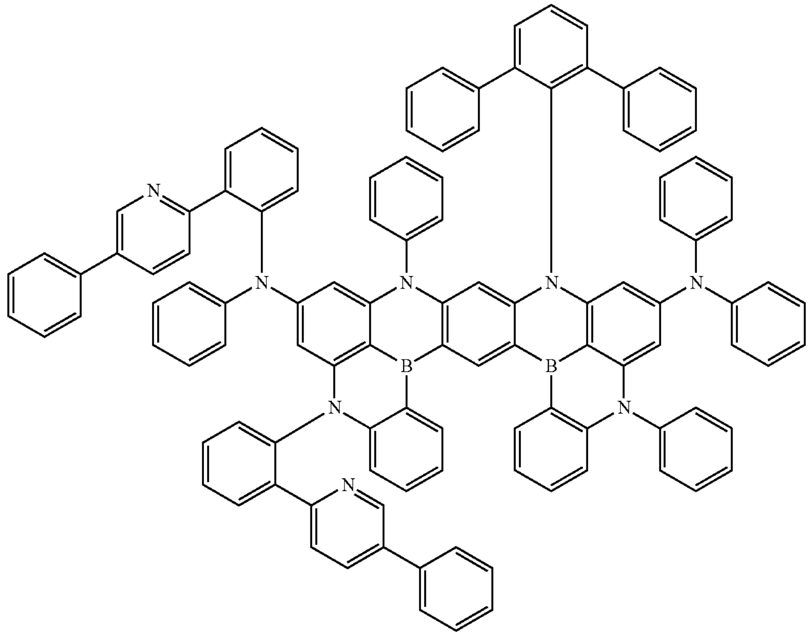
70
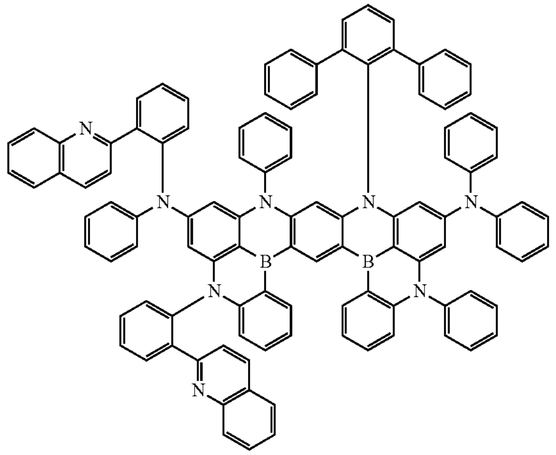
71
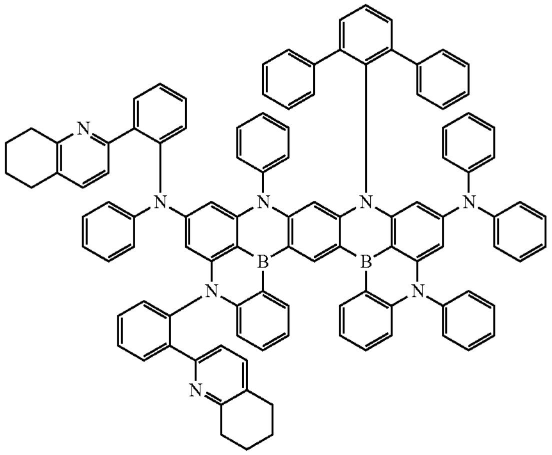

-continued
72
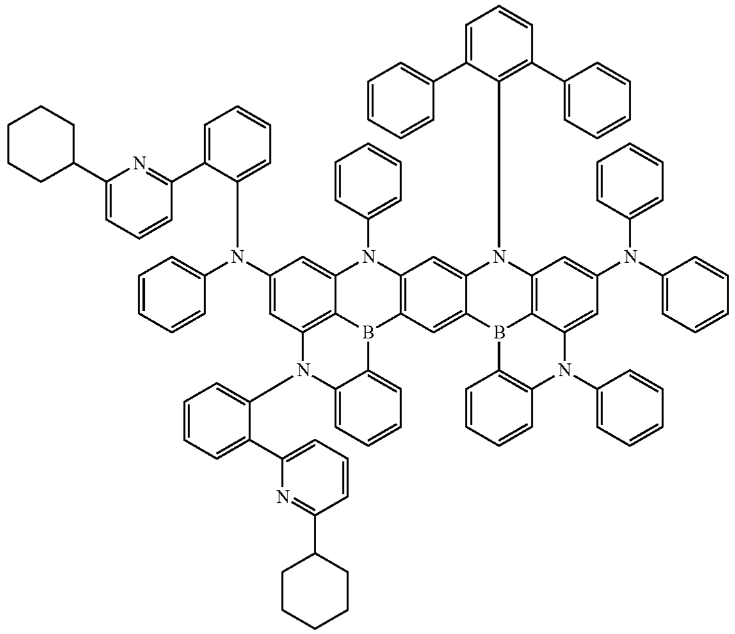
73
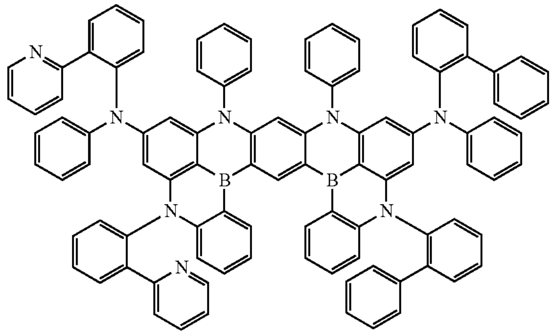
74
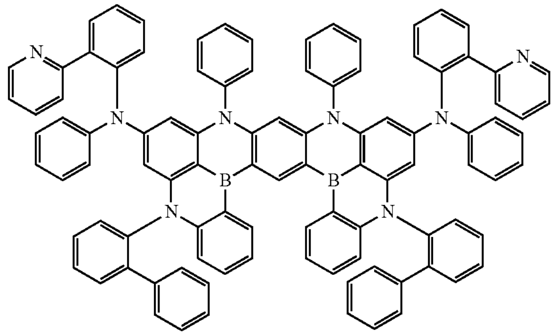
75
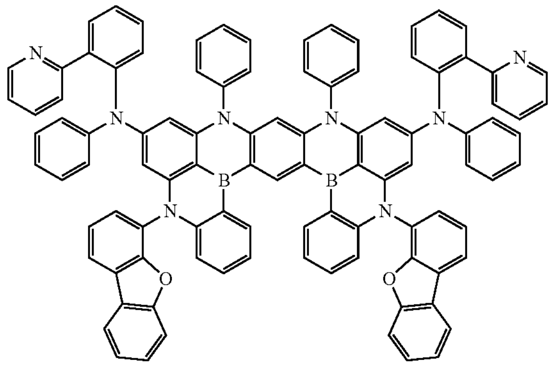
76
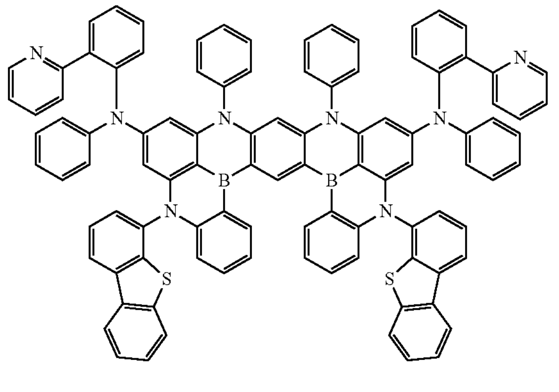

-continued
77
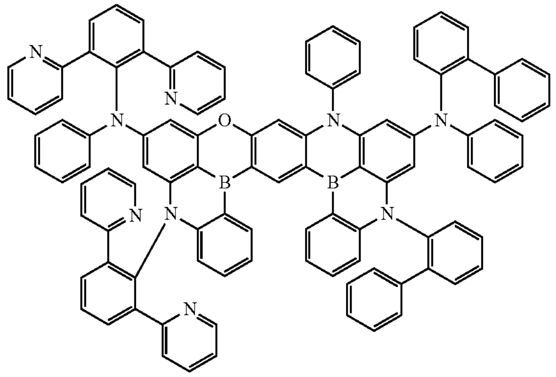
78
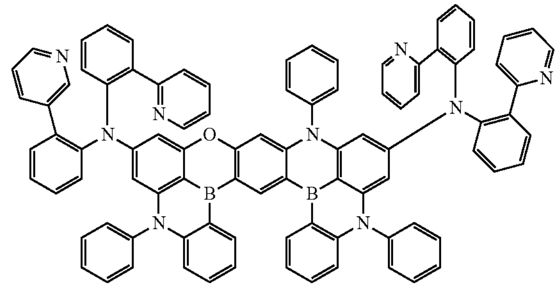
79
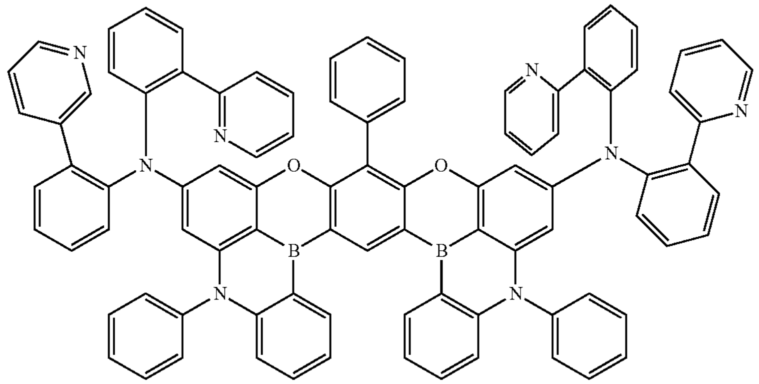
80
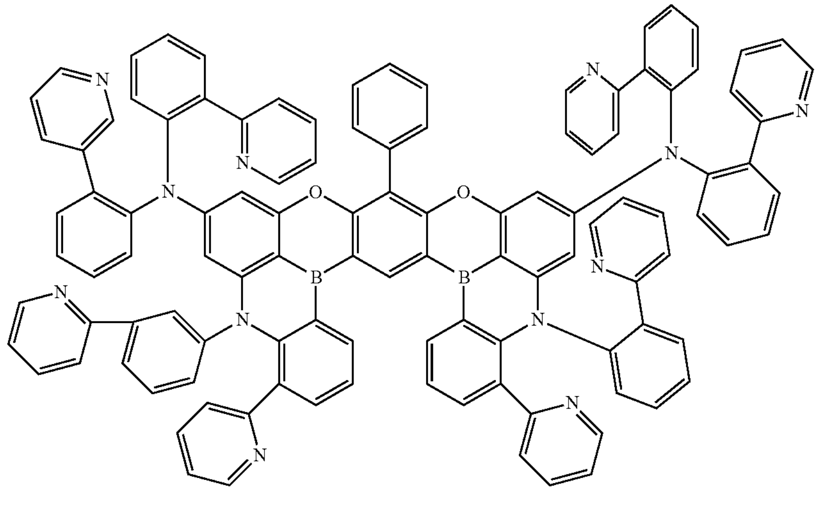

-continued
81
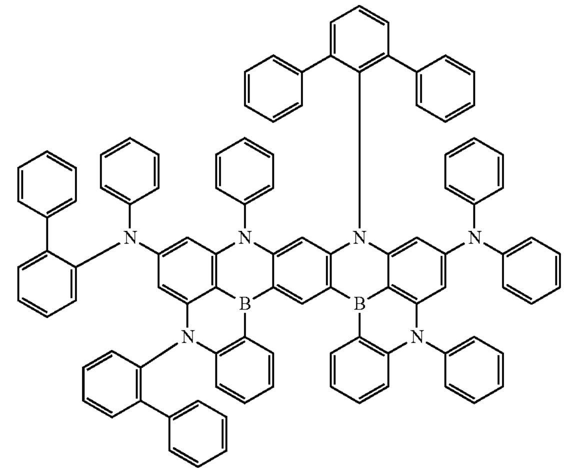
82
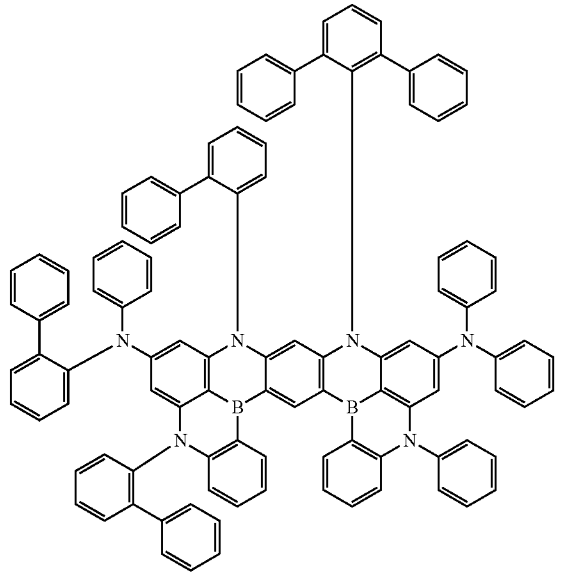
83
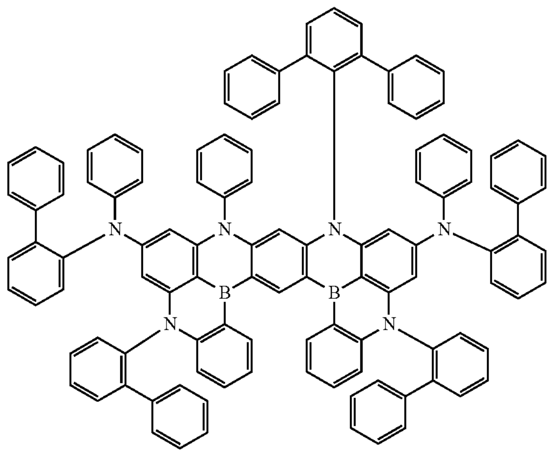
84
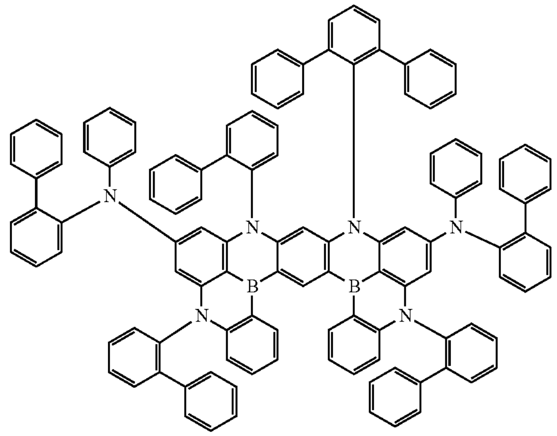
85
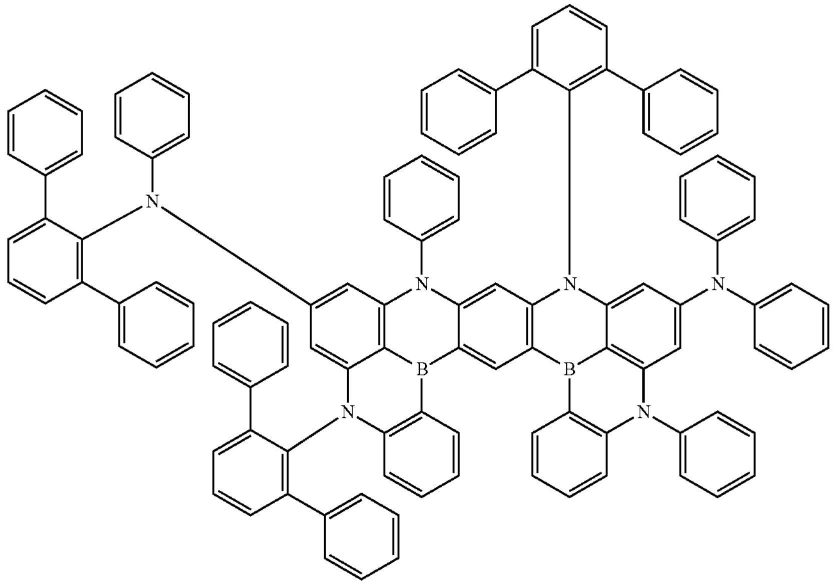

-continued
86
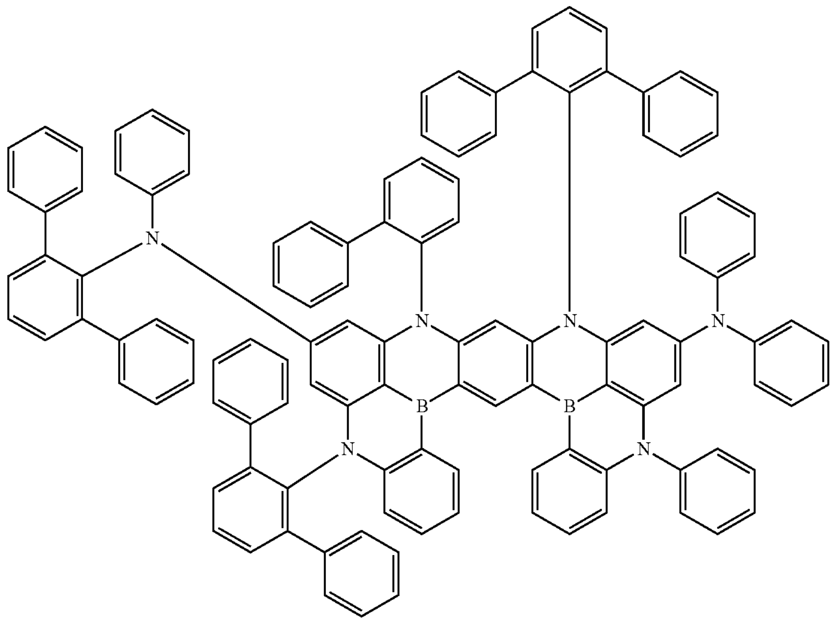
87
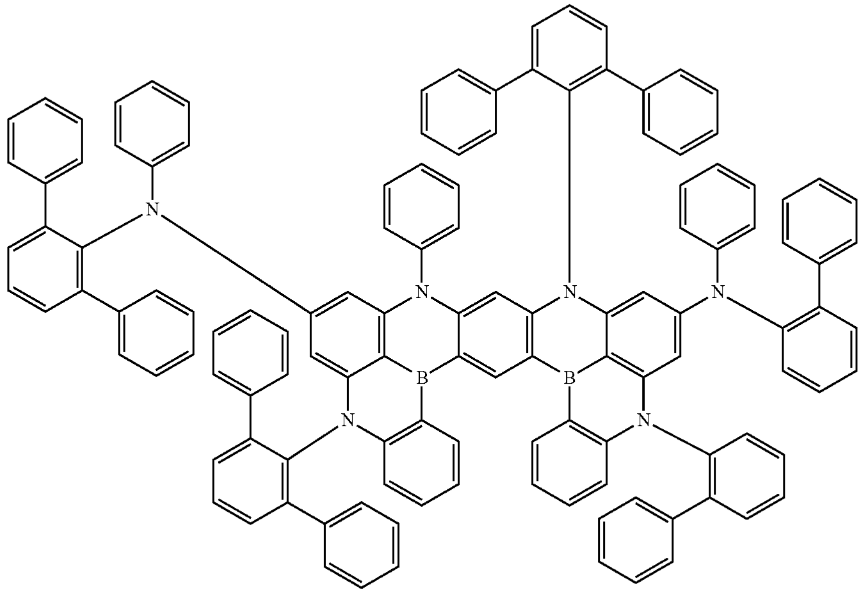

-continued
88
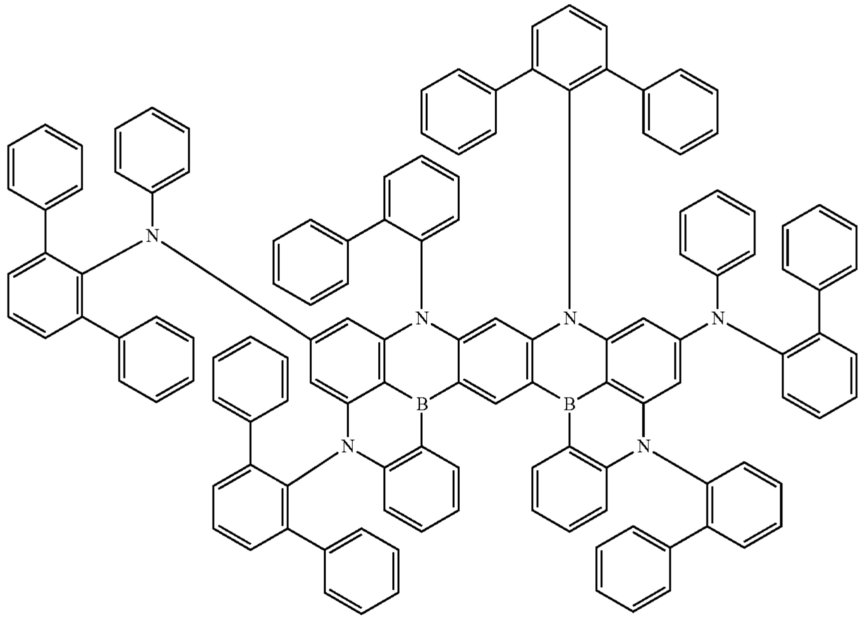
89
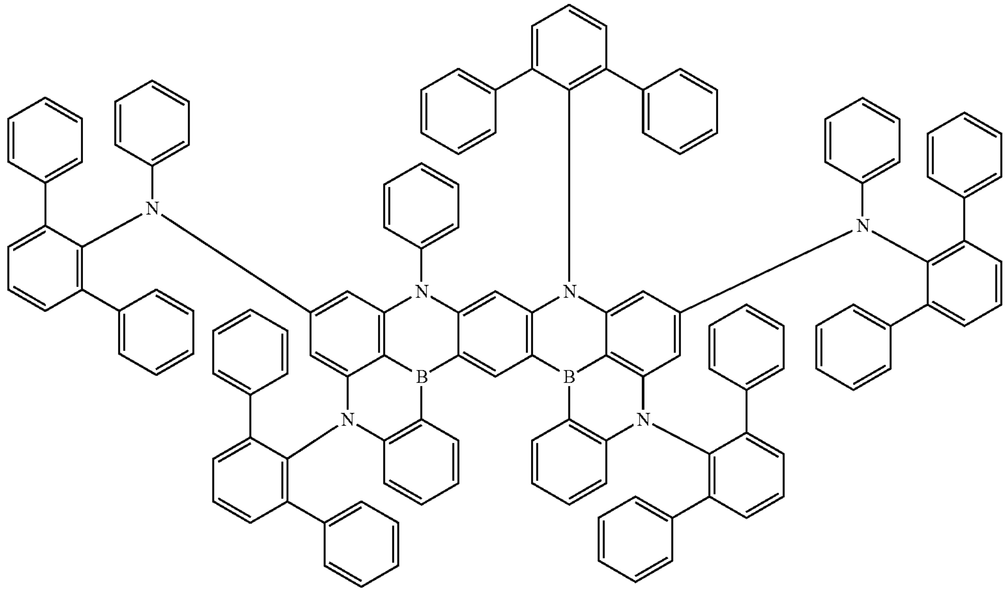

-continued
90
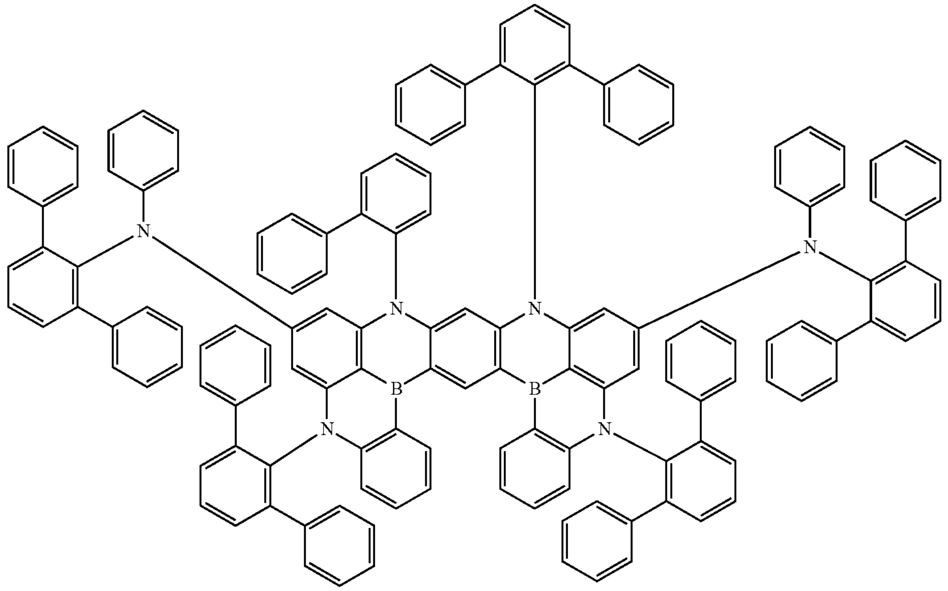
91
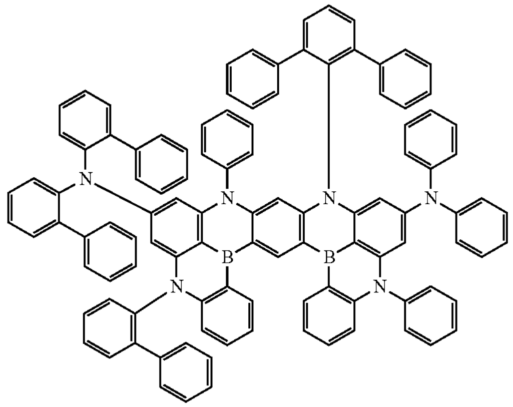
92
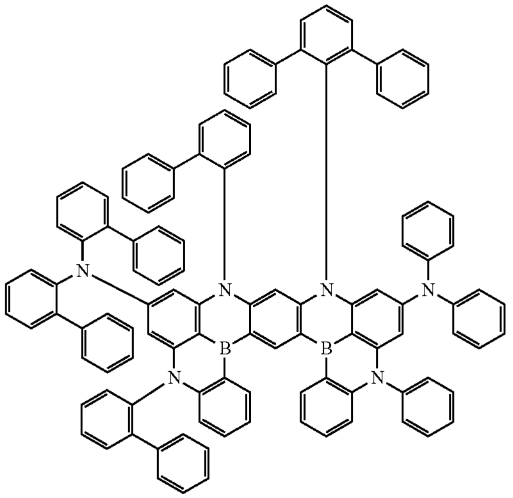
93
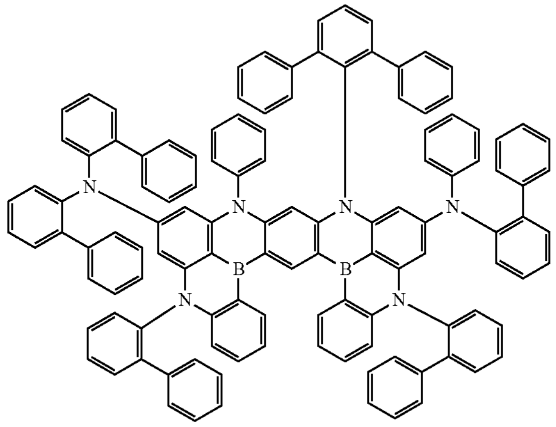
94
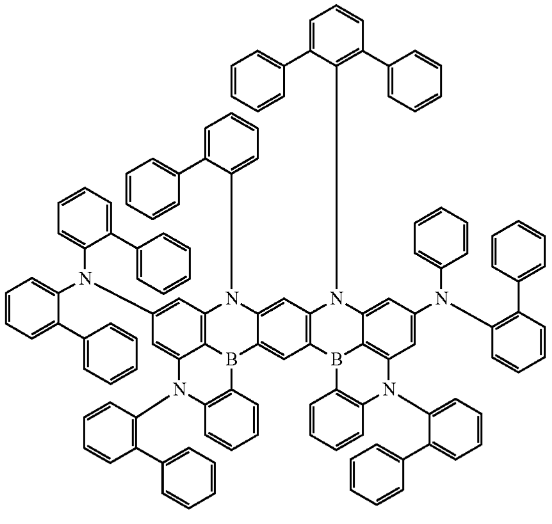

-continued
95
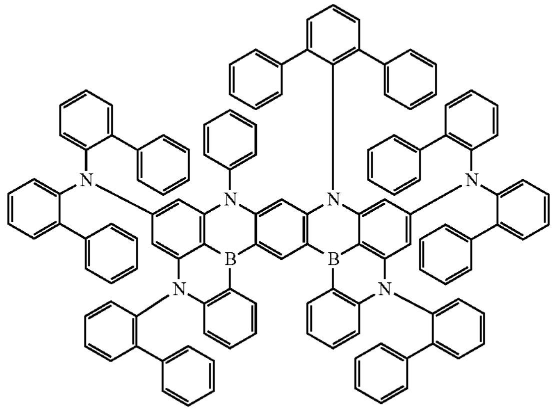
96
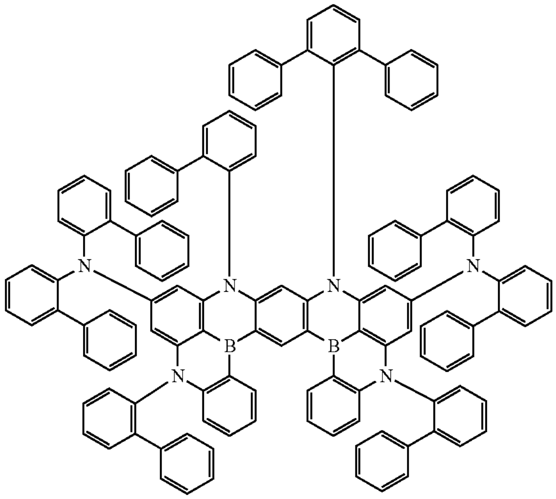
97
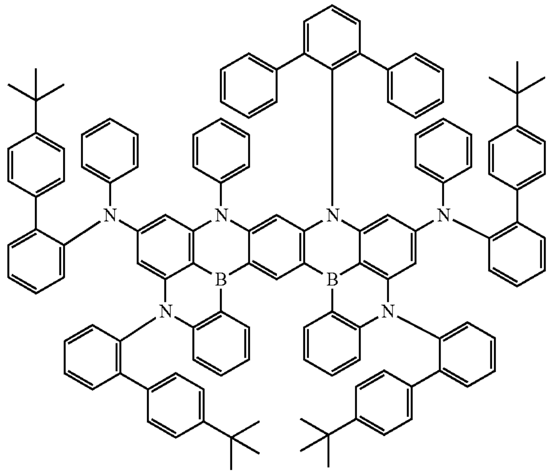
98
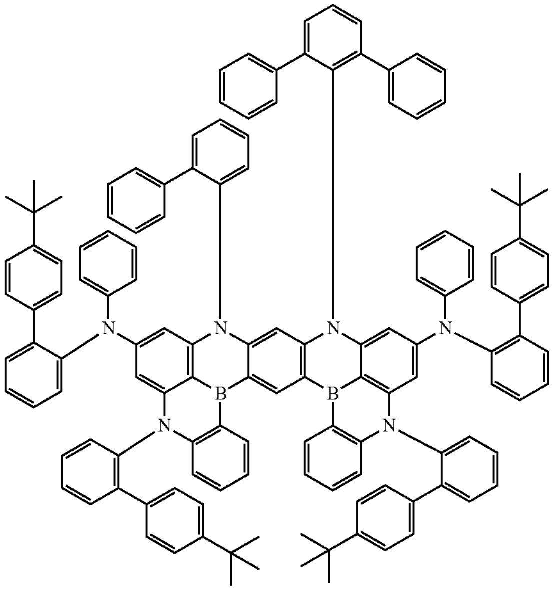

-continued
99
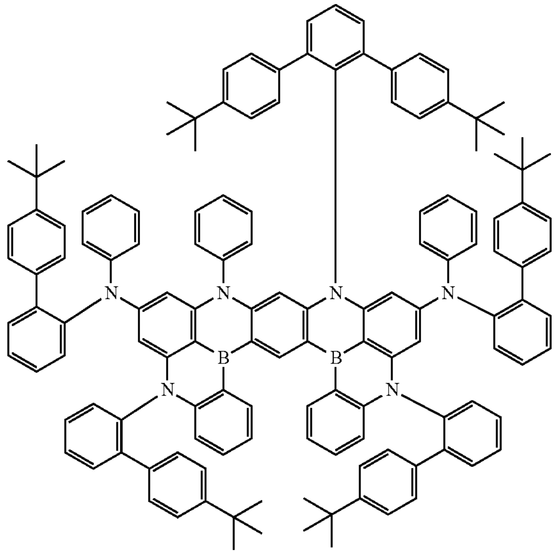
100
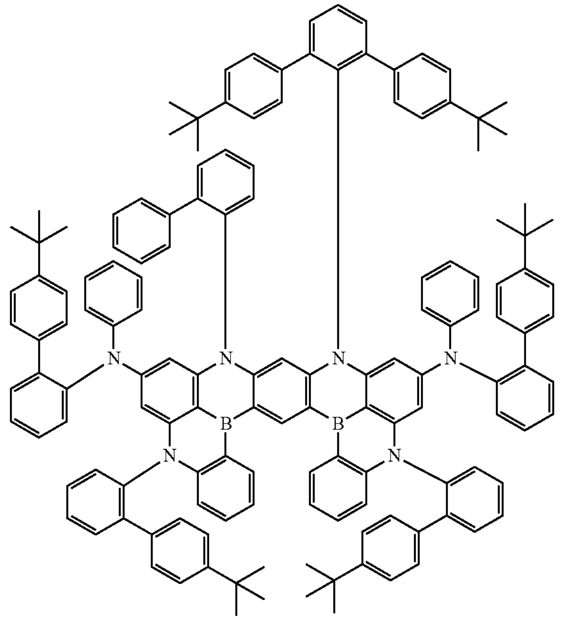
101
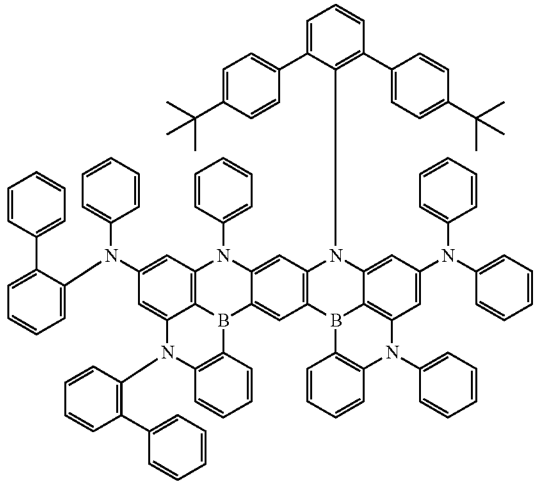
102
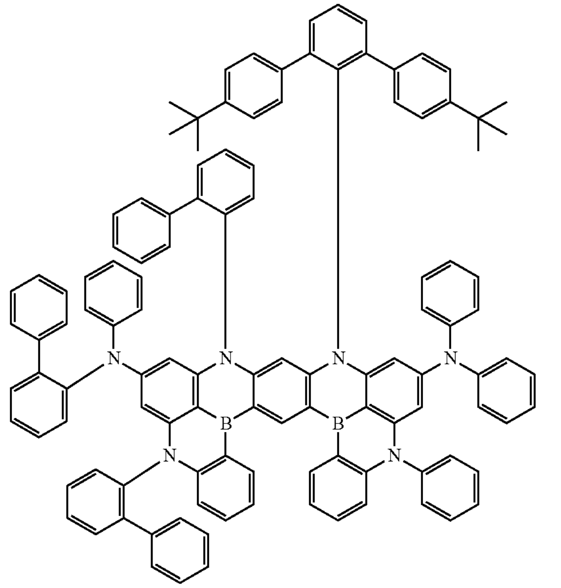

-continued
103
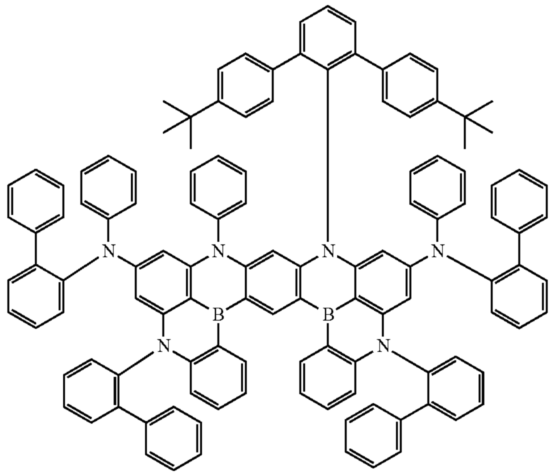
104
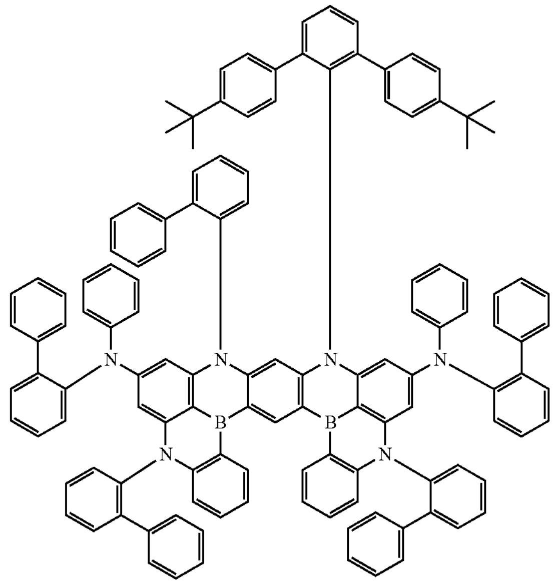
105
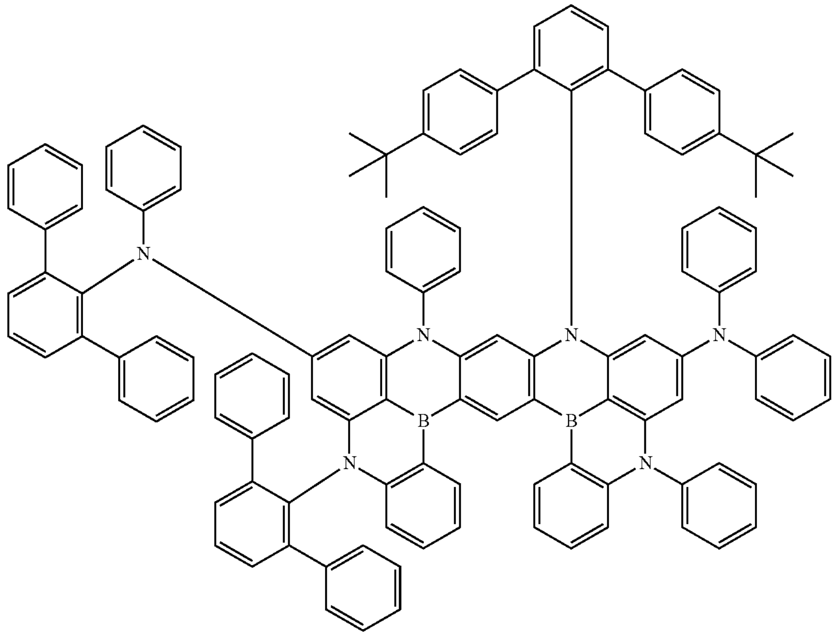

-continued
106
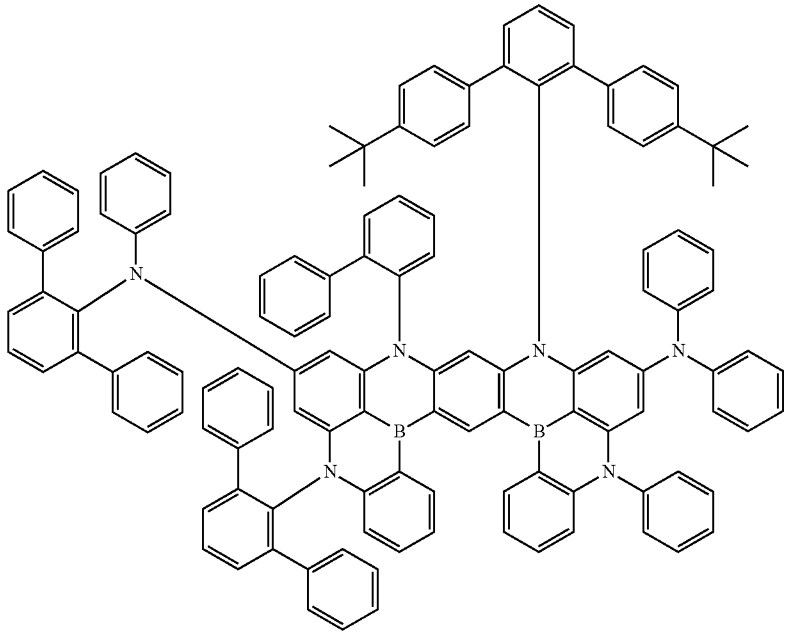
107
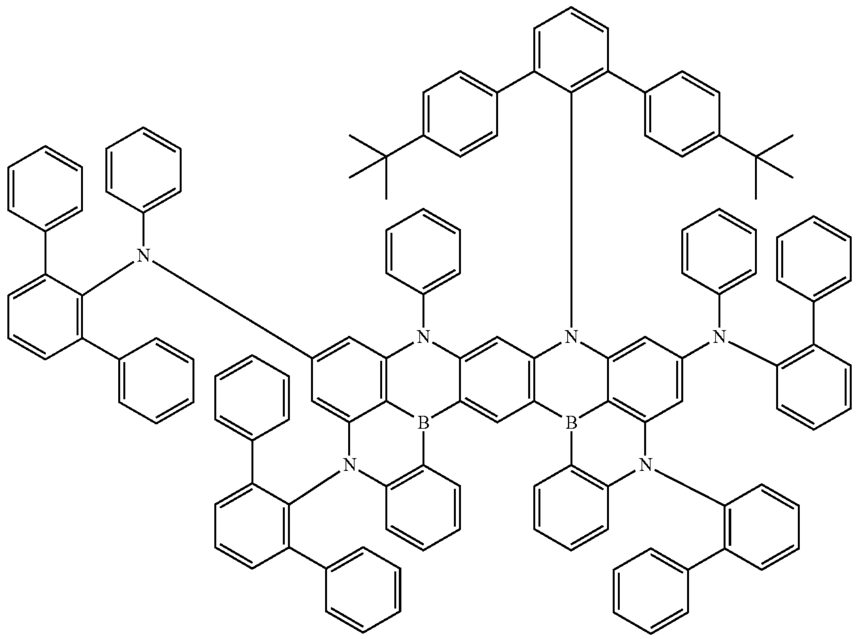

-continued
108
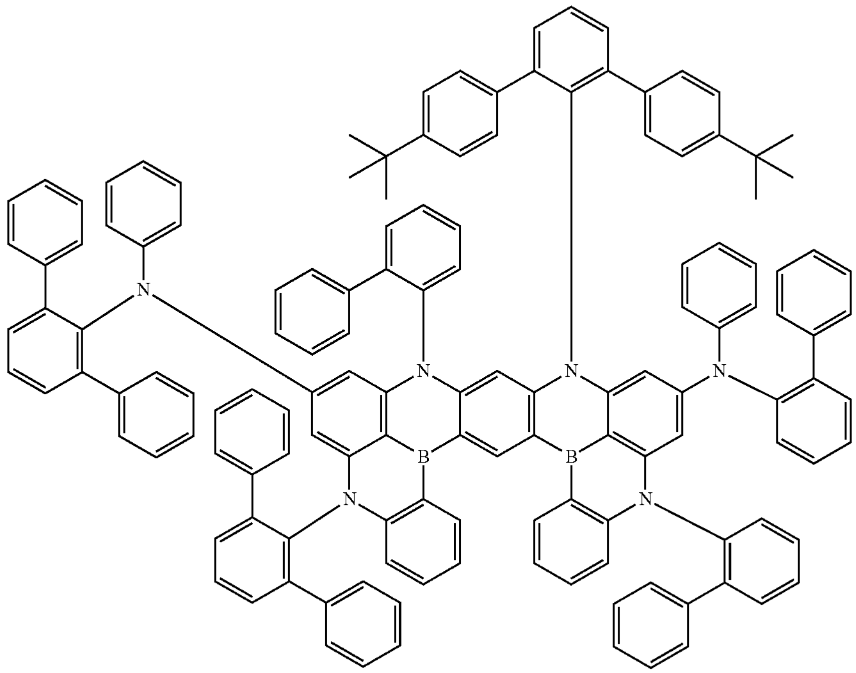
109
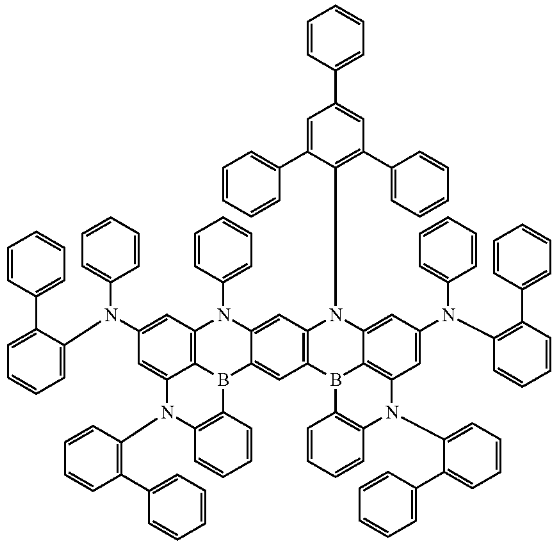
110
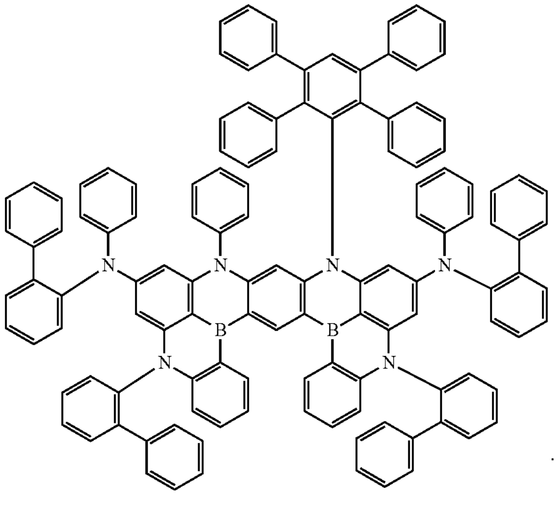
.

The heterocyclic compound represented by Formula 1-1 may include at least one group represented by Formula 1-2 as a substituent in a core structure represented by Formula 1-1:

Formula 1-1

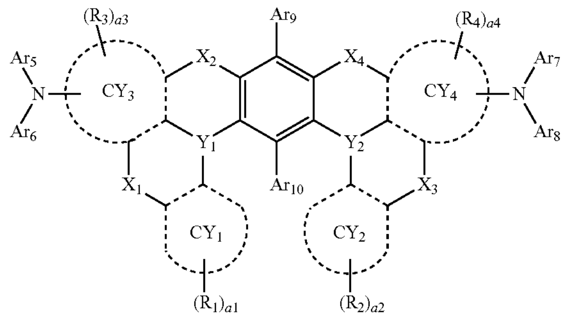

Formula 1-2

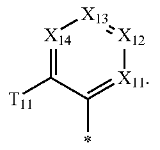

Although not wanting to be bound by theory, when the group represented by Formula 1-2 as described above is not included, B atom in a fictitious compound having a structure corresponding to Formula 1 may be combined with a nucleophile through an empty P orbital of the B atom so that a trigonal bond structure of the B atom may be transformed into a tetrahedral structure, thereby causing deterioration of an electronic device using the fictitious compound. However, the P orbital of the B atom in Formula 1 may be effectively protected through a group represented by Formula 1-2, and thus the trigonal bond structure of the B atom in Formula 1 may be effectively maintained. In addition, although the heterocyclic compound represented by Formula 1 has a multiple resonance planar structure, through a group represented by Formula 1-2, the distance between molecules may increase, causing molecular aggregation and generation of molecular excimer or molecular exciplex, and thereby decreasing the possibility of intermolecular interaction that may cause reduction in emission efficiency. Moreover, in the heterocyclic compound represented by Formula 1, when an atom in at least one of $X_{11}$ to $X_{14}$ in Formula 1-2 is "N", for example, because the lone pair electron of the N atom of the pyridine stabilizes the p orbital while showing an electron donating effect, the stability of the boron compound may be significantly improved. Therefore, the emission efficiency and/or lifespan of the electronic device including the heterocyclic compound represented by Formula 1, for example, a light-emitting device, may be improved.

The synthesis method of the heterocyclic compound represented by Formula 1 may be recognizable by one of ordinary skill in the art by referring to Synthesis Examples and/or Examples provided below.

In some embodiments, the first electrode of the light-emitting device may be an anode, the second electrode of the light-emitting device may be a cathode, the interlayer may further include a hole transport region located between the first electrode and the emission layer and an electron transport region located between the emission layer and the second electrode, the hole transport region may include a hole injection layer, a hole transport layer, an emission auxiliary layer, an electron blocking layer, or any combination thereof, and the electron transport region may include a buffer layer, a hole blocking layer, an electron control layer, an electron transport layer, an electron injection layer, or any combination thereof.

In one or more embodiments, the heterocyclic compound may be included between the first electrode and the second electrode of the light-emitting device. Accordingly, the heterocyclic compound may be included in the interlayer of the light-emitting device, for example, in the emission layer of the interlayer. The emission layer may emit red light, green light, blue light, and/or white light. For example, the emission layer may emit blue light. The blue light may have a maximum emission wavelength of, for example, about 400 nm to about 490 nm, or about 450 nm to about 470 nm. Because the blue light has a maximum emission wavelength of about 450 nm to about 470 nm, manufacturing organic light-emitting devices having high color purity is possible. In an embodiment, the emission layer may further include a host, and an amount of the host may be greater than an amount of the heterocyclic compound represented by Formula 1.

In an embodiment, the light-emitting device may include a capping layer located outside the first electrode or outside the second electrode. For example, the capping layer may include the heterocyclic compound represented by Formula 1. For example, the light-emitting device may further include at least one of a first capping layer located outside the first electrode and a second capping layer located outside the second electrode, and the heterocyclic compound represented by Formula 1 may be included in at least one of the first capping layer and the second capping layer. More details for the first capping layer and/or second capping layer are the same as described herein. In one or more embodiments, the light-emitting device may further include: a first capping layer located outside the first electrode and including the heterocyclic compound represented by Formula 1; a second capping layer located outside the second electrode and including the heterocyclic compound represented by Formula 1; or the first capping layer and the second capping layer.

The expression "(an interlayer and/or a capping layer) includes at least one heterocyclic compound" as used herein may include a case in which "(an interlayer and/or a capping layer) includes identical heterocyclic compounds represented by Formula 1" and a case in which "(an organic layer) includes two or more different heterocyclic compounds represented by Formula 1". For example, the interlayer and/or capping layer may include, as the heterocyclic compound, Compound 1 only. In this regard, Compound 1 may be present in the emission layer of the light-emitting device. In one or more embodiments, the interlayer may include, as the heterocyclic compound, Compound 1 and Compound 2. In this regard, Compound 1 and Compound 2 may be present in an identical layer (for example, Compound 1 and Compound 2 may all be present in an emission layer), or different layers (for example, Compound 1 may be present in an emission layer and Compound 2 may be present in an electron transport region).

According to another aspect of the invention an electronic apparatus including the light-emitting device may further include a thin-film transistor. In one or more embodiments, the electronic apparatus may further include a thin-film transistor including a source electrode and a drain electrode, and the first electrode of the light-emitting device may be electrically connected to the source electrode or the drain electrode. In an embodiment, the electronic apparatus may further include a color filter, a color conversion layer, a touch screen layer, a polarizing layer, or any combination thereof. More details on the electronic apparatus are the same as described herein.

According to an embodiment of the invention a heterocyclic compound is represented by Formula 1. The detailed description of Formula 1 is the same as described herein.

Description of FIG. 1

FIG. 1 is a schematic cross-sectional view of an embodiment of a light-emitting device constructed according to the principles of the invention.

Particularly, FIG. 1 is a schematic cross-sectional view of a light-emitting device 10 according to an embodiment. The light-emitting device 10 includes a first electrode 110, an interlayer 130, and a second electrode 150.

Hereinafter, the structure of the light-emitting device 10 according to an embodiment and an illustrative method of manufacturing the light-emitting device 10 will be described in connection with FIG. 1.

First Electrode 110

In FIG. 1, a substrate may be additionally located under the first electrode 110 or above the second electrode 150. As the substrate, a glass substrate or a plastic substrate may be used. In one or more embodiments, the substrate may be a flexible substrate, and may include plastics with excellent heat resistance and durability, such as a polyimide, a polyethylene terephthalate (PET), a polycarbonate, a polyethylene naphthalate, a polyarylate (PAR), a polyetherimide, or any combination thereof.

The first electrode 110 may be formed by, for example, depositing or sputtering a material for forming the first electrode 110 on the substrate. When the first electrode 110 is an anode, a material for forming the first electrode 110 may be a high work function material that facilitates injection of holes.

The first electrode 110 may be a reflective electrode, a semi-transmissive electrode, or a transmissive electrode. When the first electrode 110 is a transmissive electrode, a material for forming the first electrode 110 may include an indium tin oxide (ITO), an indium zinc oxide (IZO), a tin oxide ($SnO_2$), a zinc oxide (ZnO), or any combinations thereof. In one or more embodiments, when the first electrode 110 is a semi-transmissive electrode or a reflective electrode, magnesium (Mg), silver (Ag), aluminum (Al), aluminum-lithium (Al—Li), calcium (Ca), magnesium-indium (Mg—In), magnesium-silver (Mg—Ag), or any combinations thereof may be used as a material for forming a first electrode.

The first electrode 110 may have a single-layered structure consisting of a single layer or a multi-layered structure including a plurality of layers. For example, the first electrode 110 may have a three-layered structure of an ITO/Ag/ITO.

Interlayer 130

The interlayer 130 may be located on the first electrode 110. The interlayer 130 may include an emission layer. The interlayer 130 may further include a hole transport region placed between the first electrode 110 and the emission layer and an electron transport region placed between the emission layer and the second electrode 150.

The interlayer 130 may further include, in addition to various organic materials, metal-containing compounds such as organometallic compounds, inorganic materials such as quantum dots, and the like. In one or more embodiments, the interlayer 130 may include, i) two or more emitting units sequentially stacked between the first electrode 110 and the second electrode 150 and ii) a charge generation layer located between the two or more emitting units. When the interlayer 130 includes an emitting unit and a charge generation layer as described above, the light-emitting device 10 may be a tandem light-emitting device.

Hole Transport Region in Interlayer 130

The hole transport region may have: i) a single-layered structure consisting of a single layer consisting of a single material, ii) a single-layered structure consisting of a single layer consisting of a plurality of different materials, or iii) a multi-layered structure including a plurality of layers including different materials. The hole transport region may include a hole injection layer, a hole transport layer, an emission auxiliary layer, an electron blocking layer, or any combination thereof.

For example, the hole transport region may have a multi-layered structure including a hole injection layer/hole transport layer structure, a hole injection layer/hole transport layer/emission auxiliary layer structure, a hole injection layer/emission auxiliary layer structure, a hole transport layer/emission auxiliary layer structure, or a hole injection layer/hole transport layer/electron blocking layer structure, wherein, in each structure, layers are stacked sequentially from the first electrode 110.

The hole transport region may include a compound represented by Formula 201, a compound represented by Formula 202, or any combination thereof:

Formula 201

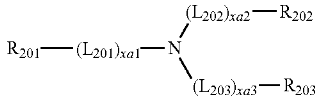

Formula 202

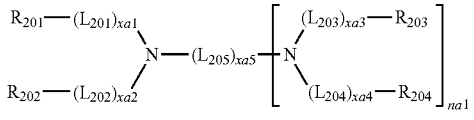

wherein, in Formulae 201 and 202, $L_{201}$ to $L_{204}$ are each independently a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, $L_{205}$ may be *—O—*', *—S—*', *—N($Q_{201}$)-*', a $C_1$-$C_{20}$ alkylene group unsubstituted or substituted with at least one $R_{10a}$, a $C_2$-$C_{20}$ alkenylene group unsubstituted or substituted with at least one $R_{10a}$, a $C_3$-$C_{60}$ carbocyclic group unsubstituted or substituted with at least one $R_{10a}$, or a $C_1$-$C_{60}$ heterocyclic group unsubstituted or substituted with at least one $R_{10a}$, xa1 to xa4 are each independently an integer from 0 to 5, xa5 is an integer from 1 to 10, $R_{201}$ to $R_{204}$ and $Q_{201}$ are each independently a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, $R_{201}$ and $R_{202}$ are optionally linked to each other, via a single bond, a $C_1$-$C_5$ alkylene group unsubstituted or substituted with at least one $R_{10a}$, or a $C_2$-$C_5$ alkenylene group unsubstituted or substituted with at least one $R_{10a}$, to form a $C_8$-$C_{60}$ polycyclic group (for example, a carbazole group or the like) unsubstituted or substituted with at least one $R_{10a}$ (for example, Compound HT16), $R_{203}$ and $R_{204}$ are optionally linked to each other, via a single bond, a $C_1$-$C_5$ alkylene group unsubstituted or substituted with at least one $R_{10a}$, or a $C_2$-$C_5$ alkenylene group unsubstituted or substituted with at least one $R_{10a}$, to form a $C_8$-$C_{60}$ polycyclic group unsubstituted or substituted with at least one $R_{10a}$, and na1 may be an integer from 1 to 4.

In one or more embodiments, each of Formulae 201 and 202 may include at least one of groups represented by Formulae CY201 to CY217.

CY201

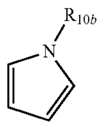

CY202

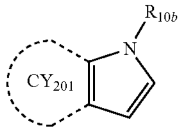

CY203

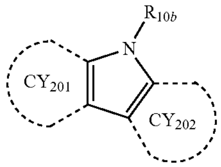

CY204

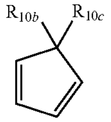

CY205

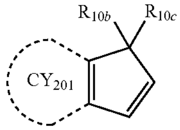

CY206

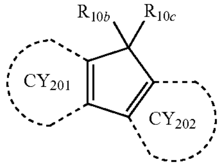

CY207

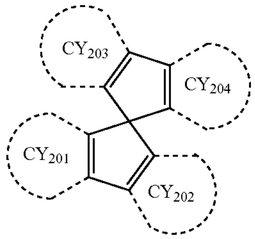

CY208

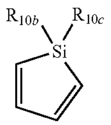

-continued

CY209

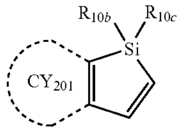

CY210

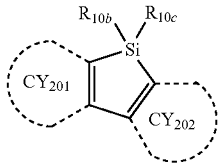

CY211

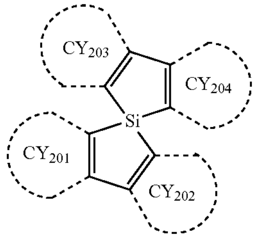

CY212

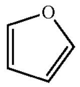

CY213

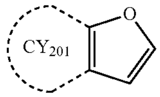

CY214

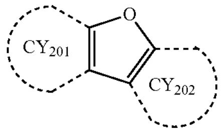

CY215

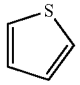

CY216

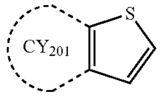

CY217

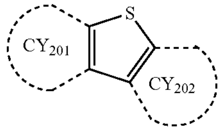

The variables $R_{10b}$ and $R_{10c}$ in Formulae CY201 to CY217 are the same as described in connection with $R_{10a}$, ring $CY_{201}$ to ring $CY_{204}$ may each independently be a $C_3$-$C_{20}$ carbocyclic group or a $C_1$-$C_{20}$ heterocyclic group, and at least one hydrogen in Formulae CY201 to CY217 may be unsubstituted or substituted with $R_{10a}$.

In an embodiment, ring $CY_{201}$ to ring $CY_{204}$ in Formulae CY201 to CY217 may each independently be a benzene group, a naphthalene group, a phenanthrene group, or an anthracene group. In one or more embodiments, each of Formulae 201 and 202 may include at least one of groups represented by Formulae CY201 to CY203.

In one or more embodiments, Formula 201 may include at least one of groups represented by Formulae CY201 to CY203 and at least one of groups represented by Formulae CY204 to CY217. In one or more embodiments, xa1 in Formula 201 is 1, $R_{201}$ is a group represented by one of Formulae CY201 to CY203, xa2 may be 0, and $R_{202}$ may be a group represented by one of Formulae CY204 to CY217. In one or more embodiments, each of Formulae 201 and 202 may not include a group represented by one of Formulae CY201 to CY203. In one or more embodiments, each of Formulae 201 and 202 may not include a group represented by one of Formulae CY201 to CY203, and may include at least one of groups represented by Formulae CY204 to CY217. In one or more embodiments, each of Formulae 201 and 202 may not include a group represented by one of Formulae CY201 to CY217.

In an embodiment, the hole transport region may include one of Compounds HT1 to HT46, 4,4',4"-tris[phenyl(m-tolyl)amino]triphenylamine (m-MTDATA), 1-N,1-N-bis[4-(diphenylamino)phenyl]-4-N,4-N-diphenylbenzene-1,4-diamine (TDATA), 4,4',4"-tris[2-naphthyl(phenyl)amino]triphenylamine (2-TNATA), bis(naphthalen-1-yl)-N,N'-bis(phenyl)benzidine (NPB or NPD), N4,N4'-di(naphthalen-2-yl)-N4,N4'-diphenyl-[1,1'-biphenyl]-4,4'-diamine (β-NPB), N,N'-bis(3-methylphenyl)-N,N'-diphenylbenzidine (TPD), N,N'-bis(3-methylphenyl)-N,N'-diphenyl-9,9-spirobifluorene-2,7-diamine (Spiro-TPD), N2,N7-di-1-naphthalenyl-N2,N7-diphenyl-9,9'-spirobi[9H-fluorene]-2,7-diamine (Spiro-NPB), N,N'-di(1-naphthyl)-N,N'-diphenyl-2,2'-dimethyl-(1,1'-biphenyl)-4,4'-diamine (methylated NPB), 4,4'-cyclohexylidenebis[N,N-bis(4-methylphenyl)benzenamine] (TAPC), N,N,N',N'-tetrakis(3-methylphenyl)-3,3'-dimethylbenzidine (HMTPD), 4,4',4"-tris(N-carbazolyl)triphenylamine (TCTA), polyaniline/dodecylbenzenesulfonic acid (PANI/DBSA), poly(3,4-ethylenedioxythiophene)/poly(4-styrenesulfonate) (PEDOT/PSS), polyaniline/camphor sulfonic acid (PANI/CSA), polyaniline/poly(4-styrenesulfonate) (PANI/PSS), 9-(4-tert-Butylphenyl)-3,6-bis(triphenylsilyl)-9H-carbazole (CzSi) or any combination thereof:

HT1

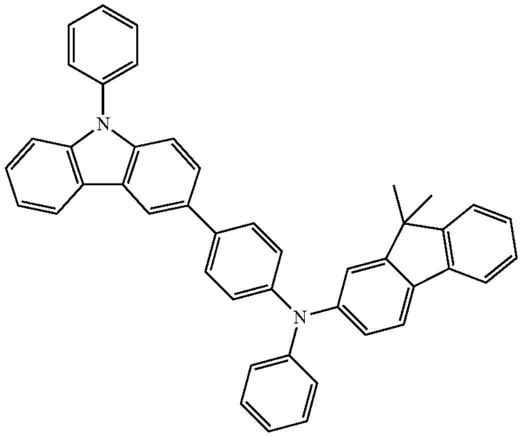

HT2

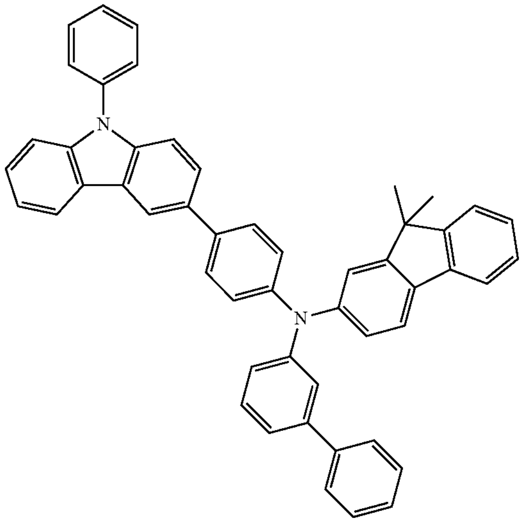

HT3

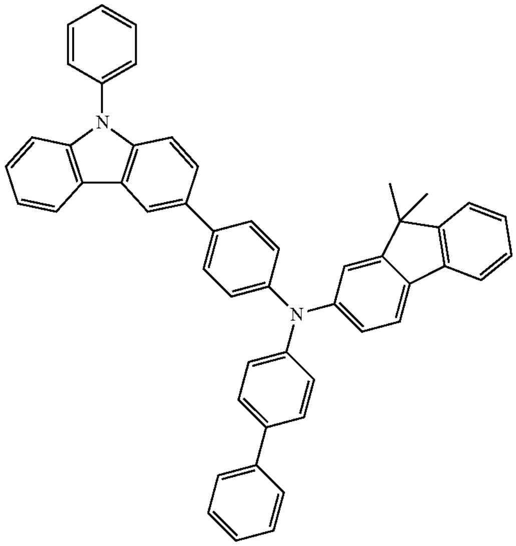

HT4

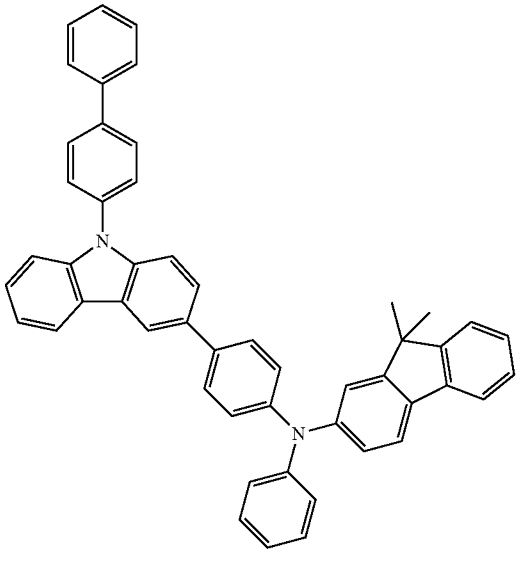

-continued
HT5
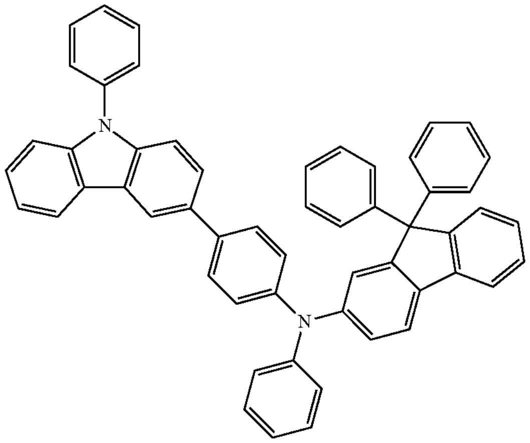
HT6
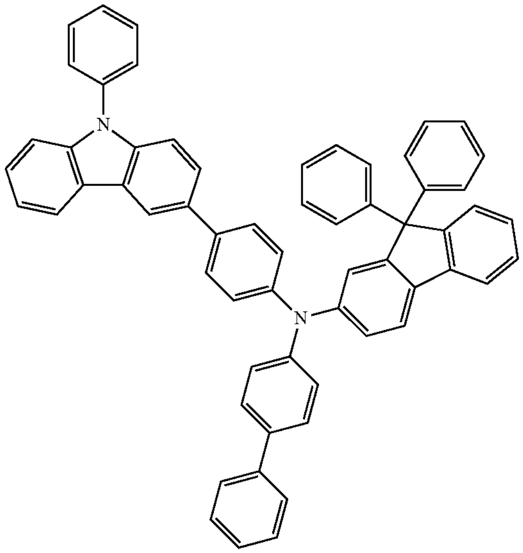
HT7
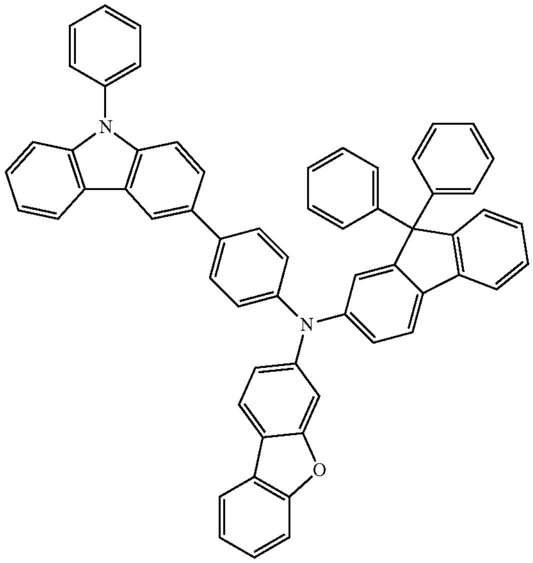
HT8
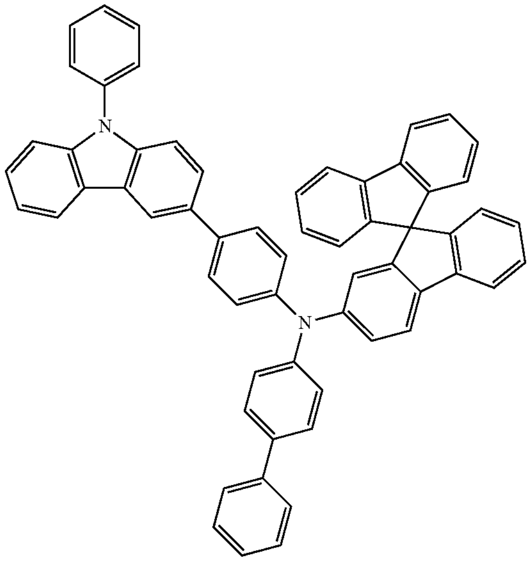

-continued
HT9
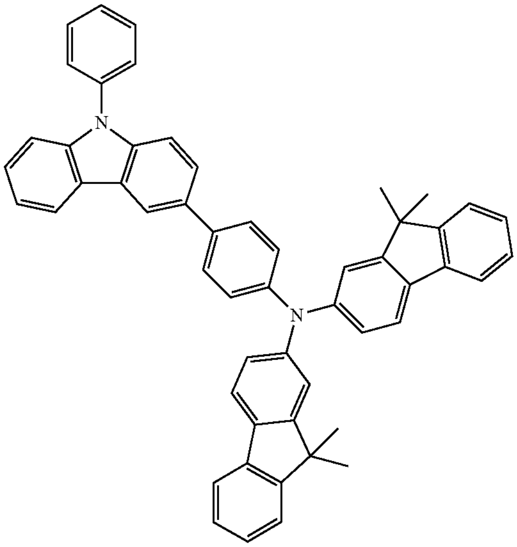
HT10
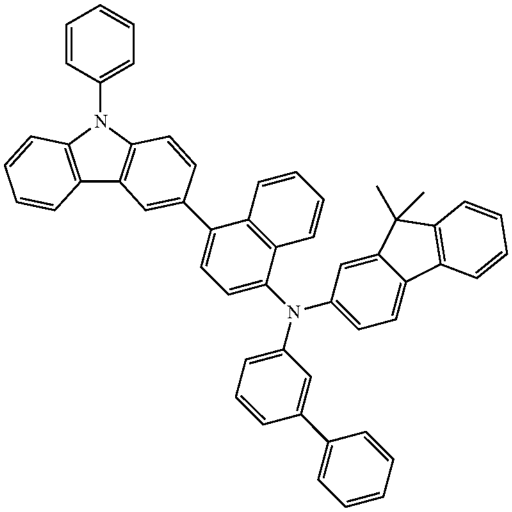
HT11
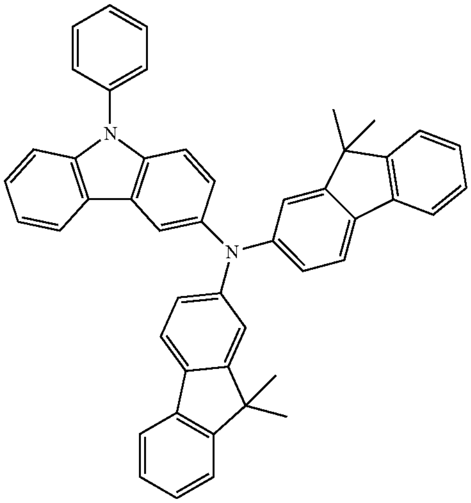
HT12
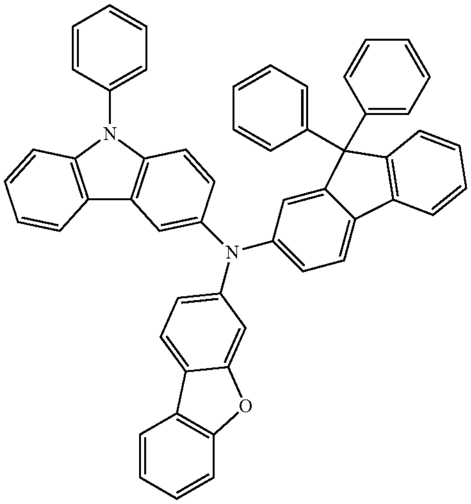
HT13
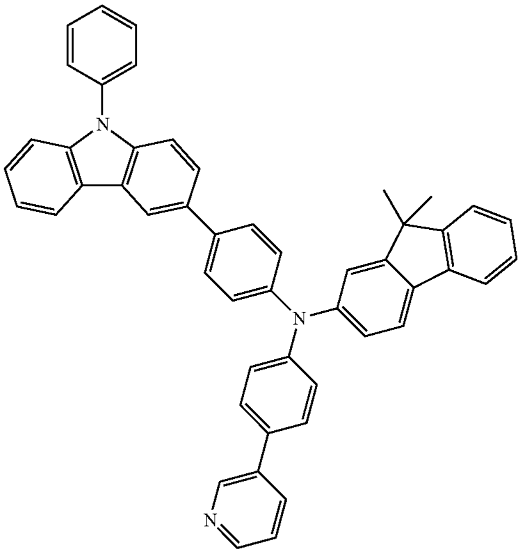
HT14
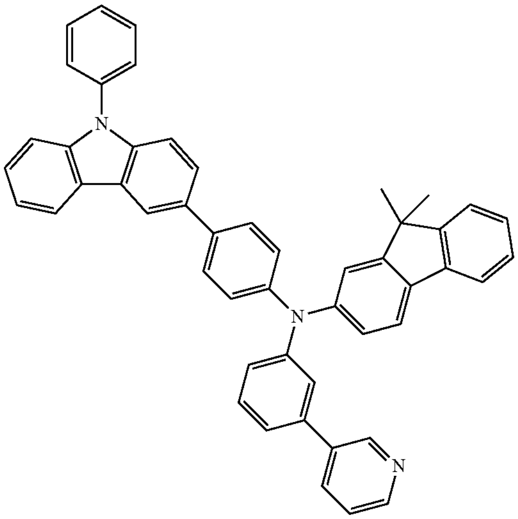

-continued
HT15
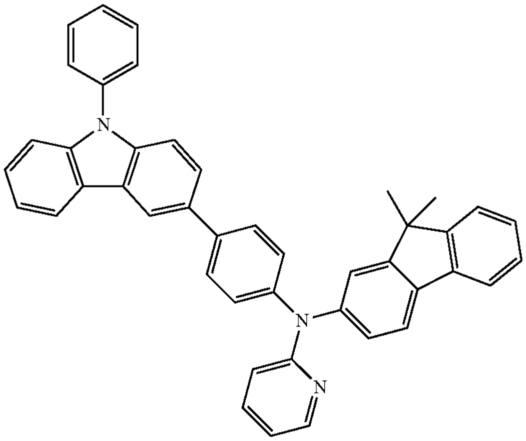
HT16
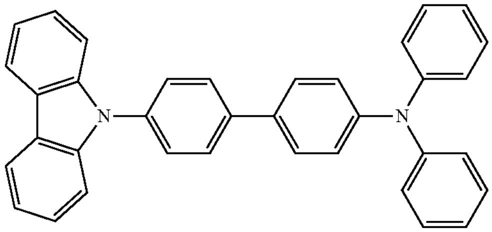
HT17
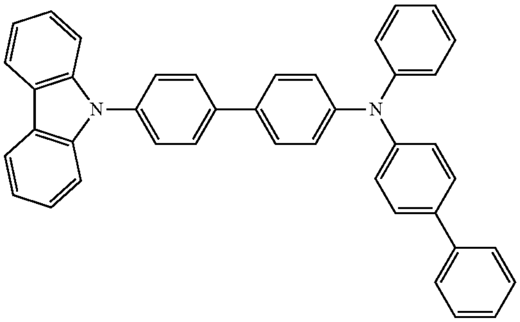
HT18
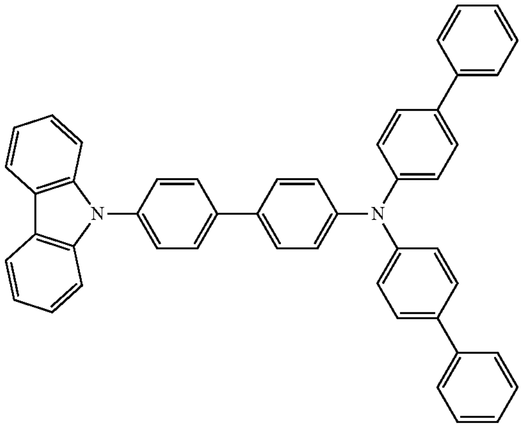
HT19
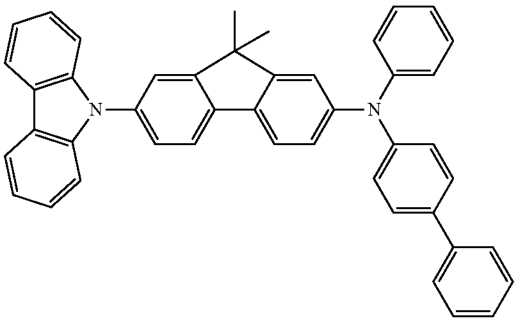
HT20
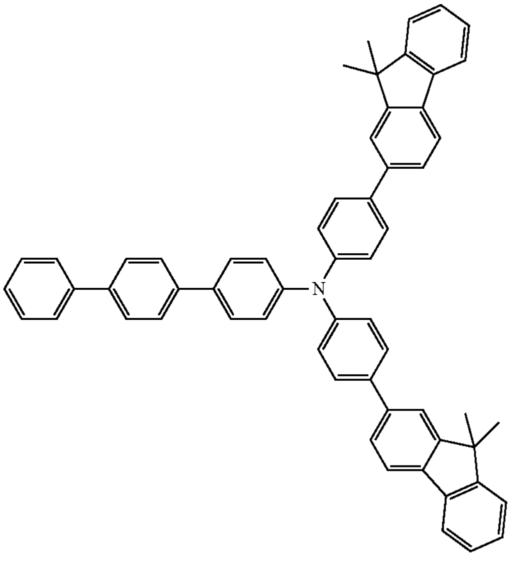

-continued
HT21
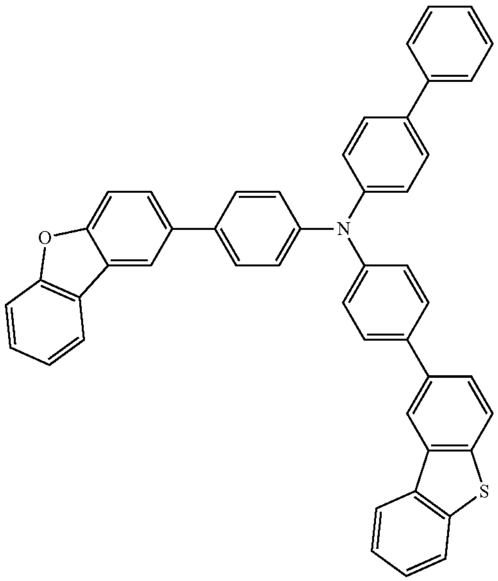
HT22
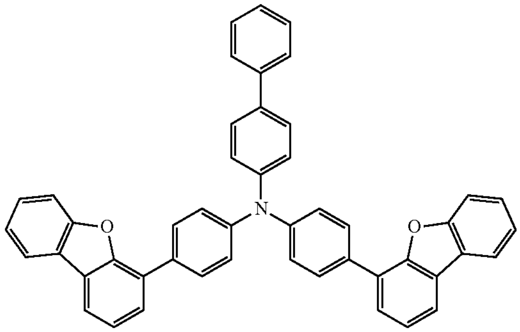
HT23
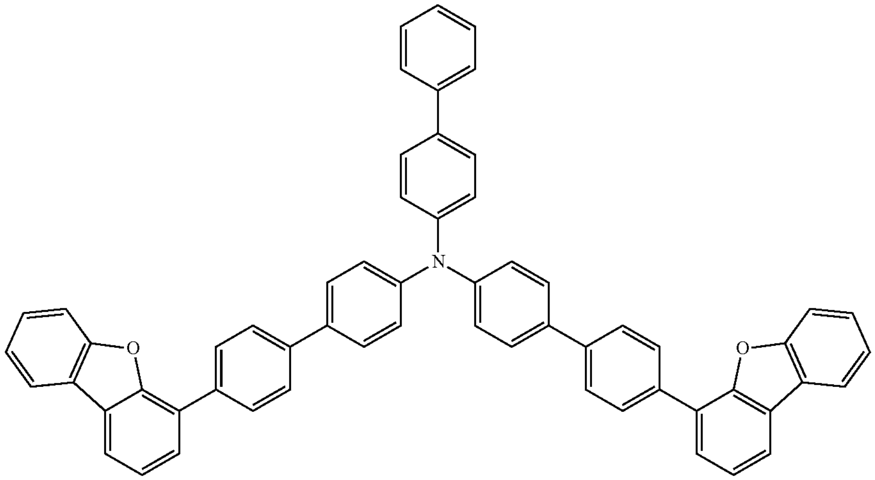
HT24
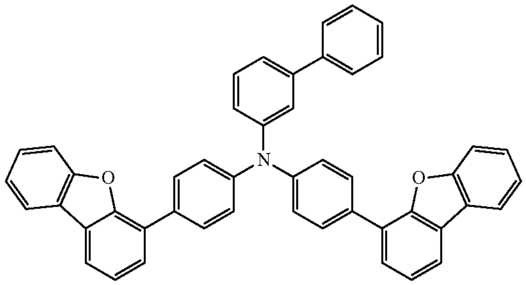
HT25
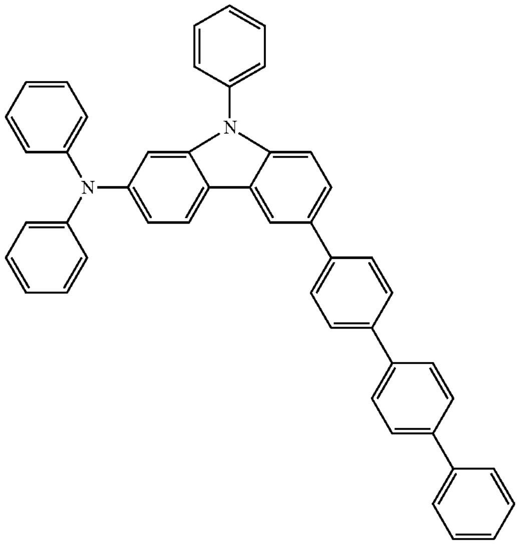

-continued
HT26
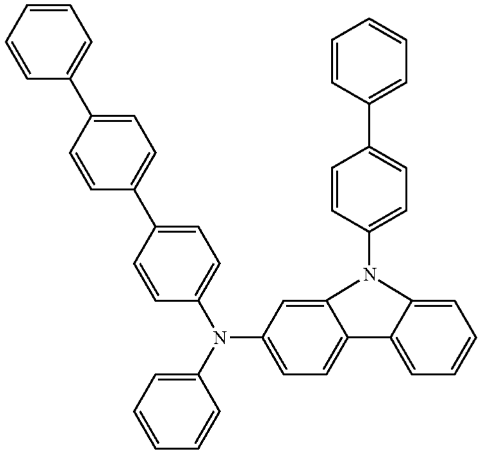
HT27
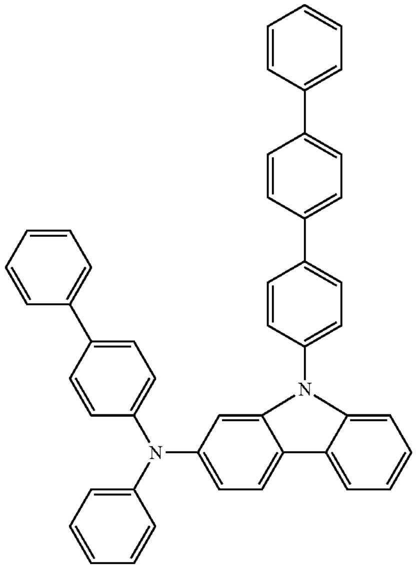
HT28
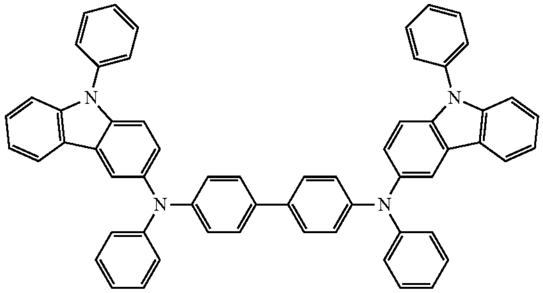
HT29
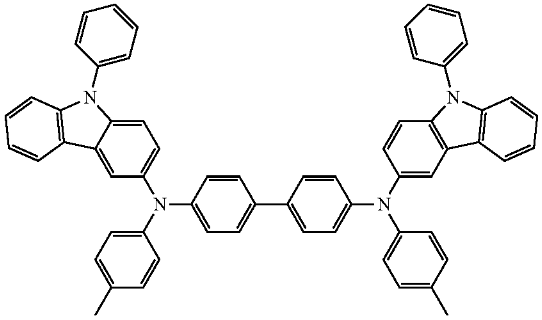
HT30
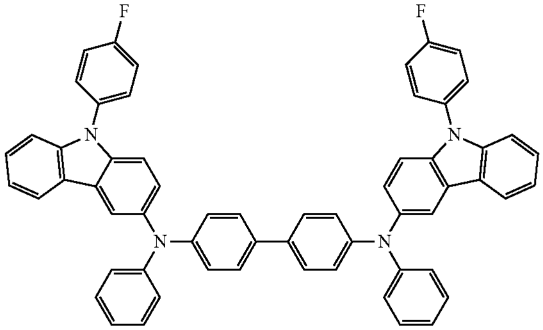
HT31
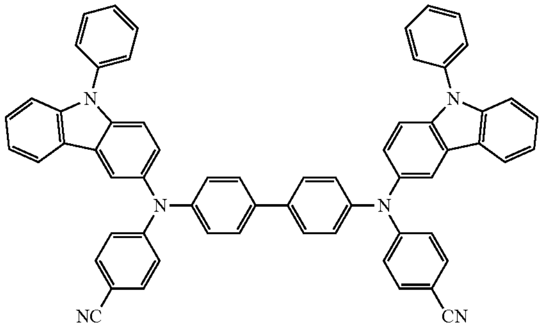

-continued
HT32
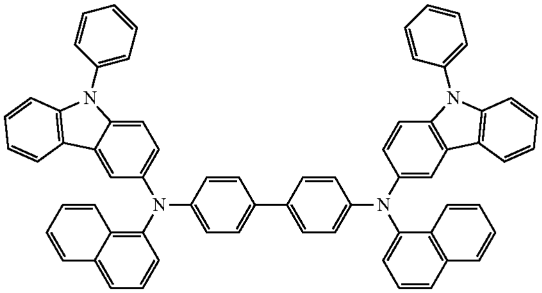
HT33
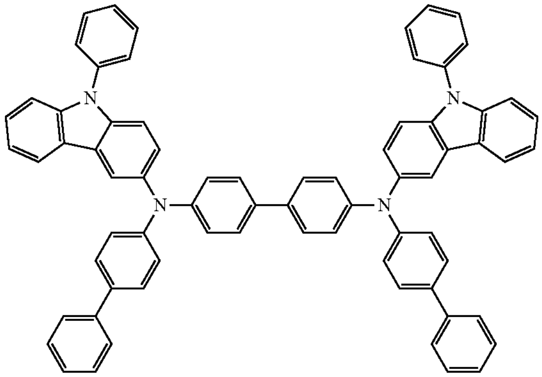
HT34
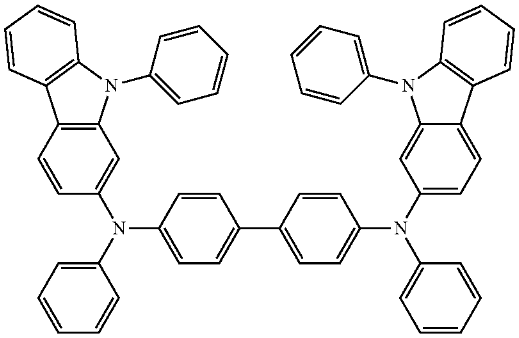
HT35
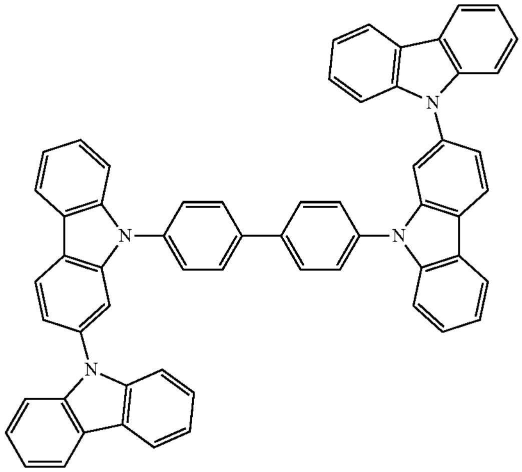
HT36
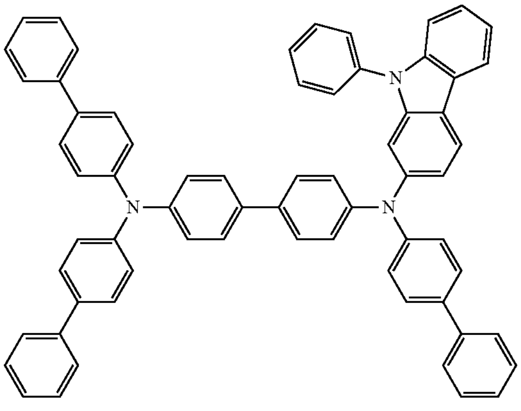
HT37
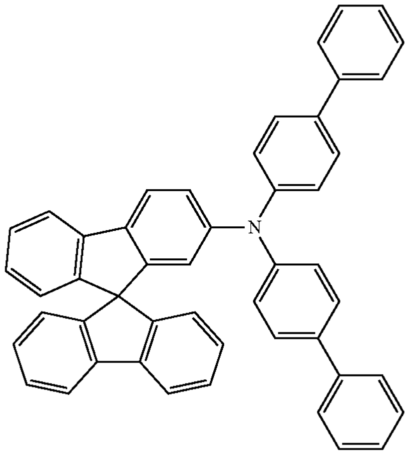

-continued
HT38
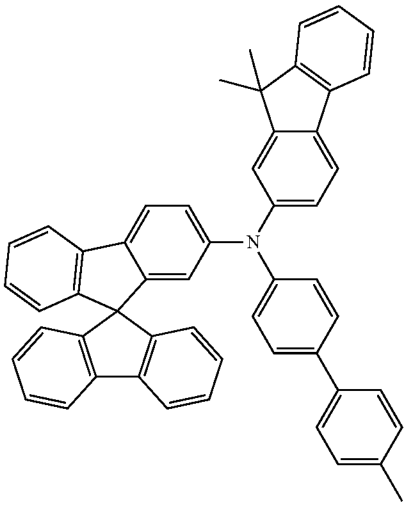
HT39
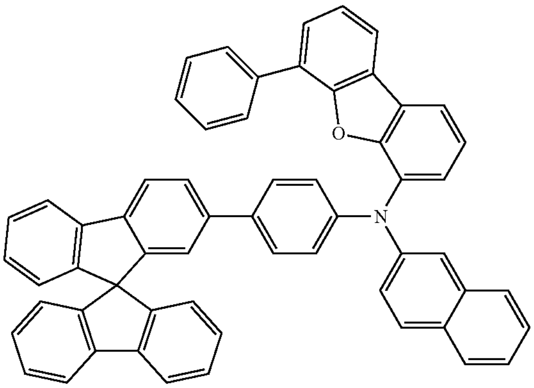
HT40
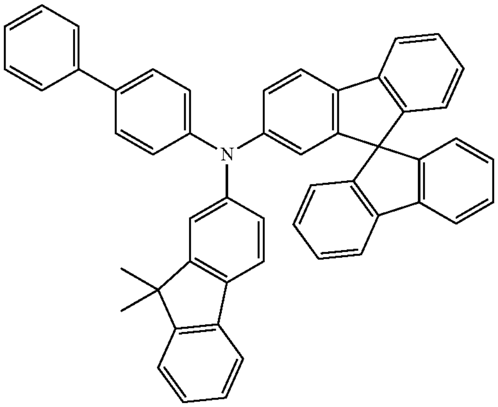
HT41
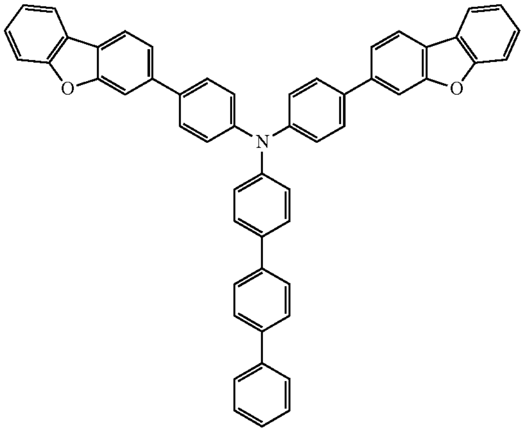
HT42
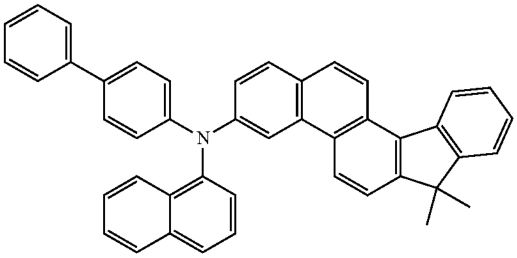
HT43
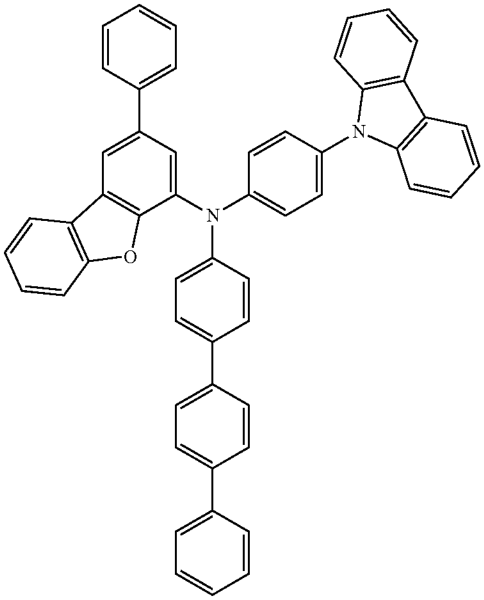

-continued
HT44
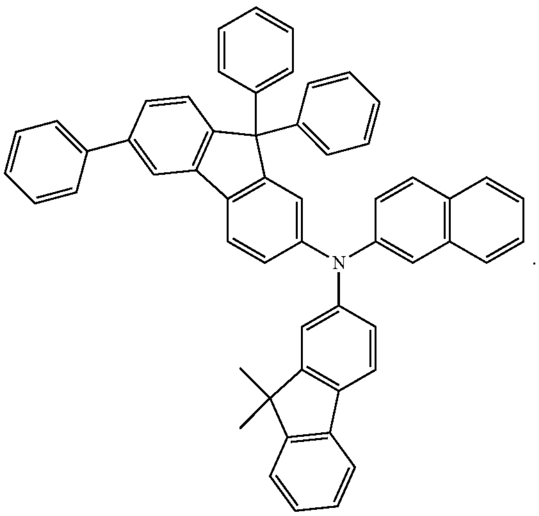
HT45
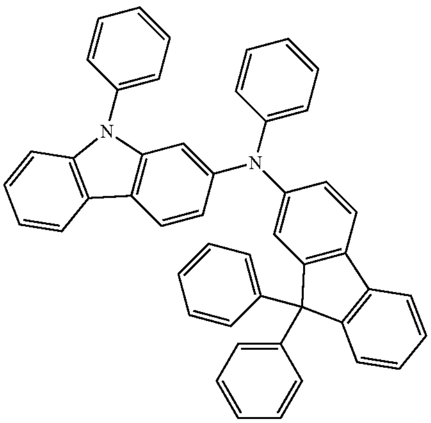
HT46
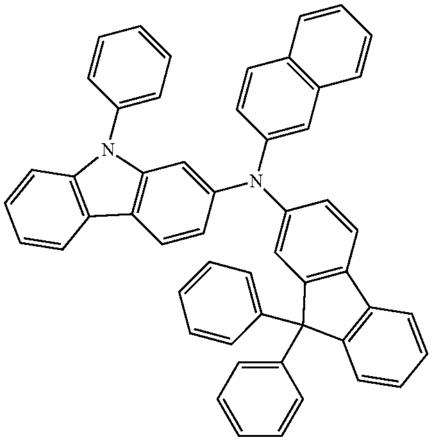
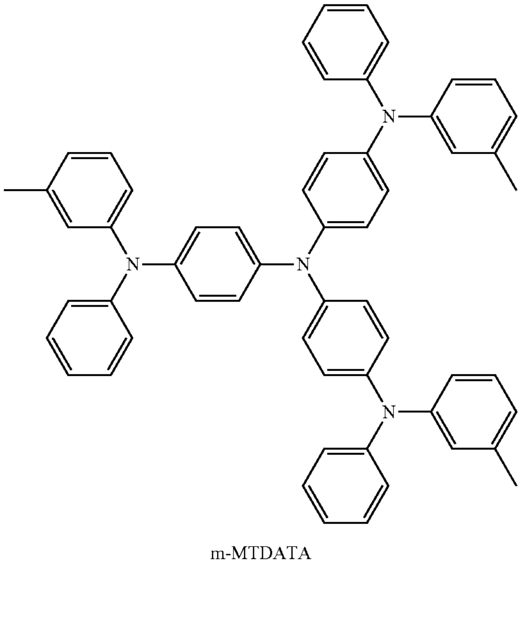
m-MTDATA
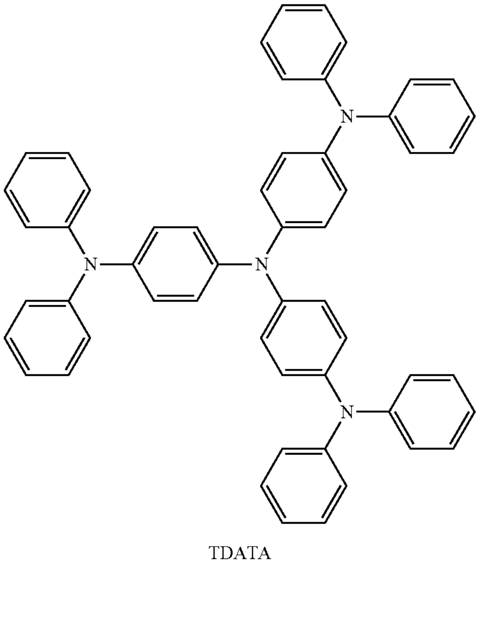
TDATA -continued
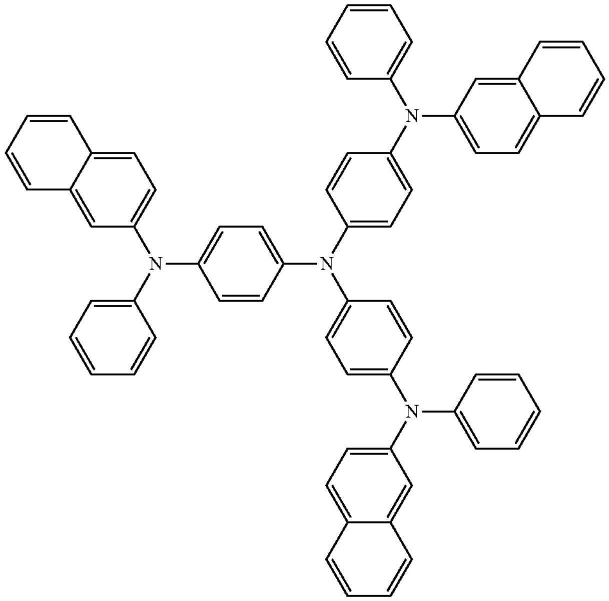
2-TNATA
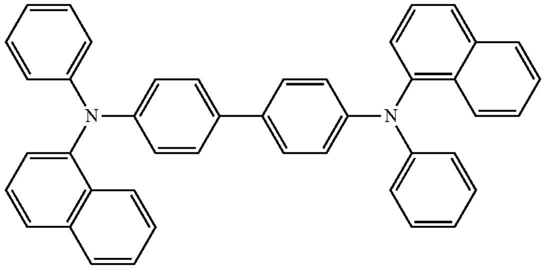
NPB
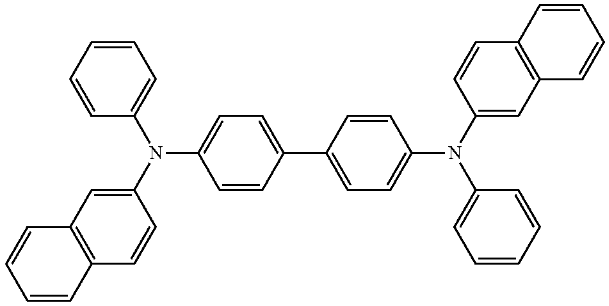
β-NPB
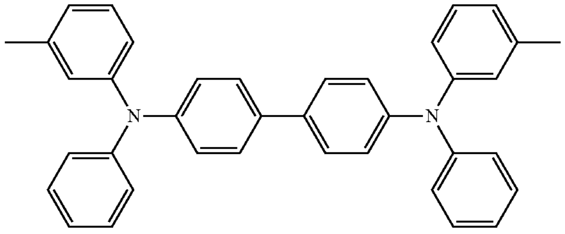
TPD
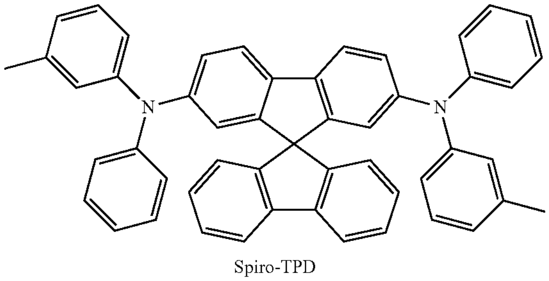
Spiro-TPD -continued

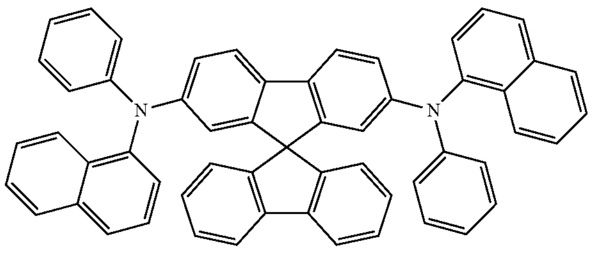

Spiro-NPB

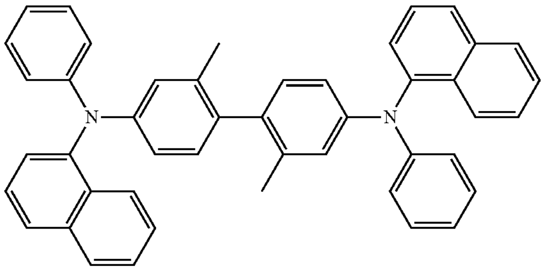

methylated-NPB

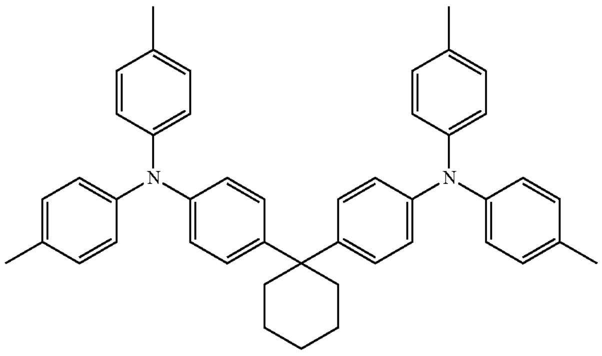

TAPC

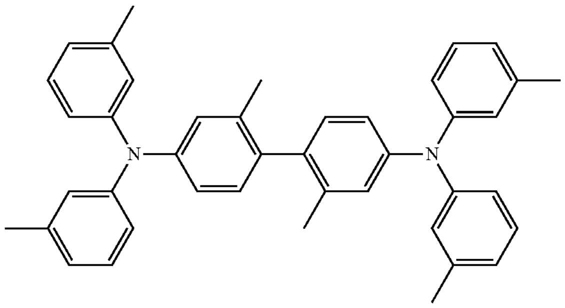

HMTPD

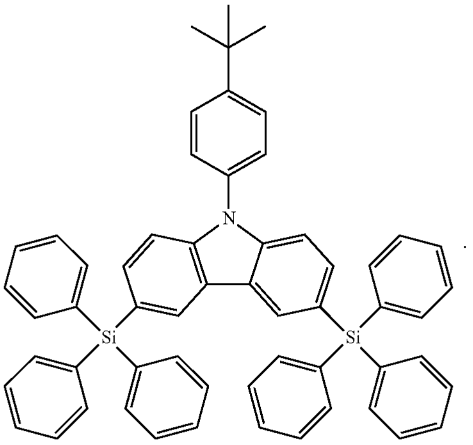

CzSi

The thickness of the hole transport region may be in a range of about 50 Å to about 10,000 Å, for example, about 100 Å to about 4,000 Å. When the hole transport region includes a hole injection layer, a hole transport layer, or any combination thereof, the thickness of the hole injection layer may be in a range of about 100 Å to about 9,000 Å, for example, about 100 Å to about 1,000 Å, and the thickness of the hole transport layer may be in a range of about 50 Å to about 2,000 Å, for example, about 100 Å to about 1,500 Å. When the thicknesses of the hole transport region, the hole injection layer and the hole transport layer are within these ranges, satisfactory hole transporting characteristics may be obtained without a substantial increase in driving voltage.

The emission auxiliary layer may increase light-emission efficiency by compensating for an optical resonance distance according to the wavelength of light emitted by an emission layer, and the electron blocking layer may block the leakage of electrons from an emission layer to a hole transport region. Materials that may be included in the hole transport region may be included in the emission auxiliary layer and the electron blocking layer.

p-Dopant

The hole transport region may further include, in addition to these materials, a charge-generation material for the improvement of conductive properties. The charge-generation material may be uniformly or non-uniformly dispersed in the hole transport region (for example, in the form of a single layer consisting of a charge-generation material). The charge-generation material may be, for example, a p-dopant.

In one or more embodiments, the lowest unoccupied molecular orbital (LUMO) energy level of the p-dopant may be about −3.5 eV or less.

In one or more embodiments, the p-dopant may include a quinone derivative, a cyano group-containing compound, a compound containing element EL1 and element EL2, or any combination thereof. Examples of the quinone derivative are tetracyanoquinodimethane (TCNQ), 2,3,5,6-tetrafluoro-7,7, 8,8-tetracyanoquinodimethane (F4-TCNQ), etc. Examples of the cyano group-containing compound are 1,4,5,8,9,12-hexaazatriphenylene-hexacarbonitrile (HAT-CN), and a compound represented by Formula 221 below.

TCNQ

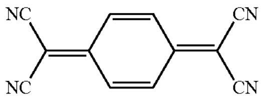

F4-TCNQ

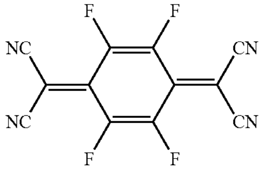

HAT-CN

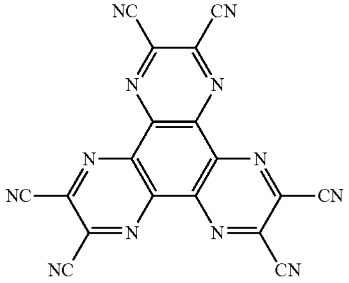

Formula 221

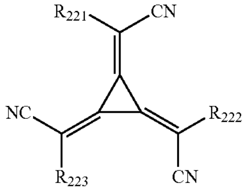

In Formula 221, $R_{221}$ to $R_{223}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, and one or more of $R_{221}$ to $R_{223}$ may each independently be a $C_3$-$C_{60}$ carbocyclic group or a $C_1$-$C_{60}$ heterocyclic group, each substituted with a cyano group; —F; —Cl; —Br; —I; a $C_1$-$C_{20}$ alkyl group substituted with a cyano group, —F, —Cl, —Br, —I, or any combination thereof; or any combination thereof.

In the compound containing element EL1 and element EL2, element EL1 may be a metal, a metalloid, or any combination thereof, and element EL2 may be a non-metal, a metalloid, or any combination thereof.

Examples of the metal are an alkali metal (for example, lithium (Li), sodium (Na), potassium (K), rubidium (Rb), cesium (Cs), etc.); an alkaline earth metal (for example, beryllium (Be), magnesium (Mg), calcium (Ca), strontium (Sr), barium (Ba), etc.); a transition metal (for example, titanium (Ti), zirconium (Zr), hafnium (Hf), vanadium (V), niobium (Nb), tantalum (Ta), chromium (Cr), molybdenum (Mo), tungsten (W), manganese (Mn), technetium (Tc), rhenium (Re), iron (Fe), ruthenium (Ru), osmium (Os), cobalt (Co), rhodium (Rh), iridium (Ir), nickel (Ni), palladium (Pd), platinum (Pt), copper (Cu), silver (Ag), gold (Au), etc.); a post-transition metal (for example, zinc (Zn), indium (In), tin (Sn), etc.); and a lanthanide metal (for example, lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), lutetium (Lu), etc.).

Examples of the metalloid are silicon (Si), antimony (Sb), and tellurium (Te). Examples of the non-metal are oxygen (O) and a halogen (for example, F, Cl, Br, I, etc.). In one or more embodiments, examples of the compound containing element EL1 and element EL2 are a metal oxide, a metal halide (for example, a metal fluoride, a metal chloride, a metal bromide, or a metal iodide), a metalloid halide (for example, a metalloid fluoride, a metalloid chloride, a metalloid bromide, or a metalloid iodide), a metal telluride, or any combination thereof.

Examples of the metal oxide are a tungsten oxide (for example, WO, $W_2O_3$, $WO_2$, $WO_3$, $W_2O_5$, etc.), a vanadium oxide (for example, VO, $V_2O_3$, $VO_2$, $V_2O_5$, etc.), a molybdenum oxide (MoO, $Mo_2O_3$, $MoO_2$, $MoO_3$, $Mo_2O_5$, etc.), and a rhenium oxide (for example, $ReO_3$, etc.). Examples of the metal halide are an alkali metal halide, an alkaline earth metal halide, a transition metal halide, a post-transition metal halide, and a lanthanide metal halide.

Examples of the alkali metal halide are LiF, NaF, KF, RbF, CsF, LiCl, NaCl, KCl, RbCl, CsCl, LiBr, NaBr, KBr, RbBr, CsBr, LiI, NaI, KI, RbI, and CsI. Examples of the alkaline earth metal halide are $BeF_2$, $MgF_2$, $CaF_2$, $SrF_2$, $BaF_2$, $BeCl_2$, $MgCl_2$, $CaCl_2$), $SrCl_2$, $BaCl_2$, $BeBr_2$, $MgBr_2$, $CaBr_2$, $SrBr_2$, $BaBr_2$, $BeI_2$, $MgI_2$, $CaI_2$, $SrI_2$, and $BaI_2$.

Examples of the transition metal halide are a titanium halide (for example, $TiF_4$, $TiCl_4$, $TiBr_4$, $TiI_4$, etc.), a zirconium halide (for example, $ZrF_4$, $ZrCl_4$, $ZrBr_4$, $ZrI_4$, etc.), a hafnium halide (for example, $HfF_4$, $HfCl_4$, $HfBr_4$, $HfI_4$, etc.), a vanadium halide (for example, $VF_3$, $VCl_3$, $VBr_3$, $VI_3$, etc.), a niobium halide (for example, $NbF_3$, $NbCl_3$, $NbBr_3$, $NbI_3$, etc.), a tantalum halide (for example, $TaF_3$, $TaCl_3$, $TaBr_3$, $TaI_3$, etc.), a chromium halide (for example, $CrF_3$, $CrCl_3$, $CrBr_3$, $CrI_3$, etc.), a molybdenum halide (for example, $MoF_3$, $MoCl_3$, $MoBr_3$, $MoI_3$, etc.), a tungsten halide (for example, $WF_3$, $WCl_3$, $WBr_3$, $WI_3$, etc.), a manganese halide (for example, $MnF_2$, $MnCl_2$, $MnBr_2$, $MnI_2$, etc.), a technetium halide (for example, $TcF_2$, $TcCl_2$, $TcBr_2$, $TcI_2$, etc.), a rhenium halide (for example, $ReF_2$, $ReCl_2$, $ReBr_2$, $ReI_2$, etc.), an iron halide (for example, $FeF_2$, $FeCl_2$, $FeBr_2$, $FeI_2$, etc.), a ruthenium halide (for example, $RuF_2$, $RuCl_2$, $RuBr_2$, $RuI_2$, etc.), an osmium halide (for example, $OsF_2$, $OsCl_2$, $OsBr_2$, $OsI_2$, etc.), a cobalt halide (for example, $CoF_2$, $CoCl_2$, $CoBr_2$, $CoI_2$, etc.), a rhodium halide (for example, $RhF_2$, $RhCl_2$, $RhBr_2$, $RhI_2$, etc.), an iridium halide (for example, $IrF_2$, $IrCl_2$, $IrBr_2$, $IrI_2$, etc.), a nickel halide (for example, $NiF_2$, $NiCl_2$, $NiBr_2$, $NiI_2$, etc.), a palladium halide (for example, $PdF_2$, $PdCl_2$, $PdBr_2$, $PdI_2$, etc.), a platinum halide (for example, $PtF_2$, $PtCl_2$, $PtBr_2$, $PtI_2$, etc.), a copper halide (for example, CuF, CuCl, CuBr, CuI, etc.), a silver halide (for example, AgF, AgCl, AgBr, AgI, etc.), and a gold halide (for example, AuF, AuCl, AuBr, AuI, etc.).

Examples of the post-transition metal halide are a zinc halide (for example, $ZnF_2$, $ZnCl_2$, $ZnBr_2$, $ZnI_2$, etc.), an indium halide (for example, $InI_3$, etc.), and a tin halide (for example, $SnI_2$, etc.). Examples of the lanthanide metal halide are YbF, $YbF_2$, $YbF_3$, $SmF_3$, YbCl, $YbCl_2$, $YbCl_3$, $SmCl_3$, YbBr, $YbBr_2$, $YbBr_3$, $SmBr_3$, YbI, $YbI_2$, $YbI_3$, and $SmI_3$. An example of the metalloid halide is an antimony halide (for example, $SbCl_5$, etc.).

Examples of the metal telluride are an alkali metal telluride (for example, $Li_2Te$, a $na_2Te$, $K_2Te$, $Rb_2Te$, $Cs_2Te$, etc.), an alkaline earth metal telluride (for example, BeTe, MgTe, CaTe, SrTe, BaTe, etc.), a transition metal telluride (for example, $TiTe_2$, $ZrTe_2$, $HfTe_2$, $V_2Te_3$, $Nb_2Te_3$, $Ta_2Te_3$, $Cr_2Te_3$, $Mo_2Te_3$, $W_2Te_3$, MnTe, TcTe, ReTe, FeTe, RuTe, OsTe, CoTe, RhTe, IrTe, NiTe, PdTe, PtTe, $Cu_2Te$, CuTe, $Ag_2Te$, AgTe, $Au_2Te$, etc.), a post-transition metal telluride (for example, ZnTe, etc.), and a lanthanide metal telluride (for example, LaTe, CeTe, PrTe, NdTe, PmTe, EuTe, GdTe, TbTe, DyTe, HoTe, ErTe, TmTe, YbTe, LuTe, etc.).

Emission Layer in Interlayer 130

When the light-emitting device 10 is a full-color light-emitting device, the emission layer may be patterned into a red emission layer, a green emission layer, and/or a blue emission layer, according to a sub-pixel. In one or more embodiments, the emission layer may have a stacked structure of two or more layers of a red emission layer, a green emission layer, and a blue emission layer, in which the two or more layers contact each other or are separated from each other. In one or more embodiments, the emission layer may include two or more materials of a red light-emitting material, a green light-emitting material, and a blue light-emitting material, in which the two or more materials are mixed with each other in a single layer to emit white light. For example, the emission layer may emit blue light.

In an embodiment, the emission layer may include the heterocyclic compound represented by Formula 1 as described herein. The emission layer may include a host and a dopant. In an embodiment, the dopant may include the heterocyclic compound represented by Formula 1 as described herein. In this regard, the dopant may include, in addition to the heterocyclic Compound represented by Formula 1, a phosphorescent dopant, a fluorescent dopant, or any combination thereof. The phosphorescent dopant and fluorescent dopant that may be further included in the emission layer in addition to the heterocyclic compound represented by Formula 1 are the same as described below.

The amount of the dopant in the emission layer may be from about 0.01 parts by weight to about 15 parts by weight based on 100 parts by weight of the host. In one or more embodiments, the emission layer may include a quantum dot. The emission layer may include a delayed fluorescence material. The delayed fluorescence material may act as a host or a dopant in the emission layer. The thickness of the emission layer may be in a range of about 100 Å to about 1,000 Å, for example, about 200 Å to about 600 Å. When the thickness of the emission layer is within these ranges, excellent light-emission characteristics may be obtained without a substantial increase in driving voltage.

Host

The host may include, for example, a carbazole-containing compound, an anthracene-containing compound, or any combination thereof. In an embodiment, the host may include a compound represented by Formula 301 below:

$$[Ar_{301}]_{xb11}-[(L_{301})_{xb1}-R_{301}]_{xb21}$$ Formula 301 wherein, in Formula 301, $Ar_{301}$ and $L_{301}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, $L_{301}$ may each independently be a divalent $C_3$-$C_{60}$ carbocyclic group unsubstituted or substituted with at least one $R_{10a}$ or a divalent $C_1$-$C_{60}$ heterocyclic group unsubstituted or substituted with at least one $R_{10a}$, xb11 may be 1, 2, or 3, xb1 may be an integer from 0 to 5, $R_{301}$ may be hydrogen, deuterium, —F, —Cl, —Br, —I, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, $—Si(Q_{301})(Q_{302})(Q_{303})$, $—N(Q_{301})(Q_{302})$, $—B(Q_{301})(Q_{302})$, $—C(=O)(Q_{301})$, $—S(=O)_2(Q_{301})$, or $—P(=O)(Q_{301})(Q_{302})$, xb21 may be an integer from 1 to 5, and wherein $R_{10a}$ is the same as described herein, and $Q_{301}$ to $Q_{303}$ are the same as described in connection with $Q_1$.

For example, when xb11 in Formula 301 is 2 or more, two or more of $Ar_{301}$(s) may be linked to each other via a single bond. In one or more embodiments, the host may include a compound represented by Formula 301-1, a compound represented by Formula 301-2, or any combination thereof:

Formula 301-1

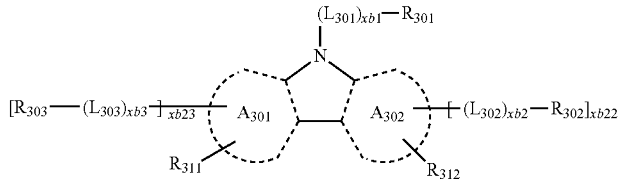

Formula 301-2

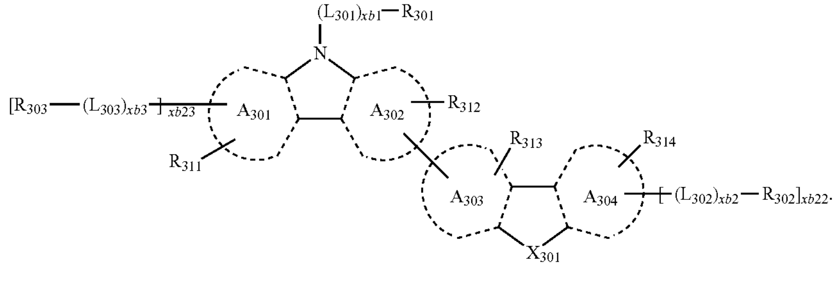

In Formulae 301-1 and 301-2, ring $A_{301}$ to ring $A_{304}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, wherein $R_{10a}$ is the same as described herein, $X_{301}$ may be O, S, N-[$(L_{304})_{xb4}$-$R_{304}$], $C(R_{304})(R_{305})$, or $Si(R_{304})(R_{305})$, xb22 and xb23 may each independently be 0, 1, or 2, $L_{301}$, xb1, and $R_{301}$ are each independently the same as described herein, $L_{302}$ to $L_{304}$ are each independently the same as described in connection with $L_{301}$, xb2 to xb4 are each independently the same as described in connection with xb1, and $R_{302}$ to $R_{305}$ and $R_{311}$ to $R_{314}$ are each independently the same as described in connection with $R_{301}$.

In one or more embodiments, the host may include an alkali earth metal complex, a post-transition metal complex, or any combination thereof. In one or more embodiments, the host may include a Be complex (for example, Compound H55), an Mg complex, a Zn complex, or any combination thereof.

In an embodiment, the host may include one of Compounds H1 to H124, 9,10-di(2-naphthyl)anthracene (ADN), 2-methyl-9,10-bis(naphthalen-2-yl)anthracene (MADN), 9,10-di-(2-naphthyl)-2-t-butyl-anthracene (TBADN), 4,4'-bis(N-carbazolyl)-1,1'-biphenyl (CBP), 1,3-di(carbazol-9-yl)benzene (mCP), 1,3,5-tri(carbazol-9-yl)benzene (TCP), or any combination thereof:

H1

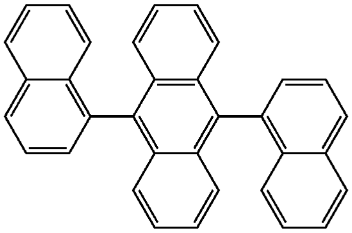

H2

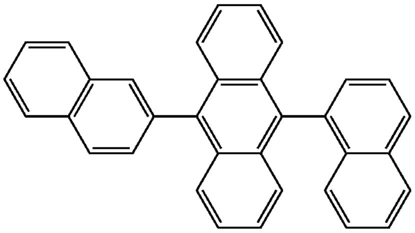

H3

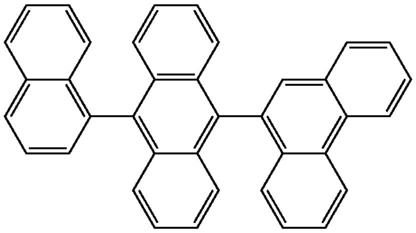

H4

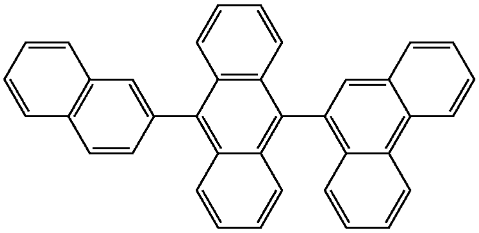

H5

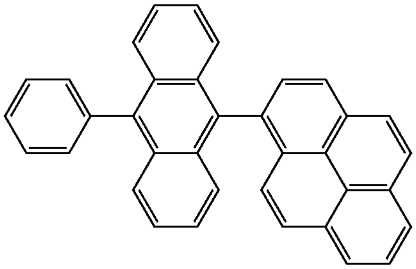

H6

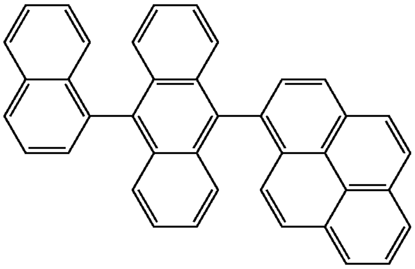

H7

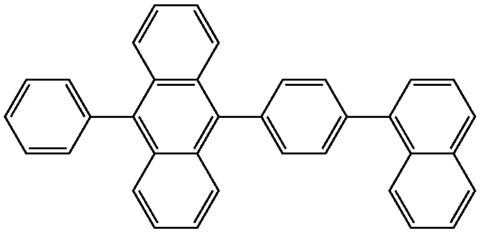

H8

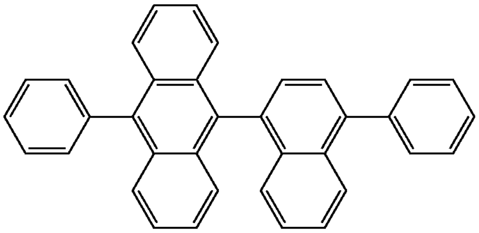

H9

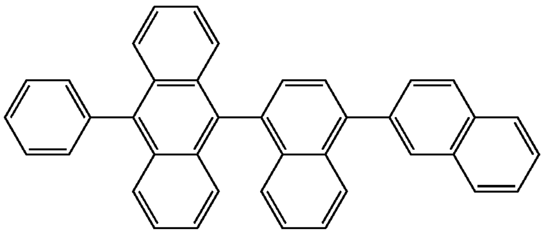

H10

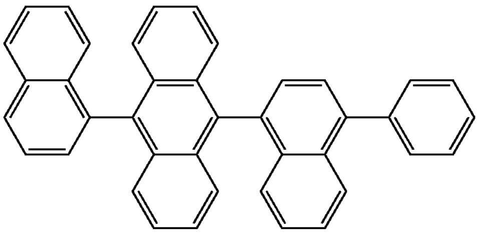

-continued
H11
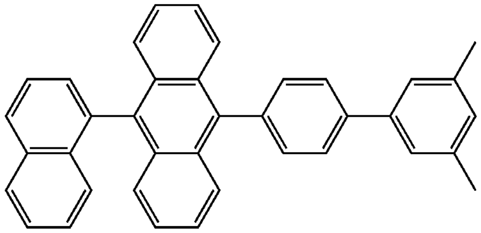
H12
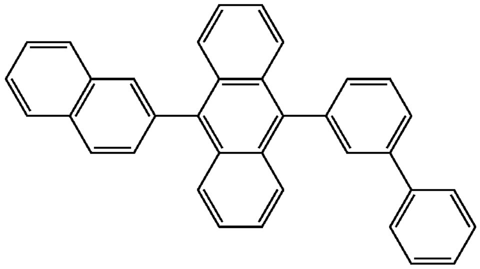
H13
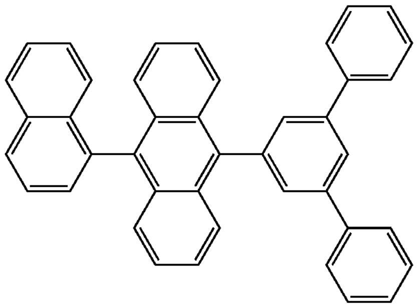
H14
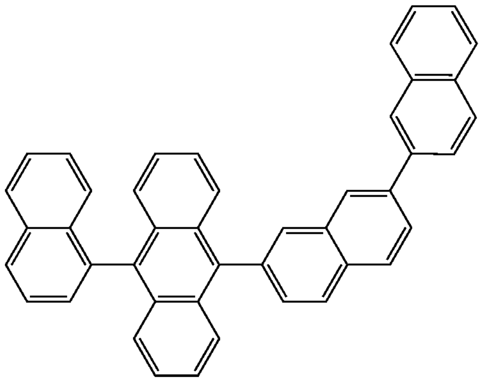
H16
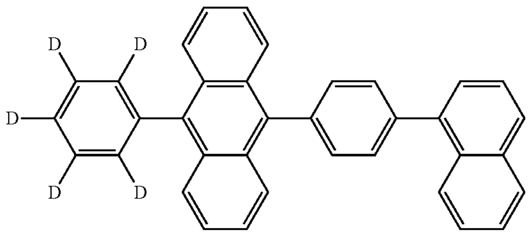
H15
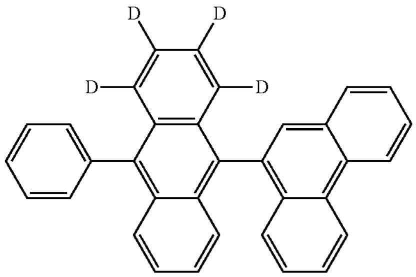
H17
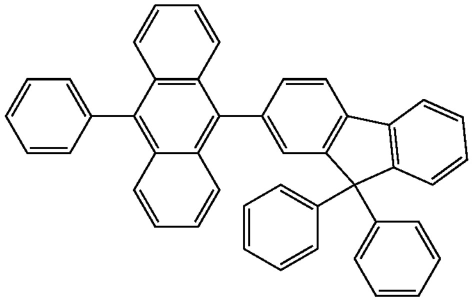
H18
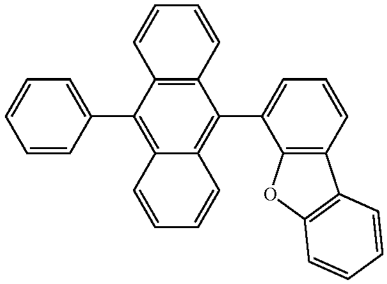
H19
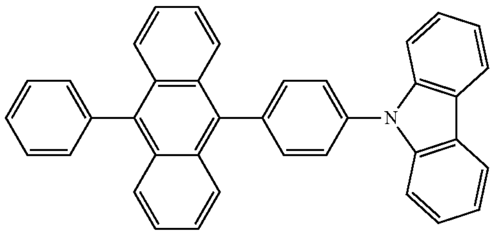
H20
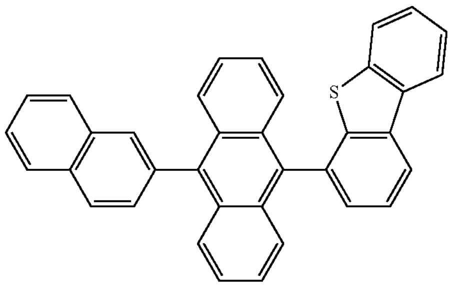

-continued
H21
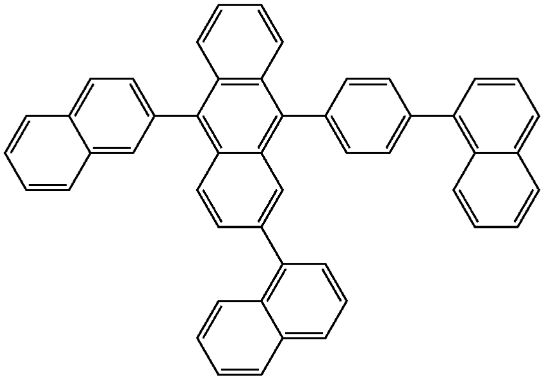
H22
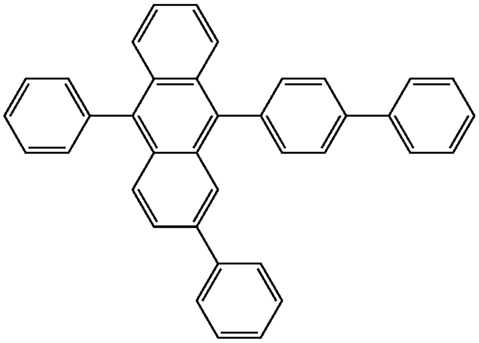
H23
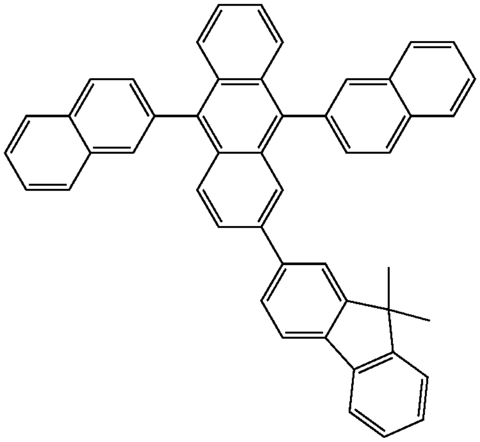
H24
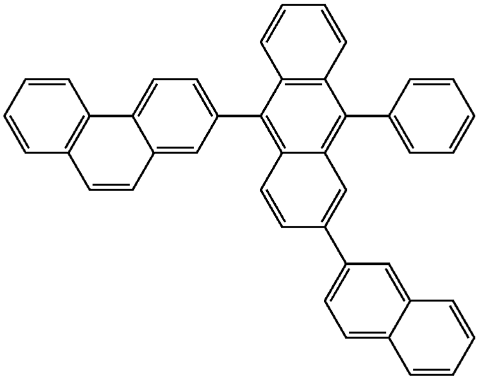
H25
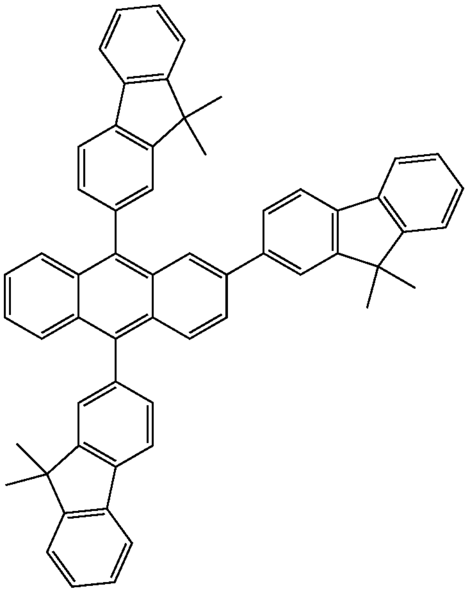
H26
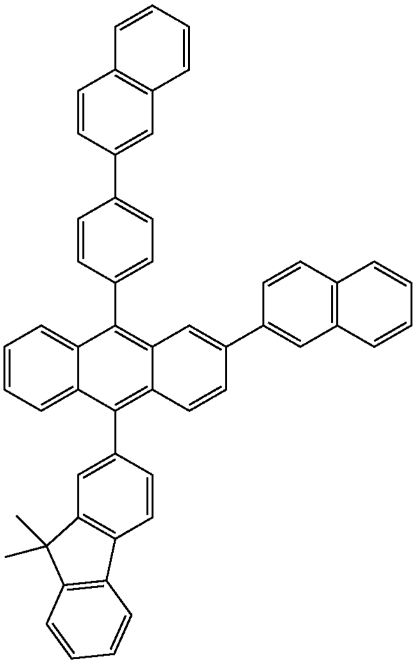

-continued
H27
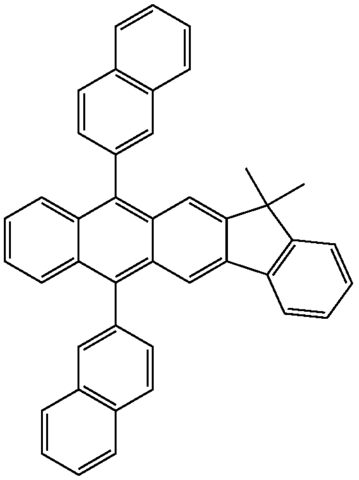
H28
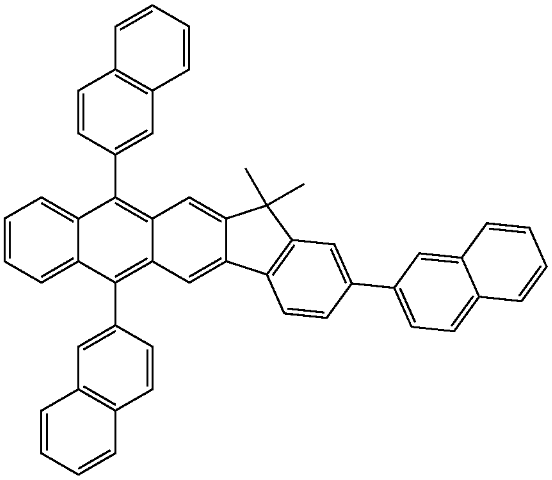
H29
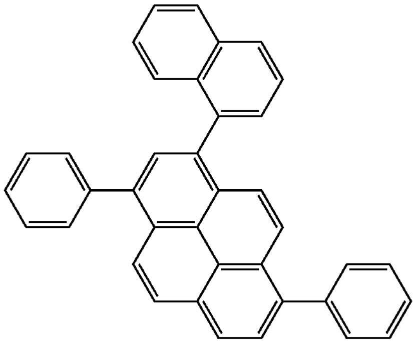
H30
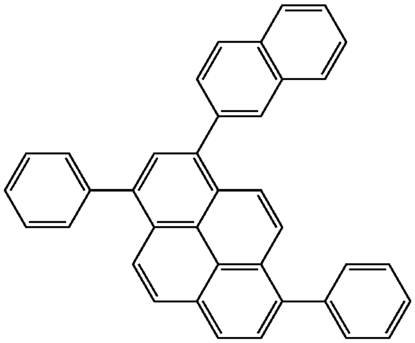
H31
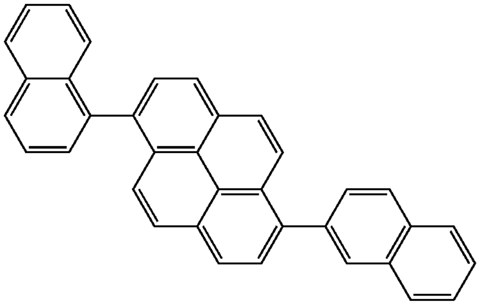
H32
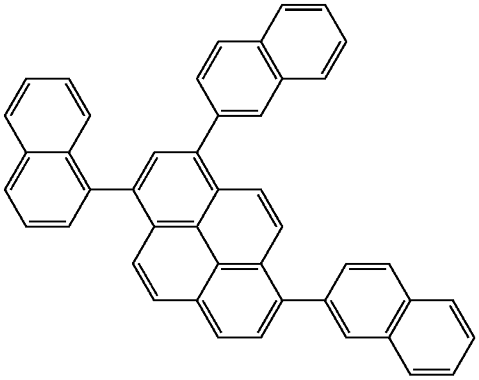
H33
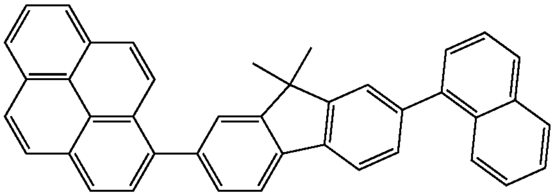

-continued
H34
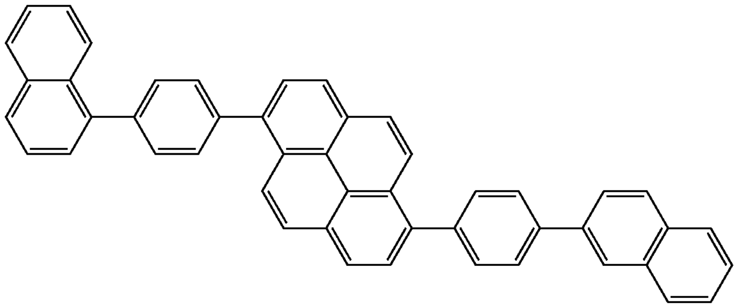
H35
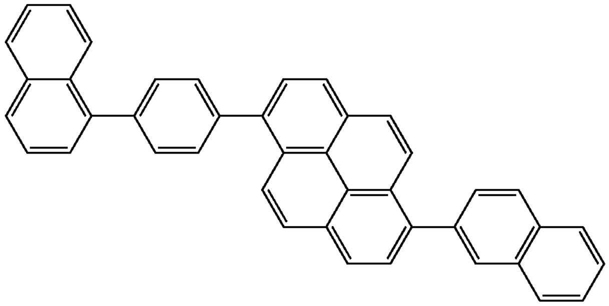
H36
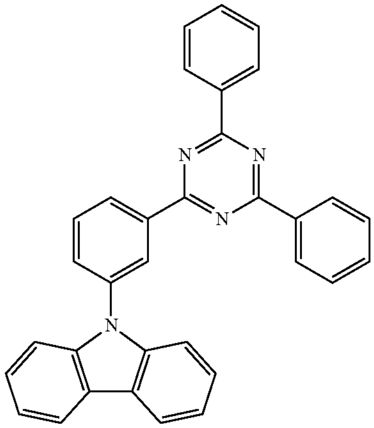
H37
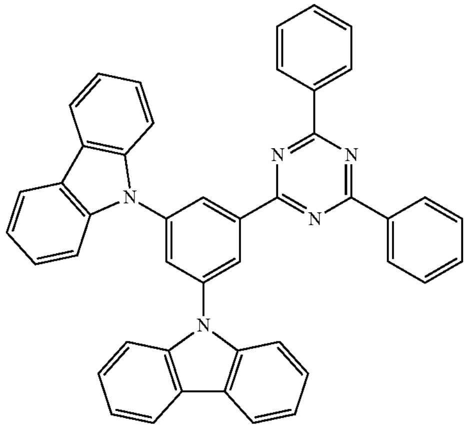
H38
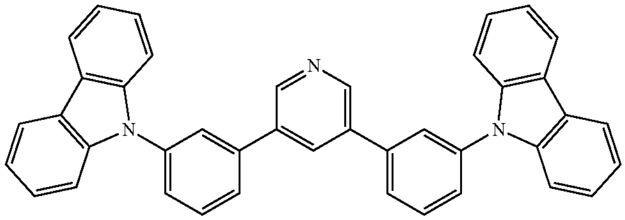

-continued
H39
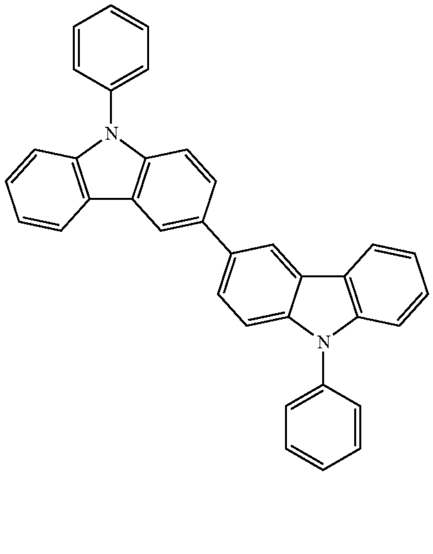
H40
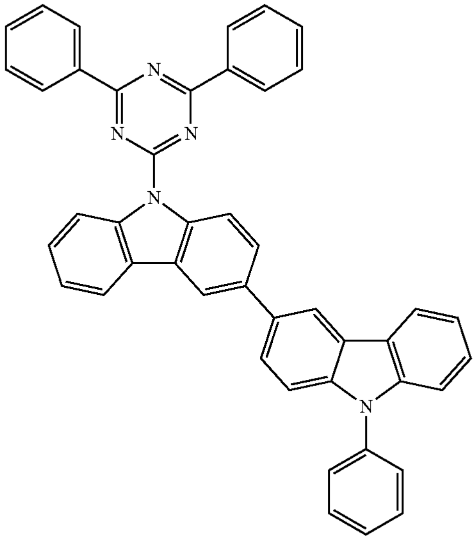
H41
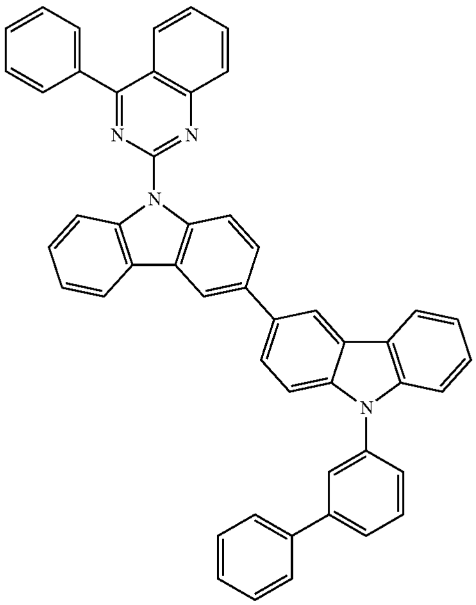
H42
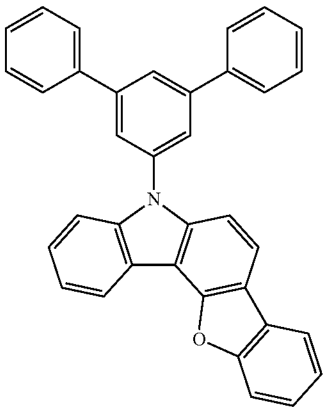
H43
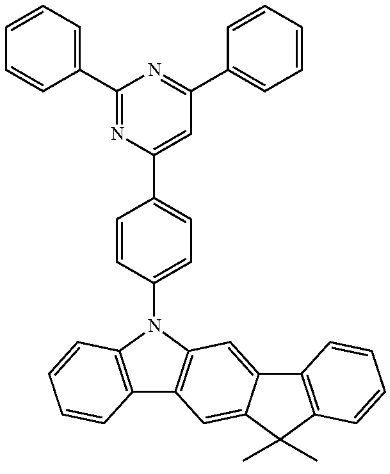
H44
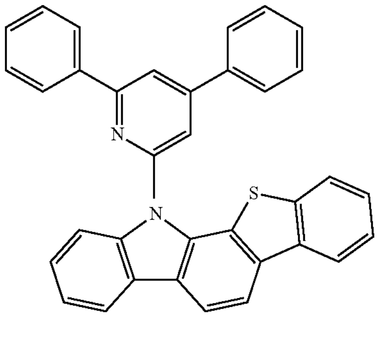

-continued
H45
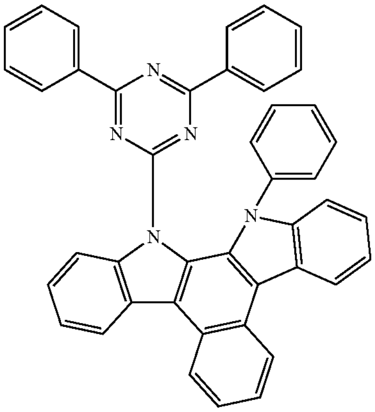
H46
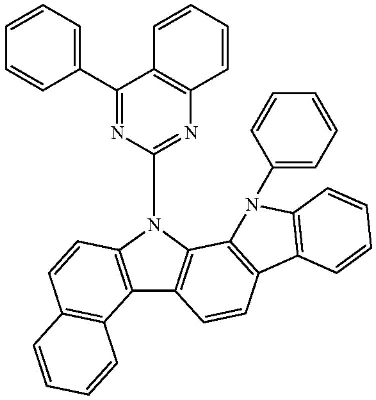
H47
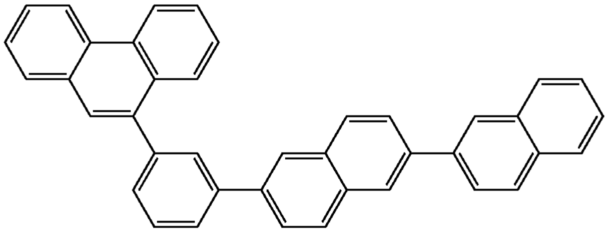
H48
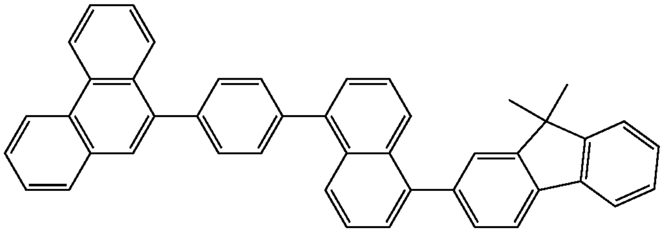
H49
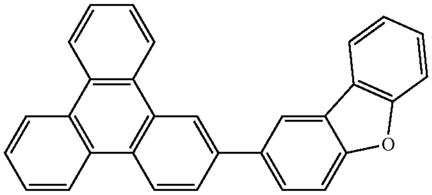
H50
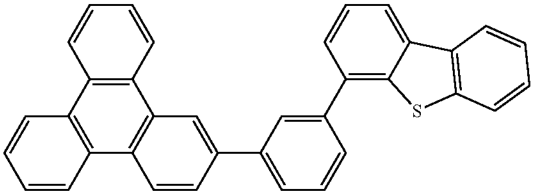
H51
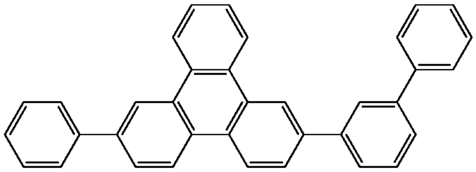
H52
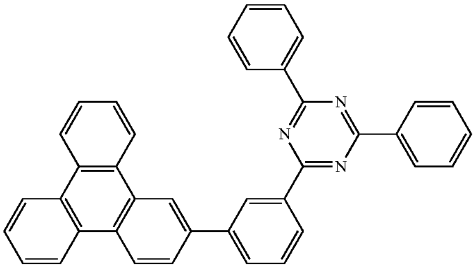

-continued
H53
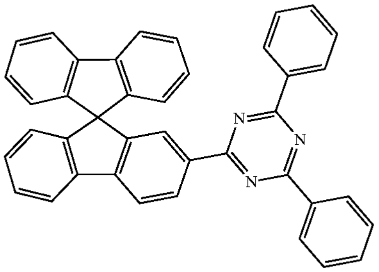
H54
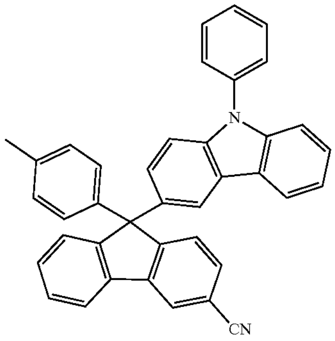
H55
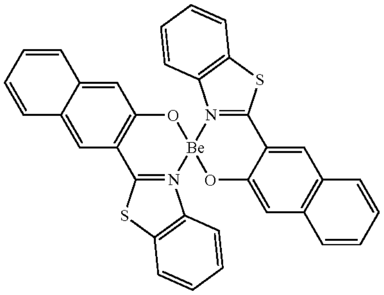
H56
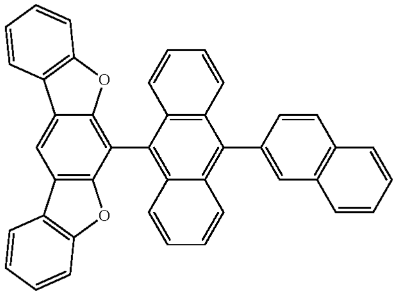
H57
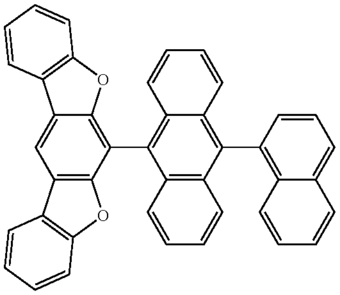
H58
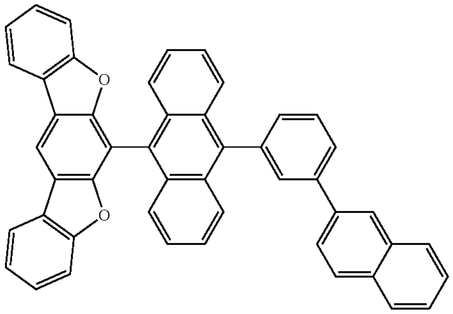
H59
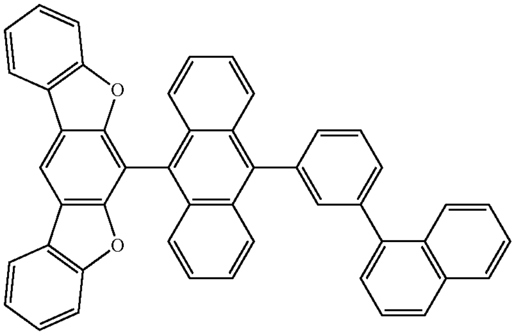
H60
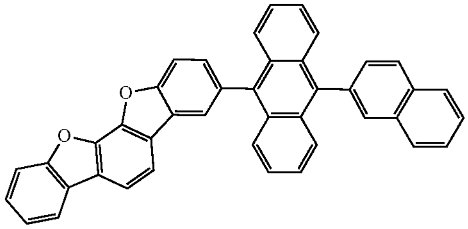
H61'
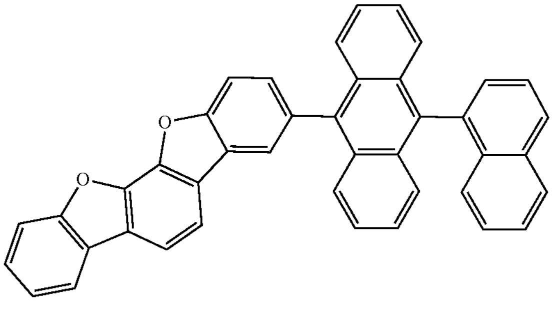

-continued
H62
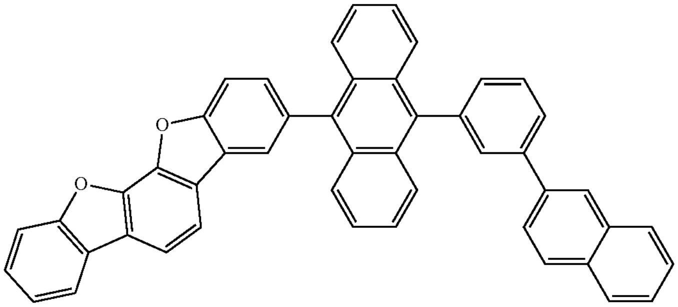
H63
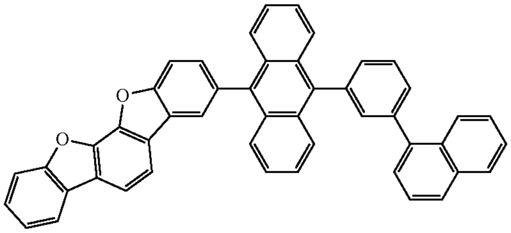
H64
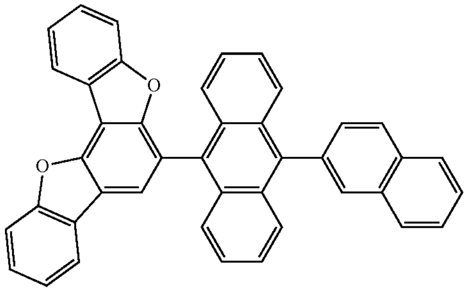
H65
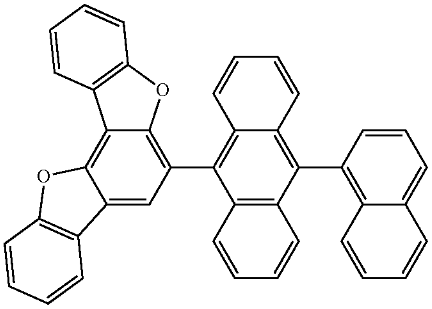
H66
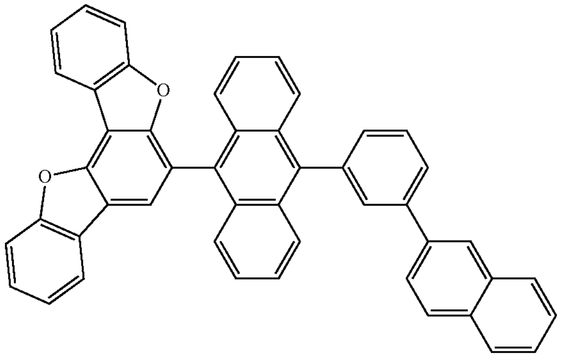
H67
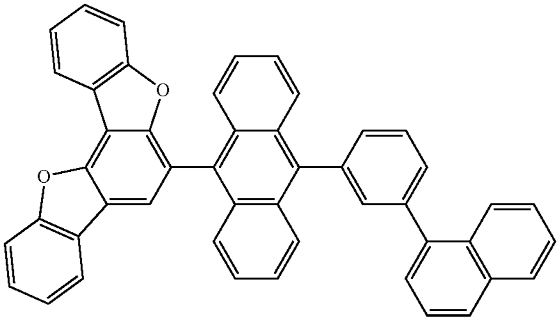
H68
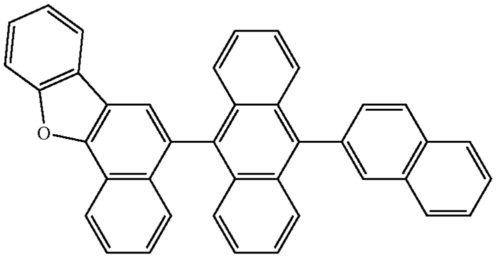
H69
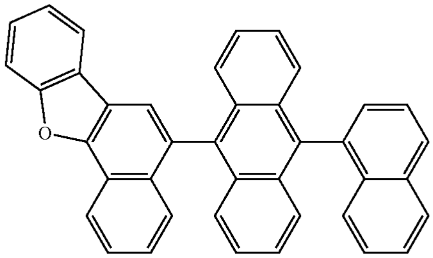

-continued
H70
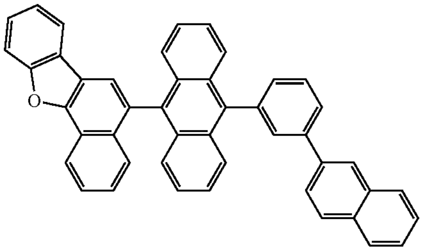
H71
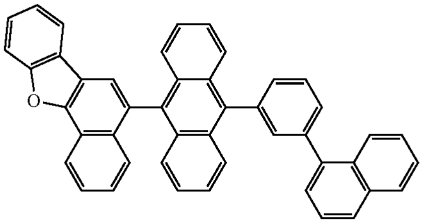
H72
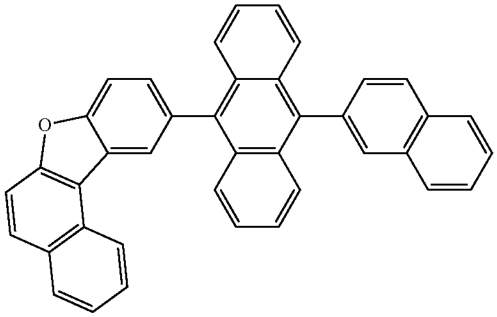
H73
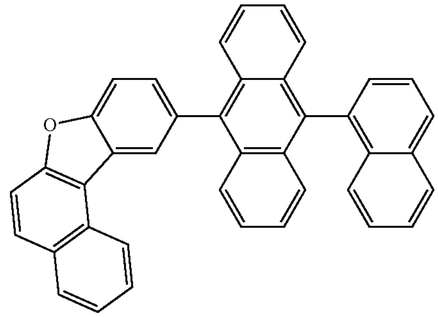
H74
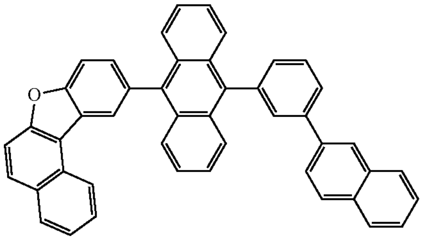
H75
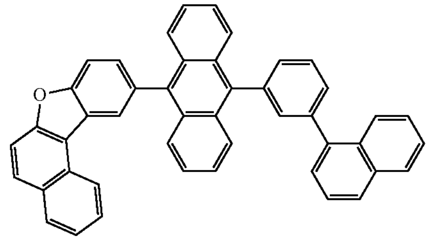
H76
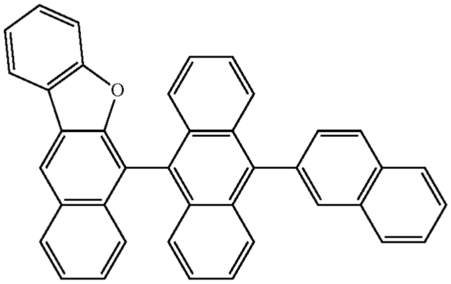
H77
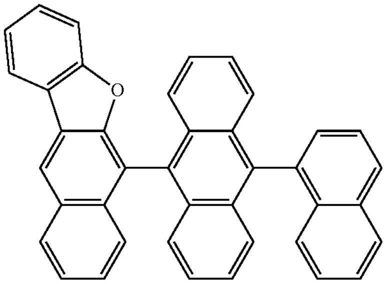
H78
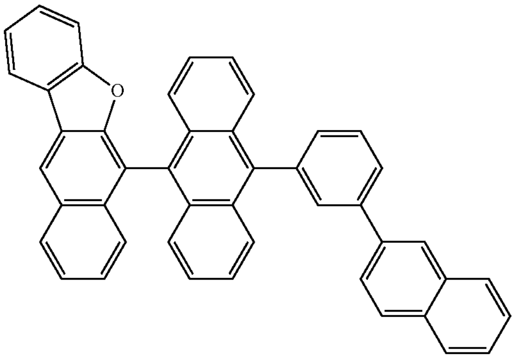
H79
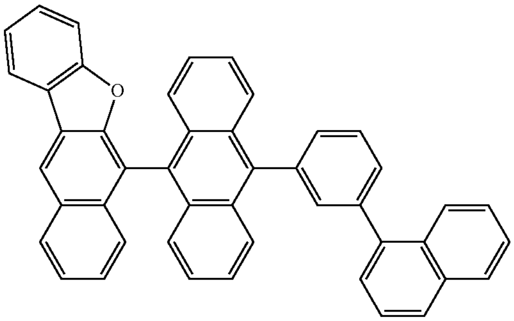

-continued
H80
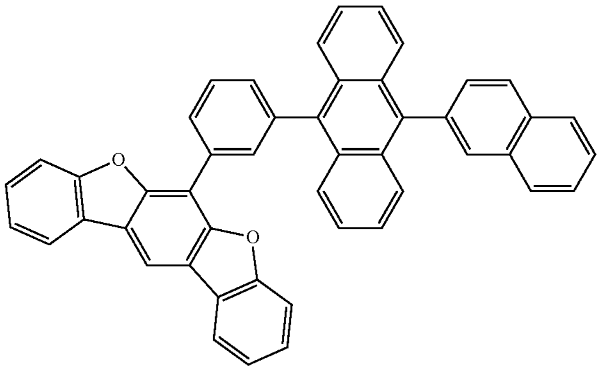
H81
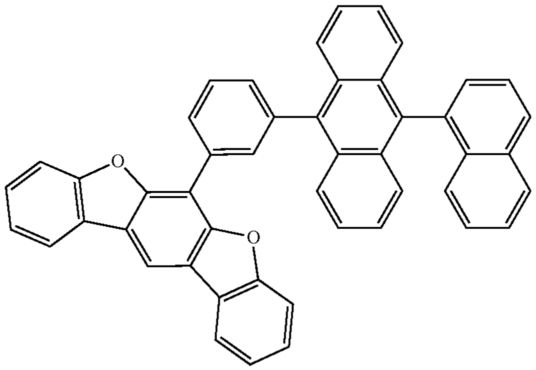
H82
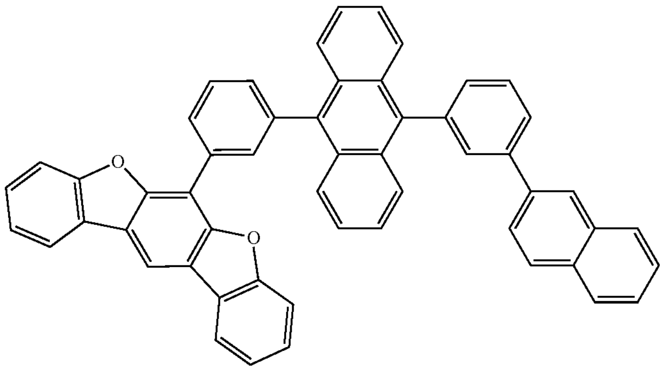
H83
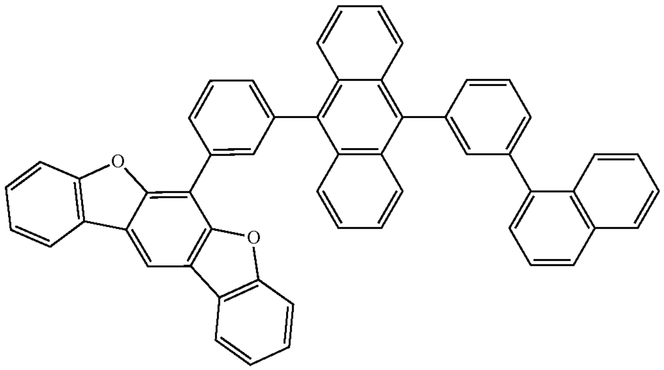

-continued
H84
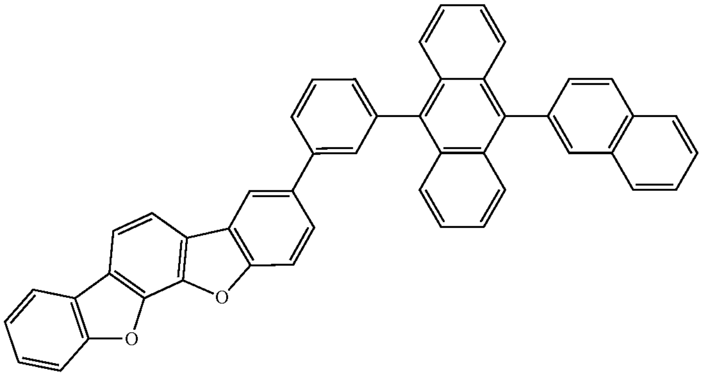
H85
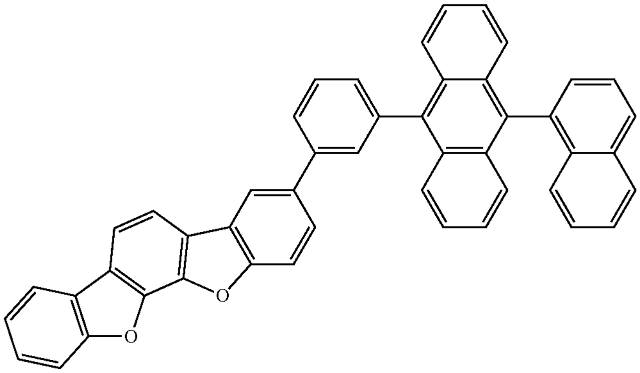
H86
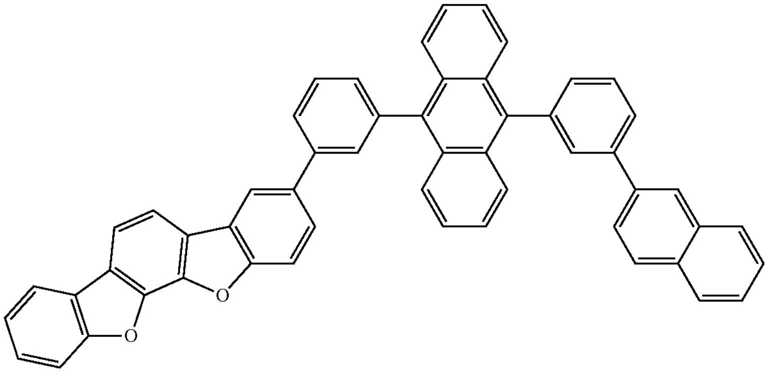
H87
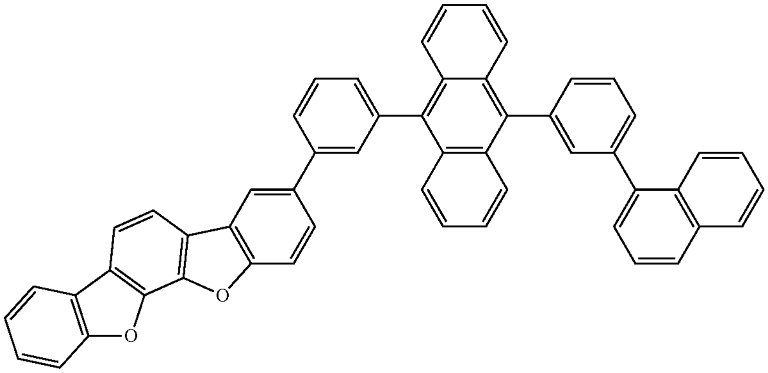

-continued
H88
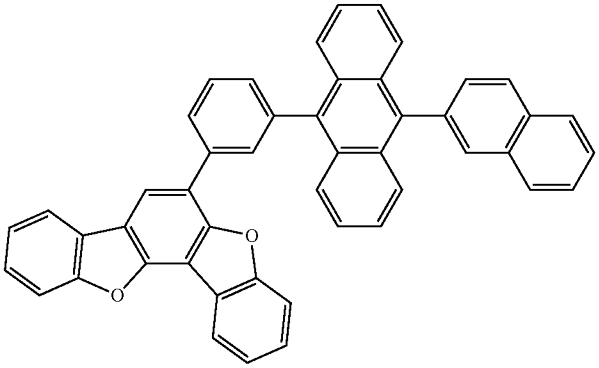
H89
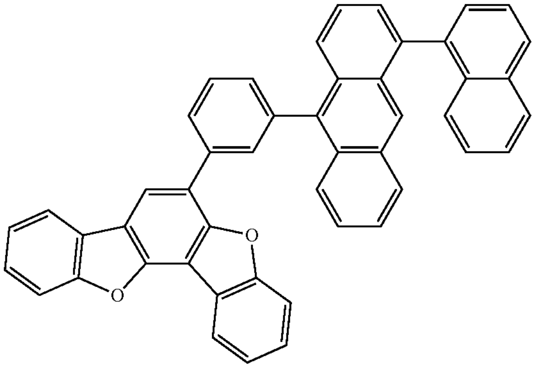
H90
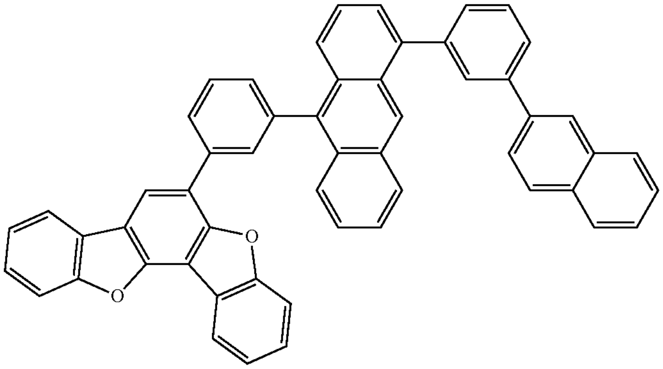
H91
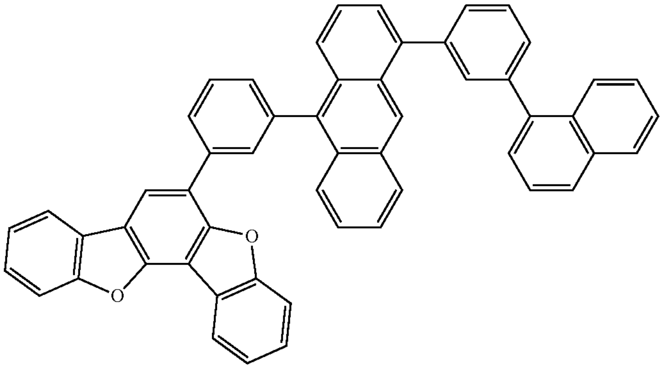

-continued
H92
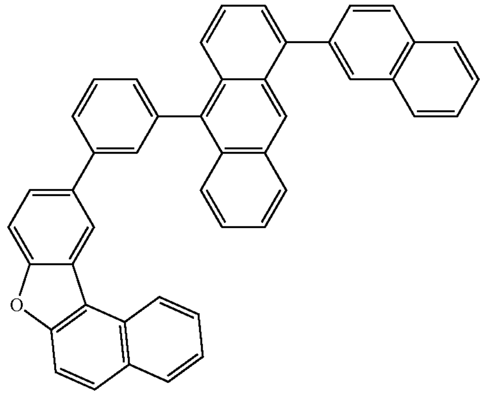
H93
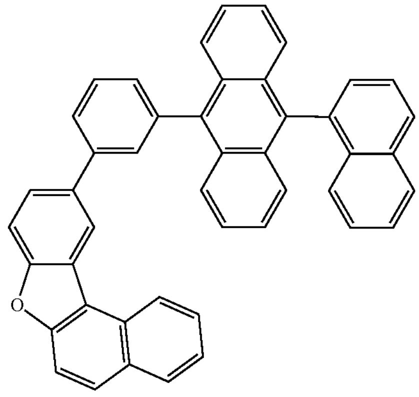
H94
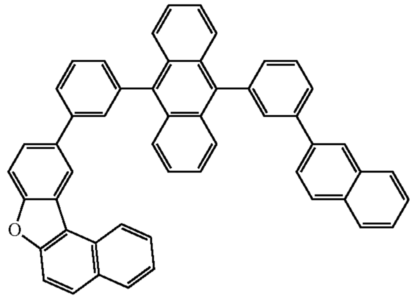
H95
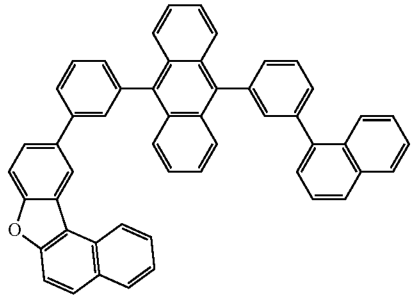
H96
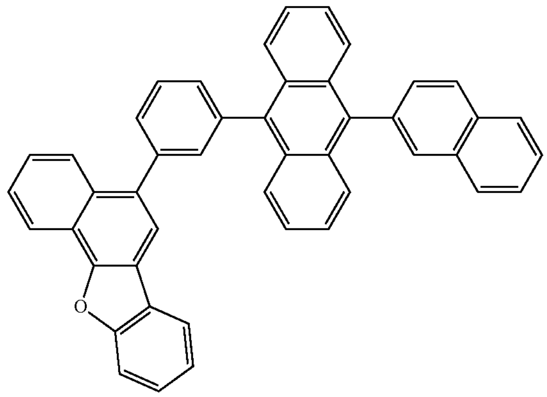
H97
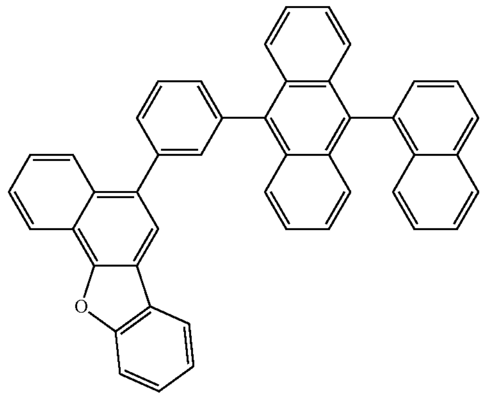
H98
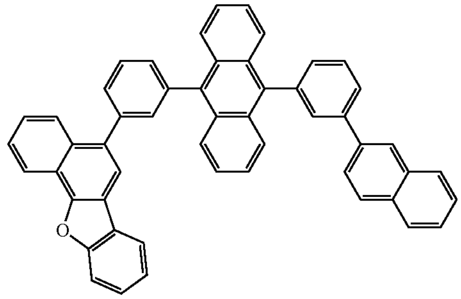
H99
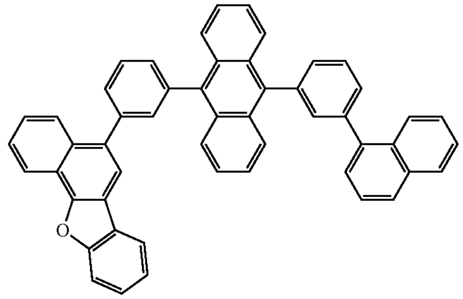

-continued
H100
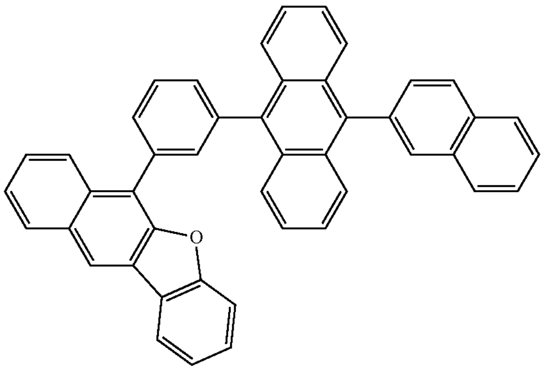
H101
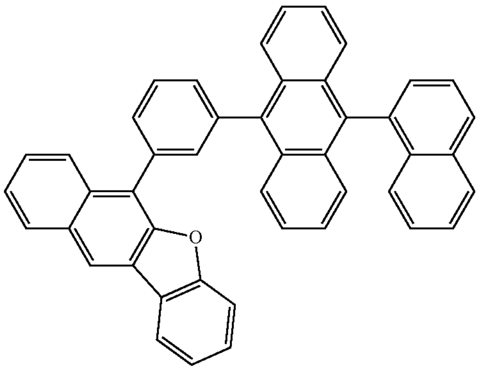
H102
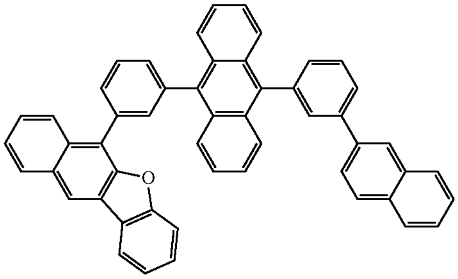
H103
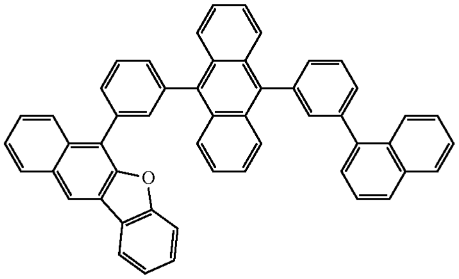
H104
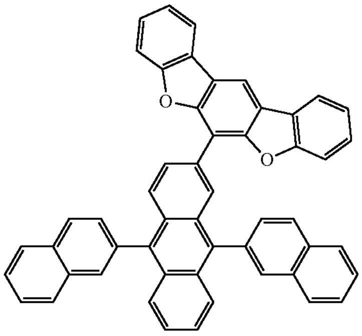
H105
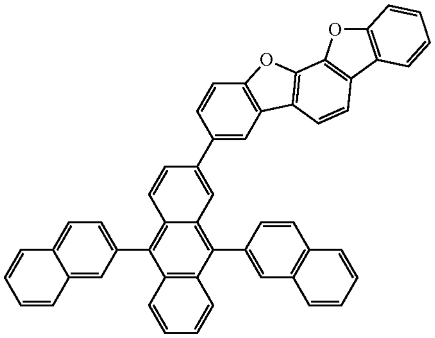
H106
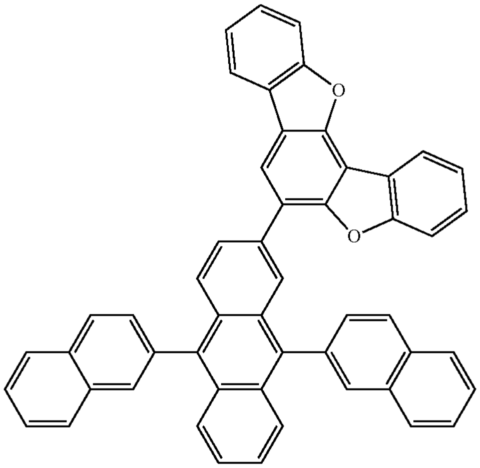
H107
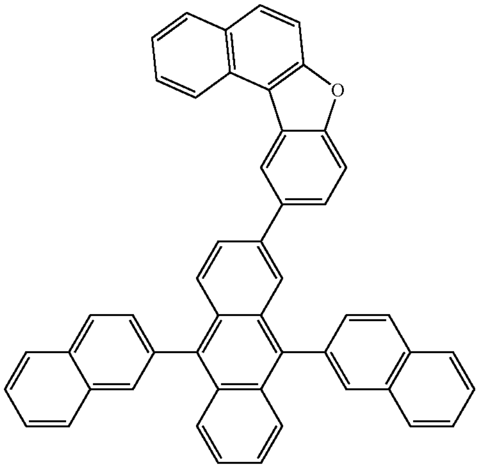

-continued
H108
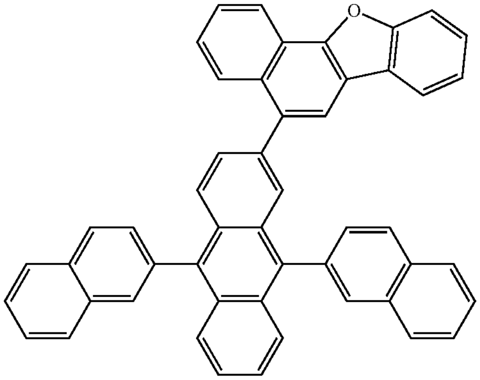
H109
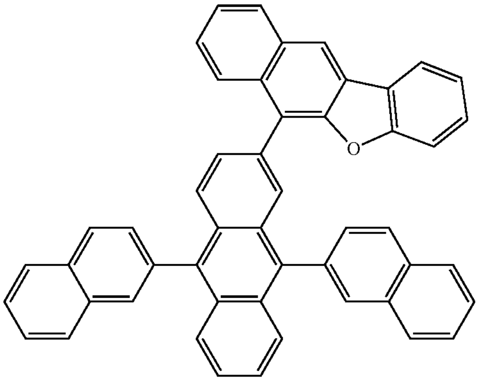
H110
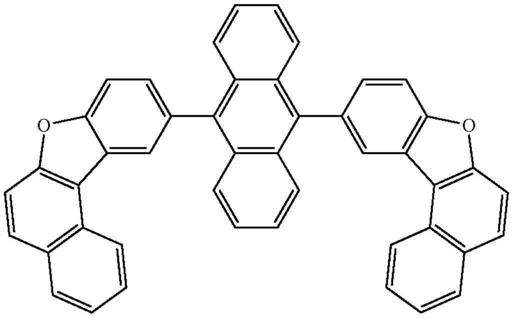
H111
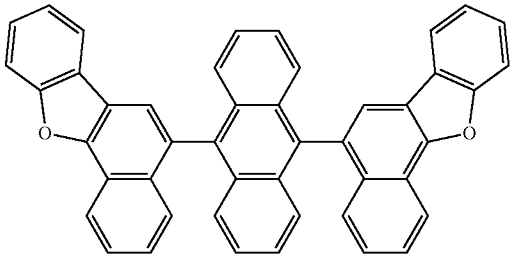
H112
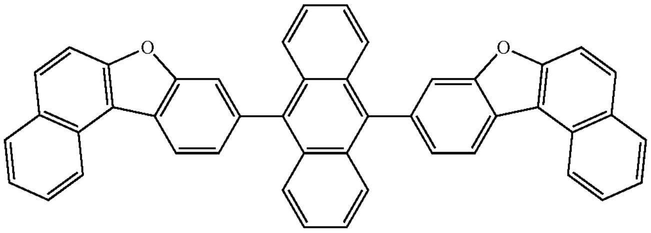
H113
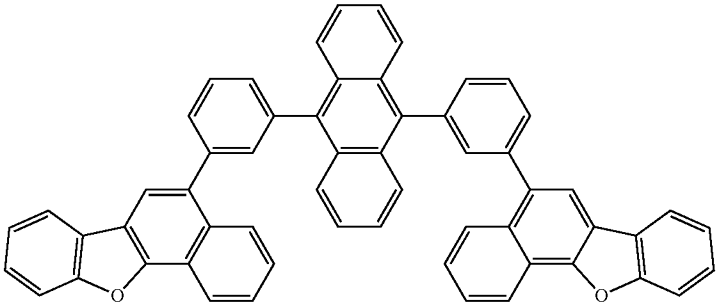
H114
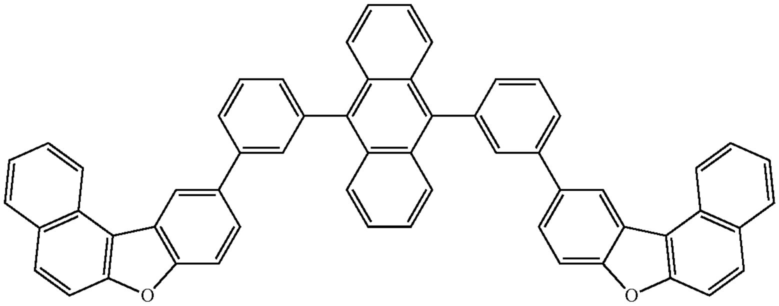

-continued
H115
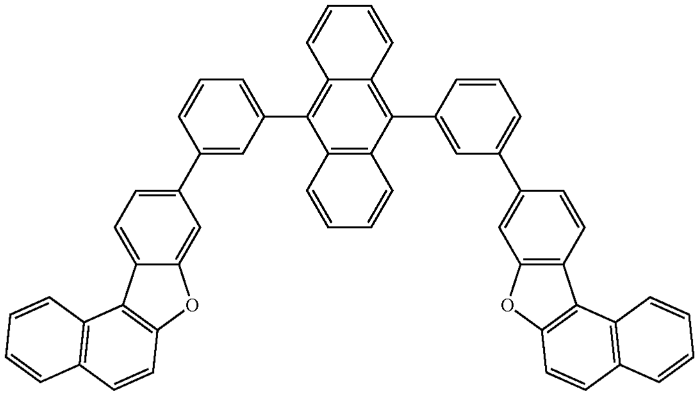
H116
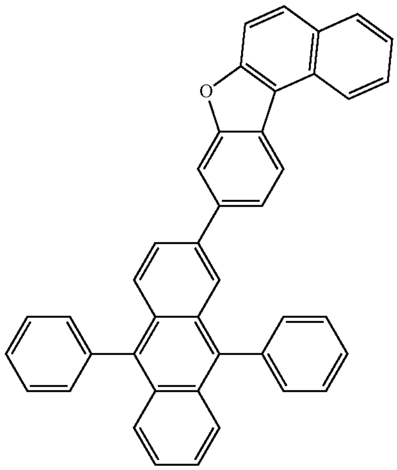
H117
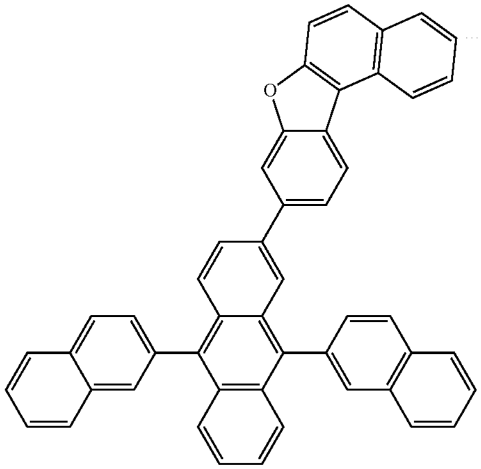

-continued
H118
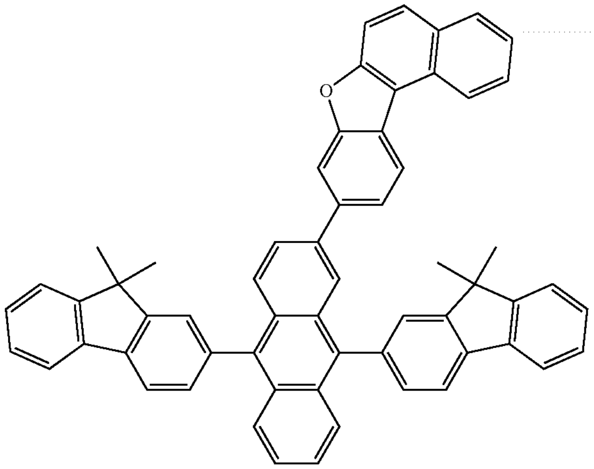
H119
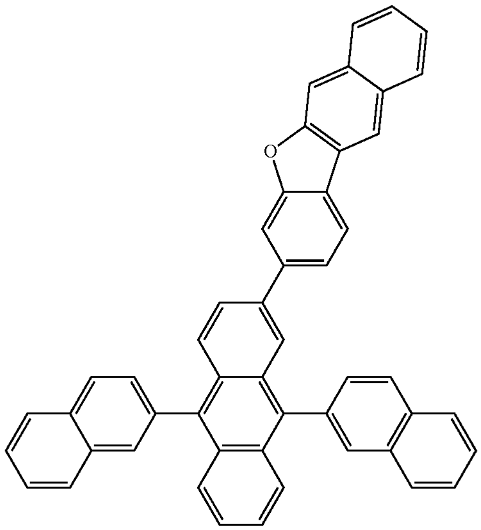
H120
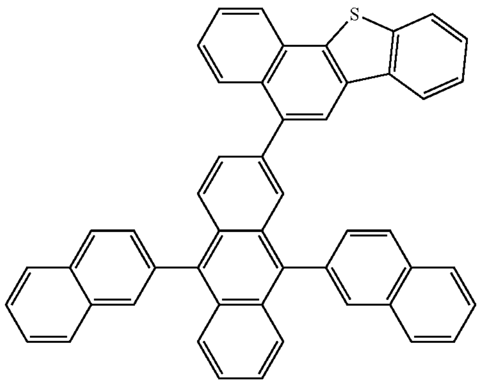
H121
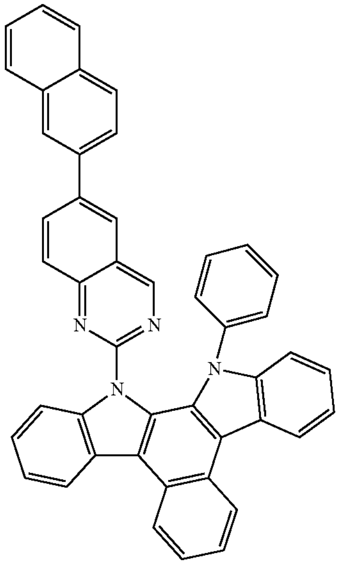
H122
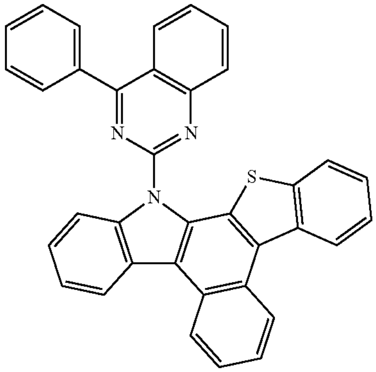

-continued

H123

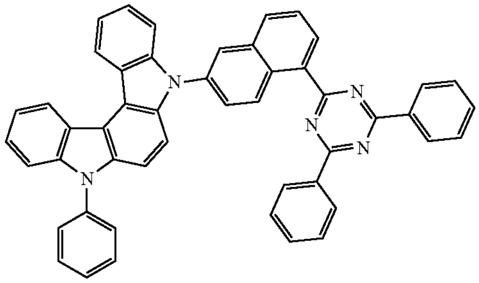

H124

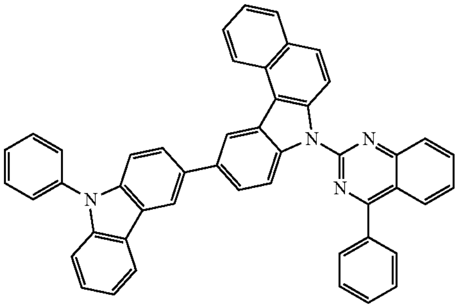

Phosphorescent Dopant

The phosphorescent dopant may include at least one transition metal as a central metal. The phosphorescent dopant may include a monodentate ligand, a bidentate ligand, a tridentate ligand, a tetradentate ligand, a pentadentate ligand, a hexadentate ligand, or any combination thereof. The phosphorescent dopant may be electrically neutral. For example, the phosphorescent dopant may include an organometallic compound represented by Formula 401:

Formula 401

$$M(L_{401})_{xc1}(L_{402})_{xc2}$$

Formula 402

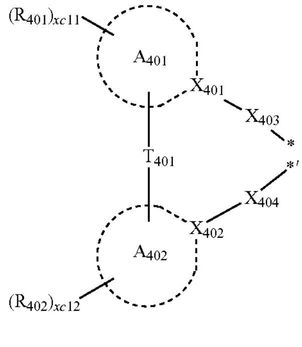

wherein, in Formulae 401 and 402,

M may be transition metal (for example, iridium (Ir), platinum (Pt), palladium (Pd), osmium (Os), titanium (Ti), gold (Au), hafnium (Hf), europium (Eu), terbium (Tb), rhodium (Rh), rhenium (Re), or thulium (Tm)), $L_{401}$ may be a ligand represented by Formula 402, and xc1 may be 1, 2, or 3, wherein when xc1 is two or more, two or more of $L_{401}$(s) may be identical to or different from each other, $L_{402}$ may be an organic ligand, and xc2 may be 0, 1, 2, 3, or 4, and when xc2 is 2 or more, two or more of $L_{402}$(s) may be identical to or different from each other, $X_{401}$ and $X_{402}$ may each independently be nitrogen or carbon, ring $A_{401}$ and ring $A_{402}$ may each independently be a $C_3$-$C_{60}$ carbocyclic group or a $C_1$-$C_{60}$ heterocyclic group, $T_{401}$ may be a single bond, *—O—*', *—S—*', *—C(=O)—*', *—N($Q_{411}$)-*', *—C($Q_{411}$)($Q_{412}$)-*', *—C($Q_{411}$)=C($Q_{412}$)-*', *—C($Q_{411}$)=*', or *=C=*', $X_{403}$ and $X_{404}$ may each independently be a chemical bond (for example, a covalent bond or a coordination bond), O, S, N($Q_{413}$), B($Q_{413}$), P($Q_{413}$), C($Q_{413}$)($Q_{414}$), or Si($Q_{413}$)($Q_{414}$), $Q_{411}$ to $Q_{414}$ are each the same as described in connection with $Q_1$, $R_{401}$ and $R_{402}$ may each independently be hydrogen, deuterium, —F, —Cl, —Br, —I, a hydroxyl group, a cyano group, a nitro group, a $C_1$-$C_{20}$ alkyl group unsubstituted or substituted with at least one $R_{10a}$, a $C_1$-$C_{20}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, —Si($Q_{401}$)($Q_{402}$)($Q_{403}$), —N($Q_{401}$)($Q_{402}$), —B($Q_{401}$)($Q_{402}$), —C(=O)($Q_{401}$), —S(=O)$_2$($Q_{401}$), or —P(=O)($Q_{401}$)($Q_{402}$), $Q_{401}$ to $Q_{403}$ are each the same as described in connection with $Q_1$, xc11 and xc12 may each independently be an integer from 0 to 10, and

* and *' in Formula 402 each indicates a binding site to M in Formula 401.

For example, in Formula 402, i) $X_{401}$ may be nitrogen, and $X_{402}$ may be carbon, or ii) each of $X_{401}$ and $X_{402}$ may be nitrogen.

In one or more embodiments, when xc1 in Formula 402 is 2 or more, two ring $A_{401}$(s) in two or more of $L_{401}$(s) may be optionally linked to each other via $T_{402}$, which is a linking group, and two ring $A_{402}$(s) are optionally linked to each other via $T_{403}$, which is a linking group (see Compounds PD1 to PD4 and PD7). The groups $T_{402}$ and $T_{403}$ are each the same as described in connection with $T_{401}$.

The group $L_{402}$ in Formula 401 may be an organic ligand. For example, $L_{402}$ may include a halogen group, a diketone group (for example, an acetylacetonate group), a carboxylic acid group (for example, a picolinate group), a —C(=O) group, an isonitrile group, a —CN group, a phosphorus group (for example, a phosphine group, a phosphite group, etc.), or any combination thereof.

The phosphorescent dopant may include, for example, one of compounds PD1 to PD39, or any combination thereof:

-continued
PD1
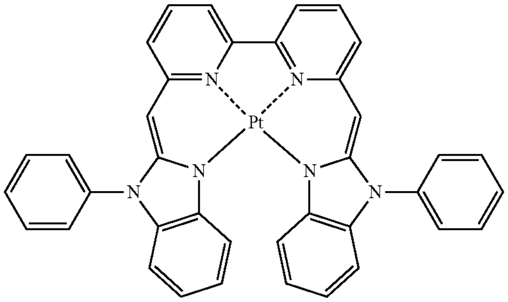
PD2
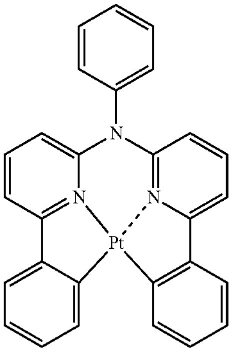
PD3
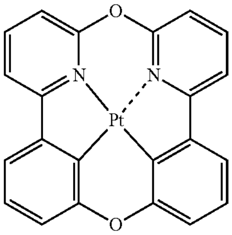
PD4
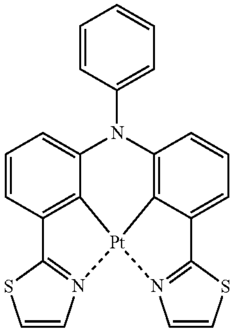
PD5
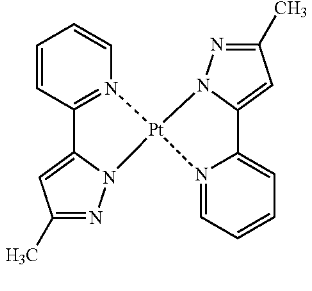
PD6
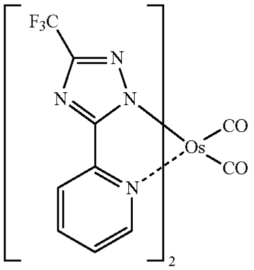
PD7
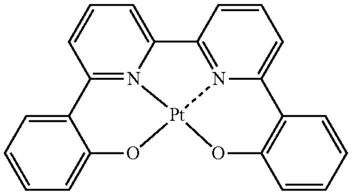
PD8
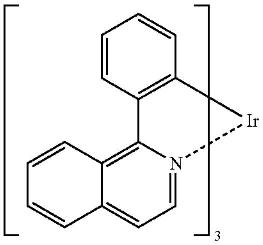
PD9
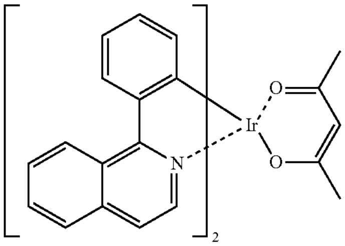
PD10
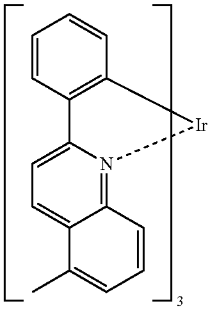
PD11
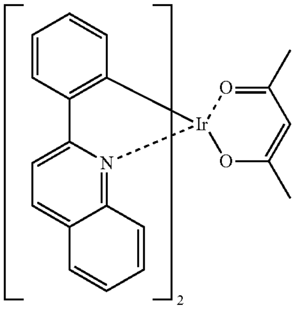

PD12
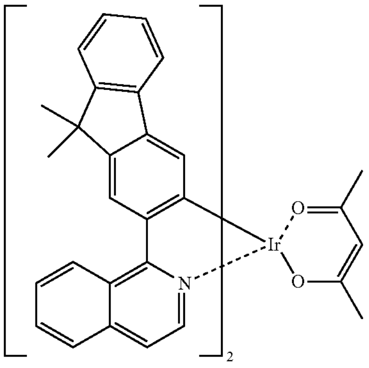
PD13
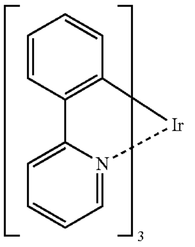
PD14
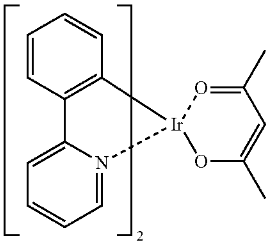
PD15
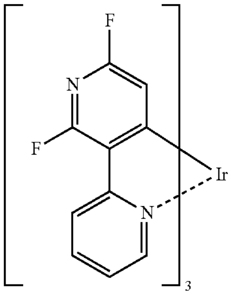
PD16
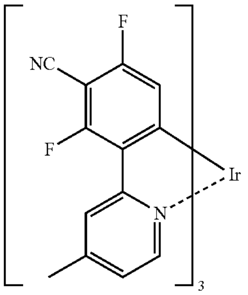
PD17
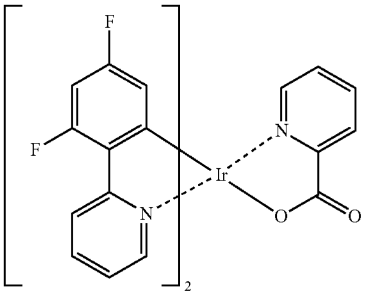
PD18
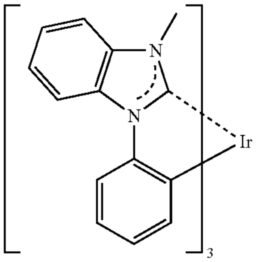
PD19
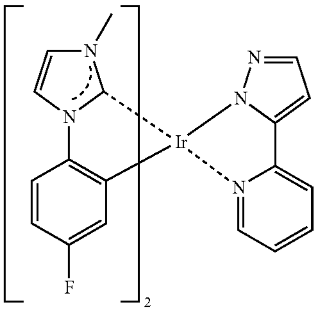
PD20
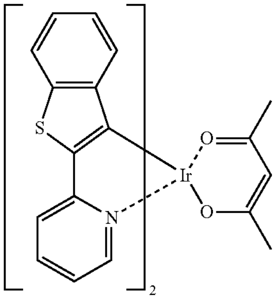
PD21
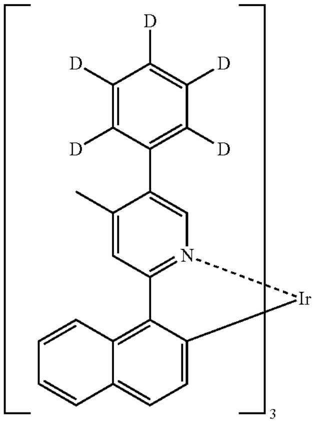

PD22
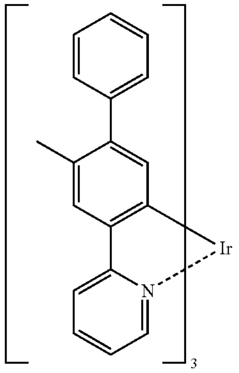
PD23
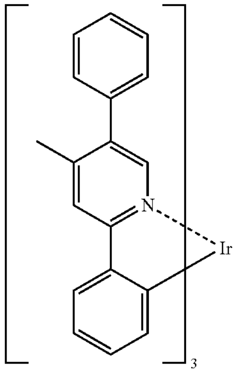
PD24
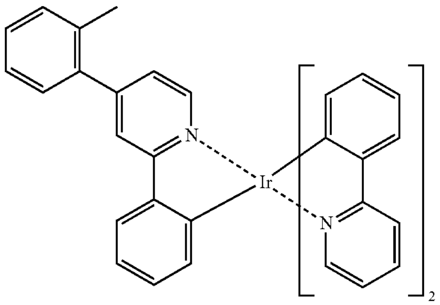
PD25
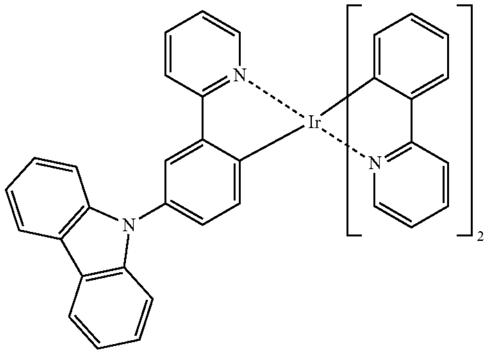
PD26
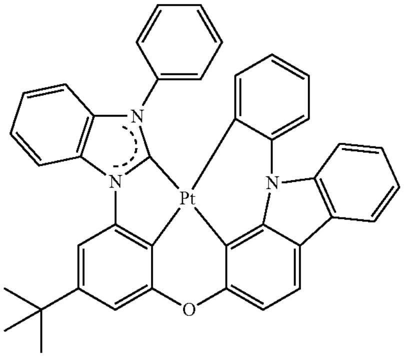
PD27
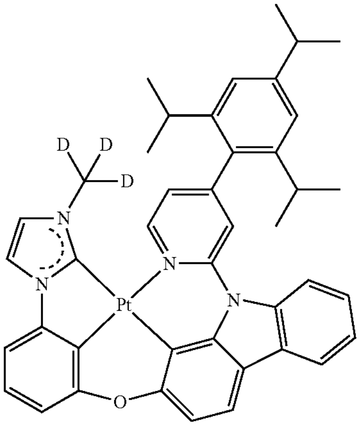
PD28
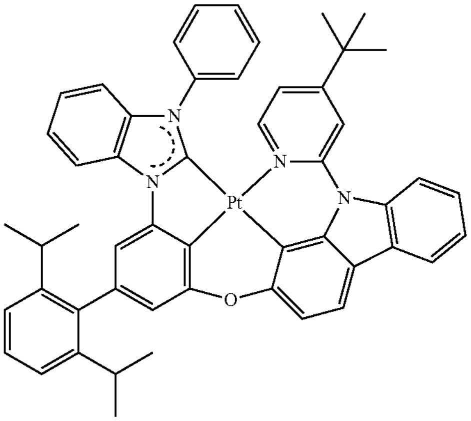
PD29
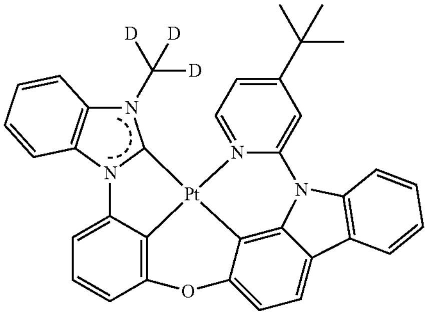

-continued
PD30
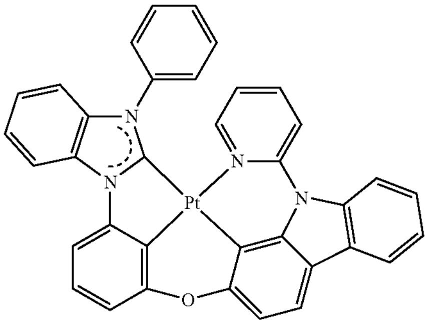
PD31
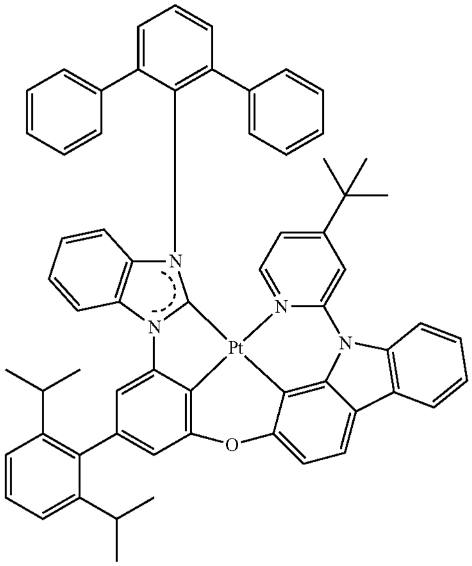
PD32
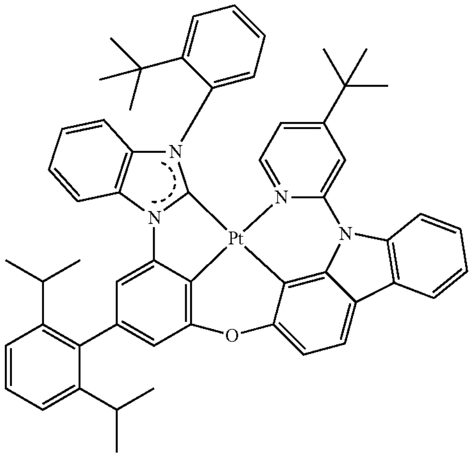
-continued
PD33
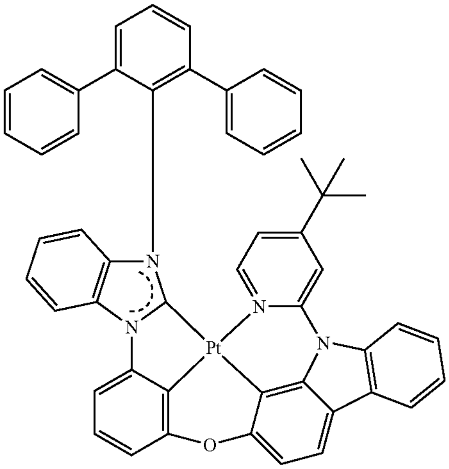
PD34
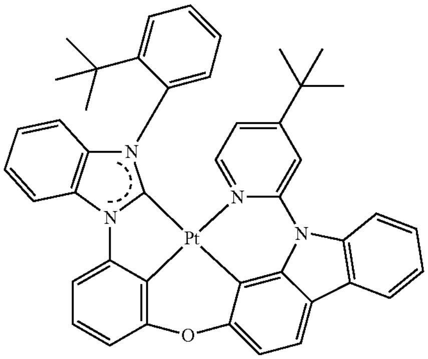
PD35
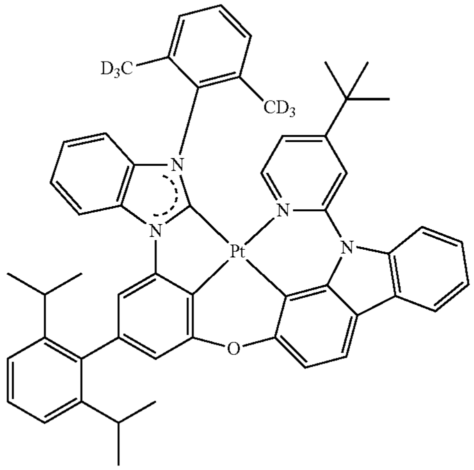

-continued

PD36

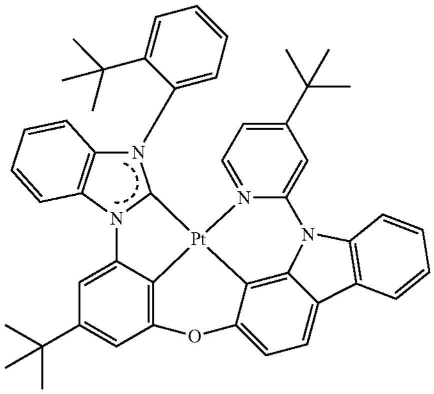

PD37

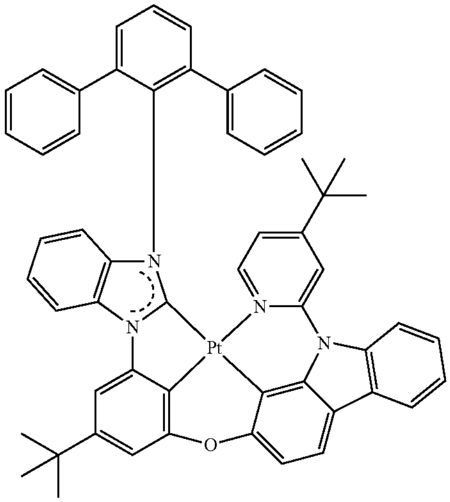

PD38

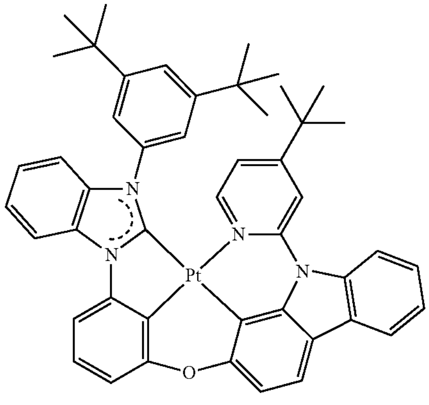

-continued

PD39

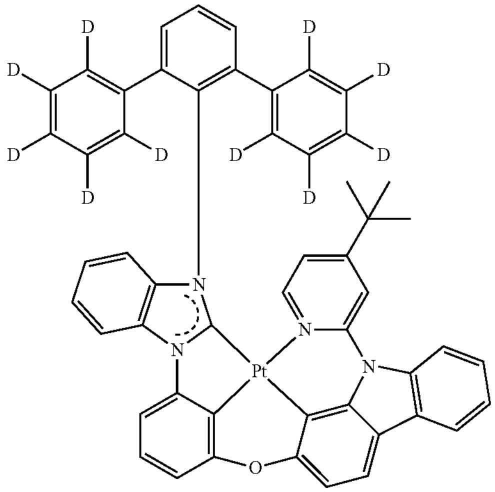

Fluorescent Dopant

The fluorescent dopant may include an amine group-containing compound, a styryl group-containing compound, or any combination thereof. In one or more embodiments, the fluorescent dopant may include a compound represented by Formula 501:

Formula 501

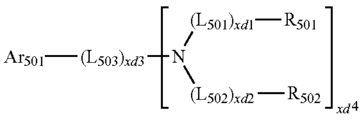

wherein, in Formula 501, $Ar_{501}$, $L_{501}$ to $L_{503}$, $R_{501}$, and $R_{502}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, $L_{501}$ to $L_{503}$ may each independently be a divalent $C_3$-$C_{60}$ carbocyclic group unsubstituted or substituted with at least one $R_{10a}$ or a divalent $C_1$-$C_{60}$ heterocyclic group unsubstituted or substituted with at least one $R_{10a}$, wherein $R_{10a}$ is the same as described herein, xd1 to xd3 may each independently be 0, 1, 2, or 3, and xd4 may be 1, 2, 3, 4, 5, or 6.

In one or more embodiments, $Ar_{501}$ in Formula 501 may be a condensed cyclic group (for example, an anthracene group, a chrysene group, or a pyrene group) in which three or more monocyclic groups are condensed together.

In one or more embodiments, xd4 in Formula 501 may be 2.

In one or more embodiments, the fluorescent dopant may include: one of Compounds FD1 to FD36; DPVBi; DPAVBi; or any combination thereof:

FD1
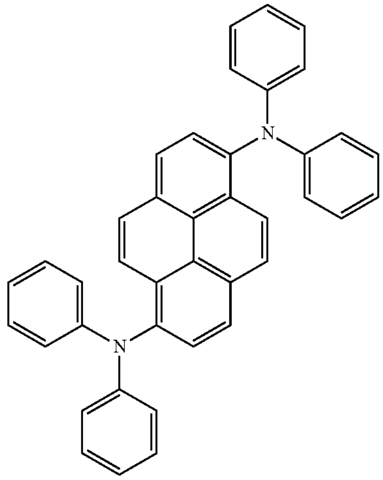
FD2
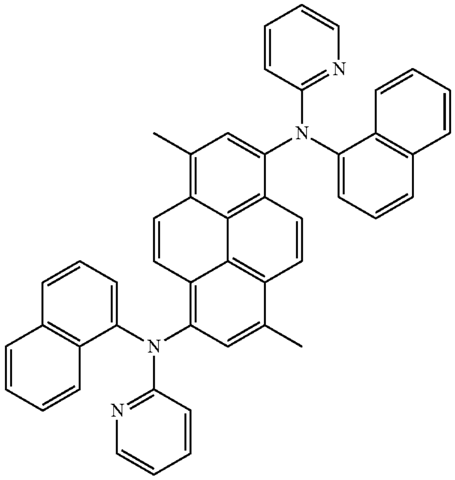
FD3
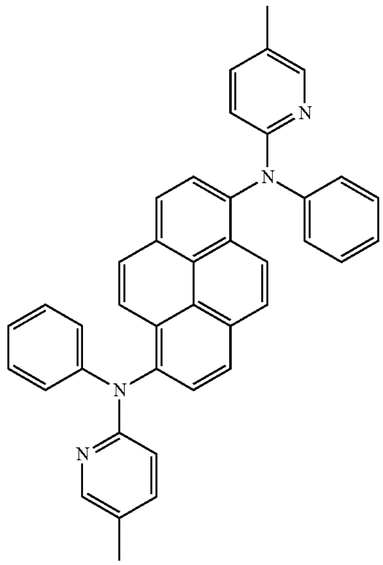
FD4
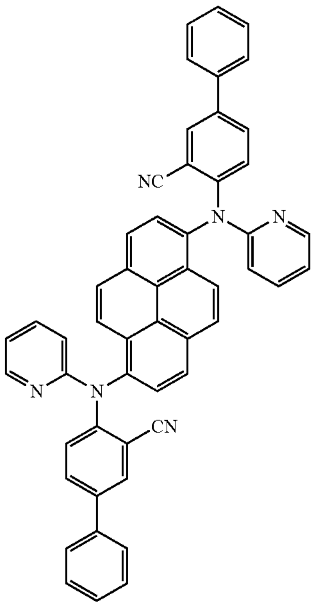
FD5
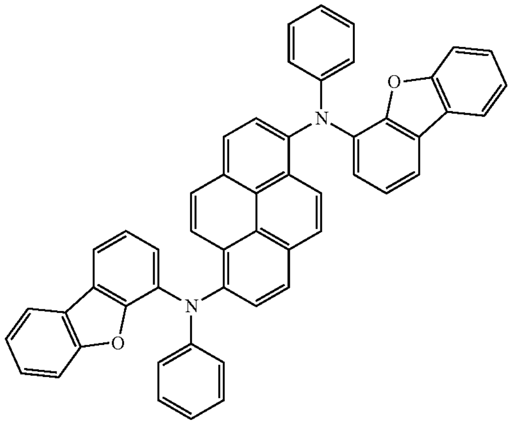
FD6
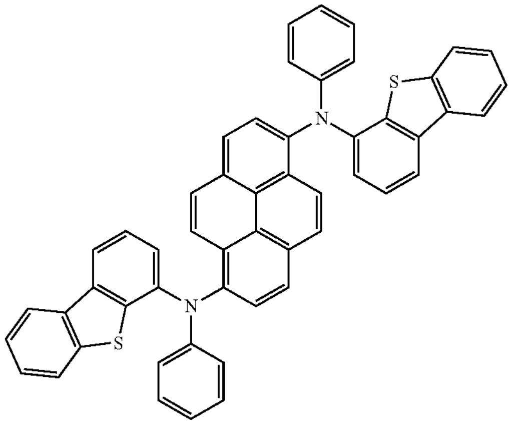

-continued
FD7
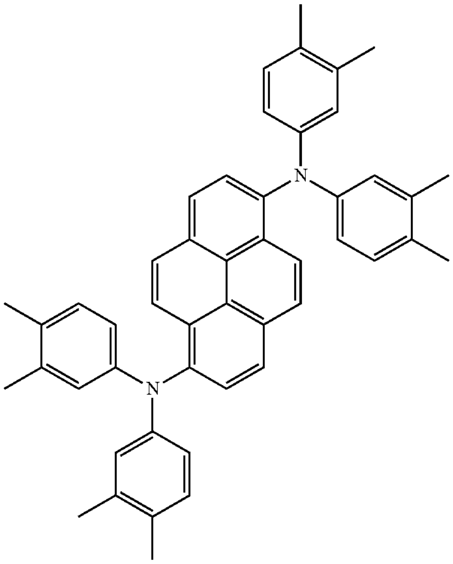
FD8
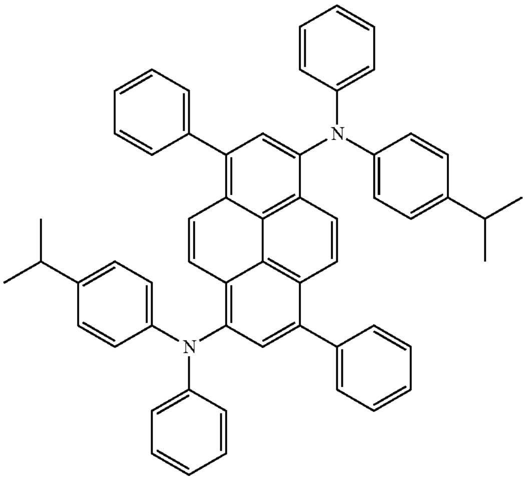
FD9
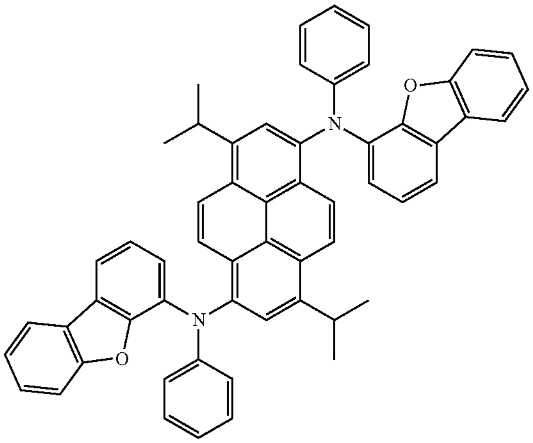
FD10
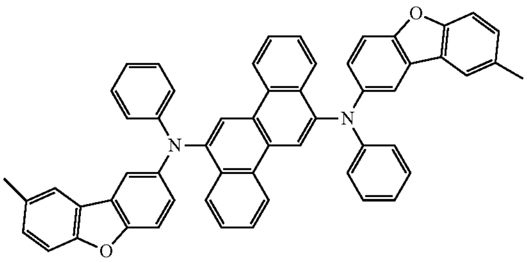
FD11
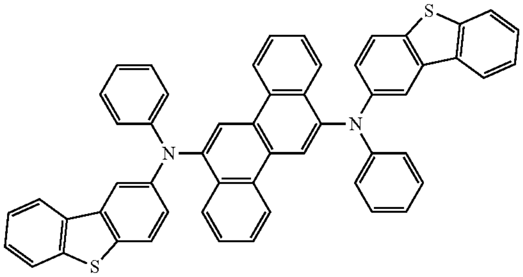
FD12
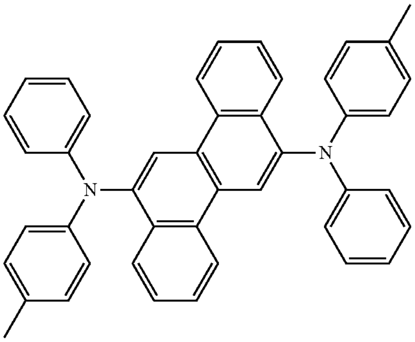

-continued
FD13
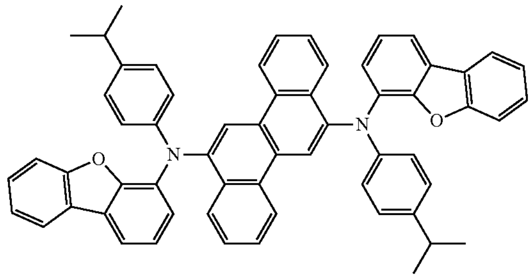
FD14
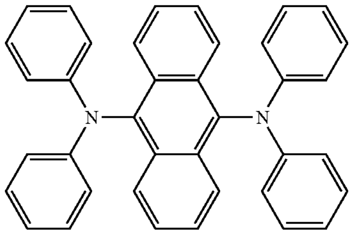
FD15
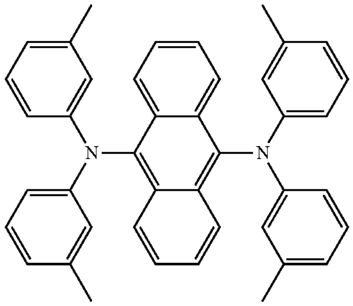
FD16
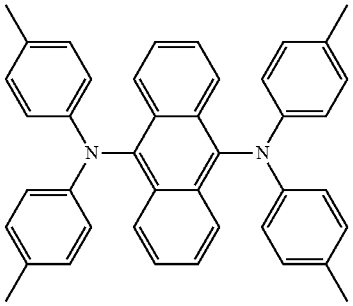
FD17
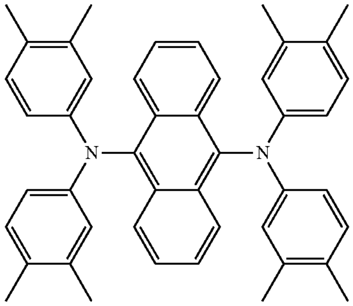
FD18
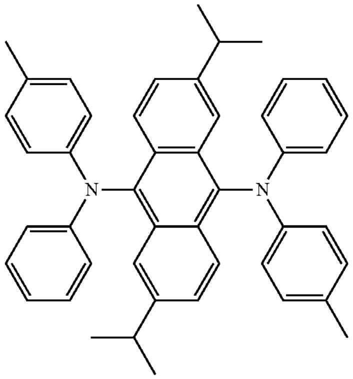
FD19
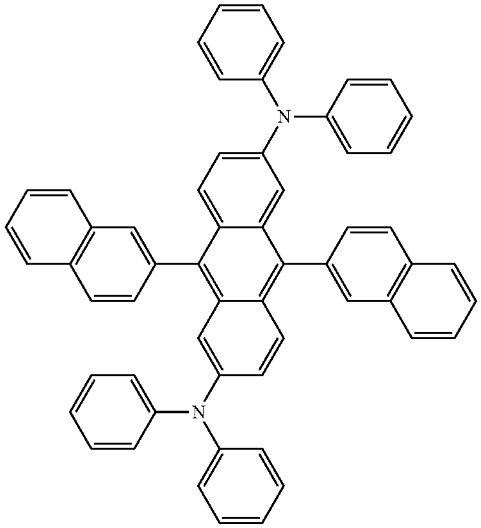
FD20
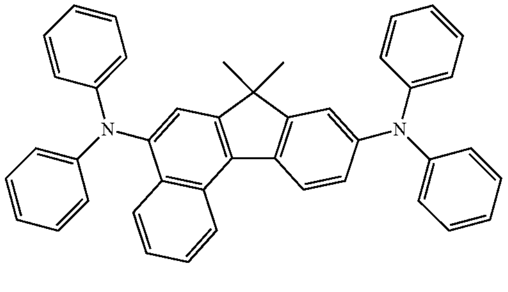

-continued
FD21
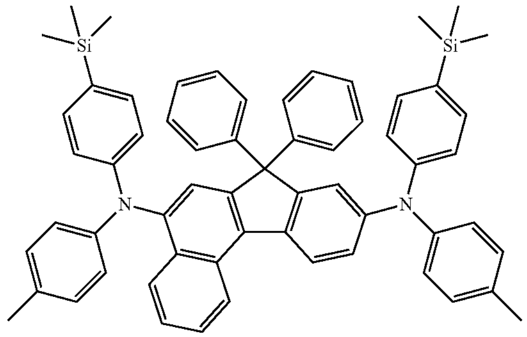
FD22
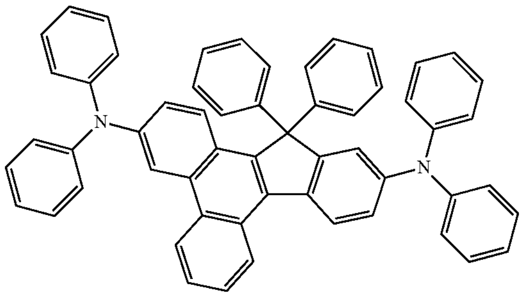
FD23
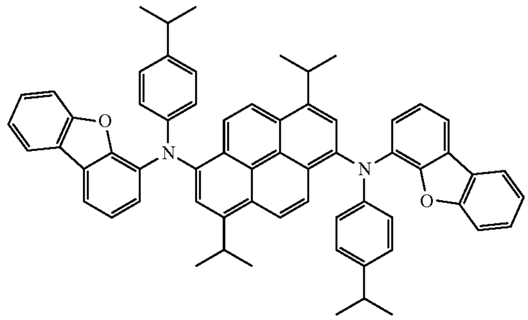
FD24
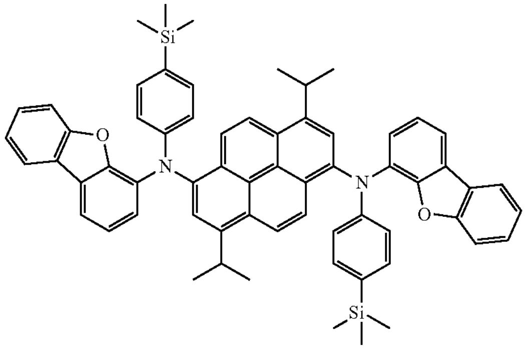
FD25
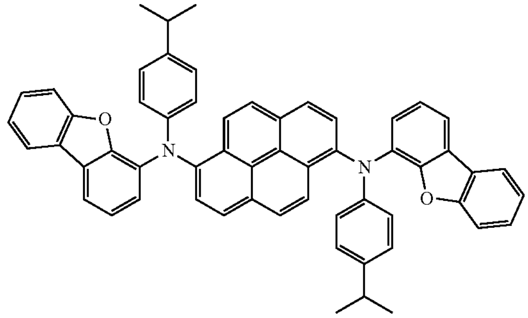
FD26
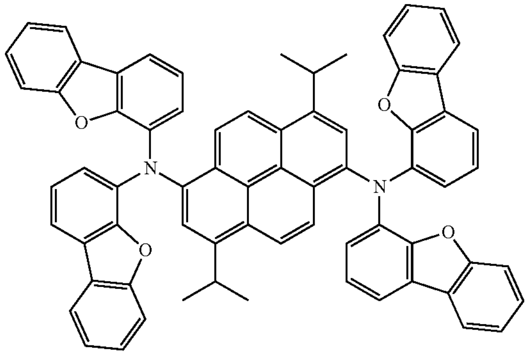
FD27
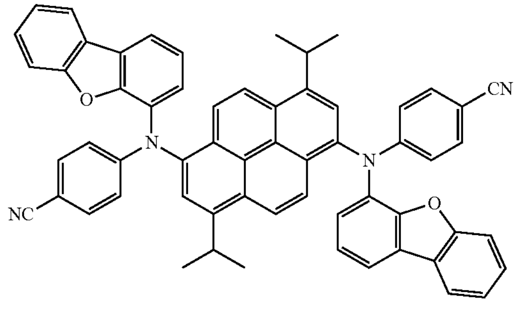
FD28
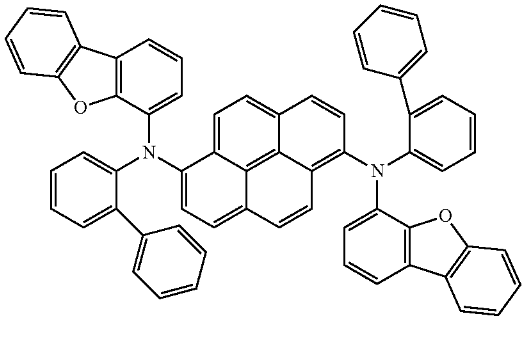

-continued
FD29
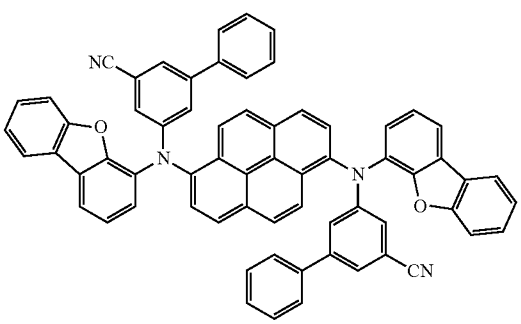
FD30
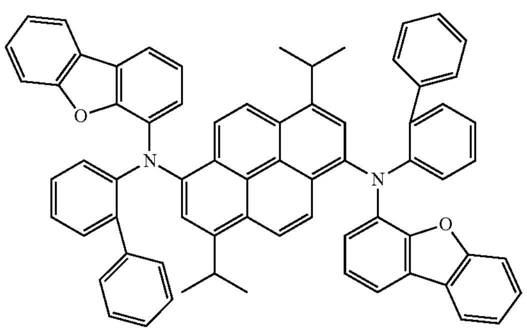
FD31
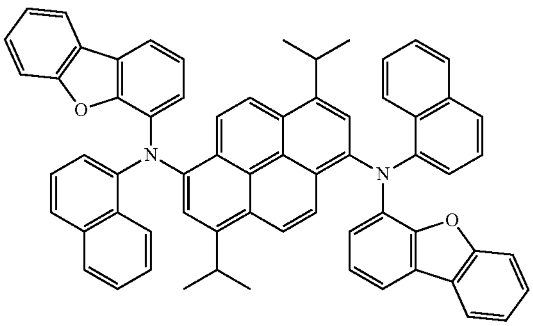
FD32
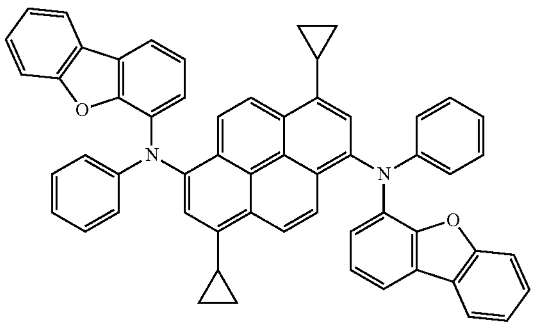
FD33
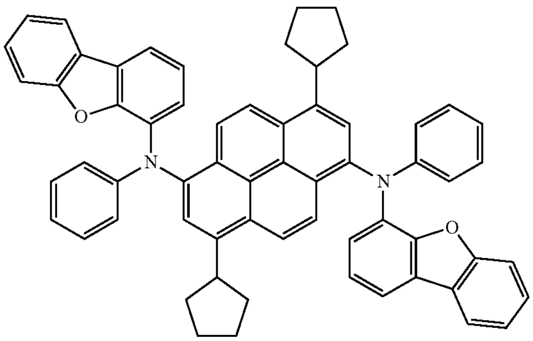
FD34
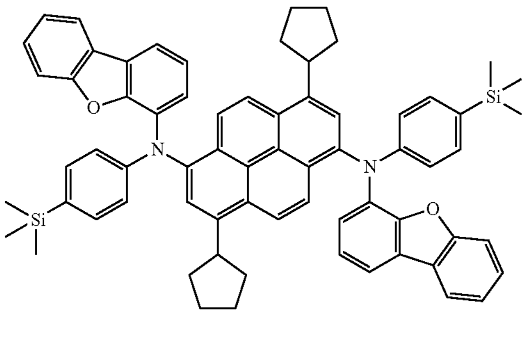
FD35
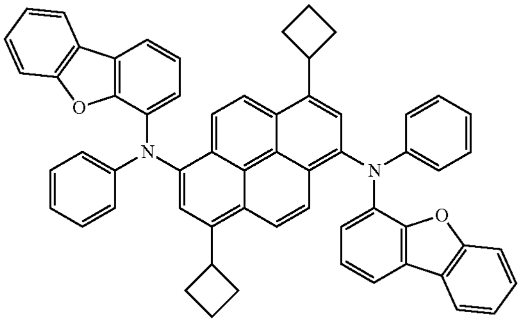
FD36
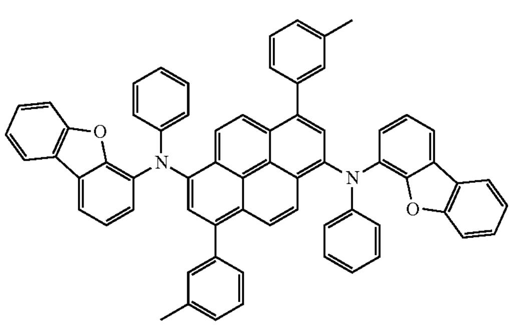

-continued

DPVBi

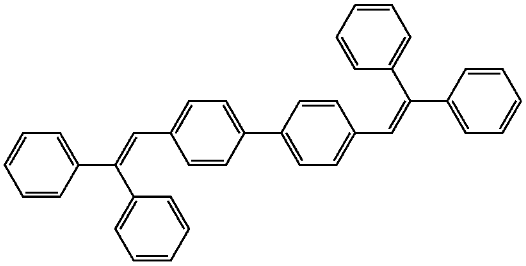

DPAVBi

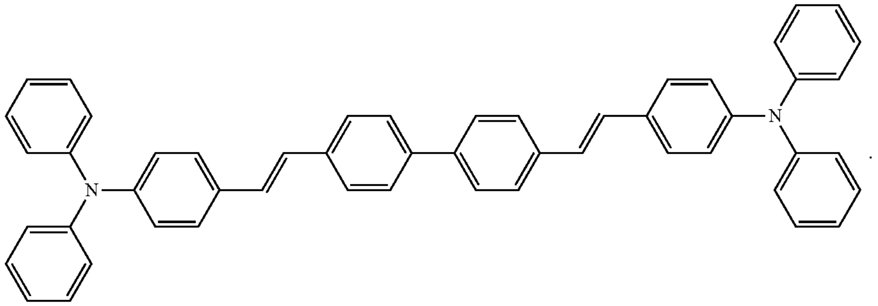

Electron Transport Region in Interlayer 130

The electron transport region may have: i) a single-layered structure consisting of a single layer consisting of a single material, ii) a single-layered structure consisting of a single layer consisting of a plurality of different materials, or iii) a multi-layered structure including a plurality of layers including different materials. The electron transport region may include a buffer layer, a hole blocking layer, an electron control layer, an electron transport layer, an electron injection layer, or any combination thereof.

In an embodiment, the electron transport region may have an electron transport layer/electron injection layer structure, a hole blocking layer/electron transport layer/electron injection layer structure, an electron control layer/electron transport layer/electron injection layer structure, or a buffer layer/electron transport layer/electron injection layer structure, wherein, for each structure, constituting layers are sequentially stacked from an emission layer.

In an embodiment, the electron transport region (for example, the buffer layer, the hole blocking layer, the electron control layer, or the electron transport layer in the electron transport region) may include a metal-free compound including at least one π electron-deficient nitrogen-containing $C_1$-$C_{60}$ cyclic group.

In an embodiment, the electron transport region may include a compound represented by Formula 601 below:

$$[Ar_{601}]_{xe11}\text{-}[(L_{601})_{xe1}\text{-}R_{601}]_{xe21}$$ Formula 601 wherein, in Formula 601, $Ar_{601}$ and $L_{601}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, $L_{601}$ may each independently be a divalent $C_3$-$C_{60}$ carbocyclic group unsubstituted or substituted with at least one $R_{10a}$ or a divalent $C_1$-$C_{60}$ heterocyclic group unsubstituted or substituted with at least one $R_{10a}$, wherein $R_{10a}$ is the same as described herein, xe11 may be 1, 2, or 3, xe1 may be 0, 1, 2, 3, 4, or 5, $R_{601}$ may be a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, —$Si(Q_{601})(Q_{602})(Q_{603})$, —$C(=O)(Q_{601})$, —$S(=O)_2(Q_{601})$, or —$P(=O)(Q_{601})(Q_{602})$, $Q_{601}$ to $Q_{603}$ are the same as described in connection with $Q_1$, xe21 may be 1, 2, 3, 4, or 5, and one or more of $Ar_{601}$, $L_{601}$, and $R_{601}$ may each independently be a π electron-deficient nitrogen-containing $C_1$-$C_{60}$ cyclic group unsubstituted or substituted with at least one $R_{10a}$.

For example, when xe11 in Formula 601 is 2 or more, two or more of $Ar_{601}$(s) may be linked via a single bond. In one or more embodiments, $Ar_{601}$ in Formula 601 may be a substituted or unsubstituted anthracene group. In an embodiment, the electron transport region may include a compound represented by Formula 601-1:

Formula 601-1

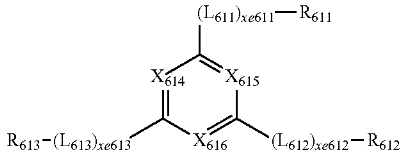

wherein, in Formula 601-1, $X_{614}$ may be N or $C(R_{614})$, $X_{615}$ may be N or $C(R_{615})$, $X_{616}$ may be N or $C(R_{616})$, one or more of $X_{614}$ to $X_{616}$ may be N, $L_{611}$ to $L_{613}$ are the same as described in connection with $L_{601}$, xe611 to xe613 are the same as described in connection with xe1, $R_{611}$ to $R_{613}$ are the same as described in connection with $R_{601}$, and $R_{614}$ to $R_{616}$ may each independently be hydrogen, deuterium, —F, —Cl, —Br, —I, a hydroxyl group, a cyano group, a nitro group, a $C_1$-$C_{20}$ alkyl group, a $C_1$-$C_{20}$ alkoxy group, a $C_3$-$C_{60}$ carbocyclic group unsubstituted or substituted with at least one $R_{10a}$, or a $C_1$-$C_{60}$ heterocyclic group unsubstituted or substituted with at least one $R_{10a}$. For example, xe1 and xe611 to xe613 in Formulae 601 and 601-1 may each independently be 0, 1, or 2.

The electron transport region may include one of Compounds ET1 to ET45, 2,9-dimethyl-4,7-diphenyl-1,10-phenanthroline (BCP), 4,7-diphenyl-1,10-phenanthroline (Bphen), tris-(8-hydroxyquinoline)aluminum ($Alq_3$), bis(2-methyl-8-quinolinolato-N1,O8)-(1,1'-biphenyl-4-olato)aluminum (BAlq), 3-(biphenyl-4-yl)-5-(4-tert-butylphenyl)-4-phenyl-4H-1,2,4-triazole (TAZ), 4-(naphthalen-1-yl)-3,5-diphenyl-4H-1,2,4-triazole (NTAZ), Diphenyl[4-(triphenylsilyl)phenyl]phosphine oxide (TSPO1), 1,3,5-Tris(1-phenyl-1H-benzo[d]imidazol-2-yl)benzene (TPBI), or any combination thereof:

ET1

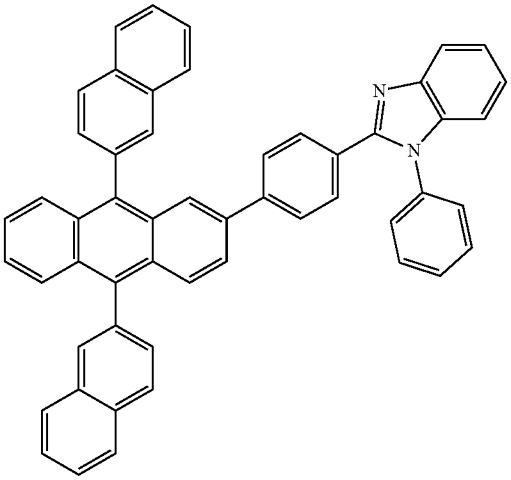

ET2

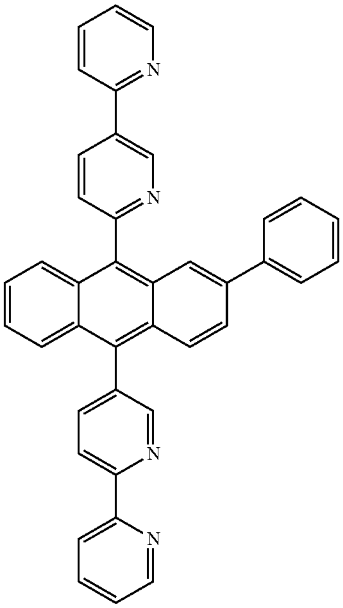

-continued

ET3

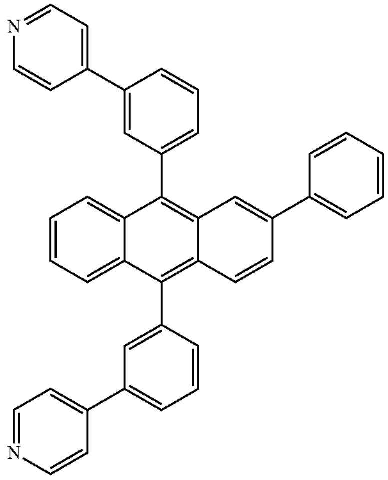

ET4

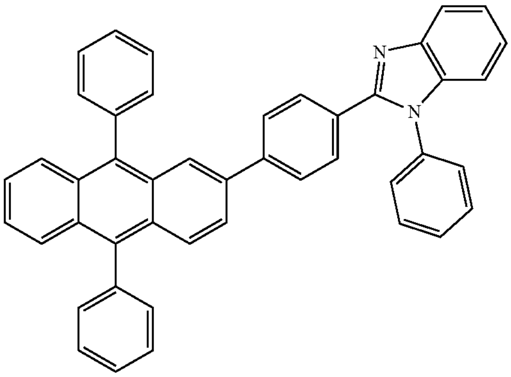

ET5

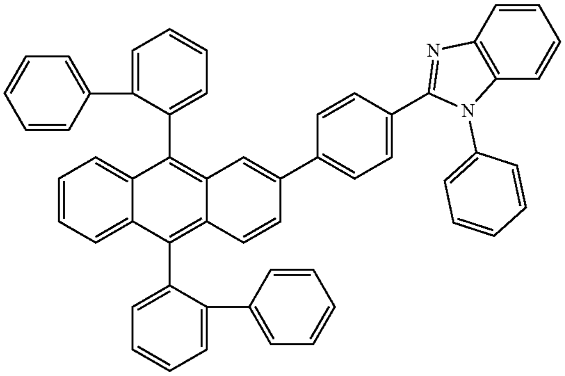

-continued
ET6
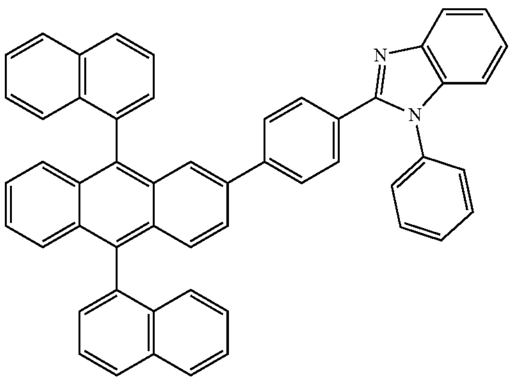
ET7
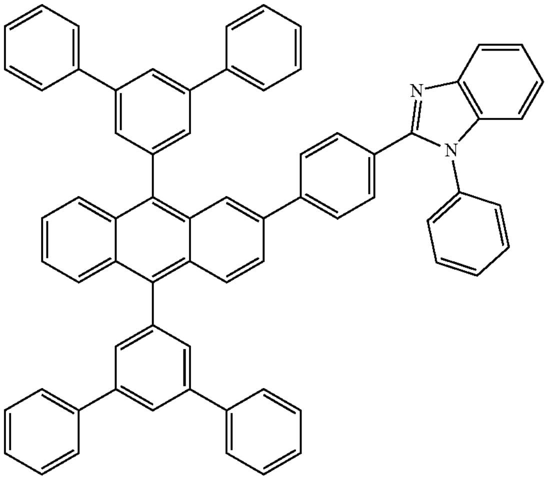
ET8
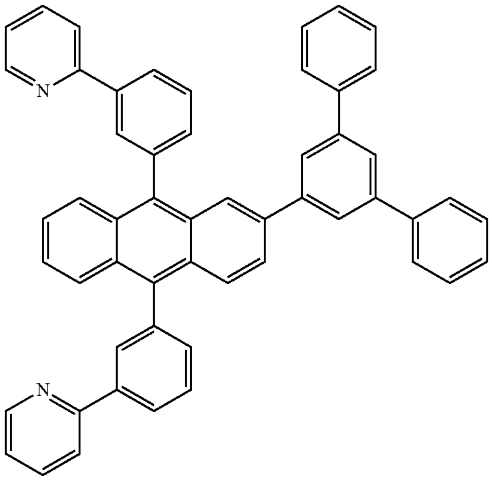
-continued
ET9
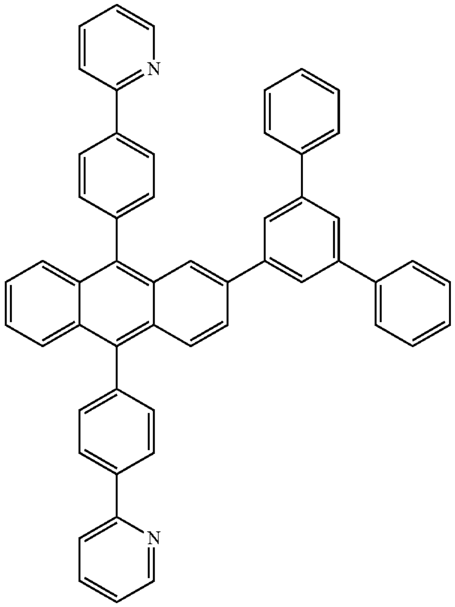
ET10
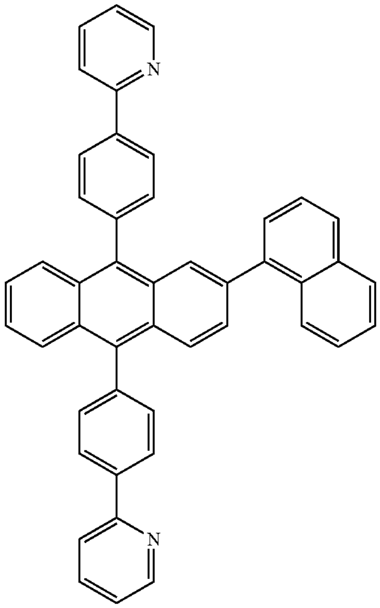

ET11
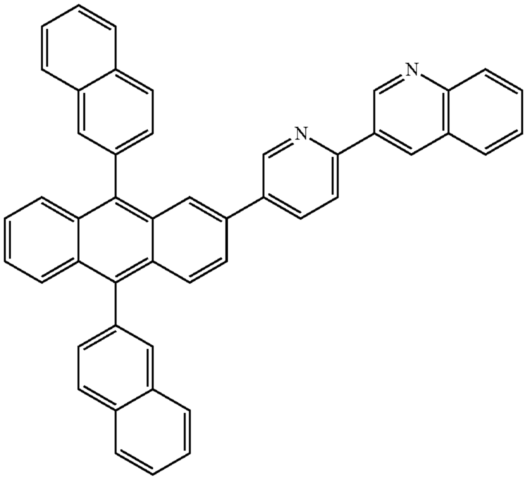
ET12
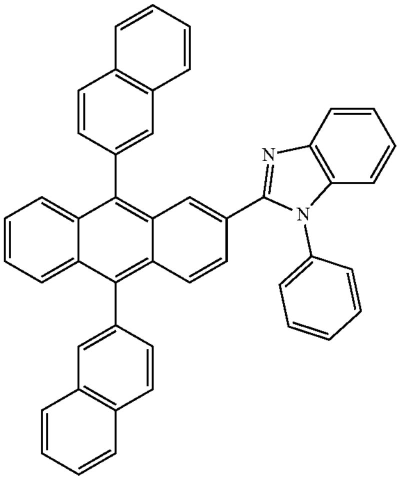
ET13
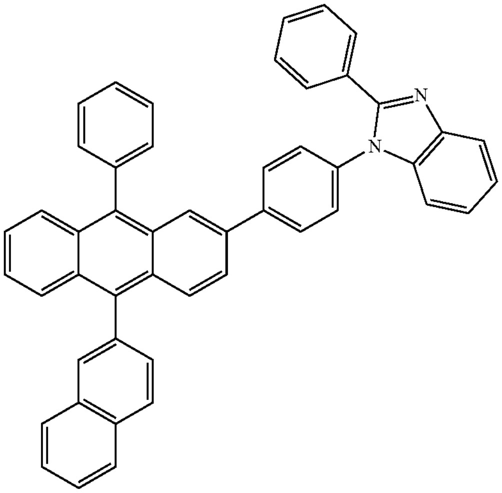
ET14
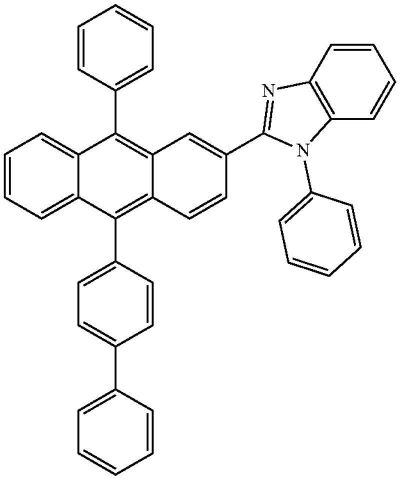
ET15
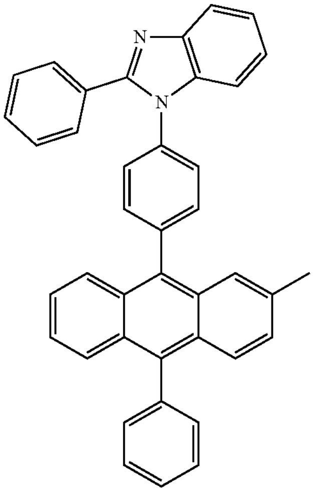
ET16
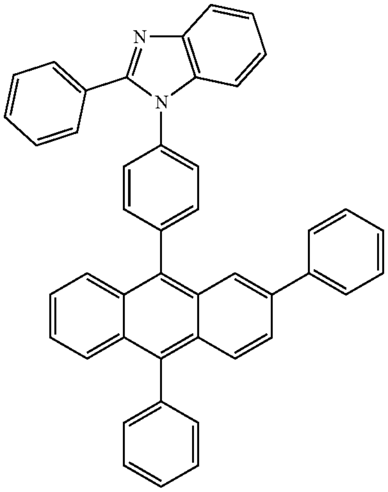

-continued
ET17
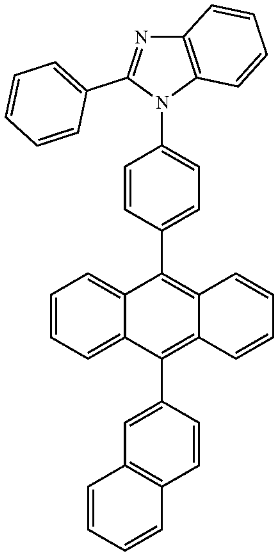
ET18
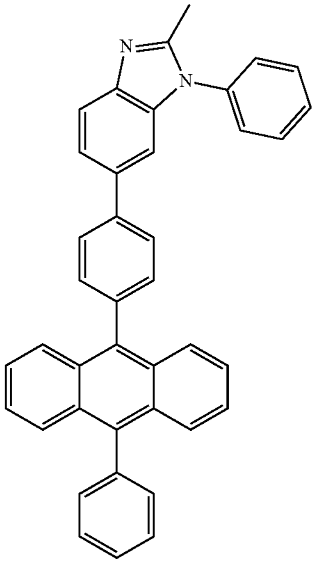
ET19
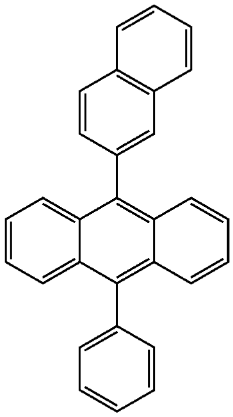
-continued
ET20
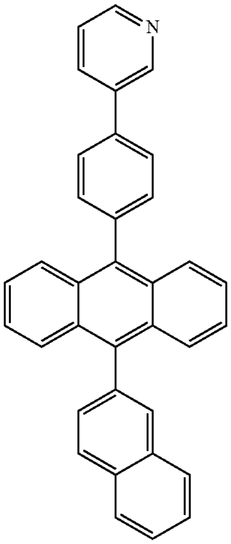
ET21
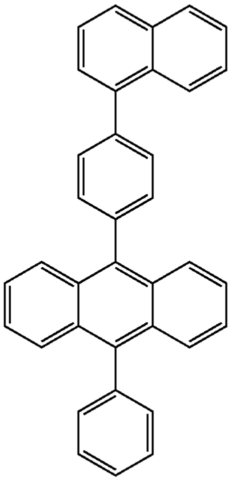
ET22
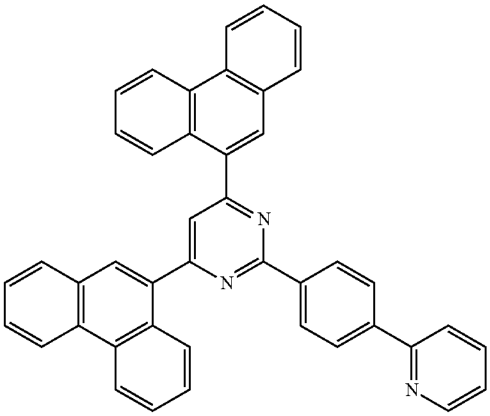

-continued
ET23
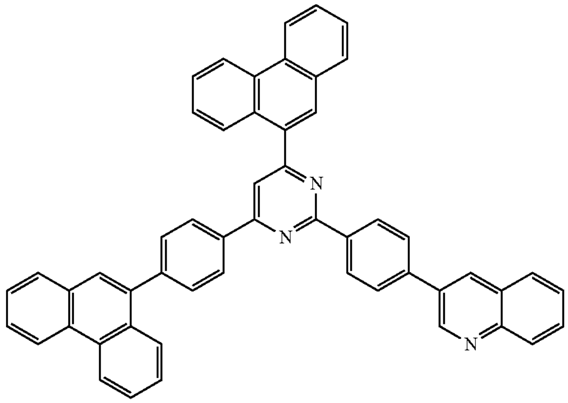
ET24
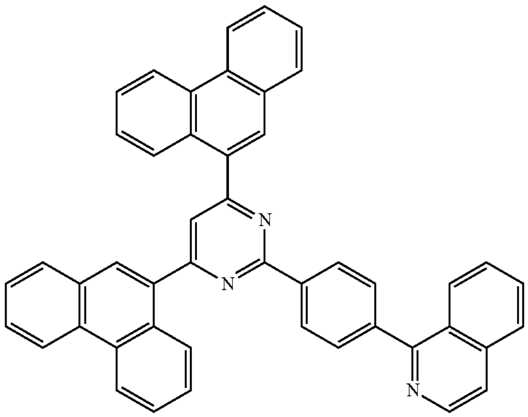
ET25
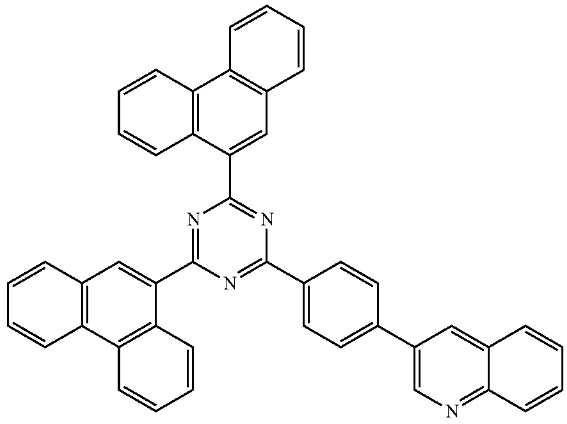
-continued
ET26
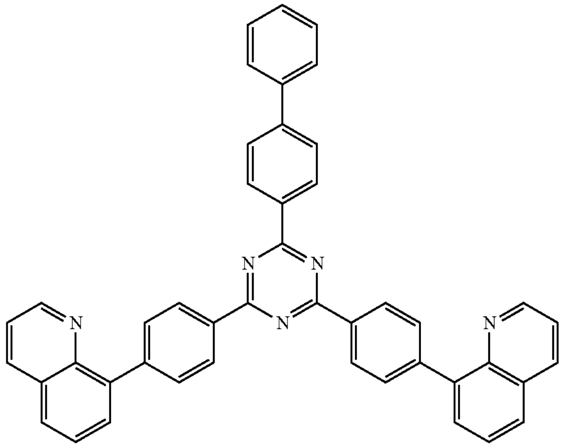
ET27
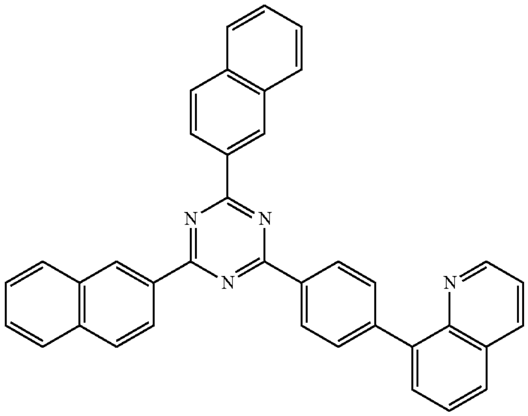
ET28
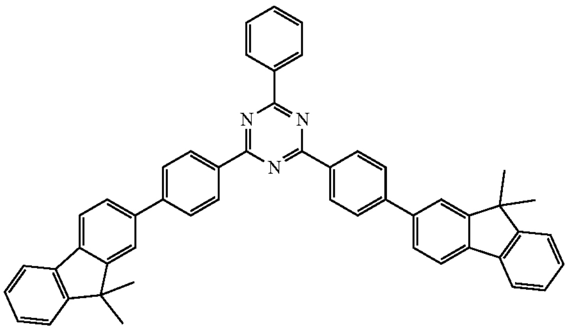

-continued
ET29
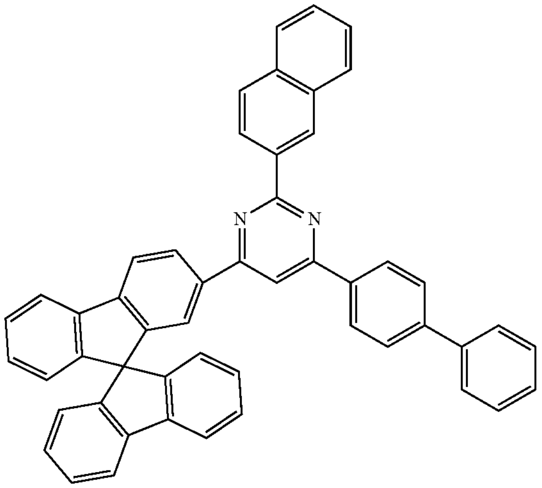
ET30
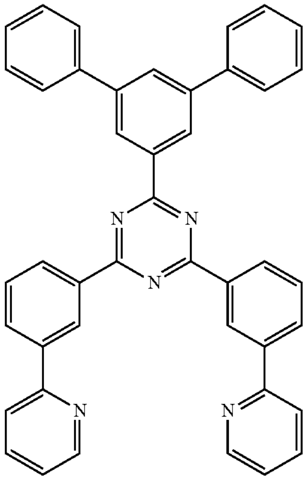
ET31
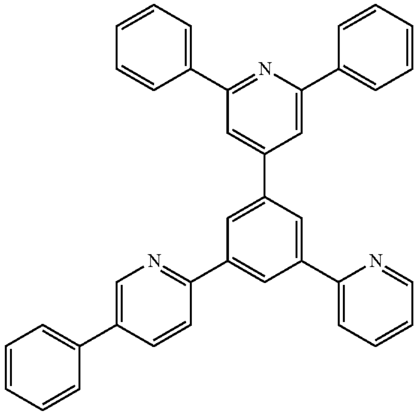
-continued
ET32
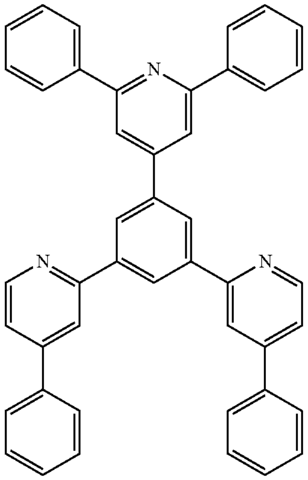
ET33
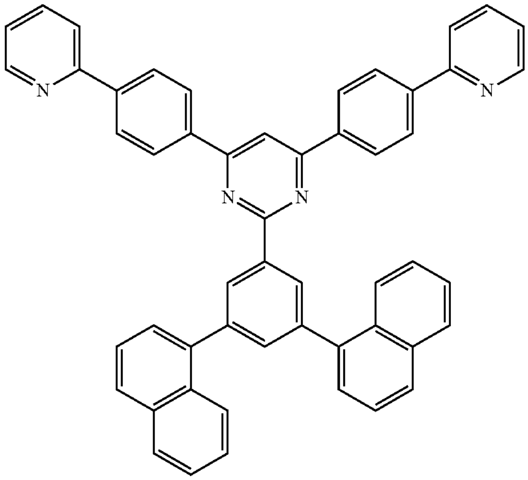
ET34
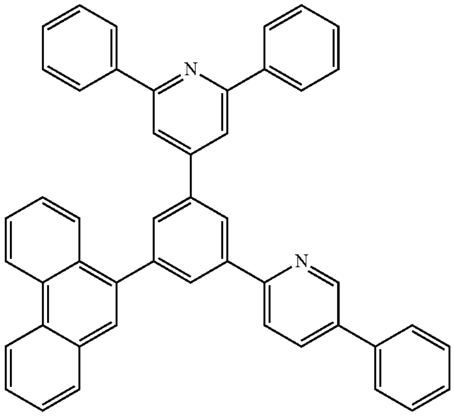

-continued
ET35
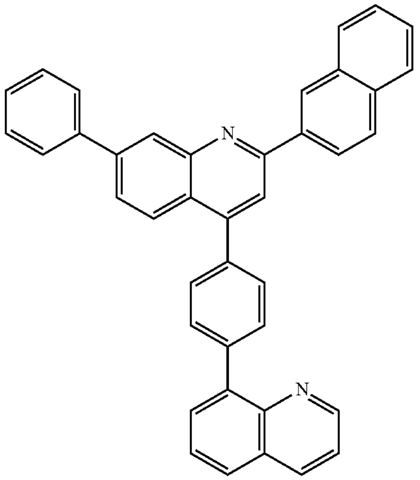
ET36
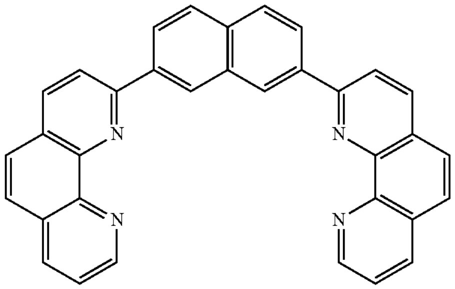
ET37
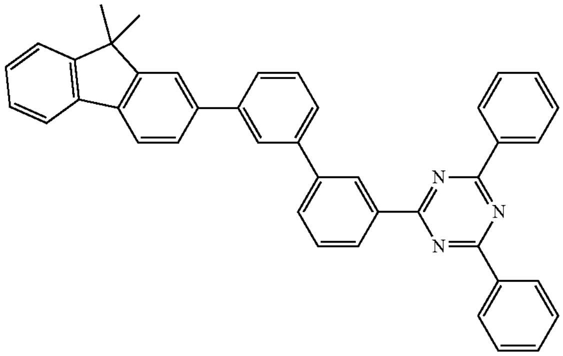
ET38
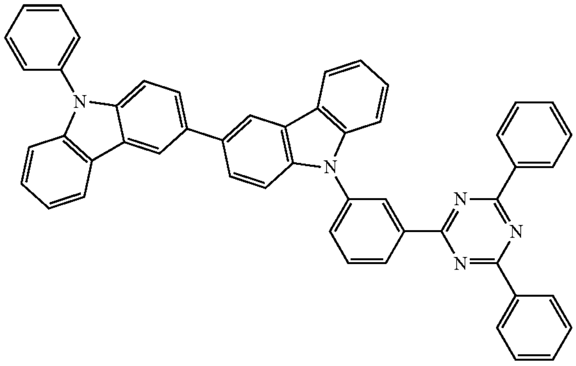
-continued
ET39
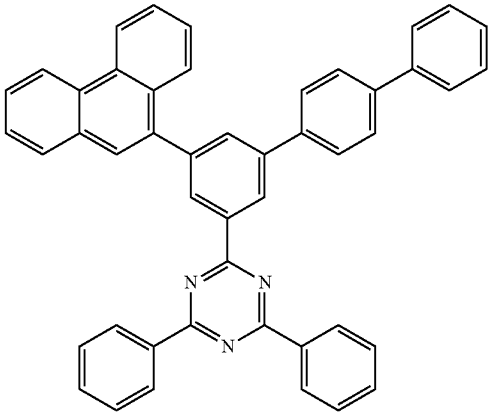
ET40
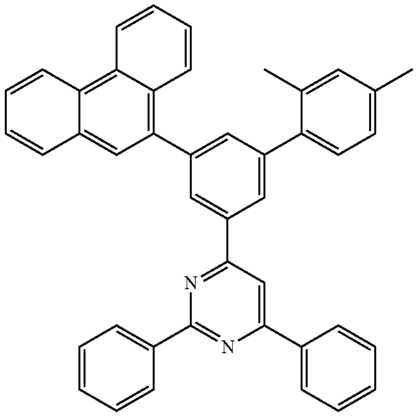
ET41
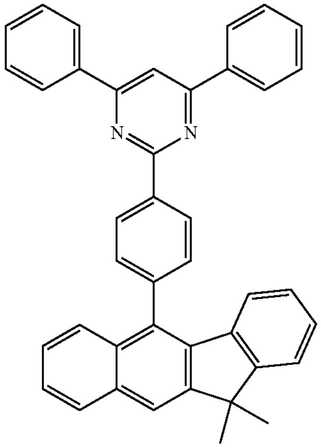

-continued
ET42
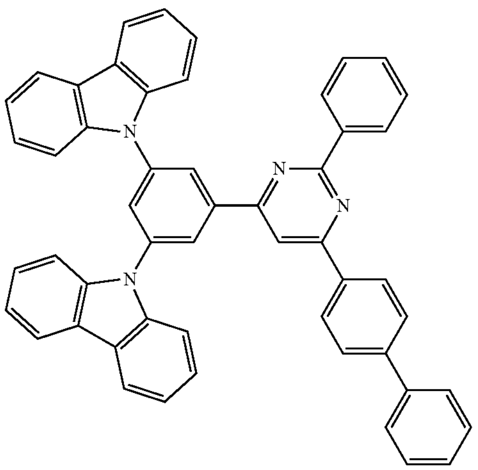
ET43
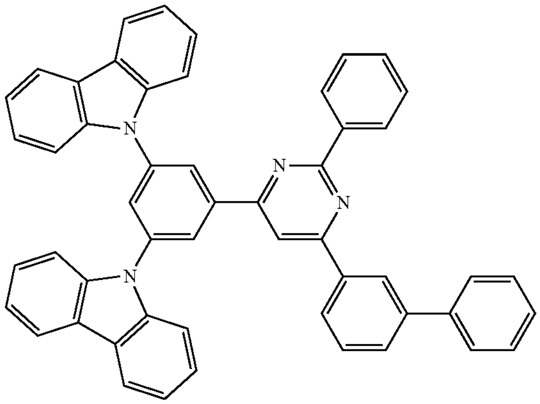
ET44
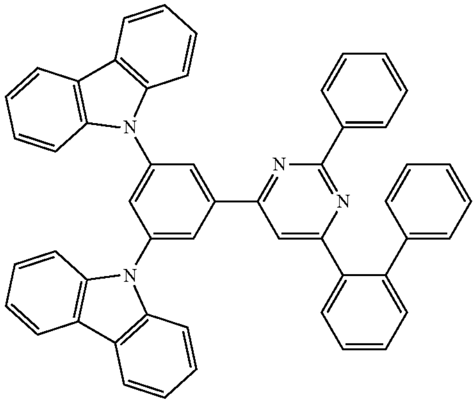
ET45
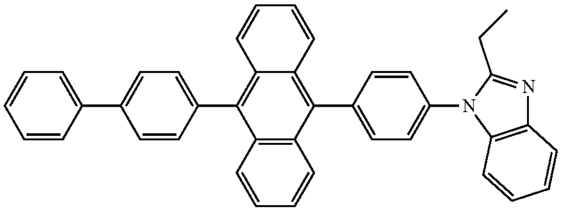
-continued
$Alq_3$
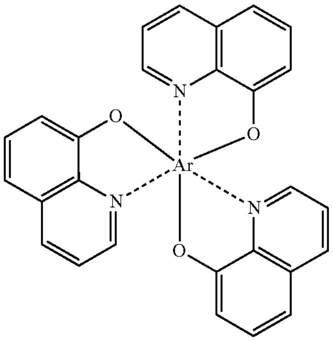
BAlq
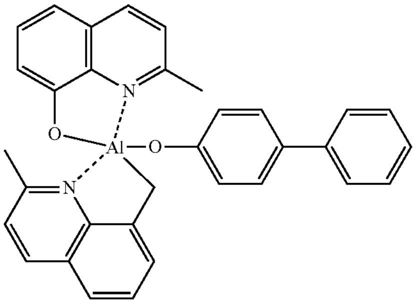
TAZ
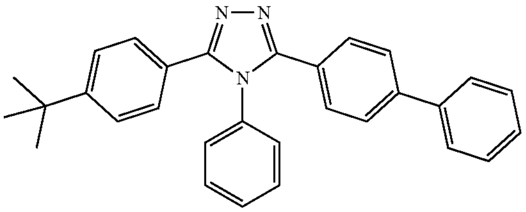
NTAZ
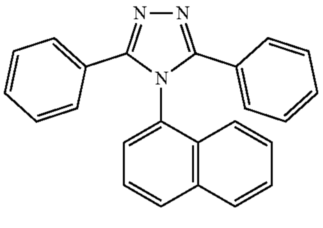
TSPO1
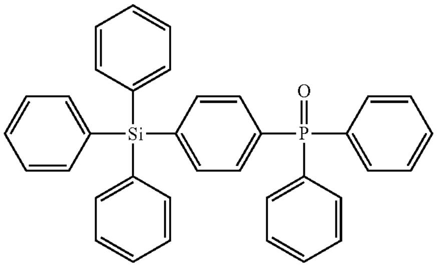

-continued

TPBI

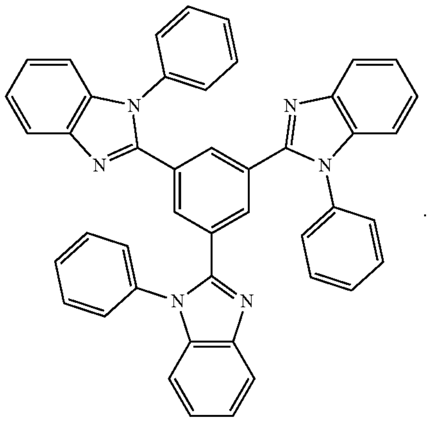

The thickness of the electron transport region may be from about 100 Å to about 5,000 Å, for example, from about 160 Å to about 4,000 Å. When the electron transport region includes the buffer layer, the hole blocking layer, the electron control layer, the electron transport layer, or any combination thereof, the thickness of the buffer layer, the hole blocking layer, or the electron control layer may each independently be from about 20 Å to about 1,000 Å, for example, about 30 Å to about 300 Å, and the thickness of the electron transport layer may be from about 100 Å to about 1,000 Å, for example, about 150 Å to about 500 Å. When the thicknesses of the buffer layer, hole blocking layer, electron control layer, electron transport layer and/or electron transport layer are within these ranges, satisfactory electron transporting characteristics may be obtained without a substantial increase in driving voltage.

The electron transport region (for example, the electron transport layer in the electron transport region) may further include, in addition to the materials described above, a metal-containing material. The metal-containing material may include an alkali metal complex, an alkaline earth metal complex, or any combination thereof. The metal ion of an alkali metal complex may be a Li ion, a Na ion, a K ion, a Rb ion, or a Cs ion, and the metal ion of the alkaline earth metal complex may be a Be ion, a Mg ion, a Ca ion, a Sr ion, or a Ba ion. A ligand coordinated with the metal ion of the alkali metal complex or the alkaline earth-metal complex may include a hydroxyquinoline, a hydroxyisoquinoline, a hydroxybenzoquinoline, a hydroxyacridine, a hydroxyphenanthridine, a hydroxyphenyloxazole, a hydroxyphenylthiazole, a hydroxyphenyloxadiazole, a hydroxyphenylthiadiazole, a hydroxyphenylpyridine, a hydroxyphenylbenzimidazole, a hydroxyphenylbenzothiazole, a bipyridine, a phenanthroline, a cyclopentadiene, or any combination thereof.

For example, the metal-containing material may include a Li complex. The Li complex may include, for example, Compound ET-D1 (lithium quinolate, LiQ) or ET-D2:

ET-D1

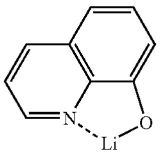

-continued

ET-D2

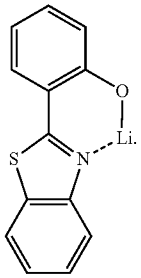

The electron transport region may include an electron injection layer that facilitates the injection of electrons from the second electrode 150. The electron injection layer may directly contact the second electrode 150.

The electron injection layer may have: i) a single-layered structure consisting of a single layer consisting of a single material, ii) a single-layered structure consisting of a single layer consisting of a plurality of different materials, or iii) a multi-layered structure including a plurality of layers including different materials.

The electron injection layer may include an alkali metal, an alkaline earth metal, a rare earth metal, an alkali metal-containing compound, an alkaline earth metal-containing compound, a rare earth metal-containing compound, an alkali metal complex, an alkaline earth metal complex, a rare earth metal complex, or any combination thereof. The alkali metal may include Li, Na, K, Rb, Cs, or any combination thereof. The alkaline earth metal may include Mg, Ca, Sr, Ba, or any combination thereof. The rare earth metal may include Sc, Y, Ce, Tb, Yb, Gd, or any combination thereof.

The alkali metal-containing compound, the alkaline earth metal-containing compound, and the rare earth metal-containing compound may be oxides, halides (for example, fluorides, chlorides, bromides, or iodides), or tellurides of the alkali metal, the alkaline earth metal, and the rare earth metal, or any combination thereof.

The alkali metal-containing compound may include alkali metal oxides, such as $Li_2O$, $Cs_2O$, or $K_2O$, alkali metal halides, such as LiF, NaF, CsF, KF, LiI, NaI, CsI, or KI, or any combination thereof. The alkaline earth metal-containing compound may include an alkaline earth metal compound, such as BaO, SrO, CaO, $Ba_xSr_{1-x}O$ (x is a real number satisfying the condition of $0<x<1$), $Ba_xCa_{1-x}O$ (x is a real number satisfying the condition of $0<x<1$), or the like. The rare earth metal-containing compound may include $YbF_3$, $ScF_3$, $Sc_2O_3$, $Y_2O_3$, $Ce_2O_3$, $GdF_3$, $TbF_3$, $YbI_3$, $ScI_3$, $TbI_3$, or any combination thereof. In one or more embodiments, the rare earth metal-containing compound may include a lanthanide metal telluride. Examples of the lanthanide metal telluride are LaTe, CeTe, PrTe, NdTe, PmTe, SmTe, EuTe, GdTe, TbTe, DyTe, HoTe, ErTe, TmTe, YbTe, LuTe, $La_2Te_3$, $Ce_2Te_3$, $Pr_2Te_3$, $Nd_2Te_3$, $Pm_2Te_3$, $Sm_2Te_3$, $Eu_2Te_3$, $Gd_2Te_3$, $Tb_2Te_3$, $Dy_2Te_3$, $Ho_2Te_3$, $Er_2Te_3$, $Tm_2Te_3$, $Yb_2Te_3$, and $Lu_2Te_3$.

The alkali metal complex, the alkaline earth-metal complex, and the rare earth metal complex may include i) one of ions of the alkali metal, the alkaline earth metal, and the rare earth metal and ii), as a ligand linked to the metal ion, for example, a hydroxyquinoline, a hydroxyisoquinoline, a hydroxybenzoquinoline, a hydroxyacridine, a hydroxyphenanthridine, a hydroxyphenyloxazole, a hydroxyphenylthiazole, a hydroxyphenyloxadiazole, a hydroxyphenylthiadiazole, a hydroxyphenylpyridine, a hydroxyphenyl benzimidazole, a hydroxyphenylbenzothiazole, a bipyridine, a phenanthroline, a cyclopentadiene, or any combination thereof.

The electron injection layer may consist of an alkali metal, an alkaline earth metal, a rare earth metal, an alkali metal-containing compound, an alkaline earth metal-containing compound, a rare earth metal-containing compound, an alkali metal complex, an alkaline earth metal complex, a rare earth metal complex, or any combination thereof, as described above. In one or more embodiments, the electron injection layer may further include an organic material (for example, a compound represented by Formula 601).

In one or more embodiments, the electron injection layer may consist of i) an alkali metal-containing compound (for example, an alkali metal halide), ii) a) an alkali metal-containing compound (for example, an alkali metal halide); and b) an alkali metal, an alkaline earth metal, a rare earth metal, or any combination thereof. In one or more embodiments, the electron injection layer may be a KI:Yb co-deposited layer, an RbI:Yb co-deposited layer, or the like.

When the electron injection layer further includes an organic material, an alkali metal, an alkaline earth metal, a rare earth metal, an alkali metal-containing compound, an alkaline earth metal-containing compound, a rare earth metal-containing compound, an alkali metal complex, an alkaline earth-metal complex, a rare earth metal complex, or any combination thereof may be homogeneously or non-homogeneously dispersed in a matrix including the organic material.

The thickness of the electron injection layer may be in a range of about 1 Å to about 100 Å, and, for example, about 3 Å to about 90 Å. When the thickness of the electron injection layer is within the range described above, the electron injection layer may have satisfactory electron injection characteristics without a substantial increase in driving voltage.

Second Electrode 150

The second electrode 150 may be located on the interlayer 130 having such a structure. The second electrode 150 may be a cathode, which is an electron injection electrode, and as the material for the second electrode 150, a metal, an alloy, an electrically conductive compound, or any combination thereof, each having a low work function, may be used.

In one or more embodiments, the second electrode 150 may include lithium (Li), silver (Ag), magnesium (Mg), aluminum (Al), aluminum-lithium (Al—Li), calcium (Ca), magnesium-indium (Mg—In), magnesium-silver (Mg—Ag), ytterbium (Yb), silver-ytterbium (Ag—Yb), an ITO, an IZO, or any combination thereof. The second electrode 150 may be a transmissive electrode, a semi-transmissive electrode, or a reflective electrode. The second electrode 150 may have a single-layered structure or a multi-layered structure including two or more layers.

Capping Layer

A first capping layer may be located outside the first electrode 110, and/or a second capping layer may be located outside the second electrode 150. In detail, the light-emitting device 10 may have a structure in which the first capping layer, the first electrode 110, the interlayer 130, and the second electrode 150 are sequentially stacked in this stated order, a structure in which the first electrode 110, the interlayer 130, the second electrode 150, and the second capping layer are sequentially stacked in this stated order, or a structure in which the first capping layer, the first electrode 110, the interlayer 130, the second electrode 150, and the second capping layer are sequentially stacked in this stated order.

Light generated in an emission layer of the interlayer 130 of the light-emitting device 10 may be extracted toward the outside through the first electrode 110, which is a semi-transmissive electrode or a transmissive electrode, and the first capping layer or light generated in an emission layer of the interlayer 130 of the light-emitting device 10 may be extracted toward the outside through the second electrode 150, which is a semi-transmissive electrode or a transmissive electrode, and the second capping layer.

Although not wanting to be bound by theory, the first capping layer and the second capping layer may increase external emission efficiency according to the principle of constructive interference. Accordingly, the light extraction efficiency of the light-emitting device 10 is increased, so that the emission efficiency of the light-emitting device 10 may be improved. Each of the first capping layer and second capping layer may include a material having a refractive index (at 589 nm) of about 1.6 or more.

The first capping layer and the second capping layer may each independently be an organic capping layer including an organic material, an inorganic capping layer including an inorganic material, or an organic-inorganic composite capping layer including an organic material and an inorganic material.

At least one selected from the first capping layer and the second capping layer may each independently include carbocyclic compounds, heterocyclic compounds, amine group-containing compounds, porphyrin derivatives, phthalocyanine derivatives, naphthalocyanine derivatives, alkali metal complexes, alkaline earth metal complexes, or any combination thereof. The carbocyclic compound, the heterocyclic compound, and the amine group-containing compound may be optionally substituted with a substituent containing O, N, S, Se, Si, F, Cl, Br, I, or any combination thereof. In one or more embodiments, at least one of the first capping layer and the second capping layer may each independently include an amine group-containing compound.

In one or more embodiments, at least one of the first capping layer and the second capping layer may each independently include a compound represented by Formula 201, a compound represented by Formula 202, or any combination thereof.

In one or more embodiments, at least one of the first capping layer and the second capping layer may each independently include one of Compounds HT28 to HT33, one of Compounds CP1 to CP6, N4,N4'-di(naphthalen-2-yl)-N4,N4'-diphenyl-[1,1'-biphenyl]-4,4'-diamine (β-NPB), or any combination thereof:

CP1
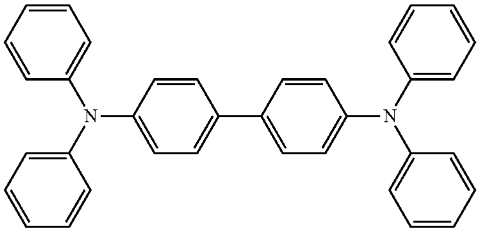
CP2
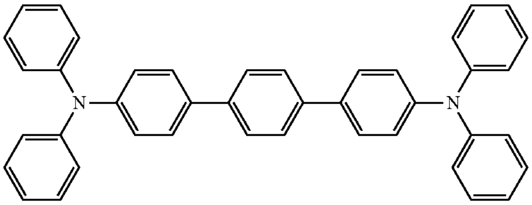
CP3
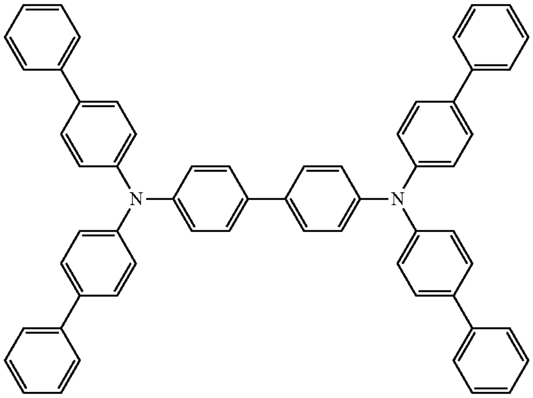
CP4
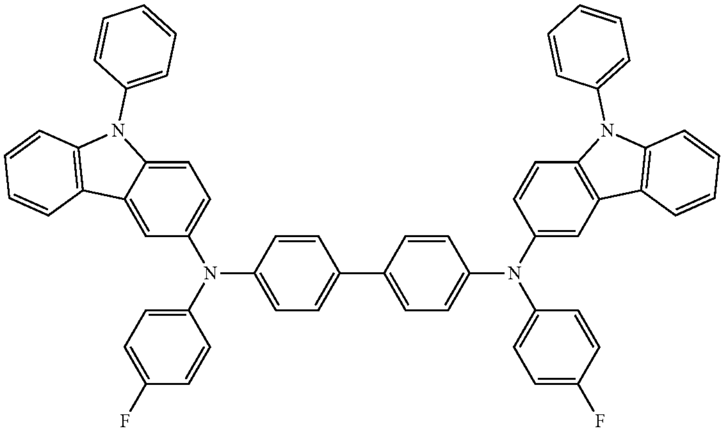
CP5
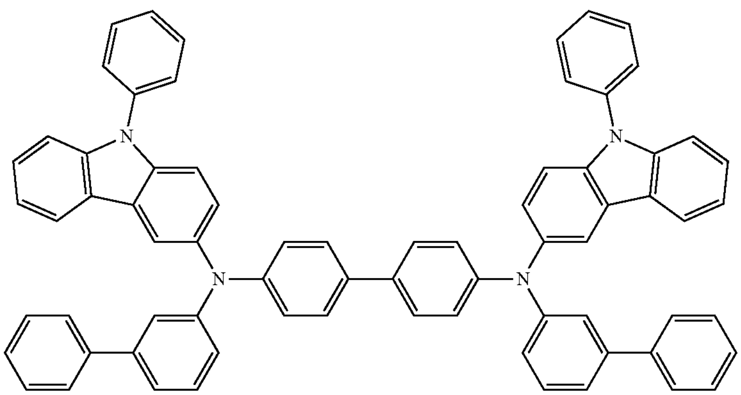

-continued

CP6

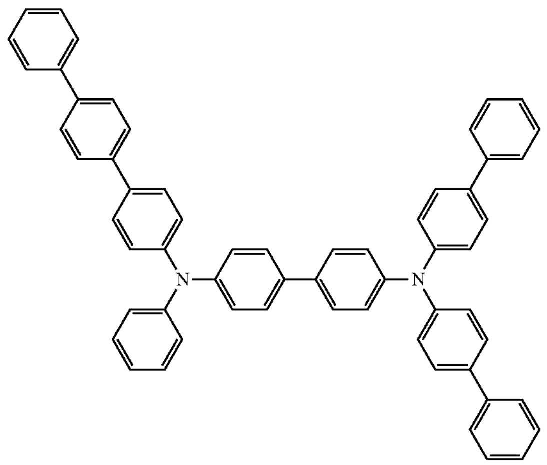

β-NPB

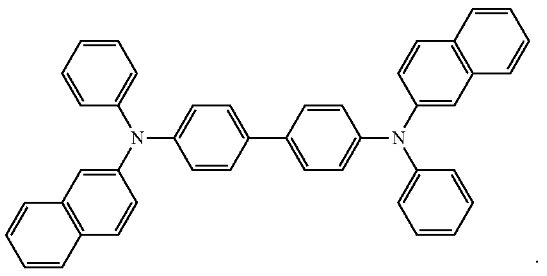

Electronic Apparatus

The light-emitting device 10 may be included in various electronic apparatuses. In one or more embodiments, the electronic apparatus including the light-emitting device may be a light-emitting apparatus, an authentication apparatus, or the like.

The electronic apparatus (for example, light-emitting apparatus) may further include, in addition to the light-emitting device 10, i) a color filter, ii) a color conversion layer, or iii) a color filter and a color conversion layer. The color filter and/or the color conversion layer may be located in at least one traveling direction of light emitted from the light-emitting device 10. In one or more embodiments, the light emitted from the light-emitting device 10 may be blue light or white light. The light-emitting device 10 may be the same as described above. In one or more embodiments, the color conversion layer may include quantum dots. The quantum dot may be, for example, a quantum dot as described herein.

The electronic apparatus may include a first substrate. The first substrate may include a plurality of subpixel areas, the color filter may include a plurality of color filter areas respectively corresponding to the subpixel areas, and the color conversion layer may include a plurality of color conversion areas respectively corresponding to the subpixel areas.

A pixel-defining film may be located among the subpixel areas to define each of the subpixel areas. The color filter may further include a plurality of color filter areas and light-shielding patterns located among the color filter areas, and the color conversion layer may include a plurality of color conversion areas and light-shielding patterns located among the color conversion areas.

The color filter areas (or the color conversion areas) may include a first area emitting first color light, a second area emitting second color light, and/or a third area emitting third color light, and the first color light, the second color light, and/or the third color light may have different maximum emission wavelengths from one another. In one or more embodiments, the first color light may be red light, the second color light may be green light, and the third color light may be blue light. In one or more embodiments, the color filter areas (or the color conversion areas) may include quantum dots. In detail, the first area may include a red quantum dot, the second area may include a green quantum dot, and the third area may not include a quantum dot. The quantum dot is the same as described herein. The first area, the second area, and/or the third area may each include a scatterer.

In one or more embodiments, the light-emitting device 10 may emit a first light, the first area may absorb the first light to emit first first-color light, the second area may absorb the first light to emit second first-color light, and the third area may absorb the first light to emit third first-color light. In this regard, the first first-color light, the second first-color light, and the third first-color light may have different maximum emission wavelengths. In detail, the first light may be blue light, the first first-color light may be red light, the second first-color light may be green light, and the third first-color light may be blue light.

The electronic apparatus may further include a thin-film transistor in addition to the light-emitting device 10 as described above. The thin-film transistor may include a source electrode, a drain electrode, and an activation layer, wherein any one of the source electrode and the drain electrode may be electrically connected to any one of the first electrode and the second electrode of the light-emitting device 10.

The thin-film transistor may further include a gate electrode, a gate insulating film, and the like. The activation layer may include a crystalline silicon, an amorphous silicon, an organic semiconductor, an oxide semiconductor, and the like.

The electronic apparatus may further include a sealing portion for sealing the light-emitting device 10. The sealing portion and/or the color conversion layer may be placed between the color filter and the light-emitting device 10. The sealing portion allows light from the light-emitting device 10 to be extracted to the outside, while simultaneously preventing ambient air and moisture from penetrating into the light-emitting device 10. The sealing portion may be a sealing substrate including a transparent glass substrate or a plastic substrate. The sealing portion may be a thin-film encapsulation layer including at least one layer of an organic layer and/or an inorganic layer. When the sealing portion is a thin film encapsulation layer, the electronic apparatus may be flexible.

Various functional layers may be additionally located on the sealing portion, in addition to the color filter and/or the color conversion layer, according to the use of the electronic apparatus. The functional layers may include a touch screen layer, a polarizing layer, and the like. The touch screen layer may be a pressure-sensitive touch screen layer, a capacitive touch screen layer, or an infrared touch screen layer. The authentication apparatus may be, for example, a biometric authentication apparatus that authenticates an individual by using biometric information of a living body (for example, fingertips, pupils, etc.). The authentication apparatus may further include, in addition to the light-emitting device 10, a biometric information collector.

The electronic apparatus may take the form of or be applied to various displays, light sources, lighting, personal computers (for example, a mobile personal computer), mobile phones, digital cameras, electronic organizers, electronic dictionaries, electronic game machines, medical instruments (for example, electronic thermometers, sphygmomanometers, blood glucose meters, pulse measurement devices, pulse wave measurement devices, electrocardiogram displays, ultrasonic diagnostic devices, or endoscope displays), fish finders, various measuring instruments, meters (for example, meters for a vehicle, an aircraft, and a vessel), projectors, and the like.

Figure 2:
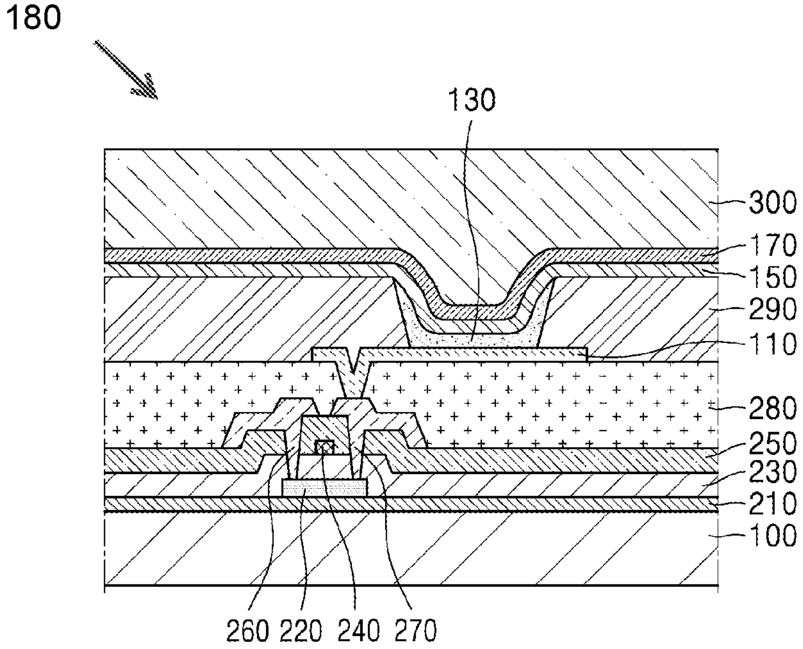
FIG. 2 is a schematic cross-sectional view of an embodiment of a light-emitting apparatus including a light-emitting device constructed according to the principles of the invention.
Figure 3:
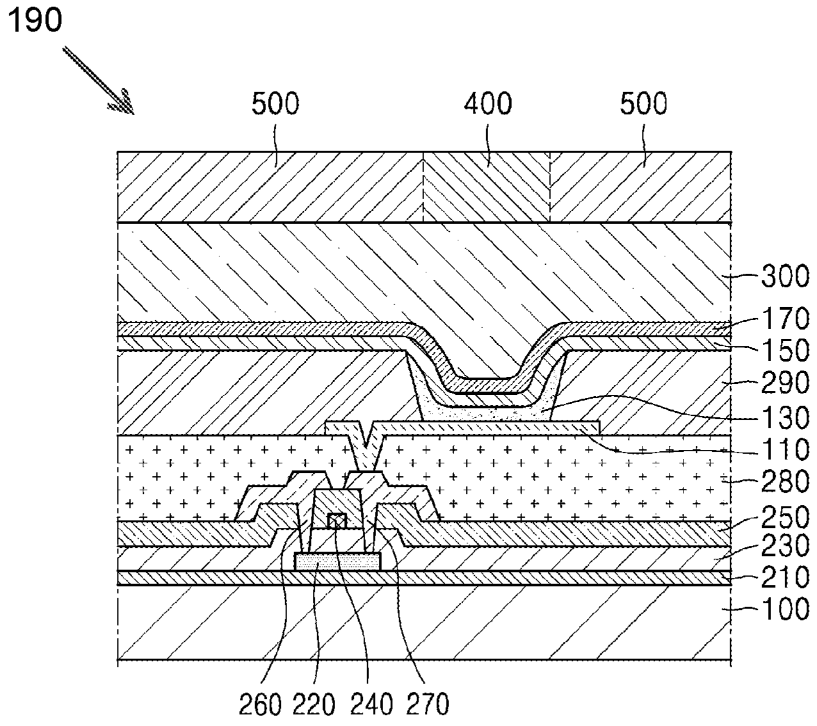
FIG. 3 is a schematic cross-sectional view of another embodiment of a light-emitting apparatus including a light-emitting device constructed according to the principles of the invention.

Description of FIGS. 2 and 3

FIG. 2 is a schematic cross-sectional view of an embodiment of a light-emitting apparatus including a light-emitting device constructed according to the principles of the invention.

The light-emitting apparatus 180 of FIG. 2 includes a substrate 100, a thin-film transistor (TFT) 200, a light-emitting device 10, and an encapsulation portion 300 that seals the light-emitting device 10.

The substrate 100 may be a flexible substrate, a glass substrate, or a metal substrate. A buffer layer 210 may be formed on the substrate 100. The buffer layer 210 may prevent penetration of impurities through the substrate 100 and may provide a substantially flat surface on the substrate 100.

The TFT 200 may be located on the buffer layer 210. The TFT 200 may include an activation layer 220, a gate electrode 240, a source electrode 260, and a drain electrode 270.

The activation layer 220 may include an inorganic semiconductor such as silicon or a polysilicon, an organic semiconductor, or an oxide semiconductor, and may include a source region, a drain region and a channel region.

A gate insulating film 230 for insulating the activation layer 220 from the gate electrode 240 may be located on the activation layer 220, and the gate electrode 240 may be located on the gate insulating film 230. An interlayer insulating film 250 is located on the gate electrode 240. The interlayer insulating film 250 may be placed between the gate electrode 240 and the source electrode 260 to insulate the gate electrode 240 from the source electrode 260 and between the gate electrode 240 and the drain electrode 270 to insulate the gate electrode 240 from the drain electrode 270.

The source electrode 260 and the drain electrode 270 may be located on the interlayer insulating film 250. The interlayer insulating film 250 and the gate insulating film 230 may be formed to expose the source region and the drain region of the activation layer 220, and the source electrode 260 and the drain electrode 270 may be in contact with the exposed portions of the source region and the drain region of the activation layer 220.

The TFT 200 is electrically connected to a light-emitting device 10 to drive the light-emitting device 10, and is covered by a passivation layer 280. The passivation layer 280 may include an inorganic insulating film, an organic insulating film, or any combination thereof. The light-emitting device 10 is provided on the passivation layer 280. The light-emitting device 10 may include a first electrode 110, an interlayer 130, and a second electrode 150.

The first electrode 110 may be formed on the passivation layer 280. The passivation layer 280 does not completely cover the drain electrode 270 and exposes a portion of the drain electrode 270, and the first electrode 110 is connected to the exposed portion of the drain electrode 270.

A pixel defining layer 290 containing an insulating material may be located on the first electrode 110. The pixel defining layer 290 exposes a region of the first electrode 110, and an interlayer 130 may be formed in the exposed region of the first electrode 110. The pixel defining layer 290 may be a polyimide or a polyacrylic organic film. At least some layers of the interlayer 130 may extend beyond the upper portion of the pixel defining layer 290 to be located in the form of a common layer.

The second electrode 150 may be located on the interlayer 130, and a capping layer 170 may be additionally formed on the second electrode 150. The capping layer 170 may be formed to cover the second electrode 150.

The encapsulation portion 300 may be located on the capping layer 170. The encapsulation portion 300 may be located on a light-emitting device 10 to protect the light-emitting device from moisture or oxygen. The encapsulation portion 300 may include: an inorganic film including a silicon nitride ($SiN_x$), a silicon oxide ($SiO_x$), an indium tin oxide, an indium zinc oxide, or any combination thereof; an organic film including a polyethylene terephthalate, a polyethylene naphthalate, a polycarbonate, a polyimide, a polyethylene sulfonate, a polyoxymethylene, a polyarylate, a hexamethyldisiloxane, an acrylic resin (for example, a polymethyl methacrylate, a polyacrylic acid, or the like), an epoxy-based resin (for example, an aliphatic glycidyl ether (AGE), or the like), or any combination thereof; or any combination of the inorganic film and the organic film.

FIG. 3 is a schematic cross-sectional view of another embodiment of a light-emitting apparatus including a light-emitting device constructed according to the principles of the invention.

The light-emitting apparatus 190 of FIG. 3 is the same as the light-emitting apparatus 180 of FIG. 2, except that a light-shielding pattern 500 and a functional region 400 are additionally located on the encapsulation portion 300. The functional region 400 may be a combination of i) a color filter area, ii) a color conversion area, or iii) a combination of the color filter area and the color conversion area. In one or more embodiments, the light-emitting device 10 included in the light-emitting apparatus 190 of FIG. 3 may be a tandem light-emitting device.

Manufacturing Method

Respective layers included in the hole transport region, the emission layer, and respective layers included in the electron transport region may be formed in a certain region by using one or more suitable methods selected from vacuum deposition, spin coating, casting, Langmuir-Blodgett (LB) deposition, ink-jet printing, laser-printing, and laser-induced thermal imaging.

When layers constituting the hole transport region, an emission layer, and layers constituting the electron transport region are formed by vacuum deposition, the deposition may be performed at a deposition temperature of about 100° C.

to about 500° C., a vacuum degree of about $10^{-8}$ torr to about $10^{-3}$ torr, and a deposition speed of about 0.01 Å/sec to about 100 Å/sec, depending on a material to be included in a layer to be formed and the structure of a layer to be formed.

Definition of Terms

As used herein, “interlayer” as used herein refers to a single layer and/or all layers between a first electrode and a second electrode of a light-emitting device. The wording “an (interlayer and/or capping layer) includes fused cyclic compound” may be interpreted as a case in which “an (interlayer and/or capping layer) includes at least one identical fused cyclic compound represented by Formula 1 or an (interlayer and/or capping layer) includes two or more different fused cyclic compounds represented by Formula 1.”

As used herein, the term “energy level” may be expressed in “electron volts” and abbreviated as “eV”.

As used herein, the term “atom” may mean an element or its corresponding radical bonded to one or more other atoms.

The terms “hydrogen” and “deuterium” refer to their respective atoms and corresponding radicals with the deuterium radical abbreviated “-D”, and the terms “—F, —Cl, —Br, and —I” are radicals of, respectively, fluorine, chlorine, bromine, and iodine.

As used herein, a substituent for a monovalent group, e.g., alkyl, may also be, independently, a substituent for a corresponding divalent group, e.g., alkylene.

The term “$C_3$-$C_{60}$ carbocyclic group” as used herein refers to a cyclic group consisting of carbon only as a ring-forming atom and having three to sixty carbon atoms, and the term “$C_1$-$C_{60}$ heterocyclic group” as used herein refers to a cyclic group that has one to sixty carbon atoms and further has, in addition to carbon, a heteroatom as a ring-forming atom. The $C_3$-$C_{60}$ carbocyclic group and the $C_1$-$C_{60}$ heterocyclic group may each be a monocyclic group consisting of one ring or a polycyclic group in which two or more rings are fused with each other. For example, the $C_1$-$C_{60}$ heterocyclic group has 3 to 61 ring-forming atoms.

The “cyclic group” as used herein may include the $C_3$-$C_{60}$ carbocyclic group, and the $C_1$-$C_{60}$ heterocyclic group.

The term “π electron-rich $C_3$-$C_{60}$ cyclic group” as used herein refers to a cyclic group that has three to sixty carbon atoms and does not include *—N=*' as a ring-forming moiety, and the term “π electron-deficient nitrogen-containing $C_1$-$C_{60}$ cyclic group” as used herein refers to a heterocyclic group that has one to sixty carbon atoms and includes *—N=*' as a ring-forming moiety.

For example, the $C_3$-$C_{60}$ carbocyclic group may be i) a group T1G or ii) a fused cyclic group in which two or more groups T1G are fused with each other, for example, a cyclopentadiene group, an adamantane group, a norbornane group, a benzene group, a pentalene group, a naphthalene group, an azulene group, an indacene group, an acenaphthylene group, a phenalene group, a phenanthrene group, an anthracene group, a fluoranthene group, a triphenylene group, a pyrene group, a chrysene group, a perylene group, a pentaphene group, a heptalene group, a naphthacene group, a picene group, a hexacene group, a pentacene group, a rubicene group, a coronene group, an ovalene group, an indene group, a fluorene group, a spirobifluorene group, a benzofluorene group, an indenophenanthrene group, or an indenoanthracene group.

The $C_1$-$C_{60}$ heterocyclic group may be i) a group T2G, ii) a fused cyclic group in which two or more groups T2G are fused with each other, or iii) a fused cyclic group in which at least one group T2G and at least one group T1G are fused with each other, for example, a pyrrole group, a thiophene group, a furan group, an indole group, a benzoindole group, a naphthoindole group, an isoindole group, a benzoisoindole group, a naphthoisoindole group, a benzosilole group, a benzothiophene group, a benzofuran group, a carbazole group, a dibenzosilole group, a dibenzothiophene group, a dibenzofuran group, an indenocarbazole group, an indolocarbazole group, a benzofurocarbazole group, a benzothienocarbazole group, a benzosilolocarbazole group, a benzoindolocarbazole group, a benzocarbazole group, a benzonaphthofuran group, a benzonaphthothiophene group, a benzonaphthosilole group, a benzofurodibenzofuran group, a benzofurodibenzothiophene group, a benzothienodibenzothiophene group, a pyrazole group, an imidazole group, a triazole group, an oxazole group, an isoxazole group, an oxadiazole group, a thiazole group, an isothiazole group, a thiadiazole group, a benzopyrazole group, a benzimidazole group, a benzoxazole group, a benzoisoxazole group, a benzothiazole group, a benzoisothiazole group, a pyridine group, a pyrimidine group, a pyrazine group, a pyridazine group, a triazine group, a quinoline group, an isoquinoline group, a benzoquinoline group, a benzoisoquinoline group, a quinoxaline group, a benzoquinoxaline group, a quinazoline group, a benzoquinazoline group, a phenanthroline group, a cinnoline group, a phthalazine group, a naphthyridine group, an imidazopyridine group, an imidazopyrimidine group, an imidazotriazine group, an imidazopyrazine group, an imidazopyridazine group, an azacarbazole group, an azafluorene group, an azadibenzosilole group, an azadibenzothiophene group, an azadibenzofuran group, etc.

The π electron-rich $C_3$-$C_{60}$ cyclic group may be i) a group T1G, ii) a fused cyclic group in which two or more groups T1G are fused with each other, iii) a group T3G, iv) a fused cyclic group in which two or more groups T3G are fused with each other, or v) a fused cyclic group in which at least one group T3G and at least one group T1G are fused with each other, for example, the $C_3$-$C_{60}$ carbocyclic group, a 1H-pyrrole group, a silole group, a borole group, a 2H-pyrrole group, a 3H-pyrrole group, a thiophene group, a furan group, an indole group, a benzoindole group, a naphthoindole group, an isoindole group, a benzoisoindole group, a naphthoisoindole group, a benzosilole group, a benzothiophene group, a benzofuran group, a carbazole group, a dibenzosilole group, a dibenzothiophene group, a dibenzofuran group, an indenocarbazole group, an indolocarbazole group, a benzofurocarbazole group, a benzothienocarbazole group, a benzosilolocarbazole group, a benzoindolocarbazole group, a benzocarbazole group, a benzonaphthofuran group, a benzonaphthothiophene group, a benzonaphthosilole group, a benzofurodibenzofuran group, a benzofurodibenzothiophene group, a benzothienodibenzothiophene group, etc.

The π electron-deficient nitrogen-containing $C_1$-$C_{60}$ cyclic group may be i) a group T4G, ii) a fused cyclic group in which two or more groups T4G are fused with each other, iii) a fused cyclic group in which at least one group T4G and at least one group T1G are fused with each other, iv) a fused cyclic group in which at least one group T4G and at least one group T3G are fused with each other, or v) a fused cyclic group in which at least one group T4G, at least one group T1G, and at least one group T3G are fused with one another, for example, a pyrazole group, an imidazole group, a triazole group, an oxazole group, an isoxazole group, an oxadiazole group, a thiazole group, an isothiazole group, a thiadiazole group, a benzopyrazole group, a benzimidazole group, a benzoxazole group, a benzoisoxazole group, a benzothiazole group, a benzoisothiazole group, a pyridine group, a pyrimidine group, a pyrazine group, a pyridazine group, a triazine group, a quinoline group, an isoquinoline group, a benzoquinoline group, a benzoisoquinoline group, a quinoxaline group, a benzoquinoxaline group, a quinazoline group, a benzoquinazoline group, a phenanthroline group, a cinnoline group, a phthalazine group, a naphthyridine group, an imidazopyridine group, an imidazopyrimidine group, an imidazotriazine group, an imidazopyrazine group, an imidazopyridazine group, an azacarbazole group, an azafluorene group, an azadibenzosilole group, an azadibenzothiophene group, an azadibenzofuran group, etc.

The group T1G may be a cyclopropane group, a cyclobutane group, a cyclopentane group, a cyclohexane group, a cycloheptane group, a cyclooctane group, a cyclobutene group, a cyclopentene group, a cyclopentadiene group, a cyclohexene group, a cyclohexadiene group, a cycloheptene group, an adamantane group, a norbornane (or a bicyclo[2.2.1]heptane) group, a norbornene group, a bicyclo[1.1.1]pentane group, a bicyclo[2.1.1]hexane group, a bicyclo[2.2.2]octane group, or a benzene group.

The group T2G may be a furan group, a thiophene group, a 1H-pyrrole group, a silole group, a borole group, a 2H-pyrrole group, a 3H-pyrrole group, an imidazole group, a pyrazole group, a triazole group, a tetrazole group, an oxazole group, an isoxazole group, an oxadiazole group, a thiazole group, an isothiazole group, a thiadiazole group, an azasilole group, an azaborole group, a pyridine group, a pyrimidine group, a pyrazine group, a pyridazine group, a triazine group, a tetrazine group, a pyrrolidine group, an imidazolidine group, a dihydropyrrole group, a piperidine group, a tetrahydropyridine group, a dihydropyridine group, a hexahydropyrimidine group, a tetrahydropyrimidine group, a dihydropyrimidine group, a piperazine group, a tetrahydropyrazine group, a dihydropyrazine group, a tetrahydropyridazine group, or a dihydropyridazine group.

The group T3G may be a furan group, a thiophene group, a 1H-pyrrole group, a silole group, or a borole group.

The group T4G may be a 2H-pyrrole group, a 3H-pyrrole group, an imidazole group, a pyrazole group, a triazole group, a tetrazole group, an oxazole group, an isoxazole group, an oxadiazole group, a thiazole group, an isothiazole group, a thiadiazole group, an azasilole group, an azaborole group, a pyridine group, a pyrimidine group, a pyrazine group, a pyridazine group, a triazine group, or a tetrazine group.

The terms "the cyclic group, the $C_3$-$C_{60}$ carbocyclic group, the $C_1$-$C_{60}$ heterocyclic group, the π electron-rich $C_3$-$C_{60}$ cyclic group, or the π electron-deficient nitrogen-containing $C_1$-$C_{60}$ cyclic group" as used herein refer to a group fused to any cyclic group or a polyvalent group (for example, a divalent group, a trivalent group, a tetravalent group, etc.), depending on the structure of a formula in connection with which the terms are used. In an embodiment, "a benzene group" may be a benzo group, a phenyl group, a phenylene group, or the like, which may be easily understand by one of ordinary skill in the art according to the structure of a formula including the "benzene group."

Examples of the monovalent $C_3$-$C_{60}$ carbocyclic group and the monovalent $C_1$-$C_{60}$ heterocyclic group are a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic fused polycyclic group, and a monovalent non-aromatic fused heteropolycyclic group, and examples of the divalent $C_3$-$C_{60}$ carbocyclic group and the monovalent $C_1$-$C_{60}$ heterocyclic group are a $C_3$-$C_{10}$ cycloalkylene group, a $C_1$-$C_{10}$ heterocycloalkylene group, a $C_3$-$C_{10}$ cycloalkenylene group, a $C_1$-$C_{10}$ heterocycloalkenylene group, a $C_6$-$C_{60}$ arylene group, a $C_1$-$C_{60}$ heteroarylene group, a divalent non-aromatic fused polycyclic group, and a substituted or unsubstituted divalent non-aromatic fused heteropolycyclic group.

The term "$C_1$-$C_{60}$ alkyl group" as used herein refers to a linear or branched aliphatic hydrocarbon monovalent group that has one to sixty carbon atoms, and examples thereof are a methyl group, an ethyl group, an n-propyl group, an isopropyl group, an n-butyl group, a sec-butyl group, an isobutyl group, a tert-butyl group, an n-pentyl group, a tert-pentyl group, a neopentyl group, an isopentyl group, a sec-pentyl group, a 3-pentyl group, a sec-isopentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, and a tert-decyl group. The term "$C_1$-$C_{60}$ alkylene group" as used herein refers to a divalent group having a structure corresponding to the $C_1$-$C_{60}$ alkyl group.

The term "$C_2$-$C_{60}$ alkenyl group" as used herein refers to a monovalent hydrocarbon group having at least one carbon-carbon double bond in the middle or at the terminus of the $C_2$-$C_{60}$ alkyl group, and examples thereof are an ethenyl group, a propenyl group, and a butenyl group. The term "$C_2$-$C_{60}$ alkenylene group" as used herein refers to a divalent group having a structure corresponding to the $C_2$-$C_{60}$ alkenyl group.

The term "$C_2$-$C_{60}$ alkynyl group" as used herein refers to a monovalent hydrocarbon group having at least one carbon-carbon triple bond in the middle or at the terminus of the $C_2$-$C_{60}$ alkyl group, and examples thereof include an ethynyl group and a propynyl group. The term "$C_2$-$C_{60}$ alkynylene group" as used herein refers to a divalent group having a structure corresponding to the $C_2$-$C_{60}$ alkynyl group.

The term "$C_1$-$C_{60}$ alkoxy group" as used herein refers to a monovalent group represented by $—OA_{101}$ (wherein $A_{101}$ is the $C_1$-$C_{60}$ alkyl group), and examples thereof include a methoxy group, an ethoxy group, and an isopropyloxy group.

The term "$C_3$-$C_{10}$ cycloalkyl group" as used herein refers to a monovalent saturated hydrocarbon cyclic group having 3 to 10 carbon atoms, and examples thereof are a cyclopropyl group, a cyclobutyl group, a cyclopentyl group, a cyclohexyl group, a cycloheptyl group, a cyclooctyl group, an adamantanyl group, a norbornanyl group (or bicyclo[2.2.1]heptyl group), a bicyclo[1.1.1]pentyl group, a bicyclo[2.1.1]hexyl group, and a bicyclo[2.2.2]octyl group. The term "$C_3$-$C_{10}$ cycloalkylene group" as used herein refers to a divalent group having a structure corresponding to the $C_3$-$C_{10}$ cycloalkyl group.

The term "$C_1$-$C_{10}$ heterocycloalkyl group" as used herein refers to a monovalent cyclic group that further includes, in addition to a carbon atom, at least one heteroatom as a ring-forming atom and has 1 to 10 carbon atoms, and examples thereof are a 1,2,3,4-oxatriazolidinyl group, a tetrahydrofuranyl group, and a tetrahydrothiophenyl group. The term "$C_1$-$C_{10}$ heterocycloalkylene group" as used herein refers to a divalent group having a structure corresponding to the $C_1$-$C_{10}$ heterocycloalkyl group.

The term $C_3$-$C_{10}$ cycloalkenyl group used herein refers to a monovalent cyclic group that has three to ten carbon atoms and at least one carbon-carbon double bond in the ring thereof and no aromaticity, and examples thereof are a cyclopentenyl group, a cyclohexenyl group, and a cycloheptenyl group. The term "$C_3$-$C_{10}$ cycloalkenylene group" as used herein refers to a divalent group having a structure corresponding to the $C_3$-$C_{10}$ cycloalkenyl group.

The term "$C_1$-$C_{10}$ heterocycloalkenyl group" as used herein refers to a monovalent cyclic group that has, in addition to a carbon atom, at least one heteroatom as a ring-forming atom, 1 to 10 carbon atoms, and at least one carbon-carbon double bond in the cyclic structure thereof. Examples of the $C_1$-$C_{10}$ heterocycloalkenyl group include a 4,5-dihydro-1,2,3,4-oxatriazolyl group, a 2,3-dihydrofuranyl group, and a 2,3-dihydrothiophenyl group. The term "$C_1$-$C_{10}$ heterocycloalkenylene group" as used herein refers to a divalent group having a structure corresponding to the $C_1$-$C_{10}$ heterocycloalkenyl group.

The term "$C_6$-$C_{60}$ aryl group" as used herein refers to a monovalent group having a carbocyclic aromatic system having six to sixty carbon atoms, and the term "$C_6$-$C_{60}$ arylene group" as used herein refers to a divalent group having a carbocyclic aromatic system having six to sixty carbon atoms. Examples of the $C_6$-$C_{60}$ aryl group are a phenyl group, a pentalenyl group, a naphthyl group, an azulenyl group, an indacenyl group, an acenaphthyl group, a phenalenyl group, a phenanthrenyl group, an anthracenyl group, a fluoranthenyl group, a triphenylenyl group, a pyrenyl group, a chrysenyl group, a perylenyl group, a pentaphenyl group, a heptalenyl group, a naphthacenyl group, a picenyl group, a hexacenyl group, a pentacenyl group, a rubicenyl group, a coronenyl group, and an ovalenyl group. When the $C_6$-$C_{60}$ aryl group and the $C_6$-$C_{60}$ arylene group each include two or more rings, the rings may be fused with each other.

The term "$C_1$-$C_{60}$ heteroaryl group" as used herein refers to a monovalent group having a heterocyclic aromatic system that has, in addition to a carbon atom, at least one heteroatom as a ring-forming atom, and 1 to 60 carbon atoms. The term "$C_1$-$C_{60}$ heteroarylene group" as used herein refers to a divalent group having a heterocyclic aromatic system that has, in addition to a carbon atom, at least one heteroatom as a ring-forming atom, and 1 to 60 carbon atoms. Examples of the $C_1$-$C_{60}$ heteroaryl group are a pyridinyl group, a pyrimidinyl group, a pyrazinyl group, a pyridazinyl group, a triazinyl group, a quinolinyl group, a benzoquinolinyl group, an isoquinolinyl group, a benzoisoquinolinyl group, a quinoxalinyl group, a benzoquinoxalinyl group, a quinazolinyl group, a benzoquinazolinyl group, a cinnolinyl group, a phenanthrolinyl group, a phthalazinyl group, and a naphthyridinyl group. When the $C_1$-$C_{60}$ heteroaryl group and the $C_1$-$C_{60}$ heteroarylene group each include two or more rings, the rings may be fused with each other.

The term "monovalent non-aromatic fused polycyclic group" as used herein refers to a monovalent group (for example, having 8 to 60 carbon atoms) having two or more rings fused to each other, only carbon atoms as ring-forming atoms, and no aromaticity in its entire molecular structure. Examples of the monovalent non-aromatic fused polycyclic group are an indenyl group, a fluorenyl group, a spiro-bifluorenyl group, a benzofluorenyl group, an indeno-phenanthrenyl group, and an indeno anthracenyl group. The term "divalent non-aromatic fused polycyclic group" as used herein refers to a divalent group having a structure corresponding to a monovalent non-aromatic fused polycyclic group.

The term "monovalent non-aromatic fused heteropolycyclic group" as used herein refers to a monovalent group (for example, having 1 to 60 carbon atoms) having two or more rings fused to each other, at least one heteroatom other than carbon atoms, as a ring-forming atom, and non-aromaticity in its entire molecular structure. Examples of the monovalent non-aromatic fused heteropolycyclic group are a pyrrolyl group, a thiophenyl group, a furanyl group, an indolyl group, a benzoindolyl group, a naphtho indolyl group, an isoindolyl group, a benzoisoindolyl group, a naphthoisoindolyl group, a benzosilolyl group, a benzothiophenyl group, a benzofuranyl group, a carbazolyl group, a dibenzosilolyl group, a dibenzothiophenyl group, a dibenzofuranyl group, an azacarbazolyl group, an azafluorenyl group, an azadibenzosilolyl group, an azadibenzothiophenyl group, an azadibenzofuranyl group, a pyrazolyl group, an imidazolyl group, a triazolyl group, a tetrazolyl group, an oxazolyl group, an isoxazolyl group, a thiazolyl group, an isothiazolyl group, an oxadiazolyl group, a thiadiazolyl group, a benzopyrazolyl group, a benzimidazolyl group, a benzoxazolyl group, a benzothiazolyl group, a benzoxadiazolyl group, a benzothiadiazolyl group, an imidazopyridinyl group, an imidazopyrimidinyl group, an imidazotriazinyl group, an imidazopyrazinyl group, an imidazopyridazinyl group, an indenocarbazolyl group, an indolocarbazolyl group, a benzofurocarbazolyl group, a benzothienocarbazolyl group, a benzosilolocarbazolyl group, a benzoindolocarbazolyl group, a benzocarbazolyl group, a benzonaphthofuranyl group, a benzonaphthothiophenyl group, a benzonaphthosilolyl group, a benzofurodibenzofuranyl group, a benzofurodibenzothiophenyl group, and a benzothienodibenzothiophenyl group. The term "divalent non-aromatic fused heteropolycyclic group" as used herein refers to a divalent group having a structure corresponding to a monovalent non-aromatic fused heteropolycyclic group.

The term "$C_6$-$C_{60}$ aryloxy group" as used herein indicates —$OA_{102}$ (wherein $A_{102}$ is the $C_6$-$C_{60}$ aryl group), and the term "$C_6$-$C_{60}$ arylthio group" as used herein indicates —$SA_{103}$ (wherein $A_{103}$ is the $C_6$-$C_{60}$ aryl group).

The term "$C_7$-$C_{60}$ aryl alkyl group" used herein refers to -$A_{104}A_{105}$ (where $A_{104}$ may be a $C_1$-$C_{54}$ alkylene group, and $A_{105}$ may be a $C_6$-$C_{59}$ aryl group), and the term $C_2$-$C_{60}$ heteroaryl alkyl group" used herein refers to -$A_{106}A_{107}$ (where $A_{106}$ may be a $C_1$-$C_{59}$ alkylene group, and $A_{107}$ may be a $C_1$-$C_{59}$ heteroaryl group).

The term "$R_{10a}$" as used herein refers to:

deuterium (-D), —F, —Cl, —Br, —I, a hydroxyl group, a cyano group, or a nitro group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each unsubstituted or substituted with deuterium, —F, —Cl, —Br, —I, a hydroxyl group, a cyano group, a nitro group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, a $C_2$-$C_{60}$ heteroaryl alkyl group, —$Si(Q_{11})(Q_{12})(Q_{13})$, —$N(Q_{11})(Q_{12})$, —$B(Q_{11})(Q_{12})$, —$C(=O)(Q_{11})$, —$S(=O)_2(Q_{11})$, —$P(=O)(Q_{11})(Q_{12})$, or any combination thereof;

a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, or a $C_2$-$C_{60}$ heteroaryl alkyl group, each unsubstituted or substituted with deuterium, —F, —Cl, —Br, —I, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, a $C_2$-$C_{60}$ heteroaryl alkyl group, —$Si(Q_{21})(Q_{22})(Q_{23})$, —$N(Q_{21})(Q_{22})$, —$B(Q_{21})(Q_{22})$, —$C(=O)(Q_{21})$, —$S(=O)_2(Q_{21})$, —$P(=O)(Q_{21})(Q_{22})$, or any combination thereof; or —$Si(Q_{31})(Q_{32})(Q_{33})$, —$N(Q_{31})(Q_{32})$, —$B(Q_{31})(Q_{32})$, —$C(=O)(Q_{31})$, —$S(=O)_2(Q_{31})$, or —$P(=O)(Q_{31})(Q_{32})$, The groups $Q_1$ to $Q_3$, $Q_{11}$ to $Q_{13}$, $Q_{21}$ to $Q_{23}$ and $Q_{31}$ to $Q_{33}$ used herein may each independently be: hydrogen; deuterium; —F; —Cl; —Br; —I; a hydroxyl group; a cyano group; a nitro group; a $C_1$-$C_{60}$ alkyl group; a $C_2$-$C_{60}$ alkenyl group; a $C_2$-$C_{60}$ alkynyl group; a $C_1$-$C_{60}$ alkoxy group; a $C_3$-$C_{60}$ carbocyclic group or a $C_1$-$C_{60}$ heterocyclic group, each unsubstituted or substituted with deuterium, —F, a cyano group, a $C_1$-$C_{60}$ alkyl group, a $C_1$-$C_{60}$ alkoxy group, a phenyl group, a biphenyl group, or any combination thereof; a $C_7$-$C_{60}$ aryl alkyl group; or a $C_2$-$C_{60}$ heteroaryl alkyl group.

The term "heteroatom" as used herein refers to any atom other than a carbon atom. Examples of the heteroatom are O, S, N, P, Si, B, Ge, Se, and any combination thereof.

The term "the third-row transition metal" used herein includes hafnium (Hf), tantalum (Ta), tungsten (W), rhenium (Re), osmium (Os), iridium (Ir), platinum (Pt), gold (Au), etc.

As used herein, the term "Ph" refers to a phenyl group, the term "Me" refers to a methyl group, the term "Et" refers to an ethyl group, the term "tert-Bu" or "$Bu^t$" refers to a tert-butyl group, and the term "OMe" refers to a methoxy group.

The term "biphenyl group" as used herein refers to "a phenyl group substituted with a phenyl group." In other words, the "biphenyl group" is a substituted phenyl group having a $C_6$-$C_{60}$ aryl group as a substituent.

The term "terphenyl group" as used herein refers to "a phenyl group substituted with a biphenyl group". In other words, the "terphenyl group" is a substituted phenyl group having, as a substituent, a $C_6$-$C_{60}$ aryl group substituted with a $C_6$-$C_{60}$ aryl group.

The abbreviation "eq." means "mole equivalent".

The symbols * and *' as used herein, unless defined otherwise, each refer to a binding site to a neighboring atom in a corresponding formula or moiety.

An expression "B is used instead of A" means that the identical molar equivalent of B was used in place of A in the same molar equivalent.

EXAMPLES

Synthesis Example 1: Synthesis of Compound 1

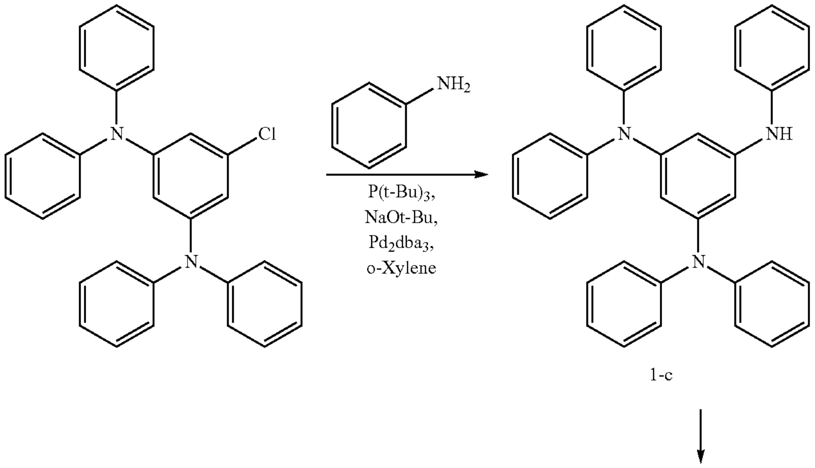

1-c

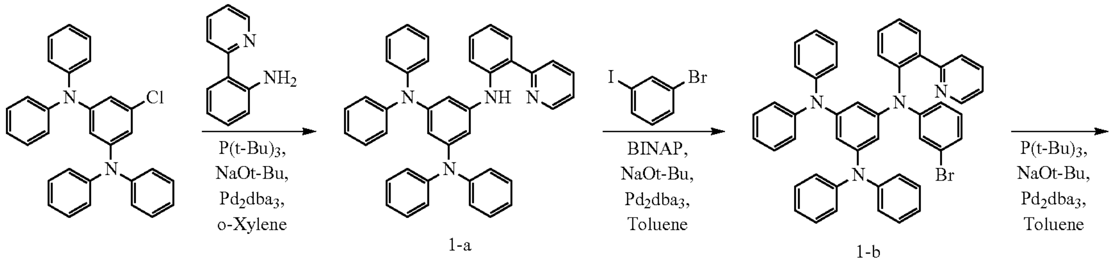

1-a 1-b

-continued

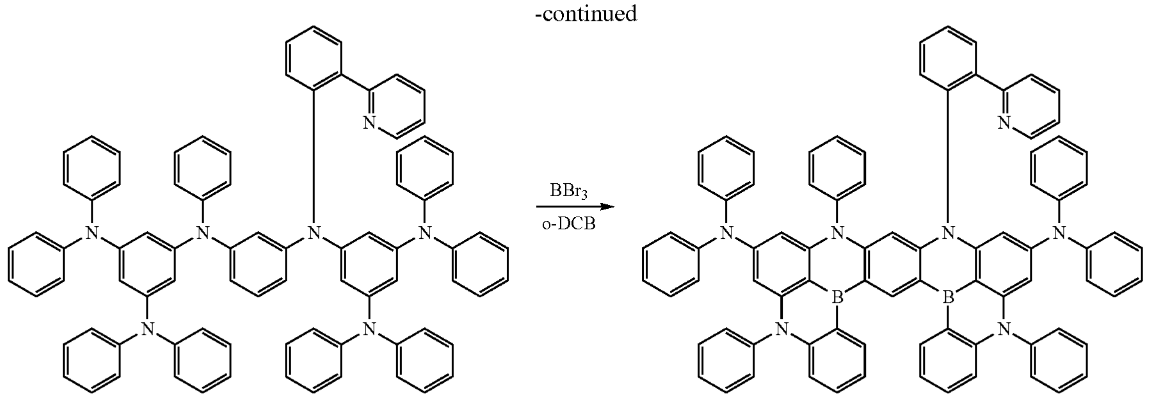

1-d 1

Synthesis of Intermediate Compound 1-a

In an argon atmosphere, 5-chloro-N1,N1,N3,N3-tetraphenylbenzene-1,3-diamine (50 gram (g), 112 millimole (mmol)), 2-(pyridine-2-yl)aniline (19 g, 112 mmol), sodium tert-butoxide (32 g, 336 mmol), tris-tert-butyl phosphine (5 ml, 11.2 mmol), and tris(dibenzylideneacetone)dipalladium (0) $Pd_2dba_3$ (5.12 g, 5.6 mmol) were added to a 2 liter (L) flask and dissolved in 1 L of o-xylene, and the reaction solution was stirred at temperature of 140° C. for 12 hours. After cooling, water (1 L) and ethylacetate (300 ml) were added thereto for extraction and collection of an organic layer, and was dried using magnesium sulfate ($MgSO_4$) and filtered. The filtered solution was placed under reduced pressure to remove solvent therefrom, and the obtained solid was purified and separated by column chromatography using silica gel and using dichloromethane ($CH_2Cl_2$) and hexane as development solvents to thereby obtain Intermediate compound 1-a (white solid, 41 g, 64%). The obtained white solid was identified by ESI-LCMS as Intermediate compound 1-a.

ESI-LCMS: $[M]^+$: $C_{41}H_{32}N_4$. 580.2612.

Synthesis of Intermediate Compound 1-b

In an argon atmosphere, Compound 1-a (40 g, 69 mmol), 3-bromo-iodobenzene (19.5 g, 69 mmol), sodium tert-butoxide (20 g, 207 mmol), 2,2'-Bis(diphenylphosphino)-1,1'-binaphthyl (BINAP in an amount of 4.3 g in 7.0 mmol), and $Pd_2dba_3$ (3.1 g, 3.5 mmol) were added to a 2 L flask and dissolved in 700 milliliter (ml) of toluene, and the reaction solution was stirred at a temperature of 100° C. for 12 hours. After cooling, water (1 L) and ethylacetate (300 ml) were added thereto for extraction and collection of an organic layer, and was dried using $MgSO_4$ and filtered. The filtered solution was placed under reduced pressure to remove solvent therefrom, and the obtained solid was purified and separated by column chromatography using silica gel using $CH_2Cl_2$ and hexane as development solvents to thereby obtain Intermediate compound 1-b (white solid, 36 g, 72%). The obtained white solid was identified by ESI-LCMS as Intermediate compound 1-b.

ESI-LCMS: $[M]^+$: $C_{47}H_{35}N_4Br$. 734.2020.

Synthesis of Intermediate Compound 1-c

In an argon atmosphere, 5-chloro-N1,N1,N3,N3-tetraphenylbenzene-1,3-diamine (50 g, 112 mmol), aniline (10.7 g, 112 mmol), sodium tert-butoxide (32 g, 336 mmol), tris-tert-butyl phosphine (5 ml, 11.2 mmol), and $Pd_2dba_3$ (3.1 g, 3.5 mmol) were added to a 2 L flask and dissolved in 1 L of o-xylene, and the reaction solution was stirred at temperature of 140° C. for 12 hours. After cooling, water (1 L) and ethylacetate (300 ml) were added thereto for extraction and collection of an organic layer, and was dried using $MgSO_4$ and filtered. The filtered solution was placed under reduced pressure to remove solvent therefrom, and the obtained solid was purified and separated by column chromatography using silica gel using $CH_2Cl_2$ and hexane as development solvents to thereby obtain Intermediate compound 1-c (white solid, 38 g, 68 wt. %). The obtained white solid was identified by ESI-LCMS as Intermediate compound 1-c.

ESI-LCMS: $[M]^+$: $C_{36}H_{29}N_3$. 503.2412.

Synthesis of Intermediate Compound 1-d

In an argon atmosphere, Compound 1-b (30 g, 41 mmol), Compound 1-c (20.5 g, 41 mmol), sodium tert-butoxide (12 g, 123 mmol), tris-tert-butyl phosphine (2.0 ml, 4.2 mmol), and $Pd_2dba_3$ (1.9 g, 2.1 mmol) were added to a 2 L flask and dissolved in 400 ml of toluene, and the reaction solution was stirred at a temperature of 100° C. for 12 hours. After cooling, water (1 L) and ethylacetate (300 ml) were added thereto for extraction and collection of an organic layer, and was dried using $MgSO_4$ and filtered. The filtered solution was placed under reduced pressure to remove solvent therefrom, and the obtained solid was purified and separated by column chromatography using silica gel using $CH_2Cl_2$ and hexane as development solvents to thereby obtain Intermediate compound 1-d (white solid, 29 g, 62%). The obtained white solid was identified by ESI-LCMS as Intermediate compound 1-d.

ESI-LCMS: $[M]^+$: $C_{83}H_{63}N_7$. 1157.5437.

Synthesis of Compound 1

In an argon atmosphere, Compound 1-d (29 g, 25 mmol) was added to a 1 L flask, dissolved in 500 ml of o-dichlorobenzene, and was cooled to 0° C. in an ice water vessel. Boron tribromide (5 eq.) was slowly added dropwise to the reaction solution, the temperature was slowly raised to room temperature, and the reaction solution was stirred for 20 minutes. The reaction solution was heated to a temperature of 180° C. and stirred for 12 hours. After cooling, triethylamine (5 ml) was slowly added dropwise thereto to terminate the reaction and solvent was removed therefrom under reduced pressure. The obtained solid was washed with methanol (MeOH) and was purified and separated by column chromatography using silica gel using $CH_2Cl_2$ and hexane as development solvents to thereby obtain Compound 1 (yellow solid, 2.6 g, 9%). The obtained yellow solid was identified by (electrospray ionization-liquid chromatography mass spectrometry (ESI-LCMS) and proton nuclear magnetic resonance ($^1H$-NMR) as Compound 1.

ESI-LCMS: $[M]^+$: $C_{83}H_{57}B_2N_7$. 1173.4936.

$^1H$-NMR (400 MHz, $CDCl_3$): 10.46 (s, 1H), 9.94 (d, 2H), 9.31 (d, 1H), 8.37 (d, 1H), 8.20 (d, 2H), 7.39 (m, 3H), 7.24 (m, 18H), 7.03 (m, 27H), 6.83 (s, 1H), 6.49 (m, 4H).

Synthesis Example 2: Synthesis of Compound 17
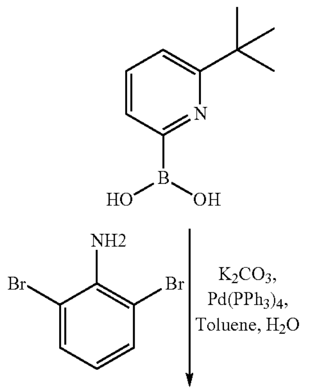
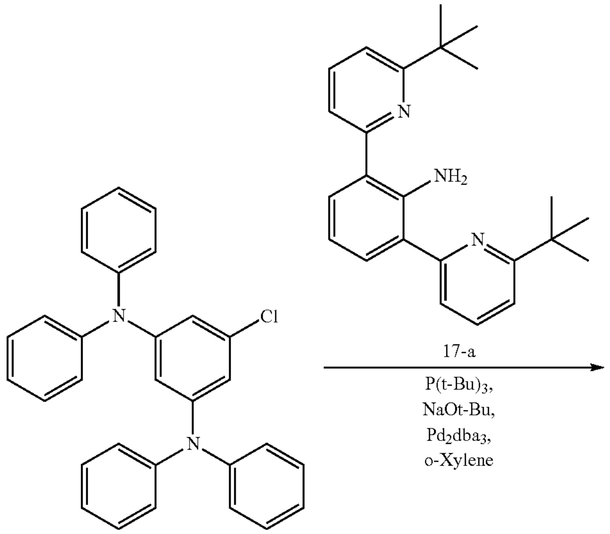
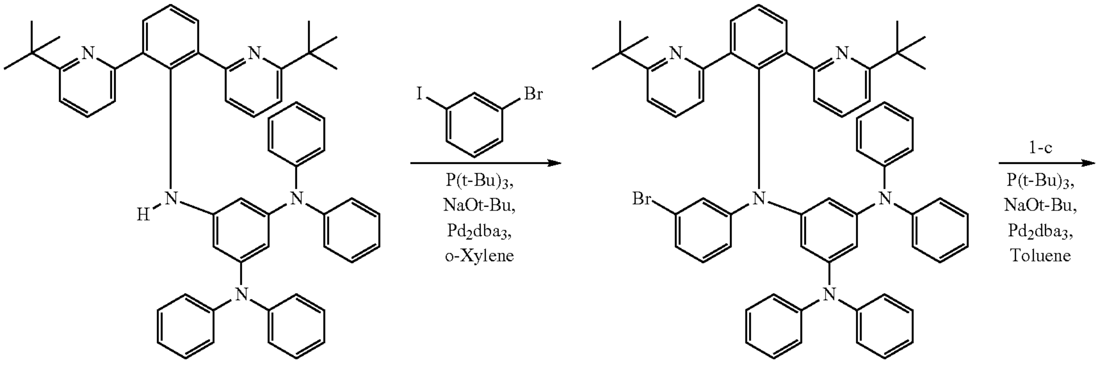
17-b 17-c -continued

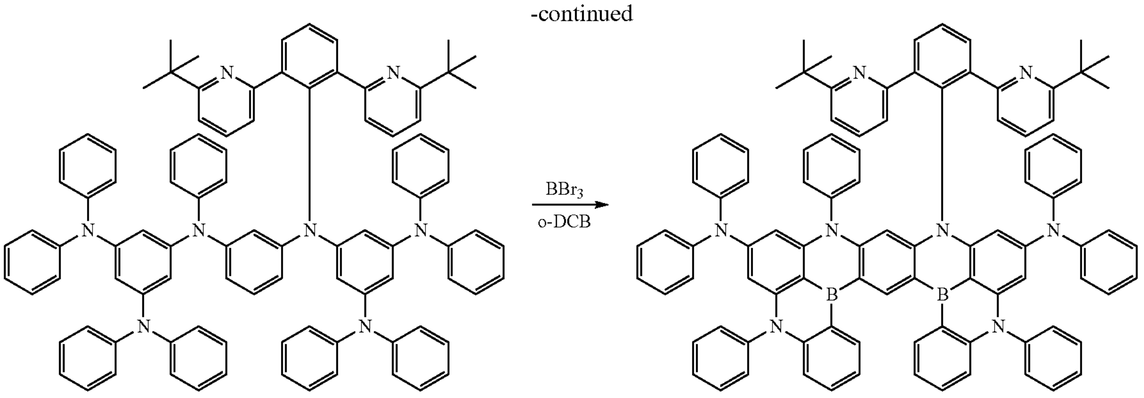

17-d 17

Synthesis of Intermediate Compound 17-a

In an argon atmosphere, 2,6-dibromoaniline (30 g, 120 mmol), (6-(tert-butyl)pyridine-2-yl)boronic acid (45 g, 250 mmol), potassium carbonate (50 g, 360 mmol), and tetrakis (triphenylphosphine)palladium(0) ($Pd(PPh_3)_4$ in amount of 4.1 g, 3.6 mmol) were added to a 2 L flask and dissolved in 1 L of toluene and 250 ml of water, and the reaction solution was stirred at a temperature of 120° C. for 12 hours. After cooling, water (1 L) and ethylacetate (300 ml) were added thereto for extraction and collection of an organic layer, and was dried using $MgSO_4$ and filtered. The filtered solution was placed under reduced pressure to remove solvent therefrom, and the obtained solid was purified and separated by column chromatography using silica gel using $CH_2Cl_2$ and hexane as development solvents to thereby obtain Intermediate compound 17-a (white solid, 24 g, 57%). The obtained white solid was identified by ESI-LCMS and $^1$H-NMR as Compound 17-a.

ESI-LCMS: $[M]^+$: $C_{24}H_{29}N_3$. 359.2424.

$^1$H-NMR (400 MHz, $CDCl_3$): 9.30 (d, 2H), 8.30 (s, 2H), 7.73 (d, 2H), 7.29 (d, 2H), 7.19 (t, 1H), 1.35 (s, 18H).

Synthesis of Intermediate Compound 17-b

In an argon atmosphere, 5-chloro-N1,N1,N3,N3-tetraphenylbenzene-1,3-diamine (50 g, 112 mmol), Compound 17-a (40 g, 112 mmol), sodium tert-butoxide (32 g, 336 mmol), tris-tert-butyl phosphine (5.1 mL, 11.2 mmol), and $Pd_2dba_3$ (5.1 g, 5.6 mmol) were added to a 2 L flask and dissolved in 1 L of o-xylene, and the reaction solution was stirred at temperature of 140° C. for 12 hours. After cooling, water (1 L) and ethylacetate (300 ml) were added thereto for extraction and collection of an organic layer, and was dried using $MgSO_4$ and filtered. The filtered solution was placed under reduced pressure to remove solvent therefrom, and the obtained solid was purified and separated by column chromatography using silica gel using $CH_2Cl_2$ and hexane as development solvents to thereby obtain Intermediate compound 17-b (white solid, 36 g, 42%). The obtained white solid was identified by ESI-LCMS as Intermediate compound 17-b.

ESI-LCMS: $[M]^+$: $C_{54}H_{51}N_5$. 769.4049.

Synthesis of Intermediate Compound 17-c

In an argon atmosphere, Compound 17-b (35 g, 45 mmol), 3-bromo-iodobenzene (63 g, 227 mmol), sodium tert-butoxide (13 g, 135 mmol), tris-tert-butyl phosphine (4.0 mL, 4.6 mmol), and $Pd_2dba_3$ (2.0 g, 2.3 mmol) were added to a 2 L flask and dissolved in 450 ml of o-xylene, and the reaction solution was stirred at a temperature of 160° C. for 36 hours. After cooling, water (1 L) and ethylacetate (300 ml) were added thereto for extraction and collection of an organic layer, and was dried using $MgSO_4$ and filtered. The filtered solution was placed under reduced pressure to remove solvent therefrom, and the obtained solid was purified and separated by column chromatography using silica gel using $CH_2Cl_2$ and hexane as development solvents to thereby obtain Intermediate compound 17-c (white solid, 21 g, 51%). The obtained white solid was identified by ESI-LCMS as Intermediate compound 17-c.

ESI-LCMS: $[M]^+$: $C_{60}H_{54}N_5Br$. 923.3119.

Synthesis of Intermediate Compound 17-d

In an argon atmosphere, Compound 17-c (20 g, 22 mmol), Compound 1-c (11 g, 22 mmol), sodium tert-butoxide (6.3 g, 66 mmol), tris-tert-butyl phosphine (1.0 mL, 2.2 mmol), and $Pd_2dba_3$ (1.0 g, 1.1 mmol) were added to a 2 L flask and dissolved in 220 ml of toluene, and the reaction solution was stirred at a temperature of 100° C. for 12 hours. After cooling, water (1 L) and ethylacetate (300 ml) were added thereto for extraction and collection of an organic layer, and was dried using $MgSO_4$ and filtered. The filtered solution was placed under reduced pressure to remove solvent therefrom, and the obtained solid was purified and separated by column chromatography using silica gel using $CH_2Cl_2$ and hexane as development solvents to thereby obtain Intermediate compound 17-d (white solid, 21.6 g, 73%). The obtained white solid was identified by ESI-LCMS as Intermediate compound 17-d.

ESI-LCMS: $[M]^+$: $C_{96}H_{82}N_8$. 1346.6071.

Synthesis of Compound 17

In an argon atmosphere, Compound 17-d (20 g, 14 mmol) was added to a 1 L flask, dissolved in 500 ml of o-dichlorobenzene, and was cooled to 0° C. in an ice water vessel. Boron tribromide (5 eq.) was slowly added dropwise to the reaction solution, the temperature was slowly raised to room temperature, and the reaction solution was stirred for 20 minutes. The reaction solution was heated to a temperature of 180° C. and stirred for 12 hours. After cooling, triethylamine (5 ml) was slowly added dropwise thereto to terminate the reaction and solvent was removed therefrom under reduced pressure. The obtained solid was washed with MeOH and was purified and separated by column chromatography using silica gel using $CH_2Cl_2$ and hexane as development solvents to thereby obtain Compound 17 (yellow solid, 1.4 g, 7%). The obtained yellow solid was identified by ESI-LCMS and $^1$H-NMR as Compound 17.

ESI-LCMS: $[M]^+$: $C_{96}H_{76}B_2N_8$. 1362.6617.

$^1$H-NMR (400 MHz, $CDCl_3$): 10.52 (s, 1H), 9.83 (d, 2H), 9.41 (d, 2H), 7.39 (t, 1H), 7.31 (m, 2H), 7.24 (m, 16H), 7.08 (m, 21H), 7.01 (t, 2H), 6.83 (s, 1H), 6.77 (d, 2H), 6.49 (m, 4H).

Synthesis Example 3: Synthesis of Compound 31
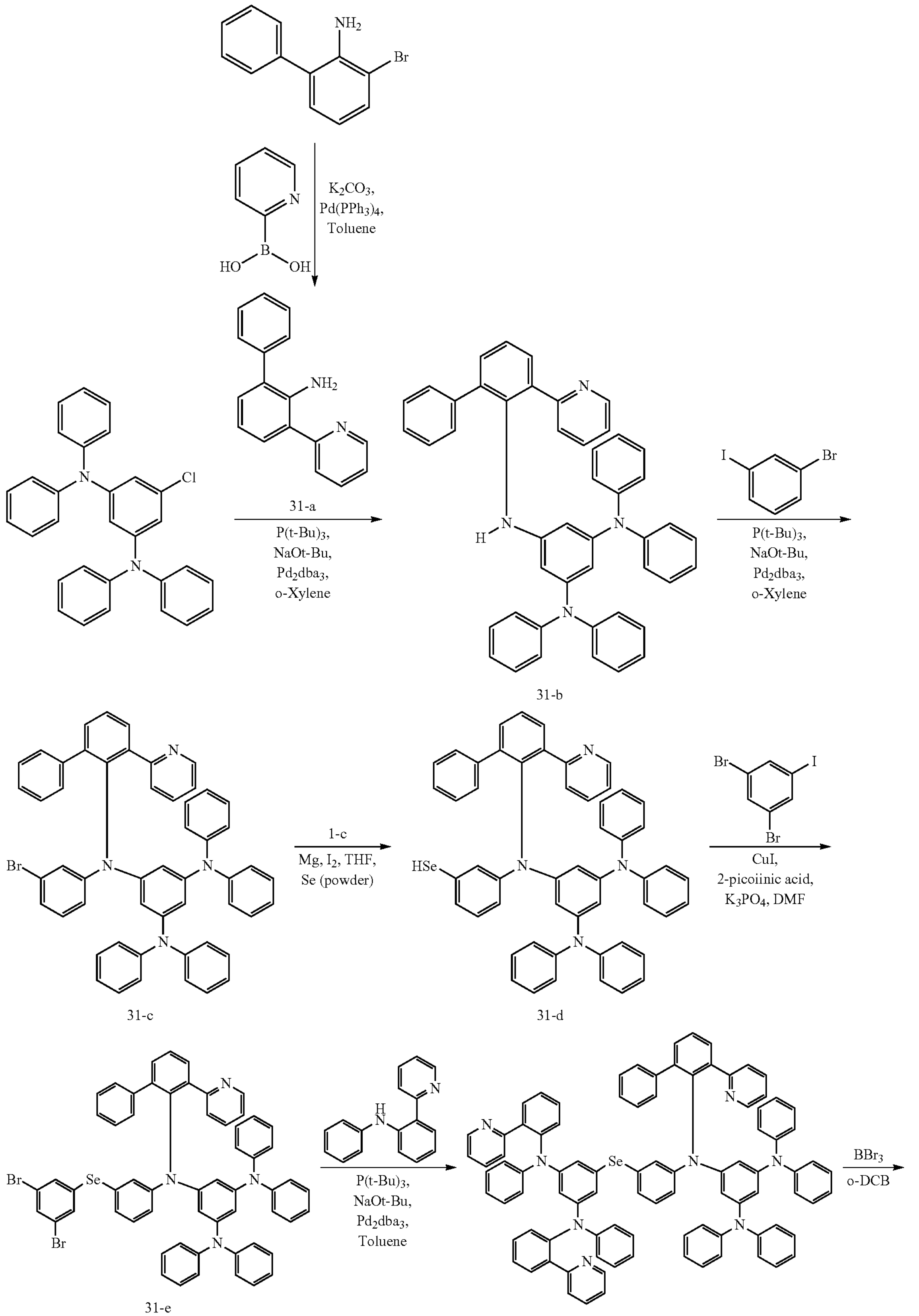
31-b
31-c
31-d
31-e
31-f -continued

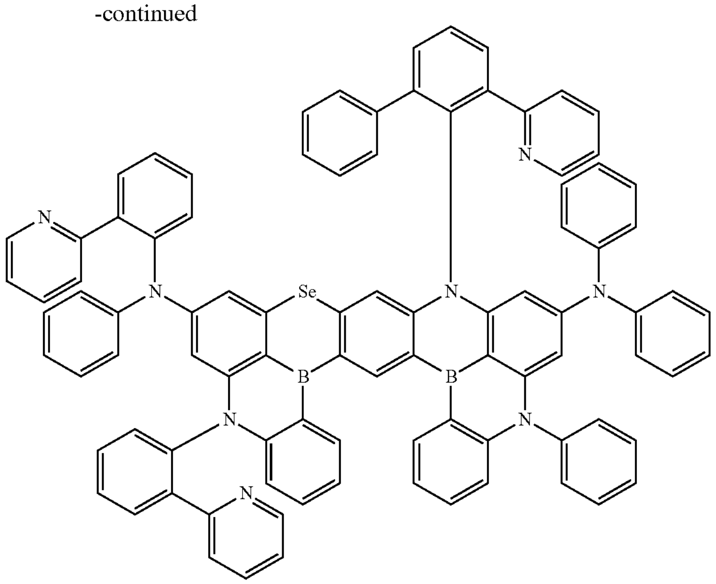

31

Synthesis of Intermediate Compound 31-a

In an argon atmosphere, 3-bromo(1,1'-biphenyl)-2-amine (30 g, 120 mmol), (5-(tert-butyl)pyridine-2-yl)boronic acid (45 g, 250 mmol), potassium carbonate (50 g, 360 mmol), and $Pd(PPh_3)_4$ (4.1 g, 3.6 mmol) were added to a 2 L flask and dissolved in 1 L of toluene and 250 ml of water, and the reaction solution was stirred at a temperature of 120° C. for 12 hours. After cooling, water (1 L) and ethylacetate (300 ml) were added thereto for extraction and collection of an organic layer, and was dried using $MgSO_4$ and filtered. The filtered solution was placed under reduced pressure to remove solvent therefrom, and the obtained solid was purified and separated by column chromatography using silica gel using $CH_2Cl_2$ and hexane as development solvents to thereby obtain Intermediate compound 31-a (white solid, 23 g, 77%). The obtained white solid was identified by ESI-LCMS and $^1$H-NMR as Compound 31-a.

ESI-LCMS: $[M]^+$: $C_{17}H_{14}N_2$. 246.1238.

$^1$H-NMR (400 MHz, $CDCl_3$): 9.30 (d, 1H), 8.37 (d, 1H), 8.09 (d, 1H), 7.42 (m, 4H), 7.08 (m, 4H), 6.90 (t, 1H).

Synthesis of Intermediate Compound 31-b

In an argon atmosphere, Compound 31-a (30 g, 121 mmol), 5-chloro-N1,N1,N3,N3-tetraphenylbenzene-1,3-diamine (54 g, 121 mmol), sodium tert-butoxide (35 g, 363 mmol), tris-tert-butyl phosphine (5.5 mL, 12 mmol), and $Pd_2dba_3$ (5.5 g, 6.0 mmol) were added to a 2 L flask and dissolved in 1 L of o-xylene, and the reaction solution was stirred at temperature of 140° C. for 12 hours. After cooling, water (1 L) and ethylacetate (300 ml) were added thereto for extraction and collection of an organic layer, and was dried using $MgSO_4$ and filtered. The filtered solution was placed under reduced pressure to remove solvent therefrom, and the obtained solid was purified and separated by column chromatography using silica gel using $CH_2Cl_2$ and hexane as development solvents to thereby obtain Intermediate compound 31-b (white solid, 43 g, 58%). The obtained white solid was identified by ESI-LCMS as Intermediate compound 31-b.

ESI-LCMS: $[M]^+$: $C_{47}H_{36}N_4$. 656.2912.

Synthesis of Intermediate Compound 31-c

In an argon atmosphere, Compound 31-b (40 g, 60 mmol), 3-bromo-iodobenzene (85 g, 300 mmol), sodium tert-butoxide (58 g, 600 mmol), tris-tert-butyl phosphine (2.7 ml, 6 mmol), and $Pd_2dba_3$ (2.7 g, 3.0 mmol) were added to a 2 L flask and dissolved in 500 ml of o-xylene, and the reaction solution was stirred at a temperature of 140° C. for 36 hours. After cooling, water (1 L) and ethylacetate (300 ml) were added thereto for extraction and collection of an organic layer, and was dried using $MgSO_4$ and filtered. The filtered solution was placed under reduced pressure to remove solvent therefrom, and the obtained solid was purified and separated by column chromatography using silica gel using $CH_2Cl_2$ and hexane as development solvents to thereby obtain Intermediate compound 31-c (white solid, 30 g, 62%). The obtained white solid was identified by ESI-LCMS as Intermediate compound 31-c.

ESI-LCMS: $[M]^+$: $C_{53}H_{39}N_4Br$. 810.2492.

Synthesis of Intermediate Compound 31-d

In an argon atmosphere, Mg (0.88 g, 37 mmol) was added to a 1 L flask and was dissolved in 150 ml of anhydrous THF. A catalytic amount of 12 (50 mg) was added thereto, and cooled when the color changed from black to gray while heating to 60° C. The reaction solution was cooled to 0° C. using an water-ice vessel, Compound 31-c (30 g, 37 mmol) was added thereto, and was stirred for 30 minutes. The reaction solution was heated to 80° C. and stirred for 30 minutes, selenium (3 eq) was added thereto, and was stirred for 2 hours at the same temperature. After cooling, the reaction solution was poured in 1 L of ice water, and 1 N HCl was added dropwise thereto to adjust pH. Ethylacetate (300 ml) was added thereto for extraction and collection of an organic layer, and was dried using $MgSO_4$ and filtered. The filtered solution was placed under reduced pressure to remove solvent therefrom, and the obtained solid was purified and separated by column chromatography using silica gel using $CH_2Cl_2$ and hexane as development solvents to thereby obtain Intermediate compound 31-d (white solid, 11.4 g, 38%). The obtained white solid was identified by ESI-LCMS as Intermediate compound 31-d.

ESI-LCMS: $[M]^+$: $C_{53}H_{40}N_4Se$. 812.1299.

Synthesis of Intermediate Compound 31-e

In an argon atmosphere, Compound 31-d (11 g, 13 mmol), 1,3-dibromo-5-iodobenzene (4.9 g, 13 mmol), CuI (2.5 g, 13 mmol), 2-picolinic acid (1.6 g, 13 mmol), and $K_3PO_4$ (14 g, 65 mmol) were added to a 1 L flask and dissolved in 150 ml of dimethylformamide (DMF). The reaction solution was stirred at a temperature of 160° C. for 12 hours, poured in diatomaceous earth (sold under the trade designation CELITE by Imerys Minerals California, Inc. of San Jose, CA (hereinafter "celite"), and filtered. Ethylacetate (300 ml) was added thereto for extraction and collection of an organic layer, and was dried using $MgSO_4$ and filtered. The filtered solution was placed under reduced pressure to remove solvent therefrom, and the obtained solid was purified and separated by column chromatography using silica gel using $CH_2Cl_2$ and hexane as development solvents to thereby obtain Intermediate compound 31-e (white solid, 8.4 g, 62%). The obtained white solid was identified by ESI-LCMS as Intermediate compound 31-e.

ESI-LCMS: $[M]^+$: $C_{59}H_{42}N_4SeBr_2$. 1044.0917.

Synthesis of Intermediate Compound 31-f

In an argon atmosphere, Compound 31-e (8 g, 7.6 mmol), N-phenyl-2-(pyridin-2-yl)aniline (3.7 g, 15 mmol), sodium tert-butoxide (2.2 g, 23 mmol), tris-tert-butyl phosphine (0.4 mL, 6.8 mmol), and $Pd_2dba_3$ (0.34 g, 3.4 mmol) were added to a 2 L flask and dissolved in 100 ml of toluene, and the reaction solution was stirred at a temperature of 140° C. for 12 hours. After cooling, water (1 L) and ethylacetate (300 ml) were added thereto for extraction and collection of an organic layer, and was dried using $MgSO_4$ and filtered. The filtered solution was placed under reduced pressure to remove solvent therefrom, and the obtained solid was purified and separated by column chromatography using silica gel using $CH_2Cl_2$ and hexane as development solvents to thereby obtain Intermediate compound 31-f (white solid, 7.5 g, 72%). The obtained white solid was identified by ESI-LCMS as Intermediate compound 31-f.

ESI-LCMS: $[M]^+$: $C_{93}H_{68}N_8Se$. 1376.4669.

Synthesis of Compound 31

In an argon atmosphere, Compound 31-f (7.5 g, 5.4 mmol) was added to a 1 L flask, dissolved in 200 ml of o-dichlorobenzene, and was cooled to 0° C. in an ice water vessel. Boron tribromide (5 eq.) was slowly added dropwise to the reaction solution, the temperature was slowly raised to room temperature, and the reaction solution was stirred for 20 minutes. The reaction solution was heated to a temperature of 180° C. and stirred for 12 hours. After cooling, triethylamine (5 ml) was slowly added dropwise thereto to terminate the reaction and solvent was removed therefrom under reduced pressure. The obtained solid was washed with MeOH and purified and separated by column chromatography using silica gel using $CH_2Cl_2$ and hexane as development solvents to thereby obtain Compound 31 (yellow solid, 0.8 g, 11%). The obtained yellow solid was identified by ESI-LCMS and $^1$H-NMR as Compound 31.

ESI-LCMS: $[M]^+$: $C_{93}H_{62}B_2N_8Se$. 1395.4434.

$^1$H-NMR (400 MHz, $CDCl_3$): 10.26 (s, 1H), 9.65 (d, 2H), 9.41 (d, 2H), 9.31 (d, 2H), 8.37 (d, 3H), 8.20 (m, 1H), 7.39 (m, 10H), 7.24 (m, 12H), 7.08 (m, 24H), 6.77 (s, 1H), 7.01 (t, 2H), 6.49 (s, 2H).

Synthesis Example 4: Synthesis of Compound 37

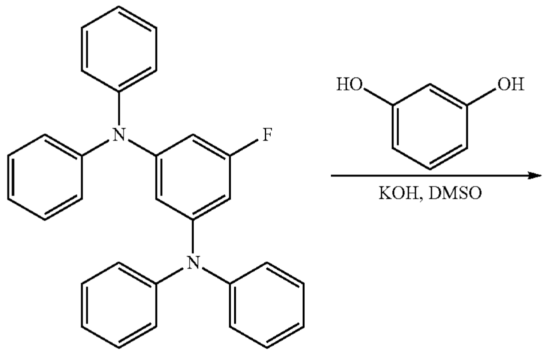

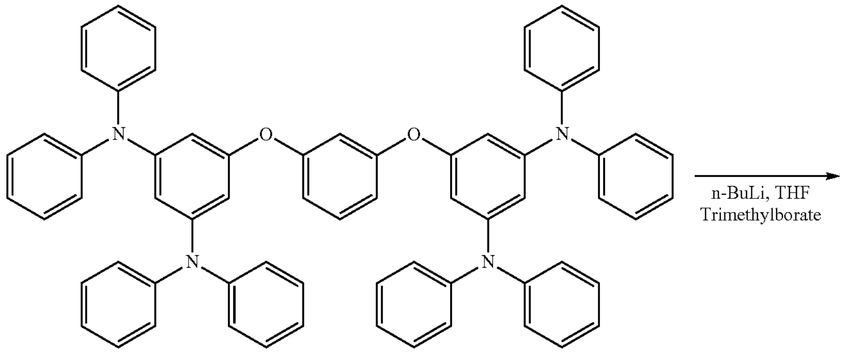

37-a

-continued

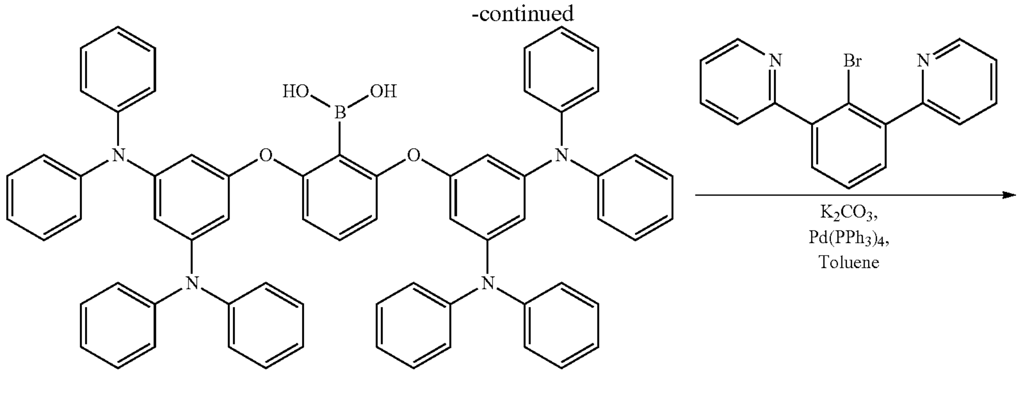

37-b

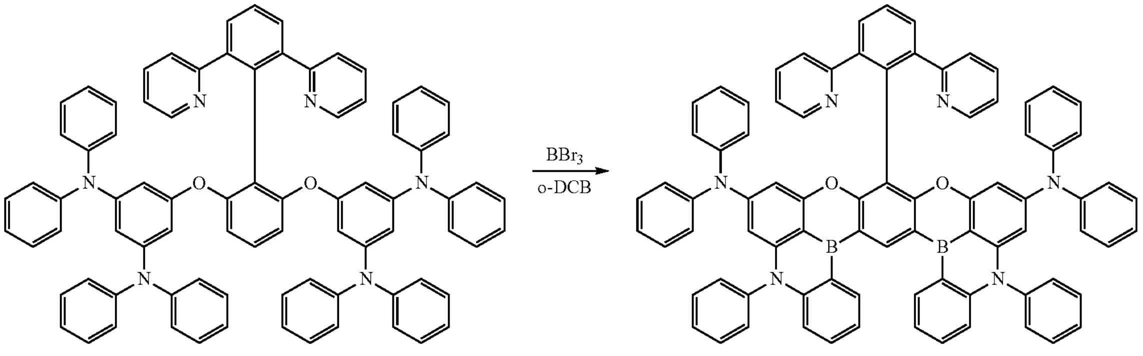

37-c 37

Synthesis of Intermediate Compound 37-a

In an argon atmosphere, 5-fluoro-N1,N1,N3,N3-tetraphenylbenzene-1,3-diamine (50 g, 116 mmol), resorcinol (6.4 g, 58 mmol), and potassium hydroxide (KOH) (6.5 g, 116 mmol) were added to a 2 L flask and dissolved in 1 L of dimethyl sulfoxide (DMSO), and the reaction solution was stirred at a temperature of 180° C. for 12 hours. After cooling, water (1 L) and ethylacetate (300 ml) were added thereto for extraction and collection of an organic layer, and was dried using $MgSO_4$ and filtered. The filtered solution was placed under reduced pressure to remove solvent therefrom, and the obtained solid was purified and separated by column chromatography using silica gel using $CH_2Cl_2$ and hexane as development solvents to thereby obtain Intermediate compound 37-a (white solid, 34 g, 64%). The obtained white solid was identified by ESI-LCMS as Intermediate compound 37-a.

ESI-LCMS: $[M]^+$: $C_{66}H_{50}N_4O_2$. 930.3912.

Synthesis of Intermediate Compound 37-b

In an argon atmosphere, Compound 37-a (30 g, 32 mmol) was added to a 1 L flask and dissolved in 300 ml of anhydrous oxolane (THF). After cooling to −78° C., N-butyllithium (n-BuLi) (1.2 eq.) was slowly added dropwise thereto for 30 minutes. Then, the reaction solution was heated to room temperature and stirred for 2 hours, cooled to −78° C. again, trimethyl borate (1.5 eq.) was added thereto, and stirred at room temperature for 12 hours. 300 ml of 0.1N hydrochloric acid (HCl) was poured to the reaction solution to terminate the reaction, ethylacetate (300 ml) was added thereto to collect an organic layer, and the reaction solution was dried using $MgSO_4$ and filtered. Solvent was removed from the filtered solution under reduced pressure, and the solid obtained therefrom was recrystallized using hexane to thereby obtain Intermediate compound 37-b (white solid, 16 g, 55%). The obtained white solid was identified by ESI-LCMS as Intermediate compound 37-b.

ESI-LCMS: $[M]^+$: $C_{66}H_{51}N_4O_4B$. 974.4001.

Synthesis of Intermediate Compound 37-c

In an argon atmosphere, Compound 37-b (16 g, 16 mmol), 2,2'-(2-bromo-1,3-phenylene)dipyridine (5.1 g, 16 mmol), potassium carbonate (6.6 g, 48 mmol), and $Pd(PPh_3)_4$ (0.55 g, 0.5 mmol) were added to a 1 L flask and dissolved in 150 ml of toluene and 50 ml of water, and the reaction solution was stirred at a temperature of 120° C. for 12 hours. After cooling, water (1 L) and ethylacetate (300 ml) were added thereto for extraction and collection of an organic layer, and was dried using $MgSO_4$ and filtered. The filtered solution was placed under reduced pressure to remove solvent therefrom, and the obtained solid was purified and separated by column chromatography using silica gel using $CH_2Cl_2$ and hexane as development solvents to thereby obtain Intermediate compound 37-c (white solid, 14 g, 74%). The obtained white solid was identified by ESI-LCMS as Intermediate compound 37-c.

ESI-LCMS: $[M]^+$: $C_{82}H_{60}N_6O_2$. 1160.4884.

Synthesis of Compound 37

In an argon atmosphere, Compound 37-c (14 g, 12 mmol) was added to a 1 L flask, dissolved in 300 ml of o-dichlorobenzene, and was cooled to 0° C. in an ice water vessel. Boron tribromide (5 eq.) was slowly added dropwise to the reaction solution, the temperature was slowly raised to room temperature, and the reaction solution was stirred for 20 minutes. The reaction solution was heated to a temperature of 180° C. and stirred for 12 hours. After cooling, triethylamine (5 ml) was slowly added dropwise thereto to terminate the reaction and solvent was removed therefrom under reduced pressure. The obtained solid was washed with MeOH and was purified and separated by column chromatography using silica gel using $CH_2Cl_2$ and hexane as development solvents to thereby obtain Compound 37 (yellow solid, 1.7 g, 12%). The obtained yellow solid was identified by ESI-LCMS and $^1$H-NMR as Compound 37.

ESI-LCMS: $[M]^+$: $C_{82}H_{54}B_2N_6O_2$. 1176.0157.

$^1$H-NMR (400 MHz, $CDCl_3$): 10.31 (s, 1H), 9.42 (d, 2H), 8.45 (d, 2H), 8.37 (d, 2H), 7.83 (t, 1H), 7.38 (m, 4H), 7.24 (m, 12H), 7.08 (m, 12H), 6.90 (m, 9H), 6.83 (t, 1H), 6.52 (d, 4H).

Synthesis Example 5: Synthesis of Compound 41

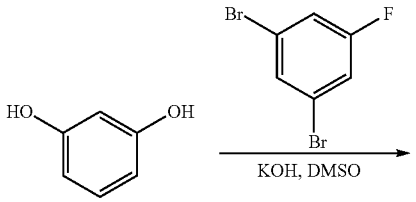

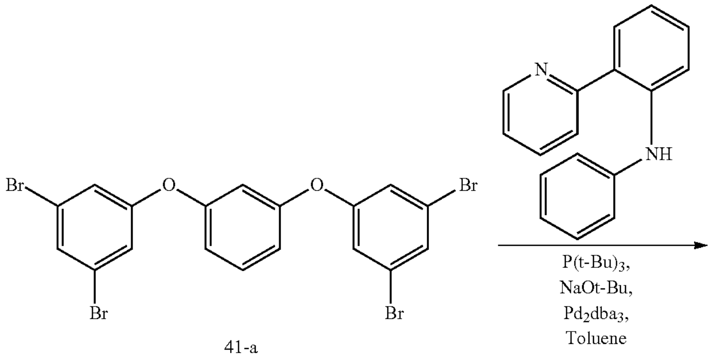

41-a

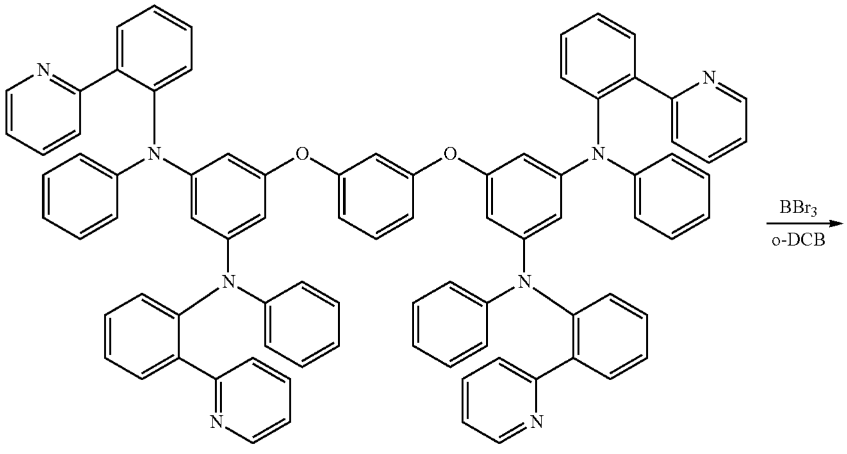

41-b

-continued

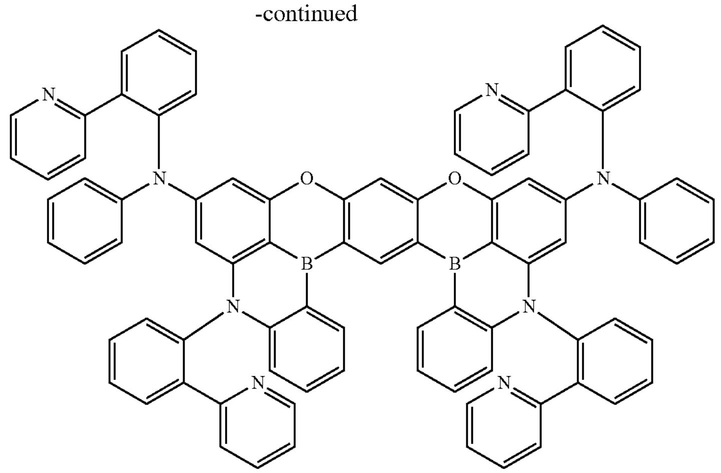

41

Synthesis of Intermediate Compound 41-a

In an argon atmosphere, 3,5-dibromo-fluorobenzene (50 g, 197 mmol), resorcinol (10 g, 90 mmol), and KOH (11.7 g, 180 mmol) were added to a 2 L flask and dissolved in 1 L of DMSO, and the reaction solution was stirred at a temperature of 180° C. for 12 hours. After cooling, water (1 L) and ethylacetate (300 ml) were added thereto for extraction and collection of an organic layer, and was dried using $MgSO_4$ and filtered. The filtered solution was placed under reduced pressure to remove solvent therefrom, and the obtained solid was purified and separated by column chromatography using silica gel using $CH_2Cl_2$ and hexane as development solvents to thereby obtain Intermediate compound 41-a (white solid, 22 g, 43%). The obtained white solid was identified by ESI-LCMS and $^1$H-NMR as Intermediate compound 41-a.

ESI-LCMS: $[M]^+$: $C_{18}H_{10}Br_4O_2$. 573.7473.

$^1$H-NMR (400 MHz, $CDCl_3$): 7.70 (s, 2H), 7.28 (m, 5H), 7.00 (d, 2H), 6.52 (s, 1H).

Synthesis of Intermediate Compound 41-b

In an argon atmosphere, Compound 41-a (20 g, 35 mmol), N-phenyl-2-(pyridin-2-yl)aniline (51 g, 207 mmol), sodium tert-butoxide (10 g, 105 mmol), tris-tert-butyl phosphine (0.4 mL, 7.0 mmol), and $Pd_2dba_3$ (0.34 g, 3.5 mmol) were added to a 2 L flask and dissolved in 500 ml of toluene, and the reaction solution was stirred at a temperature of 110° C. for 12 hours. After cooling, water (1 L) and ethylacetate (300 ml) were added thereto for extraction and collection of an organic layer, and was dried using $MgSO_4$ and filtered. The filtered solution was placed under reduced pressure to remove solvent therefrom, and the obtained solid was purified and separated by column chromatography using silica gel using $CH_2Cl_2$ and hexane as development solvents to thereby obtain Intermediate compound 41-b (white solid, 22.5 g, 52%). The obtained white solid was identified by ESI-LCMS as Intermediate compound 41-b.

ESI-LCMS: $[M]^+$: $C_{86}H_{62}N_8O_2$. 1238.5001.

Synthesis of Compound 41

In an argon atmosphere, Compound 41-b (20 g, 16 mmol) was added to a 1 L flask, dissolved in 500 ml of o-dichlorobenzene, and was cooled to 0° C. in an ice water vessel. Boron tribromide (5 eq.) was slowly added dropwise to the reaction solution, the temperature was slowly raised to room temperature, and the reaction solution was stirred for 20 minutes. The reaction solution was heated to a temperature of 180° C. and stirred for 12 hours. After cooling, triethylamine (5 ml) was slowly added dropwise thereto to terminate the reaction and solvent was removed therefrom under reduced pressure. The obtained solid was washed with MeOH and was purified and separated by column chromatography using silica gel using $CH_2Cl_2$ and hexane as development solvents to thereby obtain Compound 41 (yellow solid, 1.6 g, 8%). The obtained yellow solid was identified by ESI-LCMS and $^1$H-NMR as Compound 41.

ESI-LCMS: $[M]^+$: $C_{86}H_{56}B_2N_8O_2$. 1254.4644.

$^1$H-NMR (400 MHz, $CDCl_3$): 10.78 (s, 1H), 9.87 (d, 2H), 9.31 (d, 4H), 8.37 (d, 4H), 7.39 (m, 12H), 7.21 (m, 8H), 7.04 (m, 24H), 6.65 (s, 1H), 6.50 (d, 4H).

Synthesis Example 6: Synthesis of Compound 50

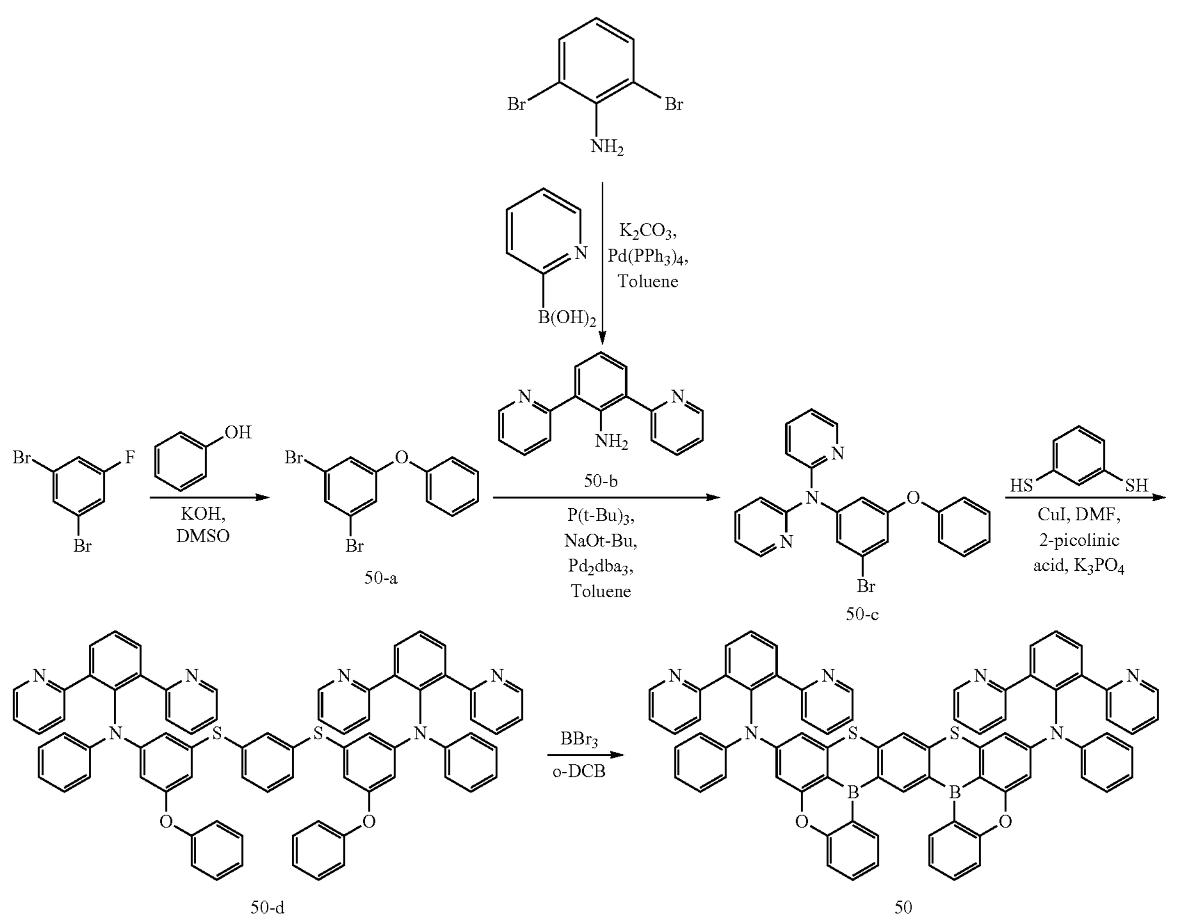

Synthesis of Intermediate Compound 50-a

In an argon atmosphere, 3,5-dibromo-fluorobenzene (23 g, 90 mmol), phenol (8.5 g, 90 mmol), and KOH (11.7 g, 180 mmol) were added to a 2 L flask and dissolved in 1 L of DMSO, and the reaction solution was stirred at a temperature of 180° C. for 12 hours. After cooling, water (1 L) and ethylacetate (300 ml) were added thereto for extraction and collection of an organic layer, and was dried using $MgSO_4$ and filtered. The filtered solution was placed under reduced pressure to remove solvent therefrom, and the obtained solid was purified and separated by column chromatography using silica gel using $CH_2Cl_2$ and hexane as development solvents to thereby obtain Intermediate compound 50-a (white solid, 22.6 g, 77%). The obtained white solid was identified by ESI-LCMS and $^1$H-NMR as Intermediate compound 50-a.

ESI-LCMS: $[M]^+$: $C_{12}H_8Br_2O$. 325.8924.

Synthesis of Intermediate Compound 50-b

In an argon atmosphere, 2,6-dibromoaniline (30 g, 120 mmol), 2-pyridinyl boronic acid (29 g, 240 mmol), potassium carbonate (50 g, 360 mmol), and $Pd(PPh_3)_4$ (4.1 g, 3.6 mmol) were added to a 2 L flask and dissolved in 1 L of toluene and 250 ml of water, and the reaction solution was stirred at a temperature of 120° C. for 12 hours. After cooling, water (1 L) and ethylacetate (300 ml) were added thereto for extraction and collection of an organic layer, and was dried using $MgSO_4$ and filtered. The filtered solution was placed under reduced pressure to remove solvent therefrom, and the obtained solid was purified and separated by column chromatography using silica gel using $CH_2Cl_2$ and hexane as development solvents to thereby obtain Intermediate compound 50-b (white solid, 24 g, 81%). The obtained white solid was identified by ESI-LCMS as Intermediate compound 50-b.

ESI-LCMS: $[M]^+$: $C_{16}H_{13}N_3$. 247.1114.

Synthesis of Intermediate Compound 50-c

In an argon atmosphere, Compound 50-a (26 g, 80 mmol), Compound 50-b (20 g, 80 mmol), sodium tert-butoxide (23 g, 240 mmol), tris-tert-butyl phosphine (3.6 ml, 8.0 mmol), and $Pd_2dba_3$ (3.6 g, 4 mmol) were added to a 2 L flask and dissolved in 800 ml of toluene, and the reaction solution was stirred at a temperature of 110° C. for 12 hours. After cooling, water (1 L) and ethylacetate (300 ml) were added thereto for extraction and collection of an organic layer, and was dried using $MgSO_4$ and filtered. The filtered solution was placed under reduced pressure to remove solvent therefrom, and the obtained solid was purified and separated by column chromatography using silica gel using $CH_2Cl_2$ and hexane as development solvents to thereby obtain Intermediate compound 50-c (white solid, 22.4 g, 67%). The obtained white solid was identified by ESI-LCMS as Intermediate compound 50-c.

ESI-LCMS: $[M]^+$: $C_{22}H_{16}N_3OBr$. 417.0443.

Synthesis of Intermediate Compound 50-d

In an argon atmosphere, Compound 50-c (20 g, 48 mmol), benzene-1,3-dithiol (3.4 g, 24 mmol), copper iodide (CuI)

(4.5 g, 24 mmol), 2-picolinic acid (3 g, 24 mmol), and $K_3PO_4$ (17 g, 72 mmol) were added to a 1 L flask and dissolved in 500 ml of DMF. The reaction solution was stirred at a temperature of 160° C. for 12 hours, poured in celite, and filtered. Ethylacetate (300 ml) was added thereto for extraction and collection of an organic layer, and was dried using $MgSO_4$ and filtered. The filtered solution was placed under reduced pressure to remove solvent therefrom, and the obtained solid was purified and separated by column chromatography using silica gel using $CH_2Cl_2$ and hexane as development solvents to thereby obtain Intermediate compound 50-d (white solid, 15 g, 58%). The obtained white solid was identified by ESI-LCMS as Intermediate compound 50-d.

ESI-LCMS: $[M]^+$: $C_{74}H_{52}N_6S_2O_2$. 1120.3636.

Synthesis of Compound 50

In an argon atmosphere, Compound 50-d (20 g, 13 mmol) was added to a 1 L flask, dissolved in 500 ml of o-dichlorobenzene, and was cooled to 0° C. in an ice water vessel. Boron tribromide (5 eq.) was slowly added dropwise to the reaction solution, the temperature was slowly raised to room temperature, and the reaction solution was stirred for 20 minutes. The reaction solution was heated to a temperature of 180° C. and stirred for 12 hours. After cooling, triethylamine (5 ml) was slowly added dropwise thereto to terminate the reaction and solvent was removed therefrom under reduced pressure. The obtained solid was washed with MeOH and purified and separated by column chromatography using silica gel using $CH_2Cl_2$ and hexane as development solvents to thereby obtain Compound 50 (yellow solid, 0.9 g, 6%). The obtained yellow solid was identified by ESI-LCMS and $^1$H-NMR as Compound 50.

ESI-LCMS: $[M]^+$: $C_{74}H_{46}B_2N_6O_2S_2$. 1136.3336.

$^1$H-NMR (400 MHz, $CDCl_3$): 10.56 (s, 1H), 9.76 (d, 2H), 9.41 (d, 4H), 8.37 (d, 4H), 7.41 (m, 6H), 7.27 (m, 8H), 7.12 (m, 14H), 6.88 (s, 2H).

Synthesis Example 7: Synthesis of Compound 55

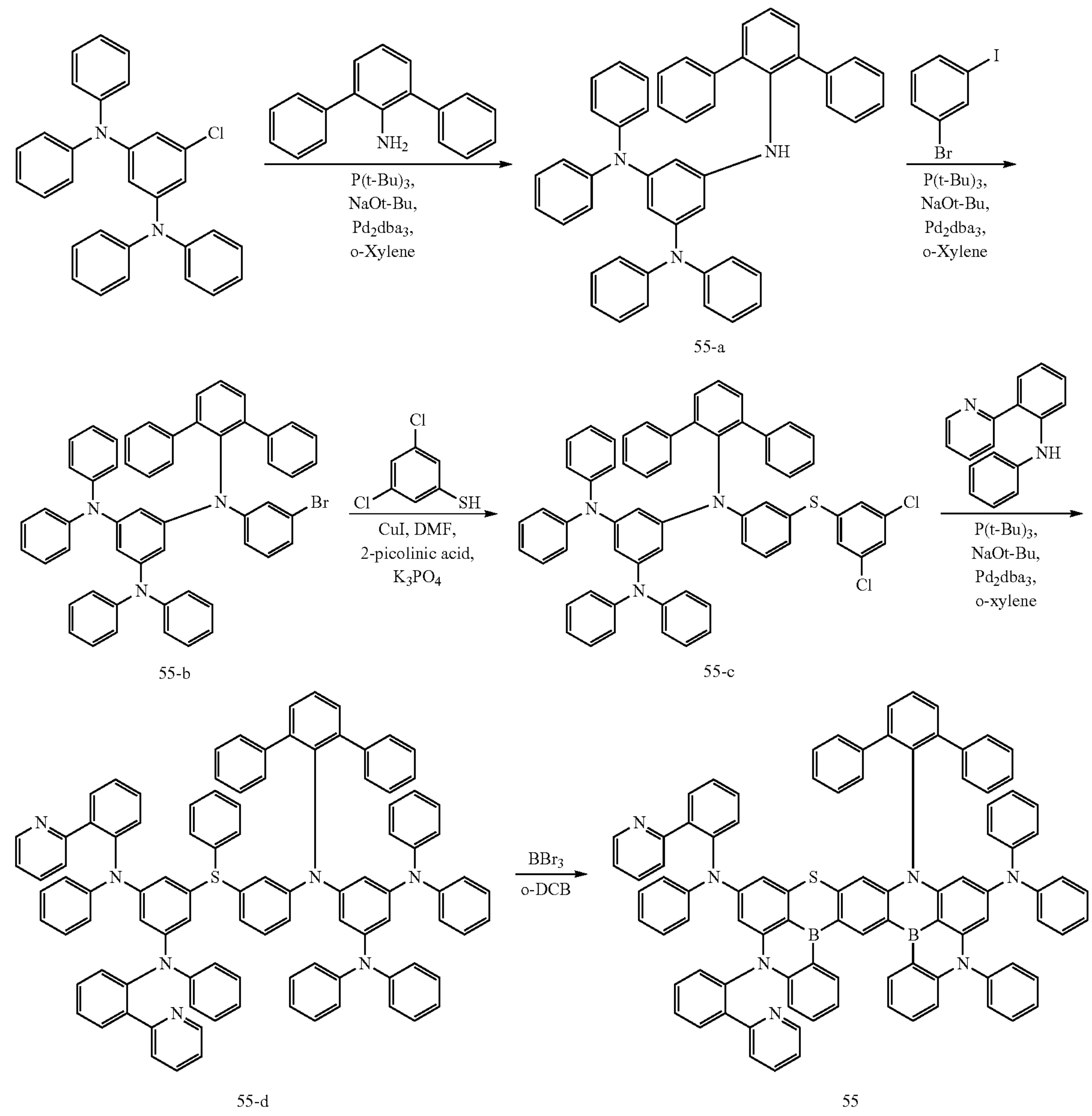

55-a 55-b 55-c 55-d

55

Synthesis of Intermediate Compound 55-a

In an argon atmosphere, [1,1':3',1"-terphenyl]-2'-amine (30 g, 122 mmol), 5-chloro-N1,N1,N3,N3-tetraphenylbenzene-1,3-diamine (58 g, 122 mmol), sodium tert-butoxide (35 g, 363 mmol), tris-tert-butyl phosphine (5.5 mL, 12 mmol), and $Pd_2dba_3$ (5.5 g, 6.0 mmol) were added to a 2 L flask and dissolved in 1 L of o-xylene, and the reaction solution was stirred at a temperature of 140° C. for 12 hours. After cooling, water (1 L) and ethylacetate (300 ml) were added thereto for extraction and collection of an organic layer, and was dried using $MgSO_4$ and filtered. The filtered solution was placed under reduced pressure to remove solvent therefrom, and the obtained solid was purified and separated by column chromatography using silica gel using $CH_2Cl_2$ and hexane as development solvents to thereby obtain Intermediate compound 55-a (white solid, 44.8 g, 66%). The obtained white solid was identified by ESI-LCMS as Intermediate compound 55-a.

ESI-LCMS: $[M]^+$: $C_{48}H_{37}N_3$. 655.3001.

Synthesis of Intermediate Compound 55-b

In an argon atmosphere, Compound 55-a (40 g, 61 mmol), 3-bromo-iodobenzene (170 g, 610 mmol), sodium tert-butoxide (17.5 g, 183 mmol), tris-tert-butyl phosphine (2.8 mL, 6.1 mmol), and $Pd_2dba_3$ (2.8 g, 3.1 mmol) were added to a 2 L flask and dissolved in 200 ml of o-xylene, and the reaction solution was stirred at a temperature of 140° C. for 36 hours. After cooling, water (1 L) and ethylacetate (300 ml) were added thereto for extraction and collection of an organic layer, and was dried using $MgSO_4$ and filtered. The filtered solution was placed under reduced pressure to remove solvent therefrom, and the obtained solid was purified and separated by column chromatography using silica gel using $CH_2Cl_2$ and hexane as development solvents to thereby obtain Intermediate compound 55-b (white solid, 22 g, 45%). The obtained white solid was identified by ESI-LCMS as Intermediate compound 55-b.

ESI-LCMS: $[M]^+$: $C_{54}H_{40}N_3Br$. 809.2412.

Synthesis of Intermediate Compound 55-c

In an argon atmosphere, Compound 55-b (22 g, 27 mmol), 1,3,5-dichlorobenzenethiol (4.9 g, 27 mmol), CuI (5.1 g, 27 mmol), 2-picolinic acid (3.3 g, 27 mmol), and $K_3PO_4$ (20 g, 81 mmol) were added to a 1 L flask and dissolved in 250 ml of DMF. The reaction solution was stirred at a temperature of 160° C. for 12 hours, poured in celite, and filtered. Ethylacetate (300 ml) was added thereto for extraction and collection of an organic layer, and was dried using $MgSO_4$ and filtered. The filtered solution was placed under reduced pressure to remove solvent therefrom, and the obtained solid was purified and separated by column chromatography using silica gel using $CH_2Cl_2$ and hexane as development solvents to thereby obtain Intermediate compound 55-c (white solid, 14 g, 56%). The obtained white solid was identified by ESI-LCMS as Intermediate compound 55-c.

ESI-LCMS: $[M]^+$: $C_{60}H_{43}N_3Cl_2S$. 907.2612.

Synthesis of Intermediate Compound 55-d

In an argon atmosphere, Compound 55-c (14 g, 15 mmol), N-phenyl-2-(pyridin-2-yl)aniline (3.8 g, 15 mmol), sodium tert-butoxide (43.5 g, 45 mmol), tris-tert-butyl phosphine (1.5 mL, 1.4 mmol), and $Pd_2dba_3$ (0.7 g, 0.8 mmol) were added to a 1 L flask and dissolved in 150 ml of o-xylene, and the reaction solution was stirred at a temperature of 140° C. for 36 hours. After cooling, water (1 L) and ethylacetate (300 ml) were added thereto for extraction and collection of an organic layer, and was dried using $MgSO_4$ and filtered. The filtered solution was placed under reduced pressure to remove solvent therefrom, and the obtained solid was purified and separated by column chromatography using silica gel using $CH_2Cl_2$ and hexane as development solvents to thereby obtain Intermediate compound 55-d (white solid, 15 g, 77%). The obtained white solid was identified by ESI-LCMS as Intermediate compound 55-d.

ESI-LCMS: $[M]^+$: $C_{94}H_{69}N_7S$. 1327.5353.

Synthesis of Compound 55

In an argon atmosphere, Compound 55-d (15 g, 11 mmol) was added to a 1 L flask, dissolved in 500 ml of o-dichlorobenzene, and was cooled to 0° C. in an ice water vessel. Boron tribromide (5 eq.) was slowly added dropwise to the reaction solution, the temperature was slowly raised to room temperature, and the reaction solution was stirred for 20 minutes. The reaction solution was heated to a temperature of 180° C. and stirred for 12 hours. After cooling, triethylamine (5 ml) was slowly added dropwise thereto to terminate the reaction and solvent was removed therefrom under reduced pressure. The obtained solid was washed with MeOH and was purified and separated by column chromatography using silica gel using $CH_2Cl_2$ and hexane as development solvents to thereby obtain Compound 55 (yellow solid, 1.2 g, 8%). The obtained yellow solid was identified by ESI-LCMS and $^1$H-NMR as Compound 55.

ESI-LCMS: $[M]^+$: $C_{94}H_{63}B_2N_7S$. 1343.5001.

$^1$H-NMR (400 MHz, $CDCl_3$): 10.43 (s, 1H), 9.58 (d, 2H), 9.31 (d, 2H), 8.37 (d, 2H), 8.20 (d, 2H), 7.76 (s, 1H), 7.41 (m, 7H), 7.25 (m, 13H), 7.12 (m, 17H), 6.57 (s, 1H), 6.49 (s, 2H).

Synthesis Example 8: Synthesis of Compound 57

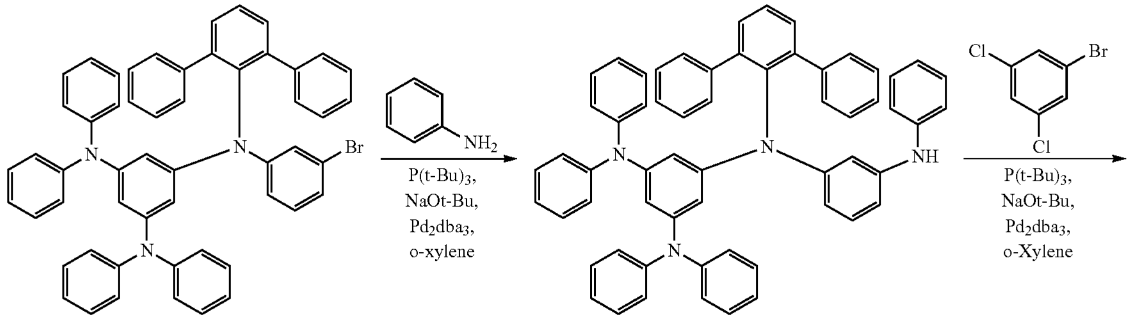

55-b 57-a

-continued

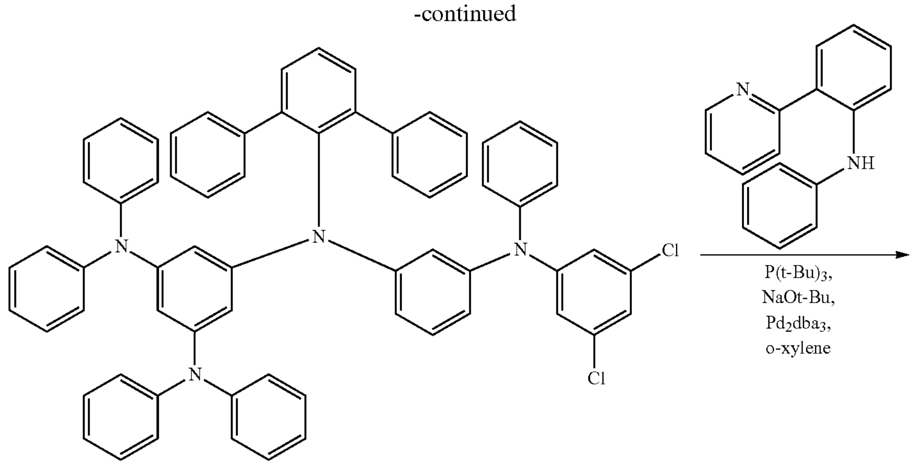

57-b

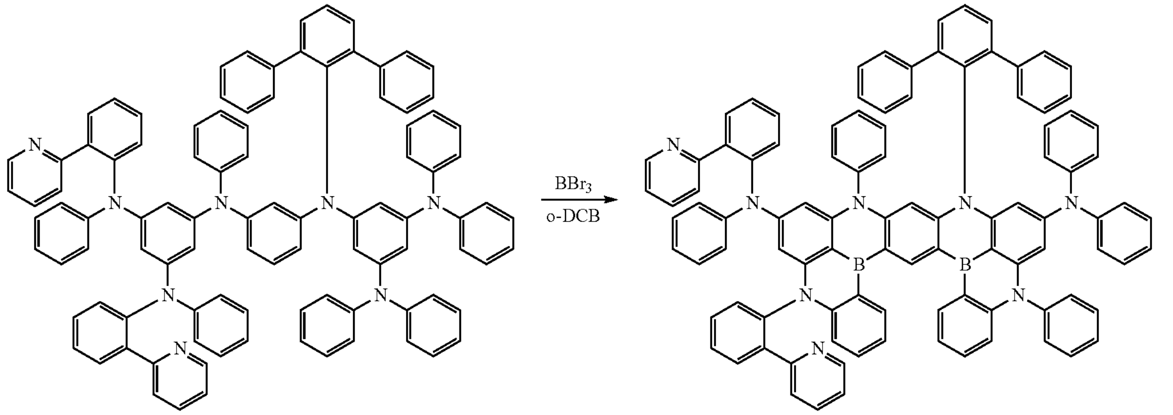

57-c 57

Synthesis of Intermediate Compound 57-a

In an argon atmosphere, Compound 55-b (30 g, 37 mmol), aniline (3.5 g, 37 mmol), sodium tert-butoxide (10.6 g, 111 mmol), tris-tert-butyl phosphine (1.7 ml, 3.8 mmol), and $Pd_2dba_3$ (1.7 g, 1.9 mmol) were added to a 1 L flask and dissolved in 400 ml of o-xylene, and the reaction solution was stirred at a temperature of 140° C. for 12 hours. After cooling, water (1 L) and ethylacetate (300 ml) were added thereto for extraction and collection of an organic layer, and was dried using $MgSO_4$ and filtered. The filtered solution was placed under reduced pressure to remove solvent therefrom, and the obtained solid was purified and separated by column chromatography using silica gel using $CH_2Cl_2$ and hexane as development solvents to thereby obtain Intermediate compound 57-a (white solid, 20 g, 68%). The obtained white solid was identified by ESI-LCMS as Intermediate compound 57-a.

ESI-LCMS: $[M]^+$: $C_{60}H_{46}N_4$. 822.3734.

Synthesis of Intermediate Compound 57-b

In an argon atmosphere, Compound 57-a (20 g, 24 mmol), 1,3-dichloro-5-bromobenzene (3.5 g, 37 mmol), sodium tert-butoxide (6.9 g, 72 mmol), tris-tert-butyl phosphine (1.1 ml, 2.4 mmol), and $Pd_2dba_3$ (1.1 g, 1.2 mmol) were added to a 1 L flask and dissolved in 250 ml of o-xylene, and the reaction solution was stirred at a temperature of 140° C. for 12 hours. After cooling, water (1 L) and ethylacetate (300 ml) were added thereto for extraction and collection of an organic layer, and was dried using $MgSO_4$ and filtered. The filtered solution was placed under reduced pressure to remove solvent therefrom, and the obtained solid was purified and separated by column chromatography using silica gel using $CH_2Cl_2$ and hexane as development solvents to thereby obtain Intermediate compound 57-b (white solid, 15 g, 65%). The obtained white solid was identified by ESI-LCMS as Intermediate compound 57-b.

ESI-LCMS: $[M]^+$: $C_{66}H_{48}N_4Cl_2$. 966.3311.

Synthesis of Intermediate Compound 57-c

In an argon atmosphere, Compound 57-b (15 g, 15 mmol), N-phenyl-2-(pyridin-2-yl)aniline (7.6 g, 30 mmol), sodium tert-butoxide (4.3 g, 45 mmol), tris-tert-butyl phosphine (0.7 mL, 1.6 mmol), and $Pd_2dba_3$ (0.7 g, 0.8 mmol) were added to a 1 L flask and dissolved in 150 ml of o-xylene, and the reaction solution was stirred at a temperature of 140° C. for 12 hours. After cooling, water (1 L) and ethylacetate (300 ml) were added thereto for extraction and collection of an organic layer, and was dried using $MgSO_4$ and filtered. The filtered solution was placed under reduced pressure to remove solvent therefrom, and the obtained solid was purified and separated by column chromatography using silica gel using $CH_2Cl_2$ and hexane as development solvents to thereby obtain Intermediate compound 57-c (white solid, 12 g, 59%). The obtained white solid was identified by ESI-LCMS as Intermediate compound 57-c.

ESI-LCMS: $[M]^+$: $C_{100}H_{74}N_8$. 1386.5997.

Synthesis of Compound 57

In an argon atmosphere, Compound 57-c (12 g, 8 mmol) was added to a 1 L flask, dissolved in 500 ml of o-dichlorobenzene, and cooled to 0° C. in an ice water vessel. Boron tribromide (5 eq.) was slowly added dropwise to the reaction solution, the temperature was slowly raised to room temperature, and the reaction solution was stirred for 20 minutes. The reaction solution was heated to a temperature of 180° C. and stirred for 12 hours. After cooling, triethylamine (5 ml) was slowly added dropwise thereto to terminate the reaction and solvent was removed therefrom under reduced pressure. The obtained solid was washed with MeOH and was purified and separated by column chromatography using silica gel using $CH_2Cl_2$ and hexane as development solvents to thereby obtain Compound 57 (yellow solid, 1.1 g, 9%). The obtained yellow solid was identified by ESI-LCMS and $^1$H-NMR as Compound 57.

ESI-LCMS: $[M]^+$: $C_{100}H_{68}B_2N_8$. 1402.5554.

$^1$H-NMR (400 MHz, $CDCl_3$): 10.59 (s, 1H), 9.68 (d, 2H), 9.31 (d, 2H), 8.37 (d, 2H), 8.20 (d, 2H), 7.76 (s, 1H), 7.43 (m, 9H), 7.27 (m, 21H), 7.12 (m, 17H), 7.03 (m, 7H), 6.83 (s, 1H), 6.49 (s, 4H).

Synthesis Example 9: Synthesis of Compound 82

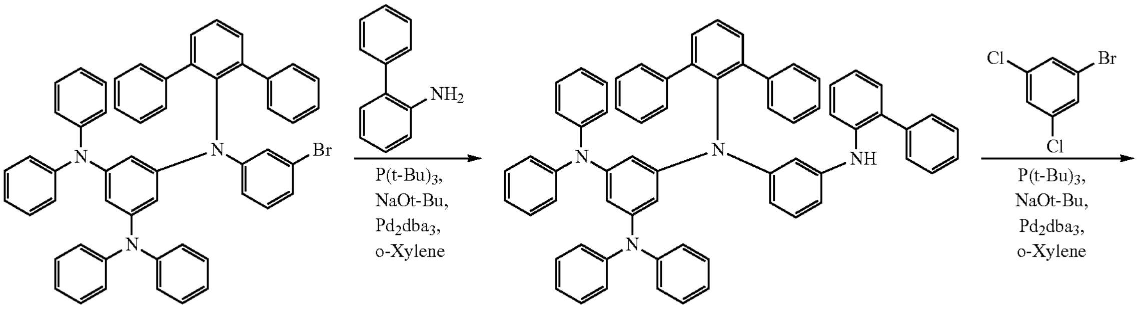

55-b 82-a

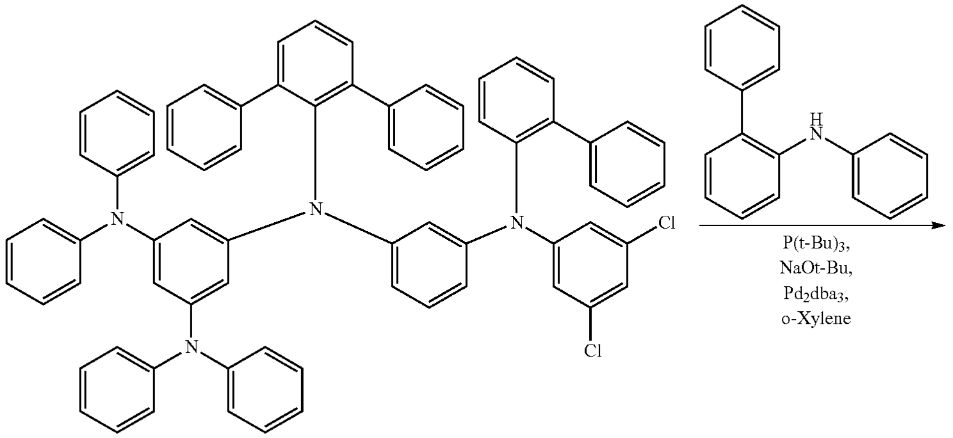

82-b

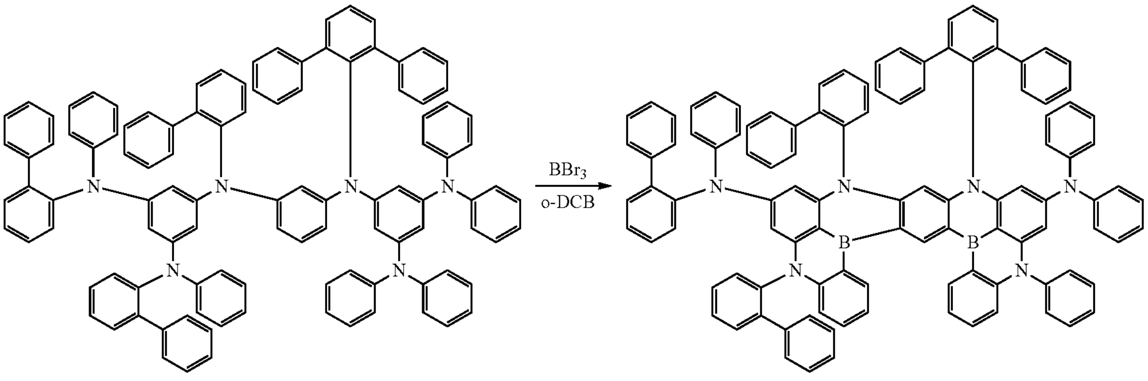

82-c 82

Synthesis of Intermediate Compound 82-a

In an argon atmosphere, Compound 55-b (30 g, 37 mmol), 2-amino biphenyl (6.3 g, 37 mmol), sodium tert-butoxide (10.6 g, 111 mmol), tris-tert-butyl phosphine (1.7 ml, 3.8 mmol), and $Pd_2dba_3$ (1.7 g, 1.9 mmol) were added to a 1 L flask and dissolved in 400 ml of o-xylene, and the reaction solution was stirred at a temperature of 140° C. for 12 hours. After cooling, water (1 L) and ethylacetate (300 ml) were added thereto for extraction and collection of an organic layer, and was dried using $MgSO_4$ and filtered. The filtered solution was placed under reduced pressure to remove solvent therefrom, and the obtained solid was purified and separated by column chromatography using silica gel using $CH_2Cl_2$ and hexane as development solvents to thereby obtain Intermediate compound 82-a (white solid, 24 g, 74%). The obtained white solid was identified by ESI-LCMS as Intermediate compound 82-a.

ESI-LCMS: $[M]^+$: $C_{66}H_{50}N_4$. 898.4006.

Synthesis of Intermediate Compound 82-b

In an argon atmosphere, Compound 82-a (24 g, 27 mmol), 1,3-dichloro-5-bromobenzene (6 g, 27 mmol), sodium tert-butoxide (7.8 g, 81 mmol), tris-tert-butyl phosphine (1.2 ml, 2.8 mmol), and $Pd_2dba_3$ (1.2 g, 1.4 mmol) were added to a 1 L flask and dissolved in 300 ml of o-xylene, and the reaction solution was stirred at a temperature of 100° C. for 12 hours. After cooling, water (1 L) and ethylacetate (300 ml) were added thereto for extraction and collection of an organic layer, and was dried using $MgSO_4$ and filtered. The filtered solution was placed under reduced pressure to remove solvent therefrom, and the obtained solid was purified and separated by column chromatography using silica gel using $CH_2Cl_2$ and hexane as development solvents to thereby obtain Intermediate compound 82-b (white solid, 18 g, 65%). The obtained white solid was identified by ESI-LCMS as Intermediate compound 82-b.

ESI-LCMS: $[M]^+$: $C_{72}H_{52}N_4Cl_2$. 1042.2437.

Synthesis of Intermediate Compound 82-c

In an argon atmosphere, Compound 82-b (18 g, 17 mmol), N-phenyl-[1,1'-biphenyl]-2-amine (8.5 g, 34 mmol), sodium tert-butoxide (4.9 g, 51 mmol), tris-tert-butyl phosphine (1.0 ml, 1.8 mmol), and $Pd_2dba_3$ (0.8 g, 0.9 mmol) were added to a 1 L flask and dissolved in 200 ml of o-xylene, and the reaction solution was stirred at a temperature of 140° C. for 12 hours. After cooling, water (1 L) and ethylacetate (300 ml) were added thereto for extraction and collection of an organic layer, and was dried using $MgSO_4$ and filtered. The filtered solution was placed under reduced pressure to remove solvent therefrom, and the obtained solid was purified and separated by column chromatography using silica gel using $CH_2Cl_2$ and hexane as development solvents to thereby obtain Intermediate compound 82-c (white solid, 17 g, 71%). The obtained white solid was identified by ESI-LCMS as Intermediate compound 82-c.

ESI-LCMS: $[M]^+$: $C_{108}H_{80}N_6$. 1460.6318.

Synthesis of Compound 82

In an argon atmosphere, Compound 82-c (17 g, 12 mmol) was added to a 1 L flask, dissolved in 500 ml of o-dichlorobenzene, and cooled to 0° C. in an ice water vessel. Boron tribromide (5 eq.) was slowly added dropwise to the reaction solution, the temperature was slowly raised to room temperature, and the reaction solution was stirred for 20 minutes. The reaction solution was heated to a temperature of 180° C. and stirred for 12 hours. After cooling, triethylamine (5 ml) was slowly added dropwise thereto to terminate the reaction and solvent was removed therefrom under reduced pressure. The obtained solid was washed with MeOH and was purified and separated by column chromatography using silica gel using $CH_2Cl_2$ and hexane as development solvents to thereby obtain Compound 82 (yellow solid, 1.9 g, 11%). The obtained yellow solid was identified by ESI-LCMS and $^1$H-NMR as Compound 82.

ESI-LCMS: $[M]^+$: $C_{108}H_{74}B_2N_6$. 1476.6551.

$^1$H-NMR (400 MHz, $CDCl_3$): 10.36 (s, 1H), 9.22 (d, 2H), 8.20 (d, 2H), 8.10 (d, 3H), 7.43 (m, 13H), 7.24 (m, 16H), 7.12 (m, 20H), 7.01 (m, 7H), 6.87 (s, 1H), 6.52 (s, 4H).

Synthesis Example 10: Synthesis of Compound 83

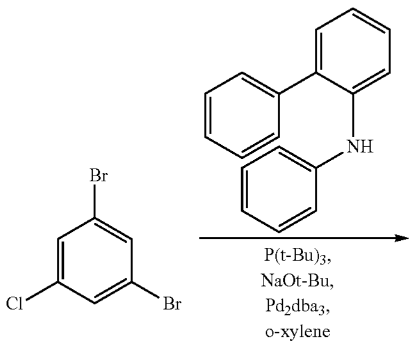

-continued
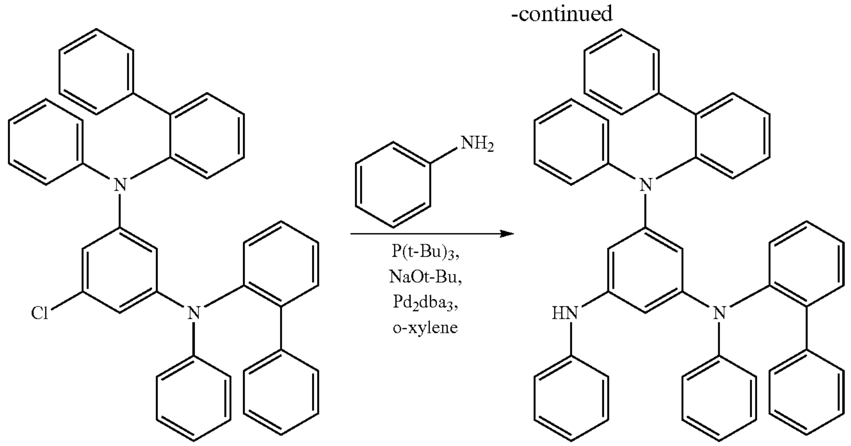
83-a 83-b
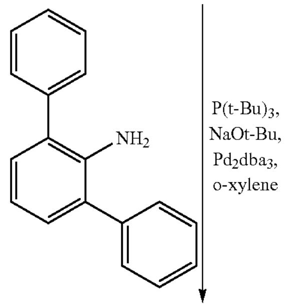
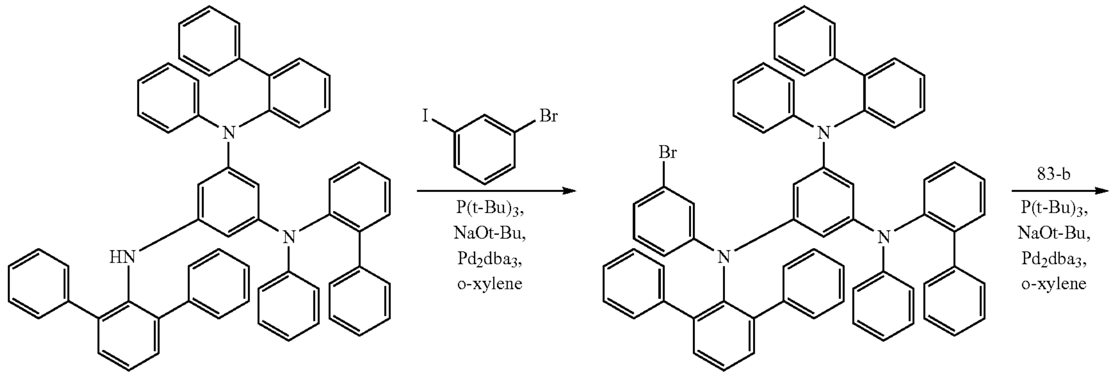
83-c 83-d

-continued

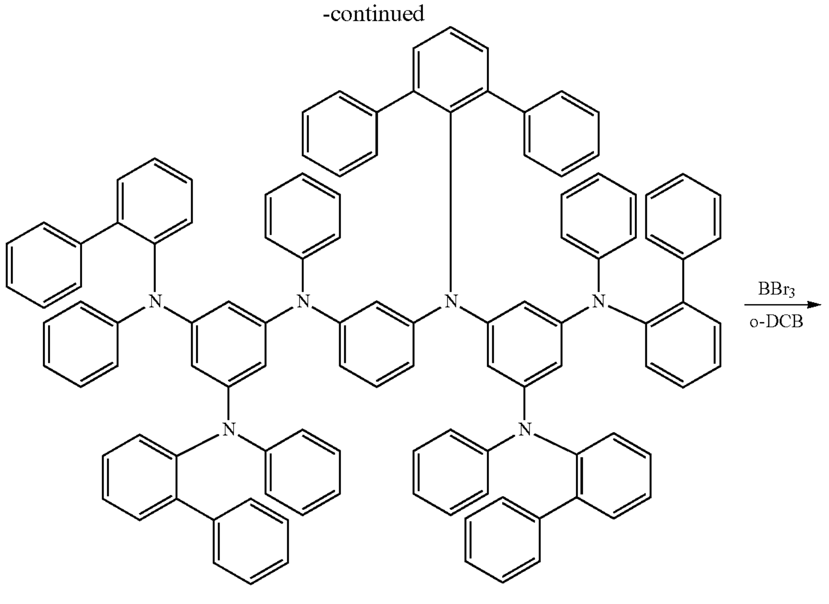

83-e

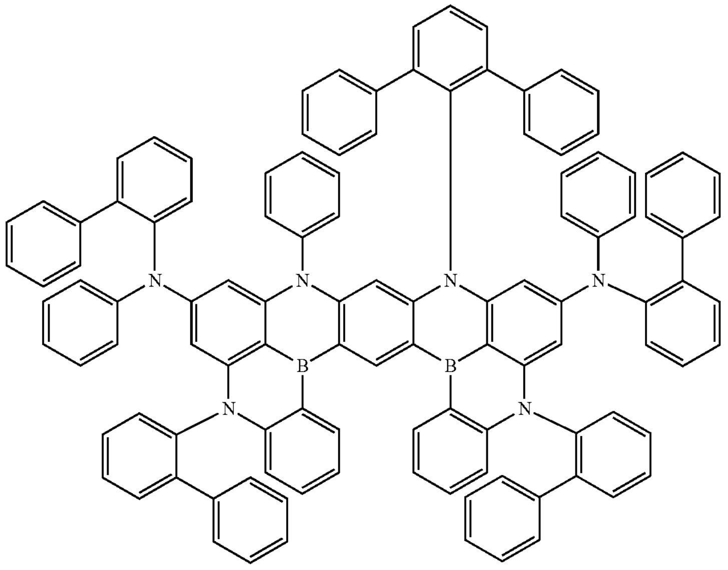

83

Synthesis of Intermediate Compound 83-a

In an argon atmosphere, 3,5-dibromo-chlorobenzene (18 g, 111 mmol), N-phenyl-[1,1'-biphenyl]-2-amine (54 g, 222 mmol), sodium tert-butoxide (32 g, 333 mmol), tris-tert-butyl phosphine (5.0 ml, 11 mmol), and $Pd_2dba_3$ (5.1 g, 5.5 mmol) were added to a 2 L flask and dissolved in 1 L of o-xylene, and the reaction solution was stirred at temperature of 100° C. for 12 hours. After cooling, water (1 L) and ethylacetate (300 ml) were added thereto for extraction and collection of an organic layer, and was dried using $MgSO_4$ and filtered. The filtered solution was placed under reduced pressure to remove solvent therefrom, and the obtained solid was purified and separated by column chromatography using silica gel using $CH_2Cl_2$ and hexane as development solvents to thereby obtain Intermediate compound 83-a (white solid, 50 g, 75%). The obtained white solid was identified by ESI-LCMS as Intermediate compound 83-a.

ESI-LCMS: $[M]^+$: $C_{42}H_{31}N_2Cl$. 598.2201.

Synthesis of Intermediate Compound 83-b

In an argon atmosphere, Compound 83-a (50 g, 83 mmol), aniline (8 g, 83 mmol), sodium tert-butoxide (24 g, 249 mmol), tris-tert-butyl phosphine (4 ml, 8.4 mmol), and $Pd_2dba_3$ (3.8 g, 4.2 mmol) were added to a 2 L flask and dissolved in 800 ml of o-xylene, and the reaction solution was stirred at a temperature of 140° C. for 12 hours. After cooling, water (1 L) and ethylacetate (300 ml) were added thereto for extraction and collection of an organic layer, and was dried using $MgSO_4$ and filtered. The filtered solution was placed under reduced pressure to remove solvent therefrom, and the obtained solid was purified and separated by column chromatography using silica gel using $CH_2Cl_2$ and hexane as development solvents to thereby obtain Intermediate compound 83-b (white solid, 38 g, 71%). The obtained white solid was identified by ESI-LCMS as Intermediate compound 83-b.

ESI-LCMS: $[M]^+$: $C_{48}H_{37}N_3$. 655.3001.

Synthesis of Intermediate Compound 83-c

In an argon atmosphere, Compound 83-a (50 g, 83 mmol), [1,1':3',1"-terphenyl]-2'-amine (20 g, 83 mmol), sodium tert-butoxide (24 g, 249 mmol), tris-tert-butyl phosphine (4 ml, 8.4 mmol), and $Pd_2dba_3$ (3.8 g, 4.2 mmol) were added to a 2 L flask and dissolved in 800 ml of o-xylene, and the reaction solution was stirred at a temperature of 140° C. for 12 hours. After cooling, water (1 L) and ethylacetate (300 ml) were added thereto for extraction and collection of an organic layer, and was dried using $MgSO_4$ and filtered. The filtered solution was placed under reduced pressure to remove solvent therefrom, and the obtained solid was purified and separated by column chromatography using silica gel using $CH_2Cl_2$ and hexane as development solvents to thereby obtain Intermediate compound 83-c (white solid, 49 g, 73%). The obtained white solid was identified by ESI-LCMS as Intermediate compound 83-c.

ESI-LCMS: $[M]^+$: $C_{60}H_{45}N_3$. 807.3535.

Synthesis of Intermediate Compound 83-d

In an argon atmosphere, Compound 83-c (45 g, 55 mmol), 3-bromo-iodobenzene (15.8 g, 55 mmol), sodium tert-butoxide (16 g, 165 mmol), tris-tert-butyl phosphine (2.5 ml, 5.6 mmol), and $Pd_2dba_3$ (2.5 g, 2.8 mmol) were added to a 2 L flask and dissolved in 800 ml of o-xylene, and the reaction solution was stirred at a temperature of 100° C. for 12 hours. After cooling, water (1 L) and ethylacetate (300 ml) were added thereto for extraction and collection of an organic layer, and was dried using $MgSO_4$ and filtered. The filtered solution was placed under reduced pressure to remove solvent therefrom, and the obtained solid was purified and separated by column chromatography using silica gel using $CH_2Cl_2$ and hexane as development solvents to thereby obtain Intermediate compound 83-d (white solid, 35 g, 67%). The obtained white solid was identified by ESI-LCMS as Intermediate compound 83-d.

ESI-LCMS: $[M]^+$: $C_{66}H_{48}N_3Br$. 961.2738.

Synthesis of Intermediate Compound 83-e

In an argon atmosphere, Compound 83-d (35 g, 36 mmol), Compound 83-b (23.6 g, 36 mmol), sodium tert-butoxide (10 g, 108 mmol), tris-tert-butyl phosphine (1.6 ml, 3.6 mmol), and $Pd_2dba_3$ (1.6 g, 1.8 mmol) were added to a 2 L flask and dissolved in 800 ml of o-xylene, and the reaction solution was stirred at a temperature of 140° C. for 12 hours. After cooling, water (1 L) and ethylacetate (300 ml) were added thereto for extraction and collection of an organic layer, and was dried using $MgSO_4$ and filtered. The filtered solution was placed under reduced pressure to remove solvent therefrom, and the obtained solid was purified and separated by column chromatography using silica gel using $CH_2Cl_2$ and hexane as development solvents to thereby obtain Intermediate compound 83-e (white solid, 32 g, 59%). The obtained white solid was identified by ESI-LCMS as Intermediate compound 83-e.

ESI-LCMS: $[M]^+$: $C_{114}H_{84}N_6$. 1536.6656.

Synthesis of Compound 83

In an argon atmosphere, Compound 83-e (32 g, 20 mmol) was added to a 1 L flask, dissolved in 500 ml of o-dichlorobenzene, and cooled to 0° C. in an ice water vessel. Boron tribromide (5 eq.) was slowly added dropwise to the reaction solution, the temperature was slowly raised to room temperature, and the reaction solution was stirred for 20 minutes. The reaction solution was heated to a temperature of 180° C. and stirred for 12 hours. After cooling, triethylamine (5 ml) was slowly added dropwise thereto to terminate the reaction and solvent was removed therefrom under reduced pressure. The obtained solid was washed with MeOH and was purified and separated by column chromatography using silica gel using $CH_2Cl_2$ and hexane as development solvents to thereby obtain Compound 83 (yellow solid, 2.2 g, 7%). The obtained yellow solid was identified by ESI-LCMS and $^1H$-NMR as Compound 83.

ESI-LCMS: $[M]^+$: $C_{114}H_{78}B_2N_6$. 1552.4437.

$^1H$-NMR (400 MHz, $CDCl_3$): 10.17 (s, 1H), 9.33 (d, 2H), 8.22 (d, 2H), 8.13 (d, 4H), 7.41 (m, 23H), 7.24 (m, 20H), 7.08 (m, 18H), 6.91 (s, 1H), 6.43 (s, 4H).

Synthesis Example 11: Synthesis of Compound 85

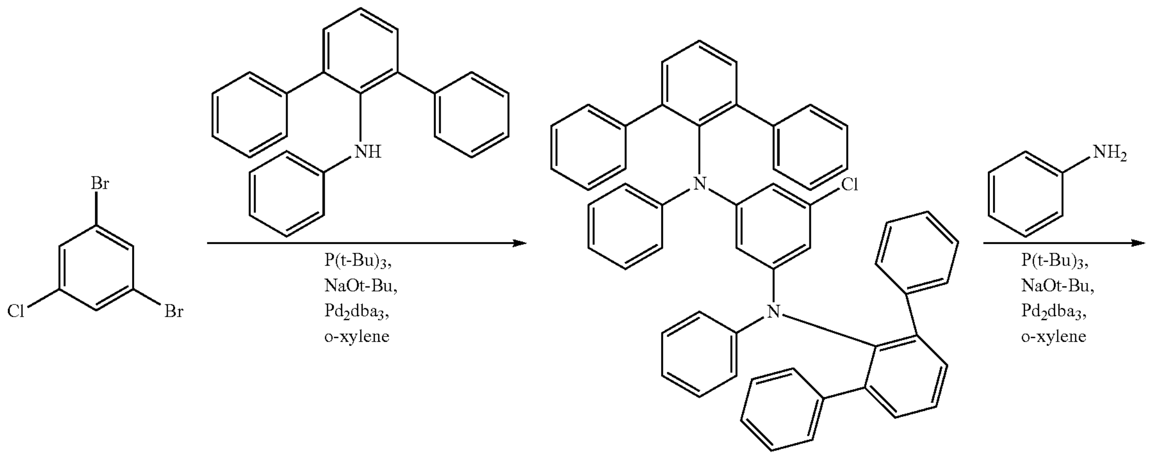

85-a

-continued

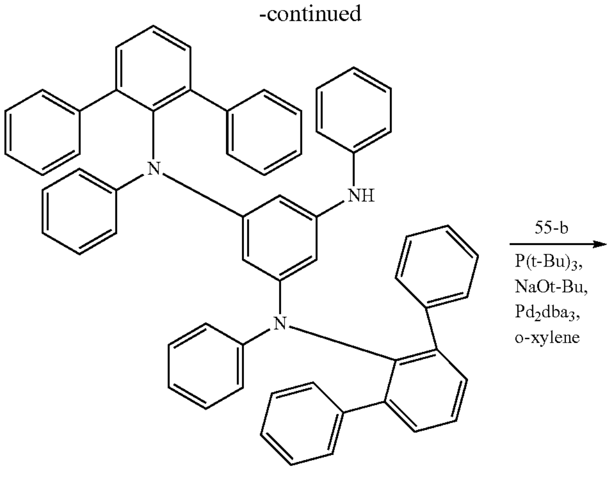

85-b

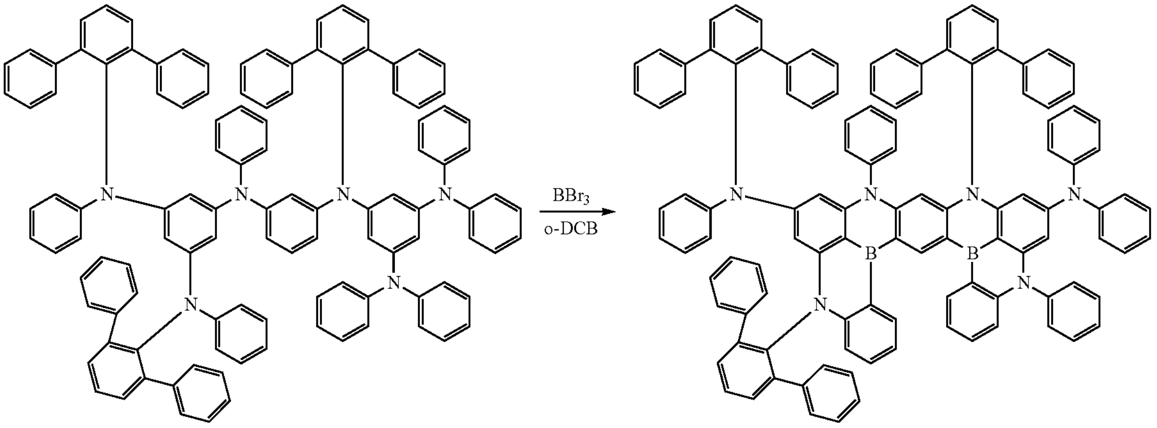

85-c 85

Synthesis of Intermediate Compound 85-a

In an argon atmosphere, 3,5-dibromo-chlorobenzene (35 g, 111 mmol), N-phenyl-[1,1':3',1"-terphenyl]-2'-amine (36 g, 111 mmol), sodium tert-butoxide (32 g, 333 mmol), tris-tert-butyl phosphine (5.1 ml, 11 mmol), and $Pd_2dba_3$ (5.1 g, 5.6 mmol) were added to a 2 L flask and dissolved in 1 L of o-xylene, and the reaction solution was stirred at temperature of 100° C. for 12 hours. After cooling, water (1 L) and ethylacetate (300 ml) were added thereto for extraction and collection of an organic layer, and was dried using $MgSO_4$ and filtered. The filtered solution was placed under reduced pressure to remove solvent therefrom, and the obtained solid was purified and separated by column chromatography using silica gel using $CH_2Cl_2$ and hexane as development solvents to thereby obtain Intermediate compound 85-a (white solid, 55 g, 67%). The obtained white solid was identified by ESI-LCMS as Intermediate compound 85-a.

ESI-LCMS: $[M]^+$: $C_{54}H_{39}N_2Cl$. 750.2812.

Synthesis of Intermediate Compound 85-b

In an argon atmosphere, Compound 85-a (55 g, 73 mmol), aniline (7 g, 111 mmol), sodium tert-butoxide (21 g, 219 mmol), tris-tert-butyl phosphine (3.3 ml, 7.2 mmol), and $Pd_2dba_3$ (3.3 g, 3.6 mmol) were added to a 2 L flask and dissolved in 700 ml of o-xylene, and the reaction solution was stirred at a temperature of 140° C. for 12 hours. After cooling, water (1 L) and ethylacetate (300 ml) were added thereto for extraction and collection of an organic layer, and was dried using $MgSO_4$ and filtered. The filtered solution was placed under reduced pressure to remove solvent therefrom, and the obtained solid was purified and separated by column chromatography using silica gel using $CH_2Cl_2$ and hexane as development solvents to thereby obtain Intermediate compound 85-b (white solid, 38 g, 64%). The obtained white solid was identified by ESI-LCMS as Intermediate compound 85-b.

ESI-LCMS: $[M]^+$: $C_{60}H_{45}N_3$. 807.3515.

Synthesis of Intermediate Compound 85-c

In an argon atmosphere, Compound 85-b (30 g, 37 mmol), Compound 55-b (30 g, 37 mmol), sodium tert-butoxide (10 g, 111 mmol), tris-tert-butyl phosphine (1.7 ml, 3.6 mmol), and $Pd_2dba_3$ (1.7 g, 1.8 mmol) were added to a 2 L flask and dissolved in 400 ml of o-xylene, and the reaction solution was stirred at a temperature of 140° C. for 12 hours. After cooling, water (1 L) and ethylacetate (300 ml) were added thereto for extraction and collection of an organic layer, and was dried using $MgSO_4$ and filtered. The filtered solution was placed under reduced pressure to remove solvent therefrom, and the obtained solid was purified and separated by column chromatography using silica gel using $CH_2Cl_2$ and hexane as development solvents to thereby obtain Intermediate compound 85-c (white solid, 24 g, 48%). The obtained white solid was identified by ESI-LCMS as Intermediate compound 85-c.

ESI-LCMS: $[M]^+$: $C_{114}H_{84}N_6$. 1536.6123.

Synthesis of Compound 85

In an argon atmosphere, Compound 85-c (24 g, 15 mmol) was added to a 1 L flask, dissolved in 500 ml of o-dichlorobenzene, and cooled to 0° C. in an ice water vessel. Boron tribromide (5 eq.) was slowly added dropwise to the reaction solution, and the temperature was slowly raised to room temperature. The reaction solution was heated to a temperature of 180° C. and stirred for 12 hours. After cooling, triethylamine (5 ml) was slowly added dropwise thereto to terminate the reaction and solvent was removed therefrom under reduced pressure. The obtained solid was washed with MeOH and was purified and separated by column chromatography using silica gel using $CH_2Cl_2$ and hexane as development solvents to thereby obtain Compound 85 (yellow solid, 1.8 g, 8%). The obtained yellow solid was identified by ESI-LCMS and $^1$H-NMR as Compound 85.

ESI-LCMS: $[M]^+$: $C_{114}H_{78}B_2N_6$. 1552.6512.

$^1$H-NMR (400 MHz, $CDCl_3$): 10.22 (s, 1H), 9.27 (d, 2H), 8.25 (d, 6H), 7.36 (m, 21H), 7.21 (m, 14H), 7.02 (m, 29H), 6.88 (s, 1H), 6.47 (s, 4H).

Synthesis Example 12: Synthesis of Compound 97

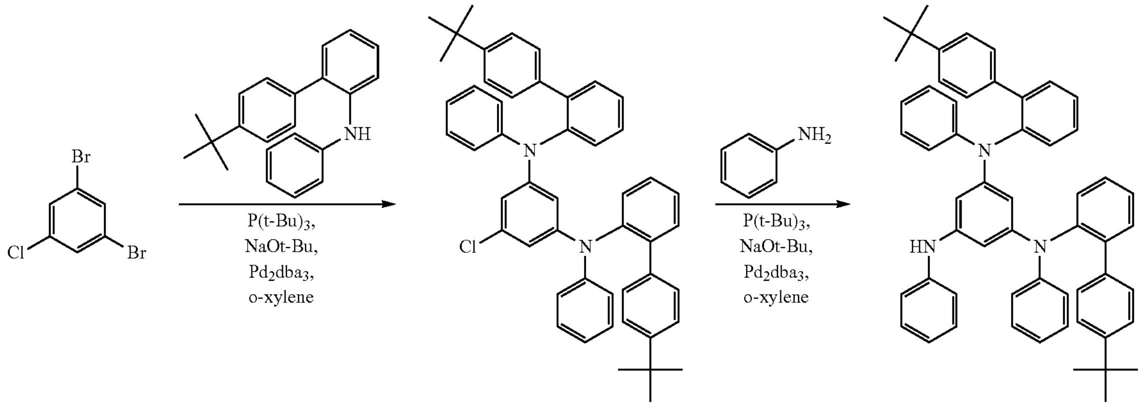

97-a 97-b

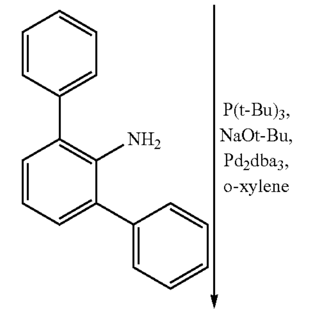

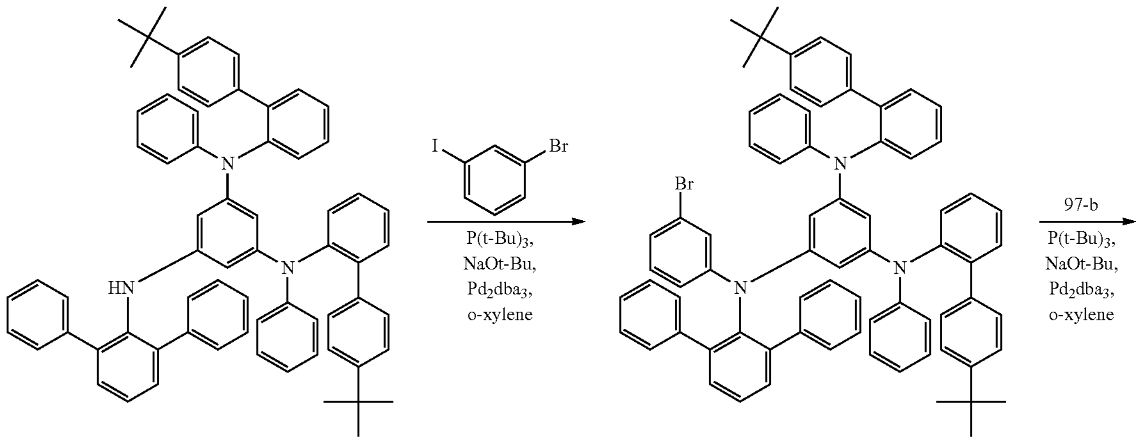

97-c 97-d

-continued

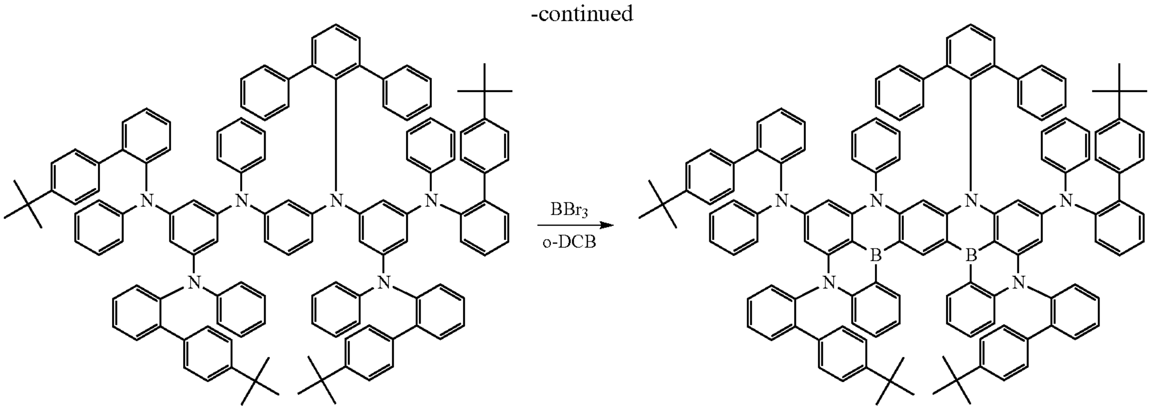

97-e

97

Synthesis of Intermediate Compound 97-a

In an argon atmosphere, 1,3-dibromo-5-chlorobenzene (30 g, 111 mmol), 4'-(tert-butyl)-N-phenyl-[1,1'-biphenyl]-2-amine (67 g, 222 mmol), sodium tert-butoxide (32 g, 333 mmol), tris-tert-butyl phosphine (5 ml, 11 mmol), and $Pd_2dba_3$ (5.1 g, 5.6 mmol) were added to a 2 L flask and dissolved in 1 L of o-xylene, and the reaction solution was stirred at temperature of 100° C. for 12 hours. After cooling, water (1 L) and ethylacetate (300 ml) were added thereto for extraction and collection of an organic layer, and was dried using $MgSO_4$ and filtered. The filtered solution was placed under reduced pressure to remove solvent therefrom, and the obtained solid was purified and separated by column chromatography using silica gel using $CH_2Cl_2$ and hexane as development solvents to thereby obtain Intermediate compound 97-a (white solid, 46 g, 59%). The obtained white solid was identified by ESI-LCMS as Intermediate compound 97-a.

ESI-LCMS: $[M]^+$: $C_{50}H_{47}N_2Cl$. 710.3336.

Synthesis of Intermediate Compound 97-b

In an argon atmosphere, Compound 97-a (45 g, 63 mmol), aniline (6.1 g, 63 mmol), sodium tert-butoxide (18 g, 190 mmol), tris-tert-butyl phosphine (3 ml, 6.4 mmol), and $Pd_2dba_3$ (2.9 g, 3.2 mmol) were added to a 2 L flask and dissolved in 600 ml of o-xylene, and the reaction solution was stirred at a temperature of 140° C. for 12 hours. After cooling, water (1 L) and ethylacetate (300 ml) were added thereto for extraction and collection of an organic layer, and was dried using $MgSO_4$ and filtered. The filtered solution was placed under reduced pressure to remove solvent therefrom, and the obtained solid was purified and separated by column chromatography using silica gel using $CH_2Cl_2$ and hexane as development solvents to thereby obtain Intermediate compound 97-b (white solid, 35 g, 72%). The obtained white solid was identified by ESI-LCMS as Intermediate compound 97-b.

ESI-LCMS: $[M]^+$: $C_{56}H_{53}N_3$. 767.4321.

Synthesis of Intermediate Compound 97-c

In an argon atmosphere, Compound 97-a (30 g, 42 mmol), [1,1':3',1"-terphenyl]-2'-amine (10 g, 42 mmol), sodium tert-butoxide (12 g, 126 mmol), tris-tert-butyl phosphine (2 ml, 4.2 mmol), and $Pd_2dba_3$ (1.9 g, 2.1 mmol) were added to a 2 L flask and dissolved in 400 ml of o-xylene, and the reaction solution was stirred at a temperature of 140° C. for 12 hours. After cooling, water (1 L) and ethylacetate (300 ml) were added thereto for extraction and collection of an organic layer, and was dried using $MgSO_4$ and filtered. The filtered solution was placed under reduced pressure to remove solvent therefrom, and the obtained solid was purified and separated by column chromatography using silica gel using $CH_2Cl_2$ and hexane as development solvents to thereby obtain Intermediate compound 97-c (white solid, 20 g, 54%). The obtained white solid was identified by ESI-LCMS as Intermediate compound 97-c.

ESI-LCMS: $[M]^+$: $C_{67}H_{59}N_3$. 905.4731.

Synthesis of Intermediate Compound 97-d

In an argon atmosphere, Compound 97-c (20 g, 22 mmol), 3-bromo-iodobenzene (10 g, 22 mmol), sodium tert-butoxide (6.4 g, 66 mmol), tris-tert-butyl phosphine (1 ml, 2.2 mmol), and $Pd_2dba_3$ (1.0 g, 1.1 mmol) were added to a 1 L flask and dissolved in 250 ml of o-xylene, and the reaction solution was stirred at a temperature of 100° C. for 12 hours. After cooling, water (1 L) and ethylacetate (300 ml) were added thereto for extraction and collection of an organic layer, and was dried using $MgSO_4$ and filtered. The filtered solution was placed under reduced pressure to remove solvent therefrom, and the obtained solid was purified and separated by column chromatography using silica gel using $CH_2Cl_2$ and hexane as development solvents to thereby obtain Intermediate compound 97-d (white solid, 16 g, 71%). The obtained white solid was identified by ESI-LCMS as Intermediate compound 97-d.

ESI-LCMS: $[M]^+$: $C_{74}H_{64}N_3Br$. 1073.2917.

Synthesis of Intermediate Compound 97-e

In an argon atmosphere, Compound 97-d (15 g, 14 mmol), Compound 97-b (9.2 g, 14 mmol), sodium tert-butoxide (4 g, 42 mmol), tris-tert-butyl phosphine (0.6 ml, 1.4 mmol), and $Pd_2dba_3$ (0.6 g, 0.7 mmol) were added to a 1 L flask and dissolved in 150 ml of o-xylene, and the reaction solution was stirred at a temperature of 100° C. for 12 hours. After cooling, water (1 L) and ethylacetate (300 ml) were added thereto for extraction and collection of an organic layer, and was dried using $MgSO_4$ and filtered. The filtered solution was placed under reduced pressure to remove solvent therefrom, and the obtained solid was purified and separated by column chromatography using silica gel using $CH_2Cl_2$ and hexane as development solvents to thereby obtain Intermediate compound 97-e (white solid, 16 g, 66%). The obtained white solid was identified by ESI-LCMS as Intermediate compound 97-e.

ESI-LCMS: $[M]^+$: $C_{130}H_{116}N_6$. 1760.9331.

Synthesis of Compound 97

In an argon atmosphere, Compound 97-e (15 g, 8.5 mmol) was added to a 1 L flask, dissolved in 500 ml of o-dichlorobenzene, and cooled to 0° C. in an ice water vessel. Boron tribromide (5 eq.) was slowly added dropwise to the reaction solution, and the temperature was slowly raised to room temperature. The reaction solution was heated to a temperature of 180° C. and stirred for 12 hours. After cooling, triethylamine (5 ml) was slowly added dropwise thereto to terminate the reaction and solvent was removed therefrom under reduced pressure. The obtained solid was washed with MeOH and was purified and separated by column chromatography using silica gel using $CH_2Cl_2$ and hexane as development solvents to thereby obtain Compound 97 (yellow solid, 1.2 g, 8%). The obtained yellow solid was identified by ESI-LCMS and $^1$H-NMR as Compound 97.

ESI-LCMS: $[M]^+$: $C_{130}H_{110}B_2N_6$. 1776.8997.

$^1$H-NMR (400 MHz, $CDCl_3$): 10.34 (s, 1H), 9.41 (d, 2H), 8.12 (d, 4H), 7.44 (m, 32H), 7.24 (m, 21H), 7.00 (m, 9H), 6.84 (s, 1H), 6.52 (s, 4H), 1.33 (s, 36H).

Synthesis Example 13: Synthesis of Compound 101

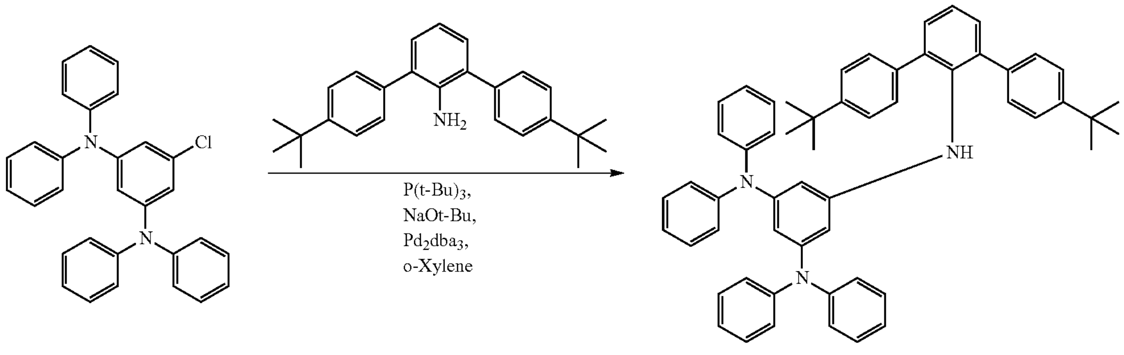

101-b

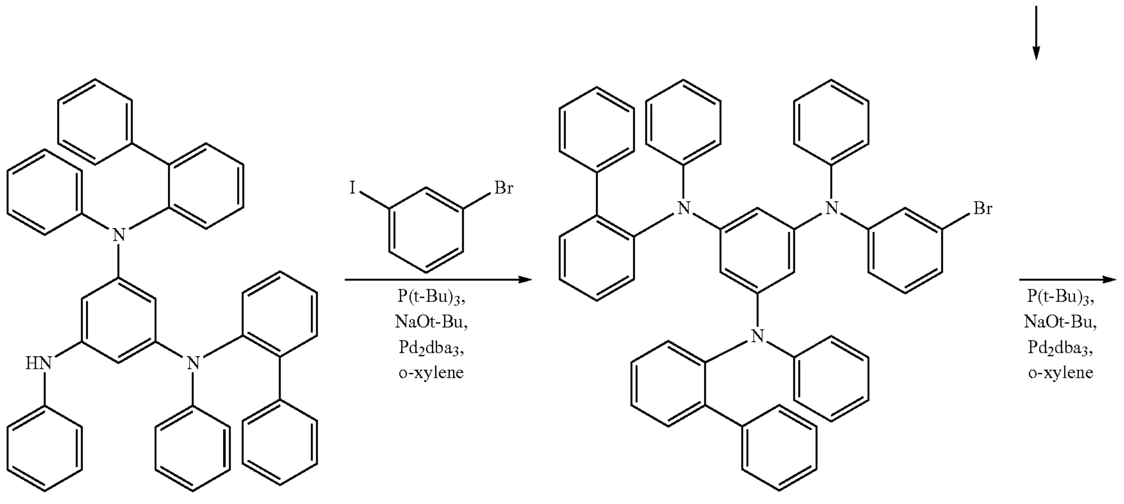

83-b 101-a

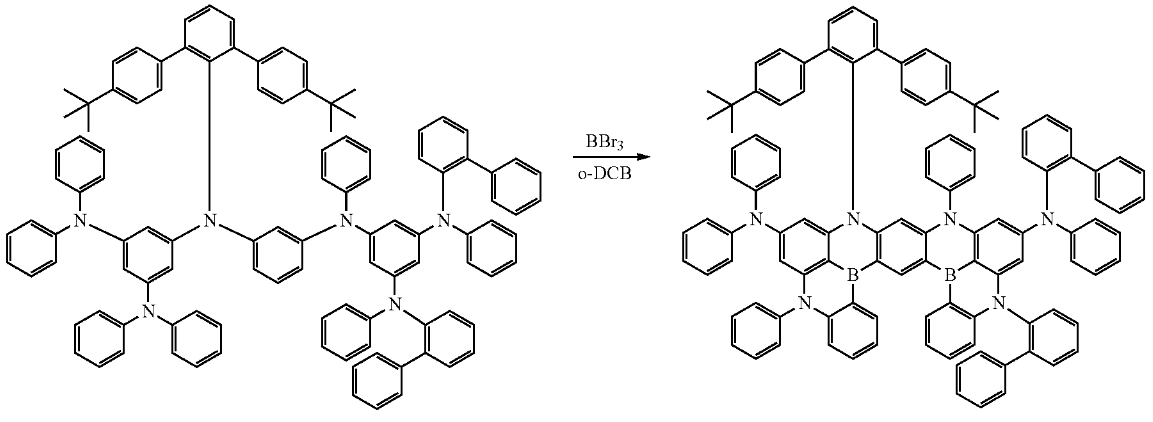

101-c

101

Synthesis of Intermediate Compound 101-a

In an argon atmosphere, Compound 83-b (30 g, 46 mmol), 3-bromo-iodobenzene (13 g, 46 mmol), sodium tert-butoxide (13 g, 138 mmol), tris-tert-butyl phosphine (2.2 ml, 4.6 mmol), and $Pd_2dba_3$ (2.1 g, 2.3 mmol) were added to a 2 L flask and dissolved in 500 ml of o-xylene, and the reaction solution was stirred at a temperature of 140° C. for 12 hours. After cooling, water (1 L) and ethylacetate (300 ml) were added thereto for extraction and collection of an organic layer, and was dried using $MgSO_4$ and filtered. The filtered solution was placed under reduced pressure to remove solvent therefrom, and the obtained solid was purified and separated by column chromatography using silica gel using $CH_2Cl_2$ and hexane as development solvents to thereby obtain Intermediate compound 101-a (white solid, 21 g, 56%). The obtained white solid was identified by ESI-LCMS as Intermediate compound 101-a.

ESI-LCMS: $[M]^+$: $C_{54}H_{40}N_3Br$. 809.2434.

Synthesis of Intermediate Compound 101-b

In an argon atmosphere, 5-chloro-N1,N1,N3,N3-tetraphenylbenzene-1,3-diamine (30 g, 67 mmol), 4,4"-di-tert-butyl-[1,1':3',1"-terphenyl]-2'-amine (24 g, 67 mmol), sodium tert-butoxide (19 g, 201 mmol), tris-tert-butyl phosphine (6 ml, 6.8 mmol), and $Pd_2dba_3$ (3 g, 3.4 mmol) were added to a 2 L flask and dissolved in 500 ml of o-xylene, and the reaction solution was stirred at a temperature of 140° C. for 12 hours. After cooling, water (1 L) and ethylacetate (300 ml) were added thereto for extraction and collection of an organic layer, and was dried using $MgSO_4$ and filtered. The filtered solution was placed under reduced pressure to remove solvent therefrom, and the obtained solid was purified and separated by column chromatography using silica gel using $CH_2Cl_2$ and hexane as development solvents to thereby obtain Intermediate compound 101-b (white solid, 37 g, 72%). The obtained white solid was identified by ESI-LCMS as Intermediate compound 101-b.

ESI-LCMS: $[M]^+$: $C_{56}H_{56}N_3$. 767.4119.

Synthesis of Intermediate Compound 101-c

In an argon atmosphere, Compound 101-a (20 g, 25 mmol), Compound 101-b (19 g, 25 mmol), sodium tert-butoxide (7.2 g, 75 mmol), tris-tert-butyl phosphine (1.2 ml, 2.6 mmol), and $Pd_2dba_3$ (1.1 g, 1.3 mmol) were added to a 2 L flask and dissolved in 250 ml of o-xylene, and the reaction solution was stirred at a temperature of 140° C. for 12 hours. After cooling, water (1 L) and ethylacetate (300 ml) were added thereto for extraction and collection of an organic layer, and was dried using $MgSO_4$ and filtered. The filtered solution was placed under reduced pressure to remove solvent therefrom, and the obtained solid was purified and separated by column chromatography using silica gel using $CH_2Cl_2$ and hexane as development solvents to thereby obtain Intermediate compound 101-c (white solid, 23.5 g, 65%). The obtained white solid was identified by ESI-LCMS as Intermediate compound 101-c.

ESI-LCMS: $[M]^+$: $C_{110}H_{52}N_6$. 1497.2331.

Synthesis of Compound 101

In an argon atmosphere, Compound 101-c (20 g, 8.5 mmol) was added to a 1 L flask, dissolved in 500 ml of o-dichlorobenzene, and cooled to 0° C. in an ice water vessel. Boron tribromide (5 eq.) was slowly added dropwise to the reaction solution, and the temperature was slowly raised to room temperature. The reaction solution was heated to a temperature of 180° C. and stirred for 12 hours. After cooling, triethylamine (5 ml) was slowly added dropwise thereto to terminate the reaction and solvent was removed therefrom under reduced pressure. The obtained solid was washed with MeOH and purified and separated by column chromatography using silica gel using $CH_2Cl_2$ and hexane as development solvents to thereby obtain Compound 101 (yellow solid, 1 g, 10%). The obtained yellow solid was identified by ESI-LCMS and $^1$H-NMR as Compound 101.

ESI-LCMS: $[M]^+$: $C_{110}H_{86}B_2N_6$. 1512.7171.

$^1$H-NMR (400 MHz, $CDCl_3$): 10.29 (s, 1H), 9.23 (d, 2H), 8.21 (d, 2H), 8.10 (d, 2H), 7.39 (m, 15H), 7.24 (m, 10H), 7.08 (m, 14H), 7.00 (m, 5H), 6.81 (s, 1H), 6.47 (s, 4H), 1.37 (s, 18H).

Proton nuclear magnetic resonance $^1$H NMR and Matrix-Assisted Laser Desorption/Ionization Time-of-Flight mass-spectrometer (MALDI-TOF MS) of the compounds synthesized according to Synthesis Examples 1 to 13 are shown in Table 1.

Synthesis methods for compounds other than the compounds shown in Synthesis Examples 1 to 13 may be easily recognized by those skilled in the technical field by referring to the synthesis paths and source materials described above.

TABLE 1

| Compound | $^1$H NMR ($CDCl_3$, 400 MHz) | ESI-MS $[M^+]$ |
|---|---|---|
| 1 | 10.46 (s, 1H), 9.94 (d, 2H), 9.31 (d, 1H), 8.37 (d, 1H), 8.20 (d, 2H), 7.39 (m, 3H), 7.24 (m, 18H), 7.03 (m, 27H), 6.83 (s, 1H), 6.49 (m, 4H). | 1173.4936. |
| 17 | 10.52 (s, 1H), 9.83 (d, 2H), 9.41 (d, 2H), 7.39 (t, 1H), 7.31 (m, 2H), 7.24 (m, 16H), 7.08 (m, 21H), 7.01 (t, 2H), 6.83 (s, 1H), 6.77 (d, 2H), 6.49 (m, 4H). | 1362.6617. |
| 31 | 10.26 (s, 1H), 9.65 (d, 2H), 9.41 (d, 2H), 9.31 (d, 2H), 8.37 (d, 3H), 8.20 (m, 1H), 7.39 (m, 10H), 7.24 (m, 12H), 7.08 (m, 24H), 6.77 (s, 1H), 7.01 (t, 2H), 6.49 (s, 2H). | 1395.4434. |
| 37 | 10.31 (s, 1H), 9.42 (d, 2H), 8.45 (d, 2H), 8.37 (d, 2H), 7.83 (t, 1H), 7.38 (m, 4H), 7.24 (m, 12H), 7.08 (m, 12H), 6.90 (m, 9H), 6.83 (t, 1H), 6.52 (d, 4H). | 1176.0157. |
| 41 | 10.78 (s, 1H), 9.87 (d, 2H), 9.31 (d, 4H), 8.37 (d, 4H), 7.39 (m, 12H), 7.21 (m, 8H), 7.04 (m, 24H), 6.65 (s, 1H), 6.50 (d, 4H). | 1254.4644. |
| 50 | 10.56 (s, 1H), 9.76 (d, 2H), 9.41 (d, 4H), 8.37 (d, 4H), 7.41 (m, 6H), 7.27 (m, 8H), 7.12 (m, 14H), 6.88 (s, 2H). | 1136.3336. |
| 55 | 10.43 (s, 1H), 9.58 (d, 2H), 9.31 (d, 2H), 8.37 (d, 2H), 8.20 (d, 2H), 7.76 (s, 1H), 7.41 (m, 7H), 7.25 (m, 13H), 7.12 (m, 17H), 6.57 (s, 1H), 6.49 (s, 2H). | 1343.5001. |
| 57 | 10.59 (s, 1H), 9.68 (d, 2H), 9.31 (d, 2H), 8.37 (d, 2H), 8.20 (d, 2H), 7.76 (s, 1H), 7.43 (m, 9H), 7.27 (m, 21H), 7.12 (m, 17H), 7.03 (m, 7H), 6.83 (s, 1H), 6.49 (s, 4H). | 1402.5554. |
| 82 | 10.36 (s, 1H), 9.22 (d, 2H), 8.20 (d, 2H), 8.10 (d, 3H), 7.43 (m, 13H), 7.24 (m, 16H), 7.12 (m, 20H), 7.01 (m, 7H), 6.87 (s, 1H), 6.52 (s, 4H). | 1476.6551. |
| 83 | 10.17 (s, 1H), 9.33 (d, 2H), 8.22 (d, 2H), 8.13 (d, 4H), 7.41 (m, 23H), 7.24 (m, 20H), 7.08 (m, 18H), 6.91 (s, 1H), 6.43 (s, 4H). | 1552.4437. |
| 85 | 10.22 (s, 1H), 9.27 (d, 2H), 8.25 (d, 6H), 7.36 (m, 21H), 7.21 (m, 14H), 7.02 (m, 29H), 6.88 (s, 1H), 6.47 (s, 4H). | 1552.6512. |

TABLE 1-continued

| Compound | $^1$H NMR ($CDCl_3$, 400 MHz) | ESI-MS [$M^+$] |
|---|---|---|
| 97 | 10.34 (s, 1H), 9.41 (d, 2H), 8.12 (d, 4H), 7.44 (m, 32H), 7.24 (m, 21H), 7.00 (m, 9H), 6.84 (s, 1H), 6.52 (s, 4H), 1.33 (s, 36H). | 1776.8997. |
| 101 | 10.29 (s, 1H), 9.23 (d, 2H), 8.21 (d, 2H), 8.10 (d, 2H), 7.39 (m, 15H), 7.24 (m, 10H), 7.08 (m, 14H), 7.00 (m, 5H), 6.81 (s, 1H), 6.47 (s, 4H), 1.37 (s, 18H). | 1512.7171. |

Example 1

As an anode, a glass substrate (product of Corning Inc. of Corning, New York (hereinafter "Corning Inc.")) with a 15 Ω/cm$^2$ (1,200 Å) ITO electrode formed thereon was cut to a size of 50 mm×50 mm×0.7 mm, sonicated with isopropyl alcohol and pure water each for 5 minutes, and then cleaned by exposure to ultraviolet rays and ozone for 30 minutes. Then, the resultant structure was mounted on a vacuum deposition apparatus.

The compound NPD was deposited on the anode to form a hole injection layer having a thickness of 300 Å, the compound HT6 was deposited on the hole injection layer to form a hole transport layer having a thickness of 200 Å, and the compound CzSi was deposited on the hole transport layer to form an emission auxiliary layer having a thickness of 100 Å.

The compound mCP (host) and Compound 1 (dopant) were co-deposited to a weight ratio of 99:1 on the emission auxiliary layer to form an emission layer having a thickness of 200 Å.

Subsequently, the compound TSPO1 was deposited on the emission layer to form a hole blocking layer having a thickness of 200 Å, the compound TPBi was deposited on the hole blocking layer to form an electron transport layer having a thickness of 300 Å, the compound lithium fluoride (LiF) was deposited on the electron transport layer to form an electron injection layer having a thickness of 10 Å, the element Al was deposited on the electron injection layer to form a cathode having a thickness of 3,000 Å, and the compound HT28 was deposited on the electrode to form a capping layer having a thickness of 700 Å, thereby completing the manufacture of a light-emitting device.

HT6

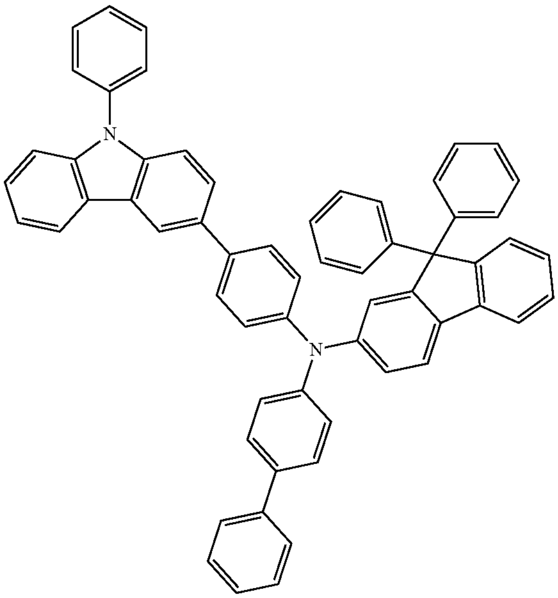

-continued

NPD

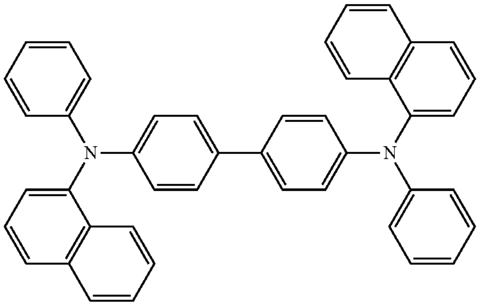

CzSi

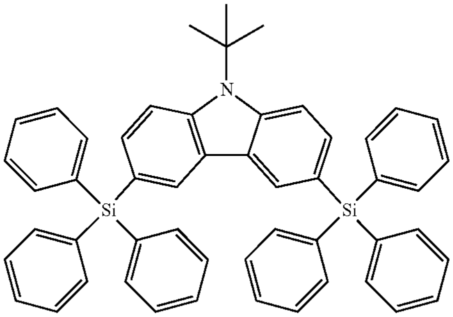

mCP

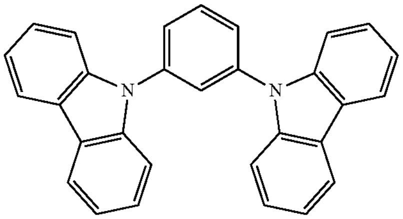

TSP01

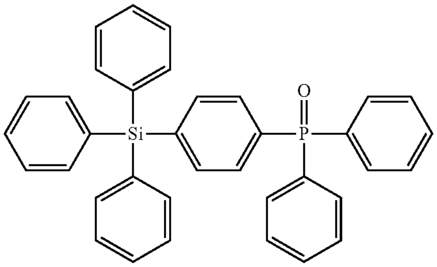

-continued

TPSi

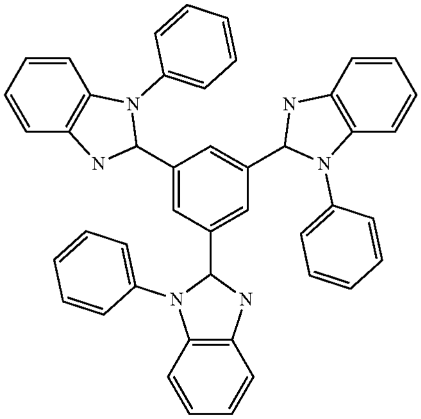

HT28

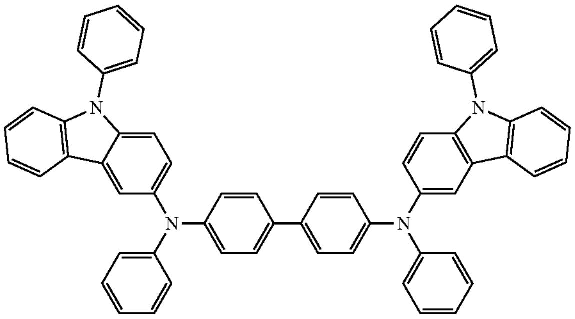

Examples 2 to 13 and Comparative Examples 1 to 3

Organic light-emitting devices were manufactured in the same manner as in Example 1, except that, in forming an emission layer, for use as a dopant, corresponding compounds shown in Table 1 were used instead of Compound 1.

Example 14

As an anode, a glass substrate (product of Corning Inc.) with a 15 Ω/$cm^2$ (1,200 Å) ITO electrode formed thereon was cut to a size of 50 mm×50 mm×0.7 mm, sonicated with isopropyl alcohol and pure water each for 5 minutes, and then cleaned by exposure to ultraviolet rays and ozone for 30 minutes. Then, the resultant structure was mounted on a vacuum deposition apparatus.

The compound NPD was deposited on the anode to form a hole injection layer having a thickness of 300 Å, the compound HT45 was deposited on the hole injection layer to form a hole transport layer having a thickness of 200 Å, and the compound CzSi was deposited on the hole transport layer to form an emission auxiliary layer having a thickness of 100 Å.

The compounds H39 and H37 (weight ratio of 5:5) used in an amount of 84 wt. % as a mixed host, the compound PD26 used in an amount of 15 wt. % as a metal phosphorescent dopant, and Compound 55 used in an amount of 1 wt. % as a dopant were co-deposited on the emission auxiliary layer to form an emission layer having a thickness of 200 Å.

Subsequently, the compound TSPO1 was deposited on the emission layer to form a hole blocking layer having a thickness of 200 Å, the compound TPBI was deposited on the hole blocking layer to form an electron transport layer having a thickness of 300 Å, the compound LiF was deposited on the electron transport layer to form an electron injection layer having a thickness of 10 Å, the element Al was deposited on the electron injection layer to form a cathode having a thickness of 3,000 Å, and the compound HT28 was deposited on the electrode to form a capping layer having a thickness of 700 Å, thereby completing the manufacture of a light-emitting device.

HT45

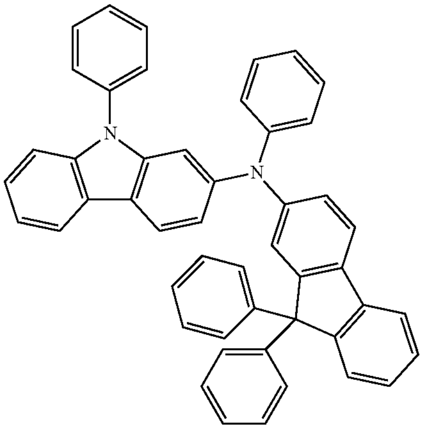

HT46

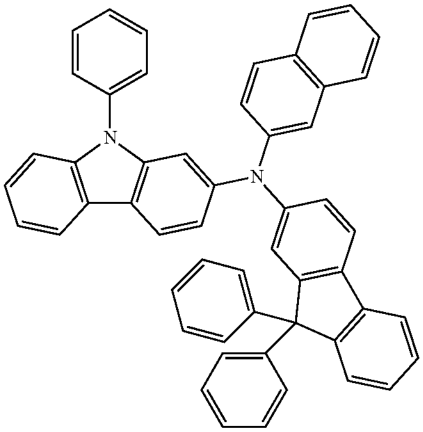

H37

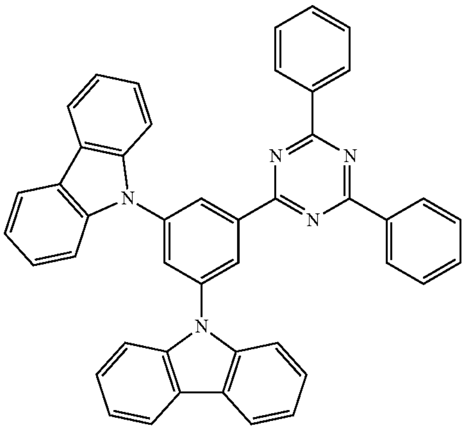

-continued

H39

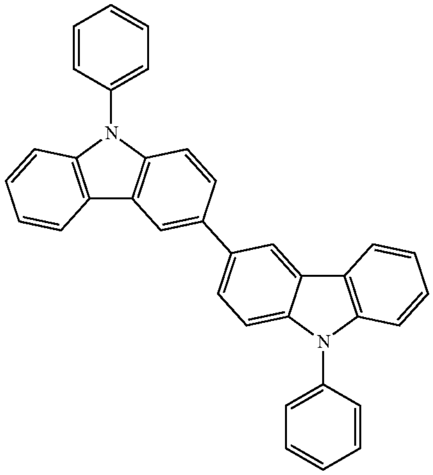

NPD

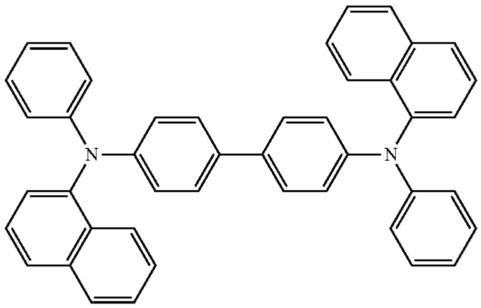

CzSi

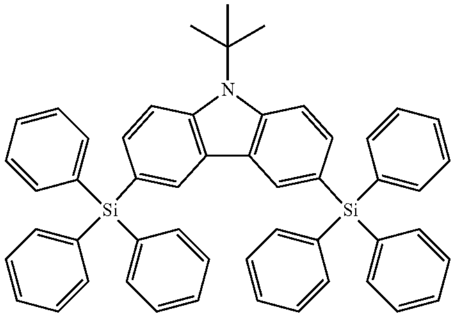

TSP01

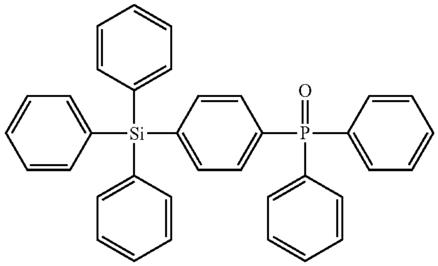

-continued

TPBi

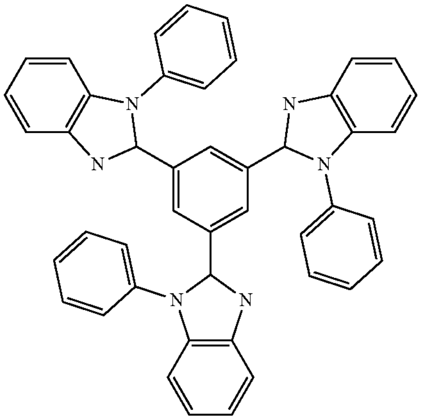

HT28

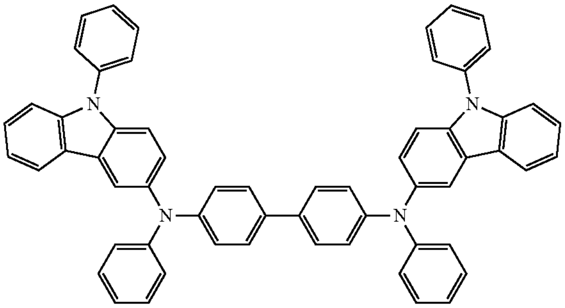

PD26

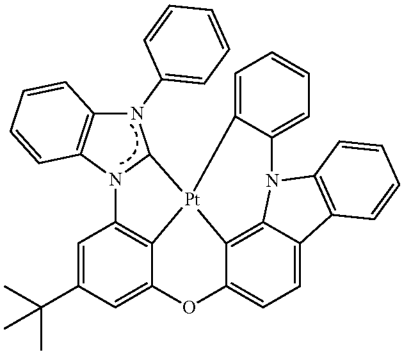

Examples 15 to 21 and Comparative Examples 4 to 6

Light-emitting devices were manufactured in the same manner as in Example 14, except that, for use as a hole transport layer material, a host, and a dopant, corresponding compounds shown in Table 2 were used.

Example 22

As an anode, a glass substrate (product of Corning Inc.) with a 15 $\Omega/cm^2$ (1,200 Å) ITO electrode formed thereon was cut to a size of 50 mm×50 mm×0.7 mm, sonicated with isopropyl alcohol and pure water each for 5 minutes, and then cleaned by exposure to ultraviolet rays and ozone for 30 minutes. Then, the resultant structure was mounted on a vacuum deposition apparatus.

The compound NPD was deposited on the anode to form a hole injection layer having a thickness of 300 Å, the compound HT45 was deposited on the hole injection layer to form a hole transport layer having a thickness of 200 Å, and the compound CzSi was deposited on the hole transport layer to form an emission auxiliary layer having a thickness of 100 Å.

The compounds H39 and H37 (weight ratio of 5:5) used in an amount of 84 wt. % as a mixed host, the compound PD26 used in an amount of 15 wt. % as a metal phosphorescent dopant, and Compound 17 used in an amount of 1 wt. % as a dopant were co-deposited on the emission auxiliary layer to form an emission layer having a thickness of 200 Å.

Subsequently, the compound TSPO1 was deposited on the emission layer to form a hole blocking layer having a thickness of 200 Å, the compound ET1 was deposited on the hole blocking layer to form an electron transport layer having a thickness of 300 Å, the compound LiF was deposited on the electron transport layer to form an electron injection layer having a thickness of 10 Å, the element Al was deposited on the electron injection layer to form a cathode having a thickness of 3,000 Å, and the compound HT28 was deposited on the electrode to form a capping layer having a thickness of 700 Å, thereby completing the manufacture of a light-emitting device.

NPD

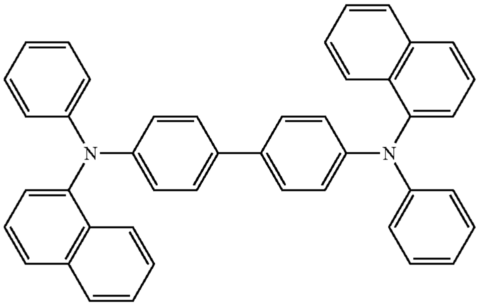

CzSi

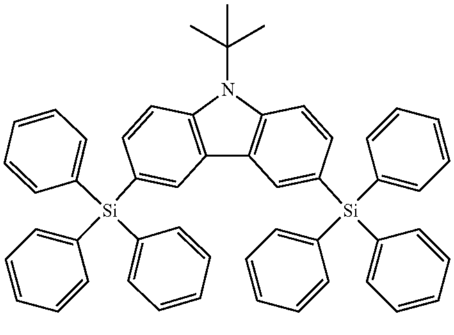

TSP01

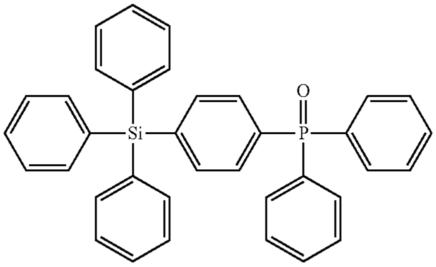

-continued

HT28

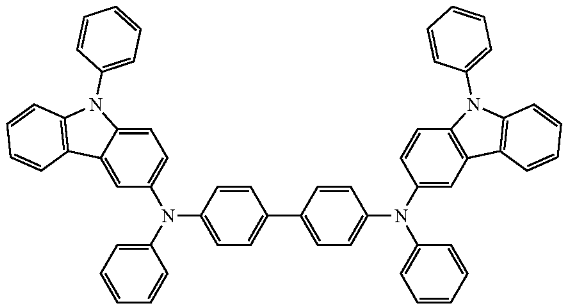

H37

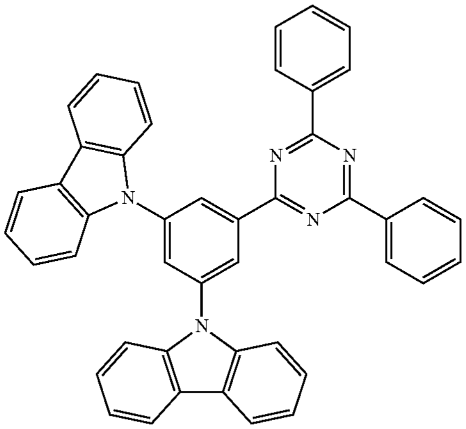

H39

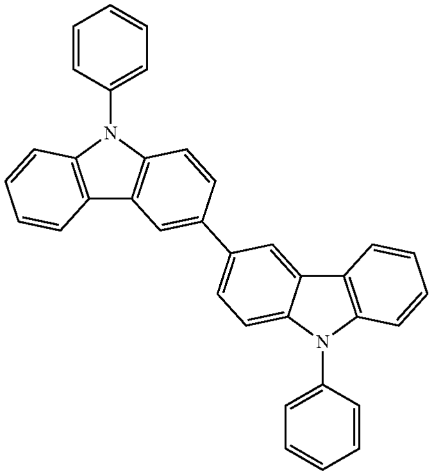

-continued

ET1

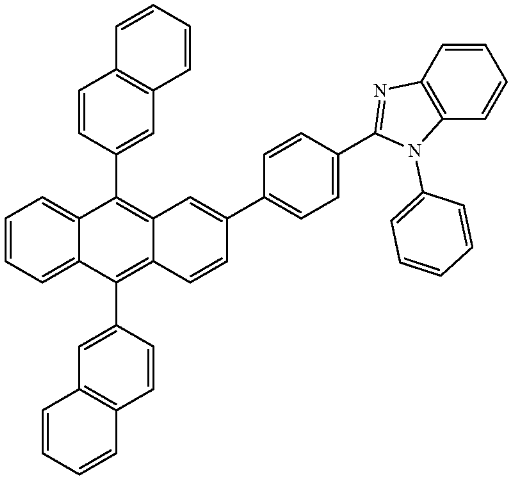

Alq3

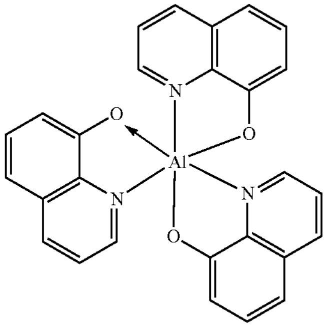

HT45

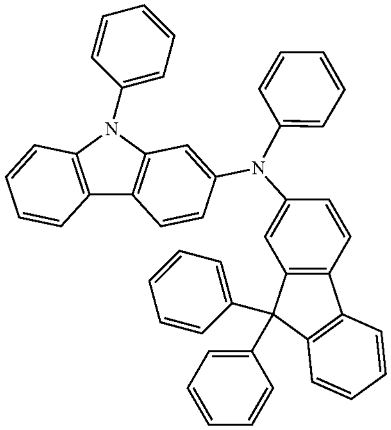

PD26

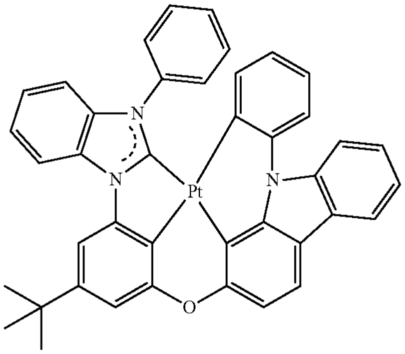

Examples 23 to 29 and Comparative Examples 7 and 8

Light-emitting devices were manufactured in the same manner as in Example 22, except that, for use as a hole transport layer material, a host, and a dopant, corresponding compounds shown in Table 4 were used.

Evaluation Example 2

The driving voltage in volt (V) at 1,000 in candela per square meter (cd/A or cd/$m^2$), emission efficiency (cd/A), and emission color of the organic light-emitting devices manufactured according to Examples 1 to 29 and Comparative Examples 1 to 8 were measured by using a source meter (sold under the trade designation Keithley MU 236, by Tektronix, Inc., of Beaverton, Oregon) and a luminance meter sold under the trade designation PR650 by Photo Research Inc. of Los Angeles, California. The ($T_{95}$) lifespan is the time it takes to achieve 95% of the initial luminance measured in hour at 100 milliamp per centimeter squared.

Results thereof are shown in Tables 2 to 4.

TABLE 2

| No. | Dopant | Driving voltage (V) | Emission efficiency (cd/A) | Emission wavelength | Lifespan ($T_{95}$)/ relative lifespan |
|---|---|---|---|---|---|
| Example 1 | 1 | 4.1 | 24.7 | 464 | 75/1.50 |
| Example 2 | 17 | 3.9 | 25.4 | 463 | 95/1.90 |
| Example 3 | 31 | 3.8 | 27.6 | 455 | 62/1.24 |
| Example 4 | 37 | 3.6 | 24.1 | 453 | 55/1.10 |
| Example 5 | 41 | 3.8 | 25.5 | 455 | 66/1.32 |
| Example 6 | 50 | 4.0 | 27.8 | 452 | 53/1.06 |
| Example 7 | 55 | 4.1 | 26.8 | 460 | 102/2.04 |
| Example 8 | 57 | 3.9 | 25.8 | 463 | 110/2.20 |
| Example 9 | 82 | 4.5 | 23.7 | 462 | 76/1.52 |
| Example 10 | 83 | 4.6 | 22.6 | 462 | 93/1.86 |
| Example 11 | 85 | 4.8 | 23.0 | 461 | 105/2.10 |
| Example 12 | 97 | 4.7 | 21.9 | 462 | 95/1.90 |
| Example 13 | 101 | 4.8 | 22.1 | 463 | 75/1.50 |
| Comparative Example 1 | A | 5.2 | 15.7 | 462 | 25/0.5 |
| Comparative Example 2 | B | 4.8 | 21.2 | 466 | 50/1.00 |
| Comparative Example 3 | C | 4.5 | 10.7 | 445 | 10/0.2 |

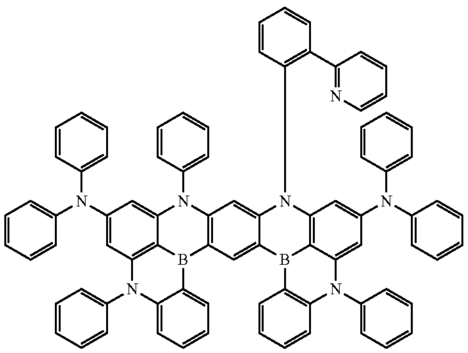

1

TABLE 2-continued
| No. | Dopant | Driving voltage (V) | Emission efficiency (cd/A) | Emission wavelength | Lifespan ($T_{95}$)/ relative lifespan |
|---|---|---|---|---|---|
| | 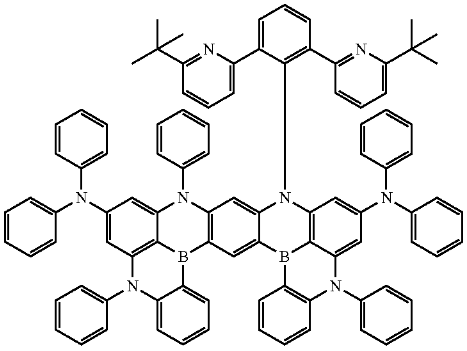 17 | | | | |
| | 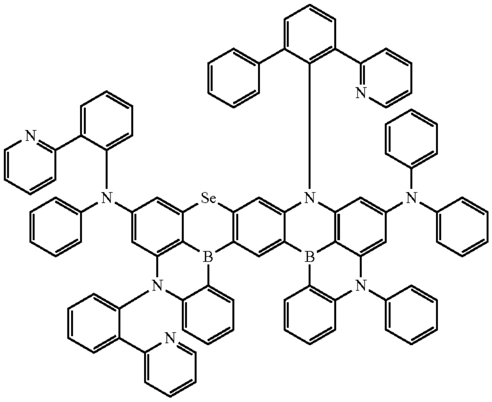 31 | | | | |
| | 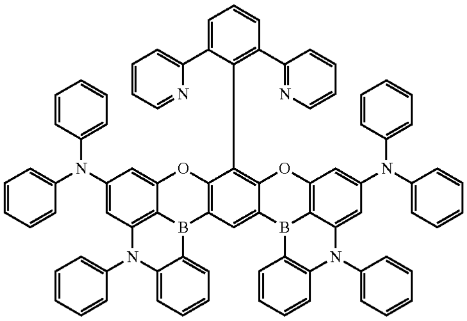 37 | | | | |
| | 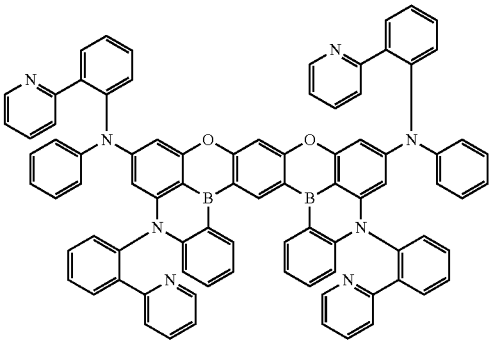 41 | | | | |
TABLE 2-continued
| No. | Dopant | Driving voltage (V) | Emission efficiency (cd/A) | Emission wavelength | Lifespan ($T_{95}$)/ relative lifespan |
|---|---|---|---|---|---|
| | 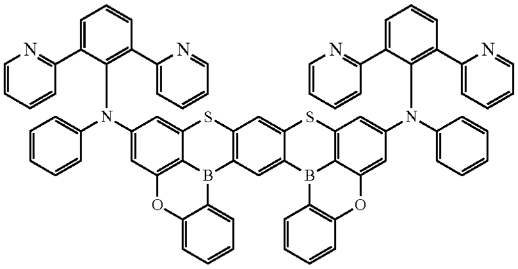 50 | | | | |
| | 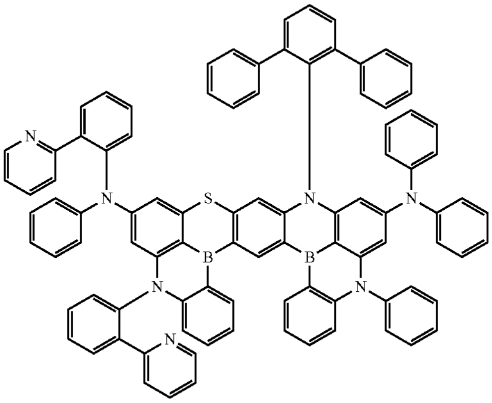 55 | | | | |
| | 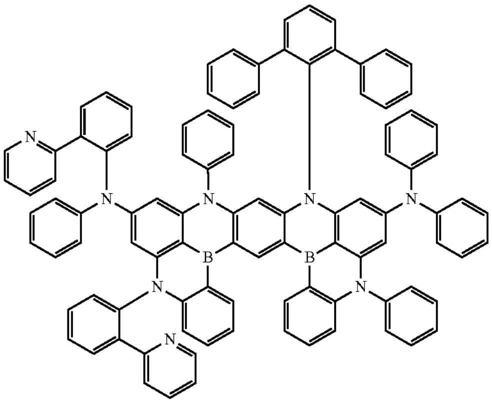 57 | | | | |

TABLE 2-continued
| No. | Dopant | Driving voltage (V) | Emission efficiency (cd/A) | Emission wavelength | Lifespan ($T_{95}$)/ relative lifespan |
|---|---|---|---|---|---|
| | 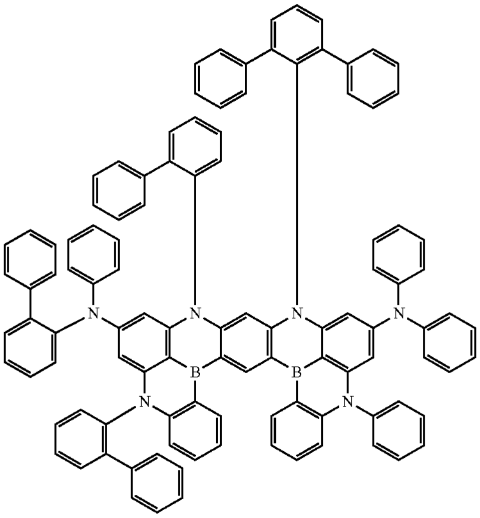 82 | | | | |
| | 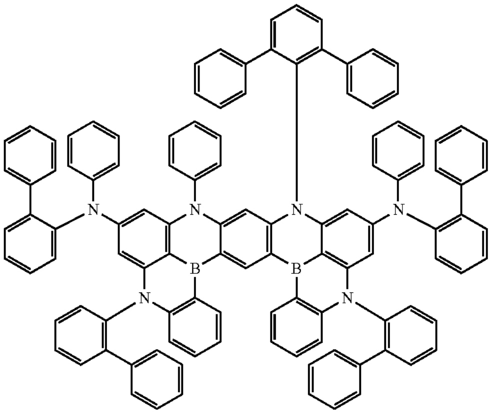 83 | | | | |
| | 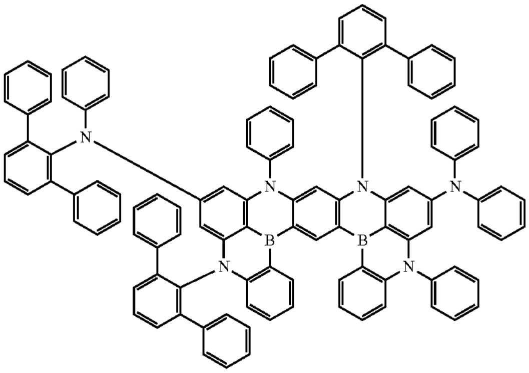 85 | | | | |
TABLE 2-continued
| No. | Dopant | Driving voltage (V) | Emission efficiency (cd/A) | Emission wavelength | Lifespan ($T_{95}$)/ relative lifespan |
|---|---|---|---|---|---|
| | 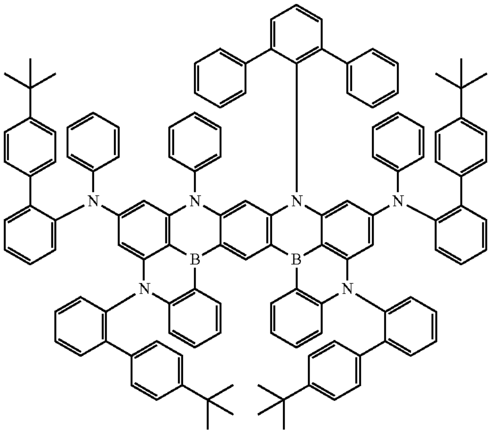 87 | | | | |
| | 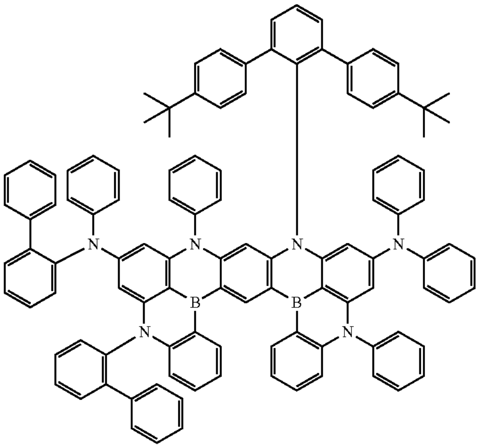 101 | | | | |
| | 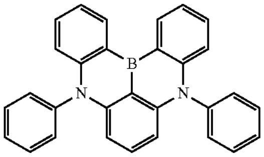 Compound A | | | | |
| | 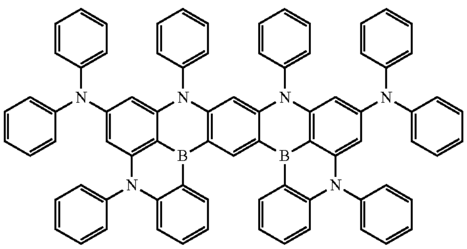 Compound B | | | | |

TABLE 2-continued

| No. | Dopant | Driving voltage (V) | Emission efficiency (cd/A) | Emission wavelength | Lifespan ($T_{95}$)/ relative lifespan |
|---|---|---|---|---|---|

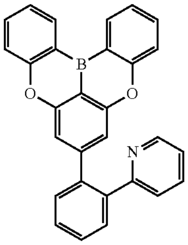

Compound C

TABLE 3

| No. | Hole transport layer | Host | Metal phos-phorescent dopant | Dopant | Driving voltage (V) | Emission efficiency (cd/A) | Emission wave-length | Lifespan ($T_{95}$)/ relative lifespan |
|---|---|---|---|---|---|---|---|---|
| Example 14 | HT45 | H39 + H37 | PD26 | 55 | 3.8 | 28.8 | 460 | 2.38 |
| Example 15 | HT45 | H39 + H37 | PD26 | 57 | 3.6 | 27.0 | 462 | 2.56 |
| Example 16 | HT45 | H39 + H37 | PD26 | 85 | 4.4 | 25.4 | 461 | 2.17 |
| Example 17 | HT45 | H39 + H37 | PD26 | 97 | 4.2 | 22.8 | 462 | 2.13 |
| Example 18 | HT46 | H39 + H37 | PD26 | 1 | 3.7 | 27.9 | 459 | 1.98 |
| Example 19 | HT46 | H39 + H37 | PD26 | 31 | 3.5 | 26.8 | 463 | 2.16 |
| Example 20 | HT46 | H39 + H37 | PD26 | 83 | 4.3 | 24.8 | 462 | 2.01 |
| Example 21 | HT46 | H39 + H37 | PD26 | 85 | 4.3 | 23 | 463 | 2.00 |
| Comparative Example 4 | HT45 | H39 + H37 | PD26 | A | 4.9 | 17.7 | 461 | 0.58 |
| Comparative Example 5 | HT45 | H39 + H37 | PD26 | B | 4.5 | 23.5 | 465 | 1.40 |
| Comparative Example 6 | HT45 | H39 + H37 | PD26 | C | 4.3 | 12.5 | 444 | 0.43 |

TABLE 4

| No. | Hole transport layer | Host | Electron transport layer | Metal phos-phorescent dopant | Dopant | Driving voltage (V) | Emission efficiency (cd/A) | Emission wave-length | Lifespan ($T_{95}$)/ relative lifespan |
|---|---|---|---|---|---|---|---|---|---|
| Example 22 | HT45 | H39 + H37 | ET1 | PD26 | 17 | 3.8 | 26.8 | 463 | 1.68 |
| Example 23 | HT45 | H39 + H37 | ET1 | PD26 | 37 | 3.6 | 25.5 | 454 | 1.09 |
| Example 24 | HT45 | H39 + H37 | ET1 | PD26 | 41 | 3.8 | 25.1 | 455 | 1.24 |
| Example 25 | HT45 | H39 + H37 | ET1 | PD26 | 101 | 4.5 | 23.8 | 463 | 1.36 |
| Example 26 | HT45 | H39 + H37 | ET1 + $Alq_3$ | PD26 | 31 | 3.6 | 26.5 | 455 | 1.48 |
| Example 27 | HT45 | H39 + H37 | ET1 + $Alq_3$ | PD26 | 41 | 3.7 | 24.8 | 455 | 1.73 |
| Example 28 | HT45 | H39 + H37 | ET1 + $Alq_3$ | PD26 | 83 | 4.5 | 24.1 | 462 | 2.21 |
| Example 29 | HT45 | H39 + H37 | ET1 + $Alq_3$ | PD26 | 85 | 4.7 | 25.0 | 461 | 2.68 |
| Comparative Example 7 | HT45 | H39 + H37 | ET1 | PD26 | C | 4.5 | 11.9 | 445 | 0.39 |
| Comparative Example 8 | HT45 | H39 + H37 | ET1 + $Alq_3$ | PD26 | C | 4.7 | 10.6 | 444 | 0.61 |

Table 2 shows that the light-emitting devices of Examples 1 to 13 emit blue light having a wavelength range of 450 nm to 470 nm and have significantly and unexpectedly improved driving voltage, emission efficiency, and lifespan characteristics as compared with the light-emitting devices of Comparative Examples 1 to 3.

Table 3 shows that the light-emitting devices of Examples 14 to 21 emit blue light having a wavelength range of 450 nm to 470 nm and have significantly and unexpectedly improved characterisitics including lower driving voltage, higher emission efficiency, and longer lifespan as compared with the light-emitting devices of Comparative Examples 4 to 6.

Table 4 shows that the light-emitting devices of Examples 22 to 29 emit blue light having a wavelength range of 450 nm to 470 nm and have significantly and unexpectedly improved characteristics including lower driving voltage, higher emission efficiency, and longer lifespan as compared with the light-emitting devices of Comparative Examples 7 and 8.

Although not wanting to be bound by theory, because the light-emitting device includes a heterocyclic compound represented by Formula 1, the light-emitting device may have low driving voltage, high emission efficiency, and high external quantum efficiency, and high-quality electronic apparatuses may be manufactured.

Although certain embodiments and implementations have been described herein, other embodiments and modifications will be apparent from this description. Accordingly, the inventive concepts are not limited to such embodiments, but rather to the broader scope of the appended claims and various obvious modifications and equivalent arrangements as would be apparent to a person of ordinary skill in the art.

What is claimed is:

1. A light-emitting device including:

a first electrode;

a second electrode facing the first electrode; and an interlayer between the first electrode and the second electrode and including an emission layer, wherein the interlayer comprises a heterocyclic compound of Formula 1, and the heterocyclic compound of Formula 1 is included in the emission layer:

Formula 1

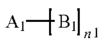

Formula 1-1

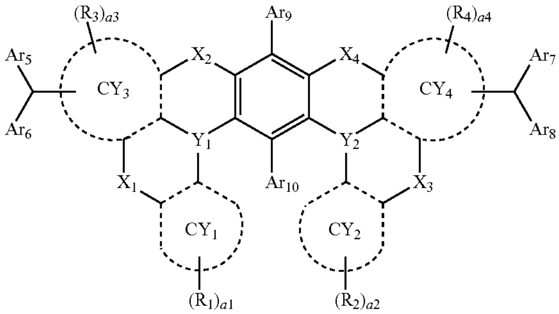

Formula 1-2

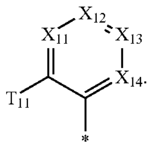

wherein, in Formulae 1-1, an 1-2, $A_1$ is a group of Formula 1-1, $B_1$ is a group of Formula 1-2, n1 is an integer from 1 to 10, $CY_1$ to $CY_4$ are each, independently from one another, a $C_5$-$C_{30}$ carbocyclic group or a $C_1$-$C_{30}$ heterocyclic group, $Y_1$ and $Y_2$ are each, independently from one another, B, P(═O), or P(═S), $X_1$ is O, S, Se, Te, N($Ar_1$), Al($Ar_1$), or P($Ar_1$), $X_2$ is O, S, Se, Te, N($Ar_2$), Al($Ar_2$), or P($Ar_2$), $X_3$ is O, S, Se, Te, N($Ar_3$), Al($Ar_3$), or P($Ar_3$), $X_4$ is O, S, Se, Te, N($Ar_4$), Al($Ar_4$), or P($Ar_4$), $Ar_1$ to $Ar_{10}$ are each, independently from one another, a binding site to $B_1$ in Formula 1, hydrogen, deuterium, —F, —Cl, —Br, —I, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, —C($Q_1$)($Q_2$)($Q_3$), —Si($Q_1$)($Q_2$)($Q_3$), -N($Q_1$)($Q_2$), —B($Q_1$)($Q_2$), —C(═O)($Q_1$), —S(═O)$_2$($Q_1$), or —P(═O)($Q_1$)($Q_2$), at least one of $Ar_1$ to $Ar_{10}$ are a binding site to $B_1$ in Formula 1, $T_{11}$ is a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, $X_{11}$ is N or C($R_{11}$), $X_{12}$ is N or C($R_{12}$), $X_{13}$ is N or C($R_{13}$), and $X_{14}$ is N or C($R_{14}$), $R_1$ to $R_4$ and Ru to $R_{14}$ are each, independently from one another, hydrogen, deuterium, —F, —Cl, —Br, —I, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, —C($Q_1$)($Q_2$)($Q_3$), —Si($Q_1$)($Q_2$)($Q_3$), —N($Q_1$)($Q_2$), —B($Q_1$)($Q_2$), —C(═O)($Q_1$), —S(═O)$_2$($Q_1$), or —P(═O)($Q_1$)($Q_2$), a1 to a4 are each, independently from one another, an integer from 0 to 10, when a1 is an integer of 2 or more, two or more of $R_1$(s) are optionally linked to each other to form a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, when a2 is an integer of 2 or more, two or more of $R_2$(s) are optionally linked to each other to form a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, when a3 is an integer of 2 or more, two or more of $R_3$(s) are optionally linked to each other to form a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, when a4 is an integer of 2 or more, two or more of $R_4$(s) are optionally linked to each other to form a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, two or more neighboring groups of $R_{11}$ to $R_{14}$ are optionally linked to each other to form a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$,

* in Formula 1-2 is a binding site to $A_1$ in Formula 1, and $R_{10a}$ is:

deuterium, —F, —Cl, —Br, —I, a hydroxyl group, a cyano group, or a nitro group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group each, independently from one another, unsubstituted or substituted with deuterium, —F, —Cl, —Br, —I, a hydroxyl group, a cyano group, a nitro group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, —Si($Q_{11}$)($Q_{12}$)($Q_{13}$), —N($Q_{11}$)($Q_{12}$), —B($Q_{11}$)($Q_{12}$), —C(═O)($Q_{11}$), —S(═O)$_2$($Q_{11}$), —P(═O)($Q_{11}$)($Q_{12}$), or any combination thereof;

a $C_3$-$C_{60}$ carbocyclic group, a $C_1$-$C_{60}$ heterocyclic group, a $C_6$-$C_{60}$ aryloxy group, or a $C_6$-$C_{60}$ arylthio group each, independently from one another, unsubstituted or substituted with deuterium, —F, —Cl, —Br, —I, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, —$Si(Q_{21})(Q_{22})(Q_{23})$, —$N(Q_{21})(Q_{22})$, —$B(Q_{21})(Q_{22})$, —$C(=O)(Q_{21})$, —$S(=O)_2(Q_{21})$, —$P(=O)(Q_{21})(Q_{22})$, or any combination thereof; or —$Si(Q_{31})(Q_{32})(Q_{33})$, —$N(Q_{31})(Q_{32})$, —$B(Q_{31})(Q_{32})$, —$C(=O)(Q_{31})$, —$S(=O)_2(Q_{31})$, or —$P(=O)(Q_{31})(Q_{32})$, wherein $Q_1$ to $Q_3$, $Q_{11}$ to $Q_{13}$, $Q_{21}$ to $Q_{23}$, and $Q_{31}$ to $Q_{33}$ are each, independently from one another: hydrogen; deuterium; —F; —Cl; —Br; —I; a hydroxyl group; a cyano group; a nitro group; a $C_1$-$C_{60}$ alkyl group; a $C_2$-$C_{60}$ alkenyl group; a $C_2$-$C_{60}$ alkynyl group; a $C_1$-$C_{60}$ alkoxy group; a $C_3$-$C_{60}$ carbocyclic group; or a $C_1$-$C_{60}$ heterocyclic group each, independently from one another, unsubstituted or substituted with deuterium, —F, a cyano group, a $C_1$-$C_{60}$ alkyl group, a $C_1$-$C_{60}$ alkoxy group, a phenyl group, a biphenyl group, or any combination thereof, wherein an organometallic compound of Formula 401 is included in the emission layer:

Formula 401

$$M(L_{401})_{xc1}(L_{402})_{xc2}$$

Formula 402

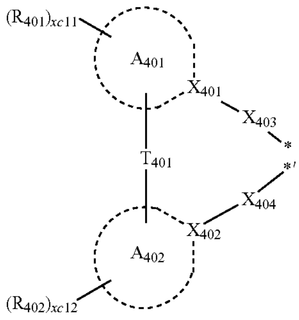

wherein, in Formulae 401 and 402,

M is a transition metal, $L_{401}$ is a ligand of Formula 402, and xc1 is 1, 2, or 3, wherein when xc1 is 2 or 3, two or more of $L_{401}$ (s) are identical to or different from each other, $L_{402}$ is an organic ligand, xc2 is 0, 1, 2, 3, or 4, and when xc2 is 2, 3 or 4, two or more of $L_{402}$(s) are identical to or different from each other, $X_{401}$ and $X_{402}$ are each, independently from one another, nitrogen or carbon, ring $A_{401}$ and ring $A_{402}$ are each, independently from one another, a $C_3$-$C_{60}$ carbocyclic group or a $C_1$-$C_{60}$ heterocyclic group, $T_{401}$ is a single bond, *—O—*, *—S—*, *—C(=O)—*', *—$N(Q_{411})$-*', *—$C(Q_{411})(Q_{412})$-*', *—$C(Q_{411})=C(Q_{412})$-*', *—$C(Q_{411})$=*', or *=C=*', $X_{403}$ and $X_{404}$ are each, independently from one another, a chemical bond, O, S, $N(Q_{413})$, $B(Q_{413})$, $P(Q_{413})$, $C(Q_{413})(Q_{414})$, or $Si(Q_{413})(Q_{414})$, $Q_{411}$ to $Q_{414}$ have, independently from one another, the same meaning as $Q_1$, $R_{401}$ and $R_{402}$ are each, independently from one another, hydrogen, deuterium, —F, —Cl, —Br, —I, a hydroxyl group, a cyano group, a nitro group, a $C_1$-$C_{20}$ alkyl group unsubstituted or substituted with at least one $R_{10a}$, a $C_1$-$C_{20}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, —$Si(Q_{401})(Q_{402})(Q_{403})$, —$N(Q_{401})(Q_{402})$, —$B(Q_{401})(Q_{402})$, —$C(=O)(Q_{401})$, —$S(=O)_2(Q_{401})$, or —$P(=O)(Q_{401})(Q_{402})$, $Q_{401}$ to $Q_{403}$ have, independently from one another, the same meaning as $Q_1$, xc11 and xc12 are each, independently from one another, an integer from 0 to 10, and

* and *' in Formula 402 each is a binding site to M in Formula 401.

2. The light-emitting device of claim 1, wherein the emission layer is configured to emit blue light.

3. The light-emitting device of claim 1, wherein the emission layer further comprises a host, and an amount of the host is greater than an amount of the heterocyclic compound of Formula 1.

4. The light-emitting device of claim 3, wherein the host comprises two different host compounds.

5. A light-emitting device including:

a first electrode;

a second electrode facing the first electrode; and an interlayer between the first electrode and the second electrode and including an emission layer, wherein the interlayer comprises a heterocyclic compound of Formula 1:

Formula 1

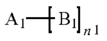

Formula 1-1

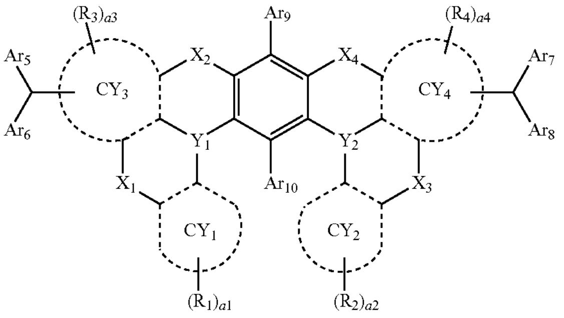

Formula 1-2

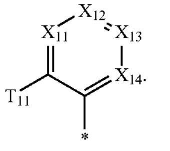

wherein, in Formulae 1, 1-1, and 1-2, $A_1$ is a group of Formula 1-1, $B_1$ is a group of Formula 1-2, n1 is an integer from 1 to 10, $CY_1$ to $CY_4$ are each, independently from one another, a $C_5$-$C_{30}$ carbocyclic group or a $C_1$-$C_{30}$ heterocyclic group, $Y_1$ and $Y_2$ are each, independently from one another, B, P(=O), or P(=S), $X_1$ is O, S, Se, Te, $N(Ar_1)$, $Al(Ar_1)$, or $P(Ar_1)$, $X_2$ is O, S, Se, Te, $N(Ar_2)$, $Al(Ar_2)$, or $P(Ar_2)$, $X_3$ is O, S, Se, Te, $N(Ar_3)$, $Al(Ar_3)$, or $P(Ar_3)$, $X_4$ is O, S, Se, Te, $N(Ar_4)$, $Al(Ar_4)$, or $P(Ar_4)$, $Ar_1$ to $Ar_{10}$ are each, independently from one another, a binding site to $B_1$ in Formula 1, hydrogen, deuterium, —F, —Cl, —Br, —I, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, —$C(Q_1)(Q_2)(Q_3)$, —$Si(Q_1)(Q_2)(Q_3)$, —$N(Q_1)(Q_2)$, —$B(Q_1)(Q_2)$, —$C(=O)(Q_1)$, —$S(=O)_2(Q_1)$, or —$P(=O)(Q_1)(Q_2)$, at least one of $Ar_1$ to $Ar_{10}$ are a binding site to $B_1$ in Formula 1, $T_{11}$ is a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, $X_{11}$ is N or $C(R_{11})$, $X_{12}$ is N or $C(R_{12})$, $X_{13}$ is N or $C(R_{13})$, and $X_{14}$ is N or $C(R_{14})$, $R_1$ to $R_4$ and $R_1$ to $R_{14}$ are each, independently from one another, hydrogen, deuterium, —F, —Cl, —Br, —I, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, —$C(Q_1)(Q_2)(Q_3)$, —$Si(Q_1)(Q_2)(Q_3)$, —$N(Q_1)(Q_2)$, —$B(Q_1)(Q_2)$, —$C(=O)(Q_1)$, —$S(=O)_2(Q_1)$, or —$P(=O)(Q_1)(Q_2)$, a1 to a4 are each, independently from one another, an integer from 0 to 10, when a1 is an integer of 2 or more, two or more of $R_1$(s) are optionally linked to each other to form a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, when a2 is an integer of 2 or more, two or more of $R_2$(s) are optionally linked to each other to form a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, when a3 is an integer of 2 or more, two or more of $R_3$(s) are optionally linked to each other to form a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, when a4 is an integer of 2 or more, two or more of $R_4$(s) are optionally linked to each other to form a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, two or more neighboring groups of $R_{11}$ to $R_{14}$ are optionally linked to each other to form a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$,

* in Formula 1-2 is a binding site to $A_1$ in Formula 1, and $R_{10a}$ is:

deuterium, —F, —Cl, —Br, —I, a hydroxyl group, a cyano group, or a nitro group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group each, independently from one another, unsubstituted or substituted with deuterium, —F, —Cl, —Br, —I, a hydroxyl group, a cyano group, a nitro group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, —$Si(Q_{11})(Q_{12})(Q_{13})$, —$N(Q_{11})(Q_{12})$, —$B(Q_{11})(Q_{12})$, —$C(=O)(Q_{11})$, —$S(=O)_2(Q_{11})$, —$P(=O)(Q_{11})(Q_{12})$, or any combination thereof;

a $C_3$-$C_{60}$ carbocyclic group, a $C_1$-$C_{60}$ heterocyclic group, a $C_6$-$C_{60}$ aryloxy group, or a $C_6$-$C_{60}$ arylthio group each, independently from one another, unsubstituted or substituted with deuterium, —F, —Cl, —Br, —I, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, —$Si(Q_{21})(Q_{22})(Q_{23})$, —$N(Q_{21})(Q_{22})$, —$B(Q_{21})(Q_{22})$, —$C(=O)(Q_{21})$, —$S(=O)_2(Q_{21})$, —$P(=O)(Q_{21})(Q_{22})$, or any combination thereof; or —$Si(Q_{31})(Q_{32})(Q_{33})$, —$N(Q_{31})(Q_{32})$, —$B(Q_{31})(Q_{32})$, —$C(=O)(Q_{31})$, —$S(=O)_2(Q_{31})$, or —$P(=O)(Q_{31})(Q_{32})$, wherein $Q_1$ to $Q_3$, $Q_{11}$ to $Q_{13}$, $Q_{21}$ to $Q_{23}$, and $Q_{31}$ to $Q_{33}$ are each, independently from one another: hydrogen; deuterium; —F; —Cl; —Br; —I; a hydroxyl group; a cyano group; a nitro group; a $C_1$-$C_{60}$ alkyl group; a $C_2$-$C_{60}$ alkenyl group; a $C_2$-$C_{60}$ alkynyl group; a $C_1$-$C_{60}$ alkoxy group; a $C_3$-$C_{60}$ carbocyclic group; or a $C_1$-$C_{60}$ heterocyclic group each, independently from one another, unsubstituted or substituted with deuterium, —F, a cyano group, a $C_1$-$C_{60}$ alkyl group, a $C_1$-$C_{60}$ alkoxy group, a phenyl group, a biphenyl group, or any combination thereof, wherein the emission layer comprises a host, and wherein the host comprises a hole transport host compound and an electron transport host compound.

6. The light-emitting device of claim 1, wherein the interlayer further comprises a hole transport region between the first electrode and the emission layer and an electron transport region between the emission layer and the second electrode, the hole transport region comprises a hole injection layer, a hole transport layer, an emission auxiliary layer, an electron blocking layer, or any combination thereof, and the electron transport region comprises a buffer layer, a hole blocking layer, an electron control layer, an electron transport layer, an electron injection layer, or any combination thereof.

7. The light-emitting device of claim 6, wherein the emission layer comprises the heterocyclic compound of Formula 1, the hole transport region comprises a compound of Formula 201, a compound of Formula 202, or any combination thereof:

Formula 201

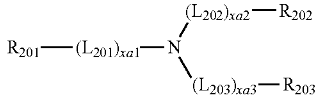

Formula 202

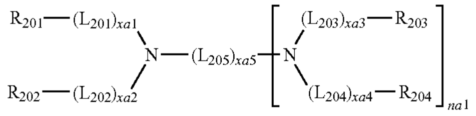

wherein, in Formulae 201 and 202, $L_{201}$ to $L_{204}$ are each, independently from one another, a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, $L_{205}$ is *—O—*', *—S—*', *—N($Q_{201}$)-*', a $C_1$-$C_{20}$ alkylene group unsubstituted or substituted with at least one $R_{10a}$, a $C_2$-$C_{20}$ alkenylene group unsubstituted or substituted with at least one $R_{10a}$, a $C_3$-$C_{60}$ carbocyclic group unsubstituted or substituted with at least one $R_{10a}$, or a $C_1$-$C_{60}$ heterocyclic group unsubstituted or substituted with at least one $R_{10a}$, xa1 to xa4 are each, independently from one another, an integer from 0 to 5, xa5 is an integer from 1 to 10, $R_{201}$ to $R_{204}$ and $Q_{201}$ are each, independently from one another, a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, $R_{201}$ and $R_{202}$ are optionally linked to each other, via a single bond, a $C_1$-$C_5$ alkylene group unsubstituted or substituted with at least one $R_{10a}$, or a $C_2$-$C_5$ alkenylene group unsubstituted or substituted with at least one $R_{10a}$, to form a $C_8$-$C_{60}$ polycyclic group unsubstituted or substituted with at least one $R_{10a}$, $R_{203}$ and $R_{204}$ are optionally linked to each other, via a single bond, a $C_1$-$C_5$ alkylene group unsubstituted or substituted with at least one $R_{10a}$, or a $C_2$-$C_5$ alkenylene group unsubstituted or substituted with at least one $R_{10a}$, to form a $C_8$-$C_{60}$ polycyclic group unsubstituted or substituted with at least one $R_{10a}$,

* and *' in $L_{205}$ each is a binding site in Formula 202, na1 is an integer from 1 to 4.

8. The light-emitting device of claim 7, wherein each of Formulae 201 and 202 includes at least one group of Formulae $CY_{201}$ to $CY_{217}$:

CY201

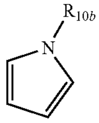

CY202

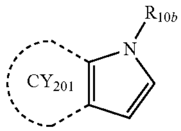

-continued

CY203

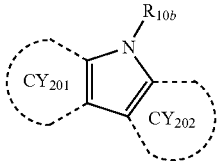

CY204

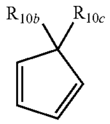

CY205

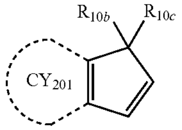

CY206

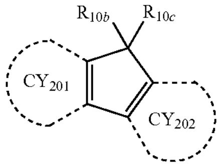

CY207

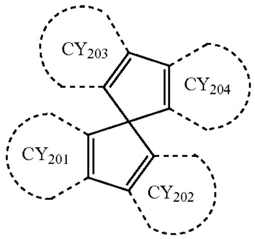

CY208

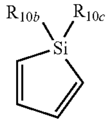

CY209

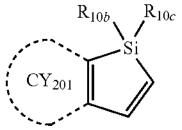

CY210

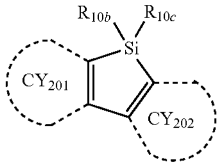

CY211

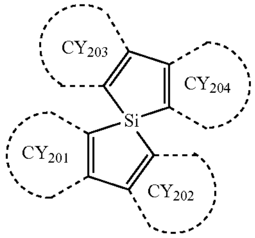

-continued

CY212

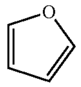

CY213

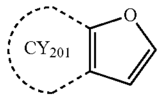

CY214

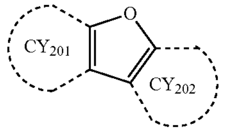

CY215

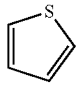

CY216

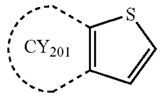

CY217

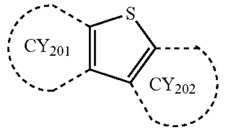

wherein, in Formulae CY201 to CY217, ring $CY_{201}$ to ring $CY_{204}$ are each, independently from one another, a $C_3$-$C_{20}$ carbocyclic group or a $C_1$-$C_{20}$ heterocyclic group, at least one hydrogen in Formulae CY201 to CY217 is unsubstituted or substituted with $R_{10a}$, and $R_{10a}$, $R_{10b}$, and $R_{10c}$ are each, independently from one another:

deuterium, —F, —Cl, —Br, —I, a hydroxyl group, a cyano group, or a nitro group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group each, independently from one another, unsubstituted or substituted with deuterium, —F, —Cl, —Br, —I, a hydroxyl group, a cyano group, a nitro group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, —Si($Q_{11}$)($Q_{12}$)($Q_{13}$), —N($Q_{11}$)($Q_{12}$), —B($Q_{11}$)($Q_{12}$), —C(═O)($Q_{11}$), —S(═O)$_2$($Q_{11}$), —P(═O)($Q_{11}$)($Q_{12}$), or any combination thereof;

a $C_3$-$C_{60}$ carbocyclic group, a $C_1$-$C_{60}$ heterocyclic group, a $C_6$-$C_{60}$ aryloxy group, or a $C_6$-$C_{60}$ arylthio group each, independently from one another, unsubstituted or substituted with deuterium, —F, —Cl, —Br, —I, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, —Si($Q_{21}$)($Q_{22}$)($Q_{23}$), —N($Q_{21}$)($Q_{22}$), —B($Q_{21}$)($Q_{22}$), —C(═O)($Q_{21}$), —S(═O)$_2$($Q_{21}$), —P(═O)($Q_{21}$)($Q_{22}$), or any combination thereof; or —Si($Q_{31}$)($Q_{32}$)($Q_{33}$), —N($Q_{31}$)($Q_{32}$), —B($Q_{31}$)($Q_{32}$), —C(═O)($Q_{31}$), —S(═O)$_2$($Q_{31}$), or —P(═O)($Q_{31}$)($Q_{32}$), wherein $Q_{11}$ to $Q_{13}$, $Q_{21}$ to $Q_{23}$, and $Q_{31}$ to $Q_{33}$ are each, independently from one another: hydrogen; deuterium; —F; —Cl; —Br; —I; a hydroxyl group; a cyano group; a nitro group; a $C_1$-$C_{60}$ alkyl group; a $C_2$-$C_{60}$ alkenyl group; a $C_2$-$C_{60}$ alkynyl group; a $C_1$-$C_{60}$ alkoxy group; a $C_3$-$C_{60}$ carbocyclic group; or a $C_1$-$C_{60}$ heterocyclic group each, independently from one another, unsubstituted or substituted with deuterium, —F, a cyano group, a $C_1$-$C_{60}$ alkyl group, a $C_1$-$C_{60}$ alkoxy group, a phenyl group, a biphenyl group, or any combination thereof.

9. The light-emitting device of claim 6, wherein the emission layer comprises the heterocyclic compound of Formula 1, the electron transport region includes a compound of Formula 601:

$$[Ar_{601}]_{xe11}\text{-}[(L_{601})_{xe1}\text{-}R_{601}]_{xe21} \qquad \text{Formula 601}$$

wherein, in Formula 601, $Ar_{601}$ and $L_{601}$ are each, independently from one another, a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, $L_{601}$ are each, independently from one another, a divalent $C_3$-$C_{60}$ carbocyclic group unsubstituted or substituted with at least one $R_{10a}$ or a divalent $C_1$-$C_{60}$ heterocyclic group unsubstituted or substituted with at least one $R_{10a}$, xe11 is 1, 2, or 3, xe1 is 0, 1, 2, 3, 4, or 5, $R_{601}$ is a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, —Si($Q_{601}$)($Q_{602}$)($Q_{603}$), —C(═O)($Q_{601}$), S(═O)$_2$($Q_{601}$), or —P(═O)($Q_{601}$)($Q_{602}$), xe21 is 1, 2, 3, 4, or 5, one or more of $Ar_{601}$, $L_{601}$, and $R_{601}$ are each, independently from one another, a π electron-deficient nitrogen-containing $C_1$-$C_{60}$ cyclic group unsubstituted or substituted with at least one $R_{10a}$, and $R_{10a}$ is:

deuterium, —F, —Cl, —Br, —I, a hydroxyl group, a cyano group, or a nitro group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group each, independently from one another, unsubstituted or substituted with deuterium, —F, —Cl, —Br, —I, a hydroxyl group, a cyano group, a nitro group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, —Si($Q_{11}$)($Q_{12}$)($Q_{13}$), —N($Q_{11}$)($Q_{12}$), —B($Q_{11}$)($Q_{12}$), —C(═O)($Q_{11}$), —S(═O)$_2$($Q_{11}$), —P(═O)($Q_{11}$)($Q_{12}$), or any combination thereof;

a $C_3$-$C_{60}$ carbocyclic group, a $C_1$-$C_{60}$ heterocyclic group, a $C_6$-$C_{60}$ aryloxy group, or a $C_6$-$C_{60}$ arylthio group each, independently from one another, unsubstituted or substituted with deuterium, —F, -Cl, —Br, —I, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), —P(=O)($Q_{21}$)($Q_{22}$), or any combination thereof; or —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), or —P(=O)($Q_{31}$)($Q_{32}$), wherein $Q_{11}$ to $Q_{13}$, $Q_{21}$ to $Q_{23}$, $Q_{31}$ to $Q_{33}$, and $Q_{601}$ to $Q_{603}$ are each, independently from one another: hydrogen; deuterium; —F; —Cl; —Br; —I; a hydroxyl group; a cyano group; a nitro group; a $C_1$-$C_{60}$ alkyl group; a $C_2$-$C_{60}$ alkenyl group; a $C_2$-$C_{60}$ alkynyl group; a $C_1$-$C_{60}$ alkoxy group; a $C_3$-$C_{60}$ carbocyclic group or a $C_1$-$C_{60}$ heterocyclic group each, independently from one another, unsubstituted or substituted with deuterium, —F, a cyano group, a $C_1$-$C_{60}$ alkyl group, a $C_1$-$C_{60}$ alkoxy group, a phenyl group, a biphenyl group, or any combination thereof.

10. The light-emitting device of claim 9, wherein an electron transport layer in the electron transport region comprises a compound of Formula 601, and the electron transport layer further comprises a material comprising a metal.

11. The light-emitting device of claim 10, wherein the material comprises a post-transition metal complex, an alkali metal complex, an alkaline earth metal complex, or any combination thereof.

12. The light-emitting device of claim 1, wherein $Y_1$ and $Y_2$ are each B.

13. The light-emitting device of claim 1, wherein Formula 1-2 is of Formula 1-2-1 or 1-2-2:

Formula 1-2-1

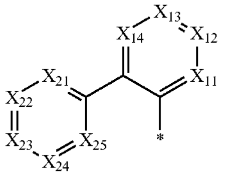

Formula 1-2-2

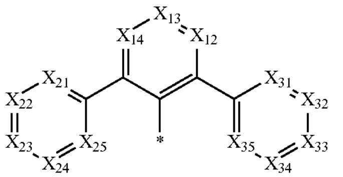

wherein, in Formulae 1-2-1 and 1-2-2, $X_{11}$ to $X_{14}$ each have, independently from one another, the same meaning as $X_{11}$ to $X_{14}$ in claim 1, $X_{21}$ is N or C($R_{21}$), $X_{22}$ is N or C($R_{22}$), $X_{23}$ is N or C($R_{23}$), $X_{24}$ is N or C($R_{24}$), and $X_{25}$ is N or C($R_{25}$), $X_{31}$ is N or C($R_{31}$), $X_{32}$ is N or C($R_{32}$), $X_{33}$ is N or C($R_{33}$), $X_{34}$ is N or C($R_{34}$), and $X_{35}$ is N or C($R_{35}$), $R_{21}$ to $R_{25}$ and $R_{31}$ to $R_{35}$ each have, independently from one another, the meaning as $R_{10a}$ in claim 1,

* has the meaning as in claim 1, two or more neighboring groups of $R_{21}$ to $R_{25}$ are optionally linked to each other to form a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, and two or more neighboring groups of $R_{31}$ to $R_{35}$ are optionally linked to each other to form a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$.

14. The light-emitting device of claim 1, wherein Formula 1-2 is one of Formulae 2-1 to 2-57:

2-1

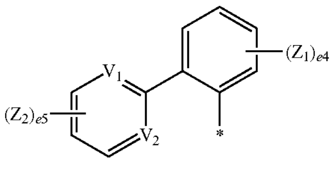

2-2

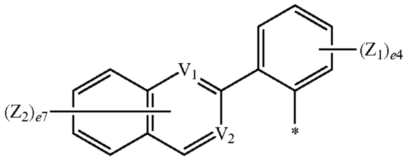

2-3

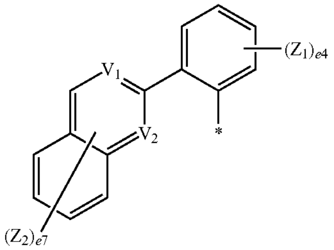

2-4

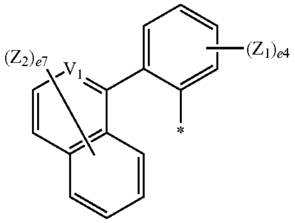

2-5

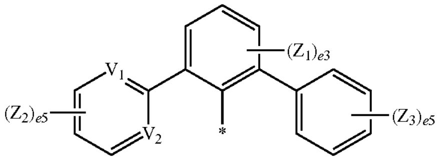

2-6

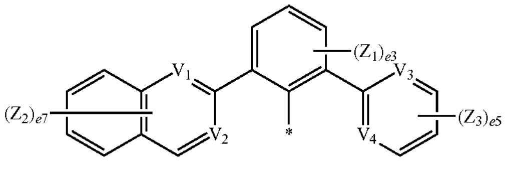

2-7

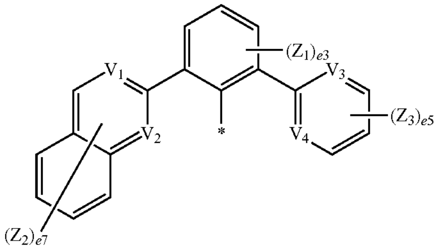

-continued
2-8
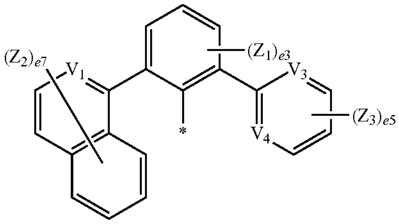
2-9
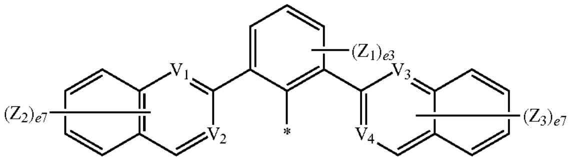
2-10
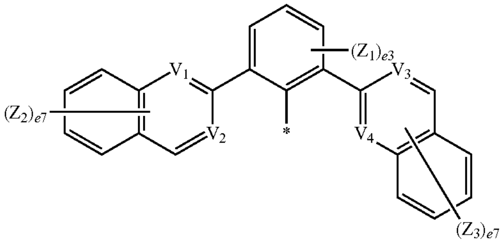
2-11
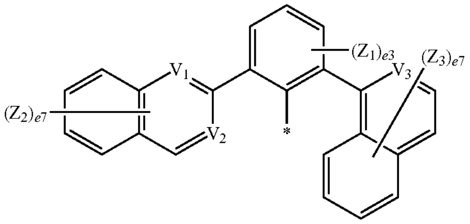
2-12
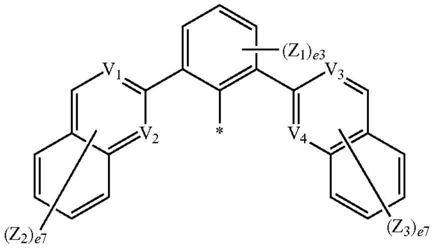
2-13
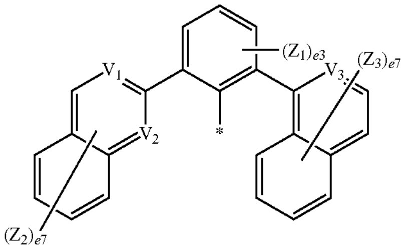
-continued
2-14
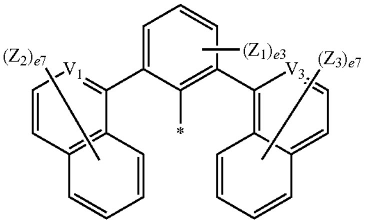
2-15
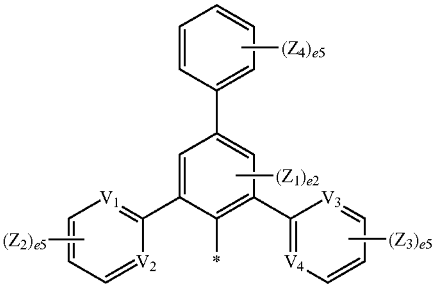
2-16
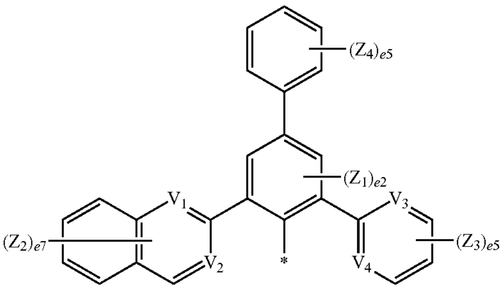
2-17
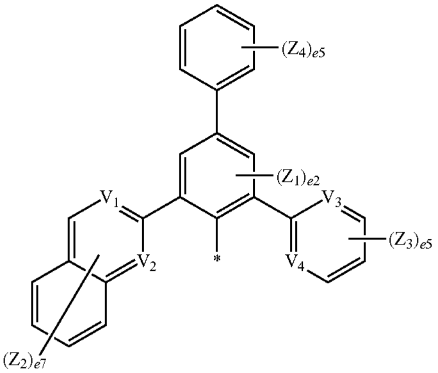
2-18
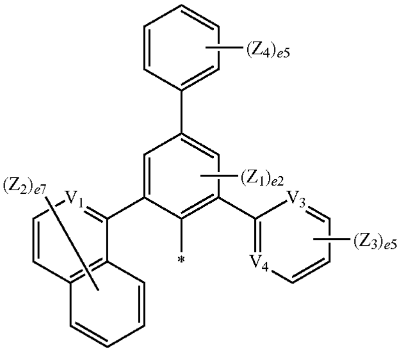

-continued
2-19
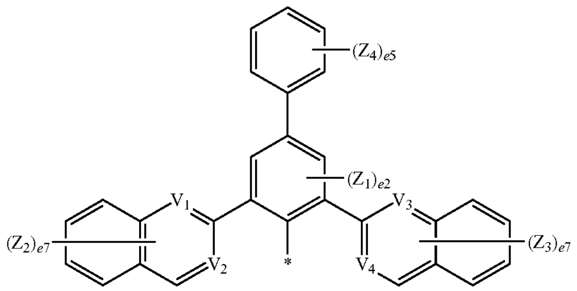
2-20
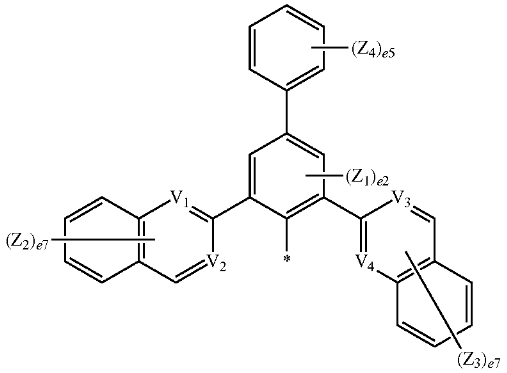
2-21
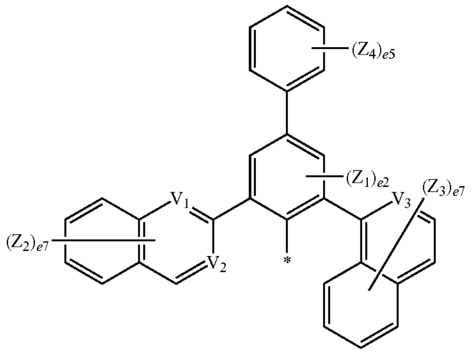
2-22
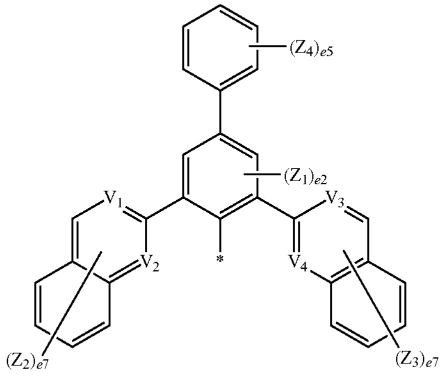
-continued
2-23
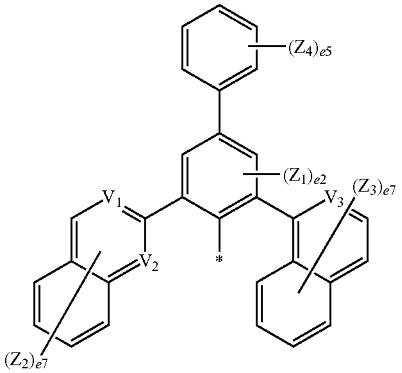
2-24
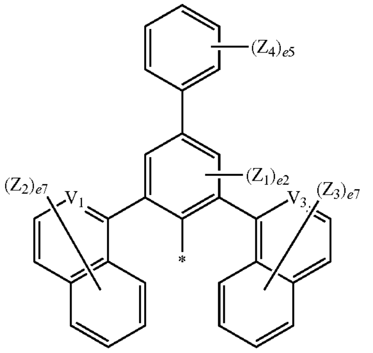
2-25
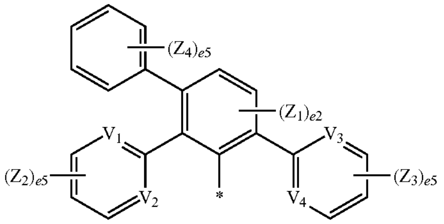
2-26
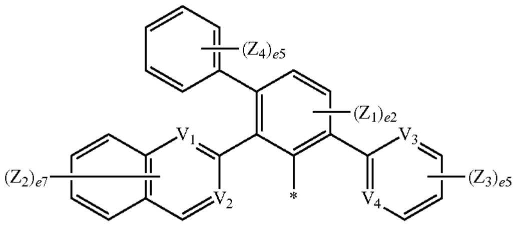
2-27
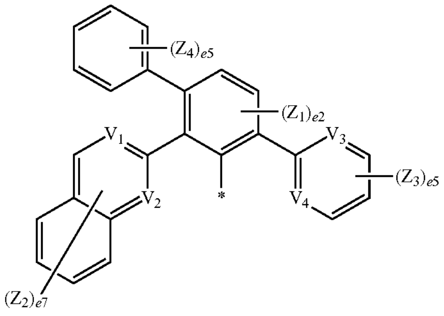

-continued
2-28
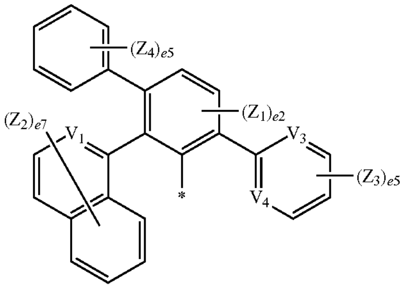
2-29
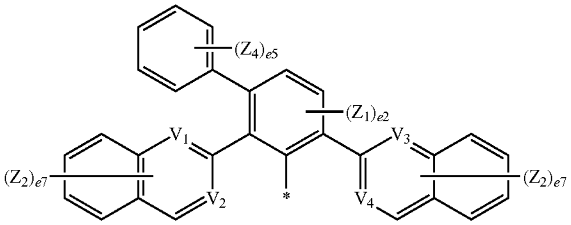
2-30
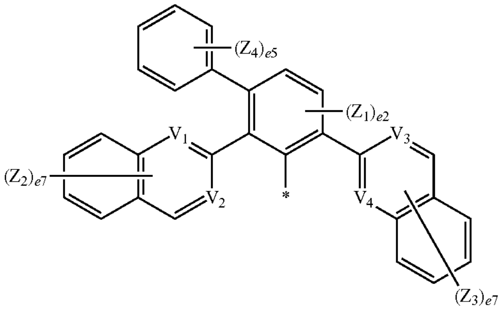
2-31
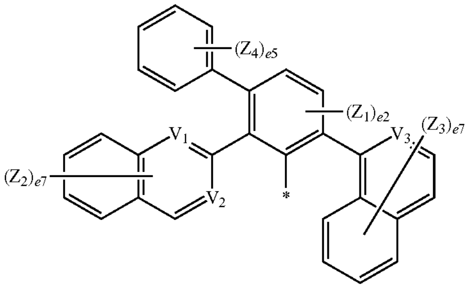
2-32
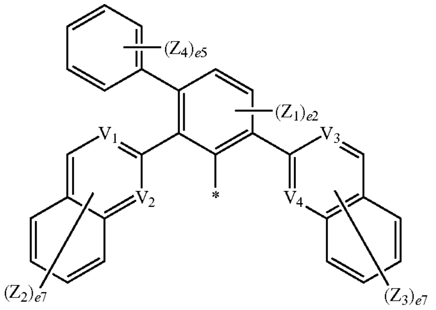
-continued
2-33
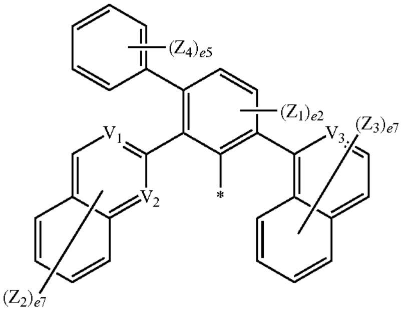
2-34
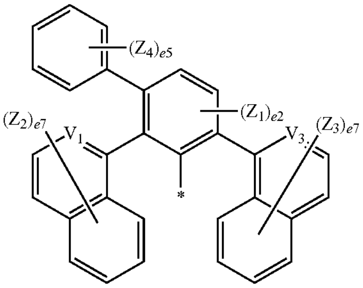
2-35
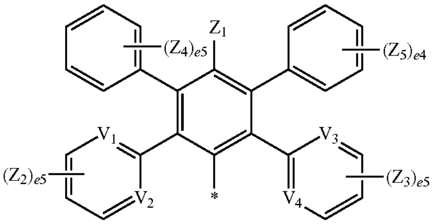
2-36
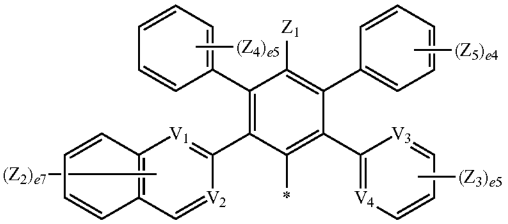
2-37
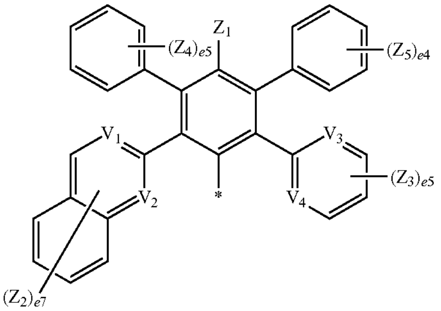

-continued
2-38
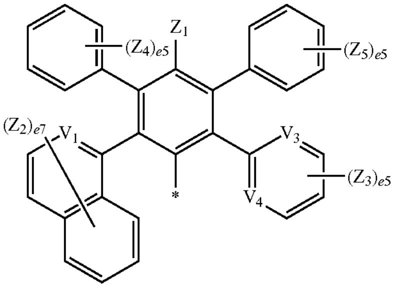
2-39
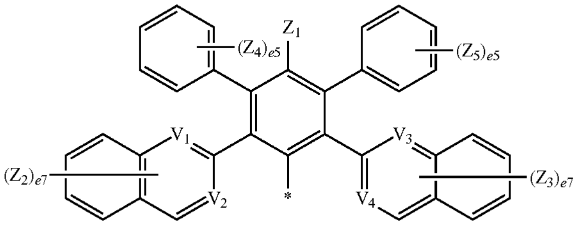
2-40
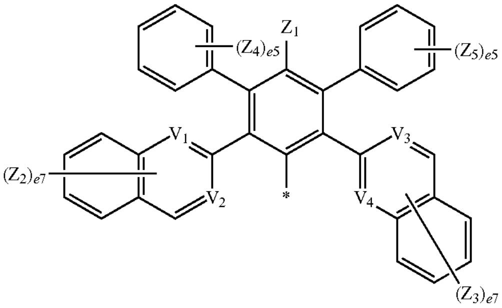
2-41
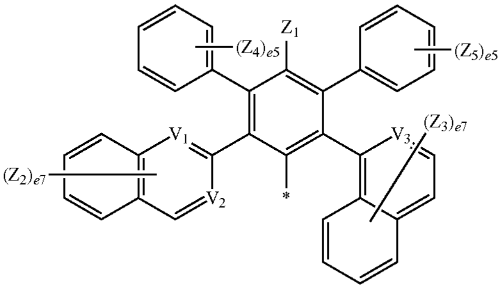
2-42
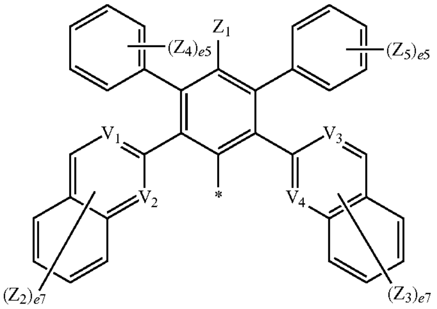
-continued
2-43
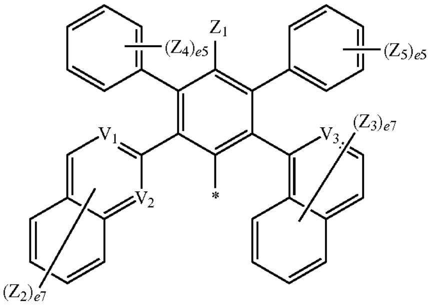
2-45
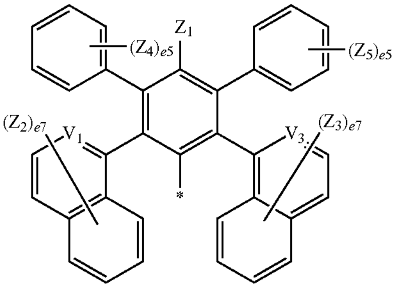
2-46
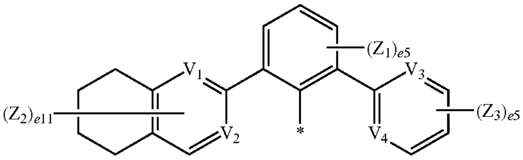
2-47
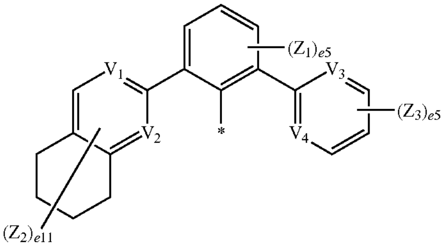
2-48
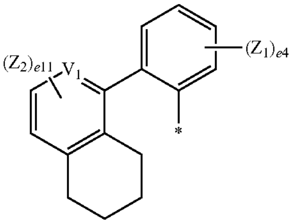
2-49
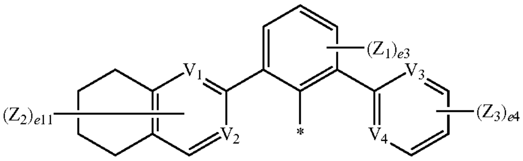

-continued 2-50

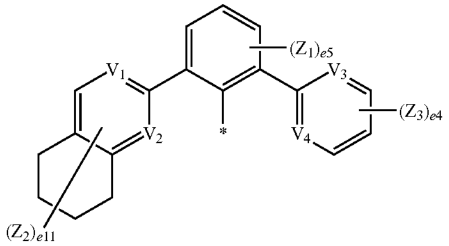

2-51

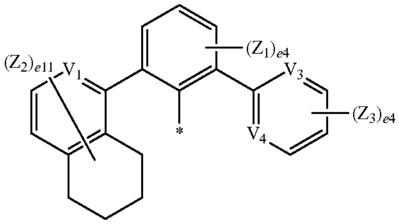

2-52

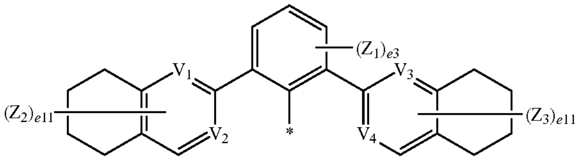

2-53

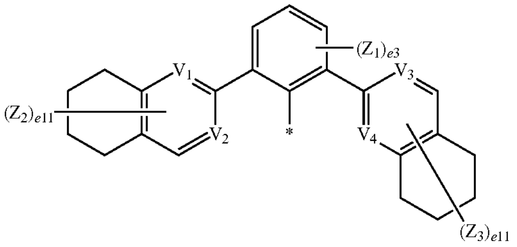

2-54

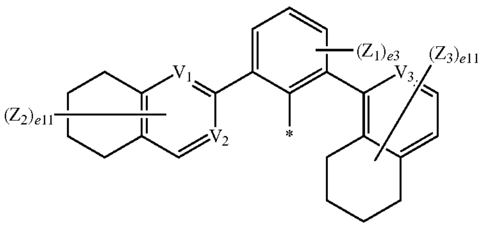

2-55

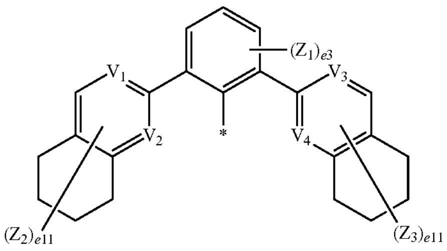

-continued 2-56

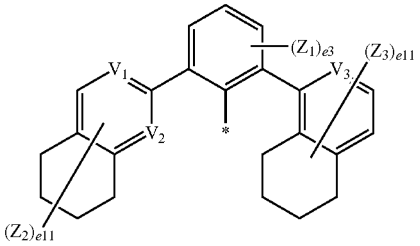

2-57

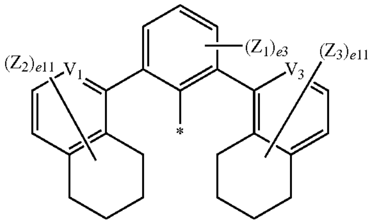

wherein, in Formulae 2-1 to 2-57, $V_1$ to $V_4$ are each, independently from one another, C or N, $Z_1$ to $Z_5$ are each, independently from one another:

deuterium, —F, —Cl, —Br, —I, a cyano group, a $C_1$-$C_{20}$ alkyl group, or a $C_1$-$C_{20}$ alkoxy group;

a $C_1$-$C_{20}$ alkyl group or a $C_1$-$C_{20}$ alkoxy group each independently from one another, substituted with deuterium, $-CD_3$, $-CD_2H$, $-CDH_2$, —F, $-CF_3$, $-CF_2H$, $-CFH_2$, —Cl, $—CCl_3$, $-CCl_2H$, $—CClH_2$, —Br, $-CBr_3$, $-CBr_2H$, $-CBrH_2$, —I, $—CI_3$, $—CI_2H$, $—CIH_2$, a cyano group, or any combination thereof;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, a terphenyl group, a $C_1$-$C_{20}$ alkylphenyl group, a naphthyl group, a fluorenyl group, a phenanthrenyl group, an anthracenyl group, a thiophenyl group, a furanyl group, an indenyl group, an isoindolyl group, an indolyl group, a carbazolyl group, a benzofuranyl group, a benzothiophenyl group, a benzosilolyl group, a dibenzofuranyl group, a dibenzothiophenyl group, a dibenzosilolyl group, a benzofluorenyl group, a benzocarbazolyl group, a naphthobenzofuranyl group, a naphthobenzothiophenyl group, a naphthobenzosilolyl group, a dibenzofluorenyl group, a dibenzocarbazolyl group, a dinaphthofuranyl group, a dinaphthothiophenyl group, a dinaphthosilolyl group, an indenocarbazolyl group, an indolocarbazolyl group, a benzofuranocarbazolyl group, a benzothienocarbazolyl group, a benzosilolocarbazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, a benzoisoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, an acridinyl group, a phenanthrolinyl group, a phenazinyl group, a phenoxazinyl group, a phenothiazinyl group, a phenoxathinyl group, a benzimidazolyl group, a benzofuranyl group, a benzothiophenyl group, a benzosilolyl group, a benzothiazolyl group, a benzoisothiazolyl group, a benzoxazolyl group, a benzoisoxazolyl group, a triazolyl group, a tetrazolyl group, a thiadiazolyl group, an oxadiazolyl group, a triazinyl group, an imidazopyridinyl group, an imidazopyrimidinyl group, an oxazolopyridinyl group, a thiazolopyridinyl group, a benzonaphthyridinyl group, an azafluorenyl group, an azaspiro-bifluorenyl group, an azacarbazolyl group, an azadibenzofuranyl group, an azadibenzothiophenyl group, an azadibenzosilolyl group, an indenopyrrolyl group, or an indolopyrrolyl group each, independently from one another, unsubstituted or substituted with deuterium, $-CD_3$, $-CD_2H$, $-CDH_2$, —F, $-CF_3$, $-CF_2H$, $-CFH_2$, —Cl, $-CCl_3$, $-CCl_2H$, $—CClH_2$, —Br, $—CBr_3$, $-CBr_2H$, $-CBrH_2$, -I, $—CI_3$, $—CI_2H$, $—CIH_2$, a cyano group, a $C_1$-$C_{20}$ alkyl group, a $C_1$-$C_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, a terphenyl group, a $C_1$-$C_{20}$ alkylphenyl group, a naphthyl group, a fluorenyl group, a phenanthrenyl group, an anthracenyl group, a thiophenyl group, a furanyl group, an indenyl group, an isoindolyl group, an indolyl group, a carbazolyl group, a benzofuranyl group, a benzothiophenyl group, a benzosilolyl group, a dibenzofuranyl group, a dibenzothiophenyl group, a dibenzosilolyl group, a benzofluorenyl group, a benzocarbazolyl group, a naphthobenzofuranyl group, a naphthobenzothiophenyl group, a naphthobenzosilolyl group, a dibenzofluorenyl group, a dibenzocarbazolyl group, a dinaphthofuranyl group, a dinaphthothiophenyl group, a dinaphthosilolyl group, an indenocarbazolyl group, an indolocarbazolyl group, a benzofuranocarbazolyl group, a benzothienocarbazolyl group, a benzosilolocarbazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, a benzoisoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, an acridinyl group, a phenanthrolinyl group, a phenazinyl group, a phenoxazinyl group, a phenothiazinyl group, a phenoxathinyl group, a benzimidazolyl group, a benzofuranyl group, a benzothiophenyl group, a benzosilolyl group, a benzothiazolyl group, a benzoisothiazolyl group, a benzoxazolyl group, a benzoisoxazolyl group, a triazolyl group, a tetrazolyl group, a thiadiazolyl group, an oxadiazolyl group, a triazinyl group, an imidazopyridinyl group, an imidazopyrimidinyl group, an oxazolopyridinyl group, a thiazolopyridinyl group, a benzonaphthyridinyl group, an azafluorenyl group, an azaspiro-bifluorenyl group, an azacarbazolyl group, an azadibenzofuranyl group, an azadibenzothiophenyl group, an azadibenzosilolyl group, an indenopyrrolyl group, an indolopyrrolyl group, $—Si(Q_{31})(Q_{32})(Q_{33})$, $—N(Q_{31})(Q_{32})$, $—B(Q_{31})(Q_{32})$, $—C(=O)(Q_{31})$, $—S(=O)_2(Q_{31})$, $—P(=O)(Q_{31})(Q_{32})$, or any combination thereof; or $—C(Q_1)(Q_2)(Q_3)$, $—Si(Q_1)(Q_2)(Q_3)$, $—N(Q_1)(Q_2)$, $—B(Q_1)(Q_2)$, $—C(=O)(Q_1)$, $—S(=O)_2(Q_1)$, or $—P(=O)(Q_1)(Q_2)$, wherein $Q_1$ to $Q_3$ and $Q_{31}$ to $Q_{33}$ are each, independently from one another: hydrogen; deuterium; —F; —Cl; —Br; —I; a hydroxyl group; a cyano group; a nitro group; a $C_1$-$C_{60}$ alkyl group; a $C_2$-$C_{60}$ alkenyl group; a $C_2$-$C_{60}$ alkynyl group; a $C_1$-$C_{60}$ alkoxy group; a $C_3$-$C_{60}$ carbocyclic group; or a $C_1$-$C_{60}$ heterocyclic group each, independently from one another, unsubstituted or substituted with deuterium, —F, a cyano group, a $C_1$-$C_{60}$ alkyl group, a $C_1$-$C_{60}$ alkoxy group, a phenyl group, a biphenyl group, or any combination thereof, e2 is an integer from 0 to 2, e3 is an integer from 0 to 3, e4 is an integer from 0 to 4, e5 is an integer from 0 to 5, e7 is an integer from 0 to 7, e11 is an integer from 0 to 11, and

* indicates a binding site to a neighboring group.

15. The light-emitting device of claim 1, wherein Formula 1-1 is of Formula 1-1-1:

Formula 1-1-1

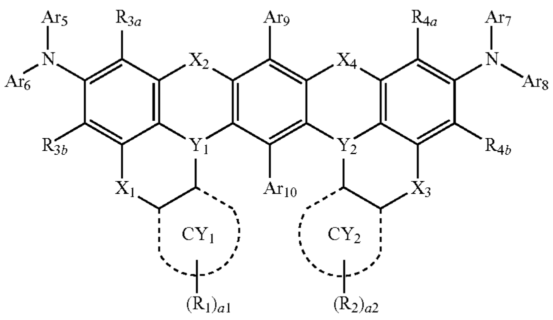

wherein, in Formula 1-1-1, $CY_1$, $CY_2$, $X_1$ to $X_4$, $Y_1$, $Y_2$, $Ar_1$ to $Ar_{10}$, $R_1$, $R_2$, a1, and a2 have, independently from one another, the same meaning as in claim 1, $R_{3a}$ and $R_{3b}$ have, independently from one another, the same meaning as $R_3$ in claim 1, and $R_{4a}$ and $R_{4b}$ have, independently from one another, the same meaning as $R_4$ in claim 1.

16. The light-emitting device of claim 1, wherein the light-emitting device further comprises a capping layer outside the first electrode or the second electrode, and the capping layer comprises one or more carbocyclic compounds, heterocyclic compounds, amine-based compounds, porphyrin derivatives, phthalocyanine derivatives, naphthalocyanine derivatives, alkali metal complexes, alkaline earth-based complexes, or any combination thereof.

17. An electronic apparatus comprising the light-emitting device of claim 1.

18. The electronic apparatus of claim 17, further comprising a thin-film transistor, wherein the thin-film transistor comprises a source electrode and a drain electrode, and the first electrode of the light-emitting device is electrically connected to at least one of the source electrode and the drain electrode of the thin-film transistor.

* * * * *